United States Patent
Bennett et al.

(10) Patent No.: US 9,765,338 B2
(45) Date of Patent: Sep. 19, 2017

(54) MODULATION OF DYSTROPHIA MYOTONICA-PROTEIN KINASE (DMPK) EXPRESSION

(71) Applicants: Isis Pharmaceuticals, Inc., Carlsbad, CA (US); University Of Rochester, Rochester, NY (US)

(72) Inventors: C. Frank Bennett, Carlsbad, CA (US); Susan M. Freier, San Diego, CA (US); Robert A. MacLeod, San Diego, CA (US); Sanjay K. Pandey, Encinitas, CA (US); Charles A. Thornton, Rochester, NY (US); Thurman Wheeler, Rochester, NY (US); Seng H. Cheng, Natick, MA (US); Andrew Leger, Boston, MA (US); Bruce M. Wentworth, Northborough, MA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/814,174

(22) Filed: Jul. 30, 2015

(65) Prior Publication Data
US 2016/0068845 A1 Mar. 10, 2016

Related U.S. Application Data

(63) Continuation of application No. 13/811,181, filed as application No. PCT/US2011/044555 on Jul. 19, 2011, now abandoned.

(60) Provisional application No. 61/365,762, filed on Jul. 19, 2010, provisional application No. 61/365,775, filed on Jul. 19, 2010, provisional application No. 61/478,021, filed on Apr. 21, 2011.

(51) Int. Cl.
*C12N 15/11* (2006.01)
*C12N 15/113* (2010.01)

(52) U.S. Cl.
CPC ........ *C12N 15/1137* (2013.01); *C12N 15/113* (2013.01); *C12Y 207/11* (2013.01); *C12N 2310/11* (2013.01); *C12N 2310/315* (2013.01); *C12N 2310/3181* (2013.01); *C12N 2310/321* (2013.01); *C12N 2310/3231* (2013.01); *C12N 2310/3341* (2013.01); *C12N 2310/341* (2013.01); *C12N 2310/346* (2013.01)

(58) Field of Classification Search
CPC ....................... C12N 15/1137; C12N 2310/113
See application file for complete search history.

(56) References Cited

U.S. PATENT DOCUMENTS

| | | | |
|---|---|---|---|
| 3,687,808 A | 8/1972 | Merigan et al. | |
| 4,845,205 A | 7/1989 | Huynh Dinh et al. | |
| 5,130,302 A | 7/1992 | Spielvogel et al. | |
| 5,134,066 A | 7/1992 | Rogers et al. | |
| 5,175,273 A | 12/1992 | Bischofberger et al. | |
| 5,367,066 A | 11/1994 | Urdea et al. | |
| 5,432,272 A | 7/1995 | Benner | |
| 5,434,257 A | 7/1995 | Matteucci | |
| 5,457,187 A | 10/1995 | Gmelner et al. | |
| 5,459,255 A | 10/1995 | Cook et al. | |
| 5,484,908 A | 1/1996 | Froehler et al. | |
| 5,502,177 A | 3/1996 | Matteucci et al. | |
| 5,525,711 A | 6/1996 | Hawkins et al. | |
| 5,552,282 A | 9/1996 | Caskey et al. | |
| 5,552,540 A | 9/1996 | Haralambidis | |
| 5,587,469 A | 12/1996 | Cook et al. | |
| 5,594,121 A | 1/1997 | Froehler et al. | |
| 5,596,091 A | 1/1997 | Switzer | |
| 5,614,617 A | 3/1997 | Cook et al. | |
| 5,645,985 A | 7/1997 | Froehler et al. | |
| 5,646,269 A | 7/1997 | Matteucci | |
| 5,681,941 A | 10/1997 | Cook et al. | |
| 5,750,692 A | 5/1998 | Cook et al. | |
| 5,763,588 A | 6/1998 | Matteucci et al. | |
| 5,801,154 A | 9/1998 | Baracchini et al. | |
| 5,830,653 A | 11/1998 | Froehler et al. | |
| 5,955,265 A | 9/1999 | Brook et al. | |
| 6,005,096 A | 12/1999 | Matteucci et al. | |
| 6,007,992 A | 12/1999 | Lin et al. | |
| 6,028,183 A | 2/2000 | Lin et al. | |
| 6,268,490 B1 | 7/2001 | Imanishi et al. | |
| 6,329,501 B1 | 12/2001 | Smith et al. | |
| 6,525,191 B1 | 2/2003 | Ramasamy | |

(Continued)

FOREIGN PATENT DOCUMENTS

| | | |
|---|---|---|
| WO | WO 99/14226 | 3/1999 |
| WO | WO 00/58332 | 10/2000 |

(Continued)

OTHER PUBLICATIONS

Van Der Burg et al., "Beyond the brain: widespread pathology in Huntington's disease", Lancet Neurology (2009) 8(8): 765-774.
Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.
Altmann et al., "Second Generation of Antisense Oligonucleotides: From Nuclease Resistance to Biological Efficacy in Animals" Chimia (1996) 50:168-176.
Altmann et al., "Second-generation antisense oligonucleotides: structure-activity relationships and the design of improved signal-transduction inhibitors" Biochem. Soc. Trans. (1996) 24:630-637.

(Continued)

*Primary Examiner* — Brian Whiteman
(74) *Attorney, Agent, or Firm* — Ionis Pharmaceuticals, Inc. Patent Dept.

(57) ABSTRACT

Provided herein are methods, compounds, and compositions for reducing expression of a DMPK mRNA and protein in an animal. Also provided herein are methods, compounds, and compositions for preferentially reducing CUGexp DMPK RNA, reducing myotonia or reducing spliceopathy in an animal. Such methods, compounds, and compositions are useful to treat, prevent, delay, or ameliorate type 1 myotonic dystrophy, or a symptom thereof.

24 Claims, No Drawings

(56) References Cited

U.S. PATENT DOCUMENTS

| | | | |
|---|---|---|---|
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,374,927 | B2 | 5/2008 | Palma et al. |
| 7,399,845 | B2 | 7/2008 | Seth et al. |
| 7,427,672 | B2 | 9/2008 | Imanishi et al. |
| 8,158,364 | B2 * | 4/2012 | Sarkar .................. C12Q 1/6883 435/4 |
| RE44,779 | E | 2/2014 | Imanishi et al. |
| 9,012,421 | B2 | 4/2015 | Migawa et al. |
| 2001/0053519 | A1 | 12/2001 | Fodor et al. |
| 2003/0158403 | A1 | 8/2003 | Manoharan et al. |
| 2003/0207804 | A1 | 11/2003 | Manoharan et al. |
| 2003/0228597 | A1 | 12/2003 | Cowsert et al. |
| 2004/0171570 | A1 | 9/2004 | Allerson et al. |
| 2007/0031844 | A1 | 2/2007 | Khvorova et al. |
| 2007/0287831 | A1 | 12/2007 | Seth et al. |
| 2008/0015158 | A1 | 1/2008 | Ichiro et al. |
| 2008/0039618 | A1 | 2/2008 | Allerson et al. |
| 2008/0242629 | A1 | 10/2008 | Crooke et al. |
| 2010/0016215 | A1 | 1/2010 | Moulton et al. |
| 2010/0047289 | A1 | 2/2010 | Fakhari et al. |
| 2010/0190837 | A1 | 7/2010 | Migawa et al. |
| 2011/0229880 | A1 | 9/2011 | Wood et al. |
| 2013/0225659 | A1 | 8/2013 | Bennett |
| 2015/0191727 | A1 | 7/2015 | Migawa et al. |

FOREIGN PATENT DOCUMENTS

| | | |
|---|---|---|
| WO | WO 02/01953 | 1/2002 |
| WO | WO 03/013437 | 2/2003 |
| WO | WO 2004/028458 | 4/2004 |
| WO | WO 2004/093783 | 11/2004 |
| WO | WO 2004/106356 | 12/2004 |
| WO | WO 2005/121368 | 12/2005 |
| WO | WO 2006/034348 | 3/2006 |
| WO | WO 2007/089584 | 8/2007 |
| WO | WO 2007/089611 | 8/2007 |
| WO | WO 2007/121272 | 10/2007 |
| WO | WO 2007/134181 | 11/2007 |
| WO | WO 2008/018795 | 2/2008 |
| WO | WO 2008/036406 | 3/2008 |
| WO | WO 2008/049085 | 4/2008 |
| WO | WO 2008/150729 | 12/2008 |
| WO | WO 2008/154401 | 12/2008 |
| WO | WO 2009/006478 | 1/2009 |
| WO | WO 2009/099326 | 8/2009 |
| WO | WO 2010/014592 | 2/2010 |
| WO | WO 2010/115993 | 10/2010 |
| WO | WO 2011/097388 | 8/2011 |

OTHER PUBLICATIONS

Altmann et al., "Second Generation Antisense Oligonucleotides—Inhibition of PKC-a and c-RAF Kinase Expression by Chimeric Oligonucleotides Incorporating 6'-Subsituted Carbocyclic Nucleosides and 2'-O-Ethylene Glycol Substituted Ribonucleosides" Nucleosides & Nucleotides (1997) 16(7-9):917-926.
Aronin et al., "Expanded CAG repeats in the crosshairs" Nature Biotechnology (2009) 27(5): 451-452.
Ascoli et al., "Identification of a novel nuclear domain" J. Cell Biol. (1991) 112(5):785-795.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Brook et al., "Molecular basis of myotonic dystrophy: Expansion of a trinucleotide (CTG) repeat at the 3' end of a transcript encoding a protein kinase family member" Cell (1992) 68(4):799-808.
Cleary et al., "The contribution of cis-elements to disease-associated repeat instability: clinical and experimental evidence" Cytogenet. Genome Res. (2003) 100:25-55.
Clemson et al., "An Architectural Role for a Nuclear Noncoding RNA: NEAT1 RNA is Essential for the Structure of Paraspeckles" Mol. Cell (2009) 33:717-726.
Conte et al., "Conformational properties and thermodynamics of the RNA duplex r(CGCAAAUUUGCG)2: comparison with the DNA analogue d(CGCAAATTTGCG)2" Nucleic Acids Res. (1997) 25(13):2627-2634.
Cooper, "RNA and Disease" Cell (2009) 136:777-793.
Costa, "Non-coding RNAs and new opportunities for the private secotr" Drug Discovery today (2009) 14:446-452.
Cremer et al., "Chromosome Territories, Interchromatin Domain Compartment, and Nuclear Matrix: An Integrated View of the Functional Nuclear Architecture" Crit. Rev. Eukaroytic Gene Expr. (2000) 10:179-212.
Crooke et al., "Basic Principles of Antisense Therapeutics" Antisense Research and Application (1998) Chapter 1:1-50.
Davis et al., "Expansion of a CUG trinucleotide repeat in the 3* untranslated region of myotonic dystrophy protein kinase transcripts results in nuclear retention of transcripts" PNAS (1997) 94:7388-7393.
Denegri et al., "Human Chromosomes 9, 12, and 15 Contain the Nucleation Sites of Stress-Induced Nuclear Bodies" Mol. Biol. Cell (2002) 13:2069-2079.
Dong et al., "Implication of snoRNA U50 in human breast cancer" Journal of Genetics and Genomics (2009) 36(8): 447-454.
Doucas et al., "The PML nuclear compartment and cancer" Biochem. Biophys. Acta (1996) 1288(3):M25-M29.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Fakan et al., "Ultrastructural Distribution of Nuclear Ribonucleoproteins as Visualized by Immunocytochemistry on Thin Sections" J. Cell Biol. (1984) 98:358-363.
Flanagan et al., "A cytosine analog that confers enhanced potency to antisense oligonucleotides" PNAS (1999) 96:3513-3518.
Fox et al., "P54nrb Forms a Heterodimer with PSP1 That Localizes to Paraspeckles in an RNA-dependent Manner" Mol. Biol. Cell (2005) 16:5304-5315.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fu et al., "Factor required for mammalian spliceosome assembly is localized to discrete regions in the nucleus" Nature (1990) 343:437-441.
Galderisi et al., Biochem. Biophys. Res. Commun. (1996) 221(3):750-754.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
Guo et al., "Inhibition of metastasis-associated lung adenocarcinoma transcript 1 in CaSki human cervical cancer cells suppresses cell proliferation and invasion" Acta Biochimica et Biophysica Sinica (2010) 42(3): 224-229.
Guttman et al., "Chromatin signature reveals over a thousand highly conserved large non-coding RNAs in mammals" Nature (2009) 458:223-227.
Hu et al., "Allele-specific silencing of mutant huntingtin and ataxin-3 genes by targeting expanded CAG repeats in mRNAs" Nature Biotechnology (2009) 27(5): 478-484.

(56) References Cited

OTHER PUBLICATIONS

Hu et al., "Allele-selective inhibition of mutant huntingtin by peptide nucleic acid-peptide conjugates, locked nucleic acid, and small interfering RNA" Annals of the New York Academy of Sciences (2009) 1175: 24-31.

Huang, "Review: Perinucleolar Structures" J. Struct. Biol. (2000) 129:233-240.

Ideue et al., "Efficient oligonucleotide-mediated degradation of nuclear noncoding RNAs in mammalian cultured cells" RNA (2009) 15(8): 1578-1587.

Ji et al., "MALAT-1, a novel noncoding RNA, and thymosin b4 predict metastasis and survival in early-stage non-small cell lung cancer" Oncogene (2003) 22:8031-8041.

Jolly et al., "In vivo binding of active heat shock transcription factor 1 to human chromosome 9 heterochromatin during stress" J. Cell Biol. (2002) 156:775-781.

Kanadia et al., "Reversal of RNA missplicing and myotonia after muscleblind overexpression in a mouse poly(CUG) model for myotonic dystrophy" PNAS (2006) 103(31):11748-11753.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Krol et al., "Ribonuclease dicer cleaves triplet repeat hairpins into shorter repeats that silence specific targets" Molecular Cell (2007) 25:575-586.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Kurchavov et al., "A New Phosphoramidite Reagent for the Incorporation of Diazaphenoxazinone Nucleoside with Enhanced Base-Pairing Properties into Oligodeoxynucleotides" Nucleosides and Nucleotides (1997) 16)10 & 11):1837-1846.

Lavorgna et al., "In search of antisense" Trends Biochem. Sci. (2004) 29:88-94.

Lee et al., "Targeted Degradation of Toxic RNA in Myotonic Dystrophy" p. 35, Abstracts of papers presented at the 2010 meeting on RNA & oligonucleotide therapeutics. Apr. 7-10, 2010.

Lehner et al., "Antisense transcripts in the human genome" Trends. Genet. (2002) 18:63-65.

Lesnik et al., "Relative Thermodynamic Stability of DNA, RNA, and DNA:RNA Hybried Duplexes: Relationship with Base Composition and Structure" Biochemistry (1995) 34:10807-10815.

Leumann, "DNA Analogues: From Supramolecular Principles to Biological Properties" Bioorg. & Med. Chem. (2002) 10:841-854.

Liang et al., "Efficient and specific knockdown of small non-coding RNAs in mammalian cells and in mice" Nucleic Acids Research (2010) 39(3): E13.

Lin et al., "Tricyclic 2'-Deoxycytidine Analogs: Synthesis and Incorporation into Oligodeoxynucleotides Which Have Enhanced Binding to Complementary RNA" J. Am. Chem. Soc. (1995) 117:3873-3874.

Lin et al., "A Cytosine Analogue Capable of Clamp-Like Binding to a Guanine in Helical Nucleic Acids" J. Am. Chem. Soc. (1998) 120:8531-8532.

Lin et al., "Failure of MBNL1-dependent post-natal splicing transitions in myotonic dystrophy" Human Mol. Genet. (2006) 15(13):2087-2097.

Liquori et al., "Myotonic Dystrophy Type 2 Caused by a CCTG Expansion in Intron 1 of ZNF9" Science (2001) 293:864-867.

Lolle, "Genome-wide non-mendelian inheritance of extra-genomic information in Arabidopsis" Nature (2005) 434:505-509.

Maher e tal., "Comparative hybrid arrest by tandem antisense oligodeoxyribonucleotides or oligodeoxyribonucleoside methylphosphonates in a cell-free system" Nuc. Acid. Res. (1988) 16:341-3358.

Mankodi et al., "Expanding CUG Repeats Trigger Aberrant Splicing of CIC-1 Chloride Channel Pre-mRNA and Hyperexcitability of Skeletal Muscle in Myotonic Dystrophy" Mol. Cell. (2002) 10:35-44.

Martin, "Ein neuer Zugang zu 2'-O-Alkylribonucleosiden and Eigenschaften deren Oligonucleotide" Helv. Chim. Acta. (1995) 78:486-504.

Mercer et al., "Specific expression of long noncoding RNAs in the mouse brain" PNAS (2008) 105(2):716-721.

Mouritzen et al., "ProbeLibrary: A new method for faster design and execution of quantitative real-time PCR" Nature Methods (2005) 2:313-317.

New England Biolabs 1998/1999 Catalog (cover page and pp. 121 and 284).

Orum et al., "Locked nucleic acids: A promising molecular family for gene-function analysis and antisense drug development" Curr. Opinion Mol. Ther. (2001) 3:239-243.

O'Rourke, "Mechanisms of RNA-mediated Disease" J. Biol. Chem. (2009) 284(12):7419-7423.

Peng et al., "The poly(A)-limiting element enhances mRNA accumulation by increasing the efficiency of pre-mRNA 3' processing" RNA (2005) 11:958-965.

Ploner et al., "Methodological obstacles in knocking down small noncoding RNAs" RNA (2009) 15(10): 1797-1804.

Prasanth et al., "Regulating Gene Expression through RNA Nuclear Retention" Celll (2005) 123(2): 249-263.

Rassoulzadegan et al., "RNA-mediated non-mendelian inheritance of an epigenetic change in the mouse" Nature (2006) 441:469-474.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Sasaki et al., "MENε/β noncoding RNAs are essential for structural integrity of nuclear paraspeckles" PNAS (2009) 106(8):2525-2530.

Scholefield et al., "Therapeutic gene silencing strategies for polyglutamine disorders" Trends in Genetics (2010) 26(1): 29-38.

Searle et al., "On the stability of nucleic acid structures in solution: enthalpy-entropy compensations, internal rotations and reversibility" Nucleic Acids Res. (1993) 21:2051-2056.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Sunwoo et al., "MEN e/b nuclear-retained non-coding RNAs are up-regulated upon muscle differentiation and are essential components of paraspeckles" Genome Res. (2009) 19:347-359.

Swayze et al., "The Medicinal Chemistry of Oligonucleotides" in Antisense Drug Technology, 2nd Edition, Chapter 6, pp. 143-182, Crooke ed., 2008.

Thiry, "Birth of a nucleolus: the evolution of nucleolar compartments" Trends. Cell Biol. (2005) 15:194-199.

Viegas et al., "Regulating the regulators: How ribonucleases dictate the rules in the control of small non-coding RNAs" RNA Biol. (2008) 5:230-243.

Wahlestedt et al., "Potent and nontoxic antisense oligonucleotide containing locked nucleic acids" Proc. Natl. Acad. Sci. USA (2000) 97: 5633-5638.

Wang et al., "Synthesis and binding property of an oligonucleotide containing tetraflurophenoxazine" Tetrahedron Lett. (1998) 39:8385-8388.

Watts e tal., "Chemically modified siRNAs: tools and applications" Drug Discovery Today (2008) 13(19-20): 842-855.

Wheeler et al., "Reversal of RNA dominance by displacement of protein sequestered on triplet repeat RNA" Science (2009) 325:336-339.

(56) References Cited

OTHER PUBLICATIONS

Wilusz et al., "3' End Processing of a Long Nuclear-Retained Noncoding RNA Yields a tRNA-like Cytoplasmic RNA" Cell (2008) 135:919-932.

Woolf et al., "Specificity of antisense oligonucleotides in vivo" PNAS (1992) 89:7305-7309.

Yelin et al., "Widespread occurrence of antisense transcription in the human genome" Nat. Biotechnol. (2003) 21(4):379-386.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

European Search Report for application EP 11740540.7 dated Aug. 19, 2014.

European Search Report for application EP 11810309.2 dated Aug. 19, 2014.

European Search Report for application EP 11810291.2 dated Feb. 4, 2014.

International Search Report for application PCT/US11/24099 dated Jun. 22, 2011.

International Search Report for application PCT/US11/44583 dated Mar. 1, 2012.

International Search Report for application PCT/US11/44555 dated Apr. 11, 2012.

Extended European Search Report in co-pending European Patent Application No. 16153949.9, dated May 11, 2016, 9 pages.

Mulders et al., "Triplet Repeat Oligonucleotide-Mediated Reversal of RNA Toxicity in Myotonic Dystrophy," Proceedings of the National Academy of Sciences (2009), 106: 13915-13928.

De Die-Smulders et al., "Age and Causes of Death in Adult-Onset Myotonic Dystrophy," Brain, 1998, 121:1557-1563.

Miller et al., "Recruitment of Human Muscleblind Proteins to (CUG)(n) Expansions Associated with Myotonic Dystrophy," EMBO J., 2000, 19:4439-4448.

Osborne et al., "RNA-Dominant Diseases," Hum Mol Genet., 2006, 15:R162-9.

Pandey et al., "Identification and Characterization of Modified Antisense Oligonucleotides Targeting DMPK in Mice and Nonhuman Primates for the Treatment of Myotonic Dystrophy Type 1," J Pharmacol Exp Ther, 2015, 355:329-340.

Ranum et al., "RNA-Mediated Neuromuscular Disorders," Annu Rev Neurosci, 2006, 29:259-277.

Wheeler et al., "Targeting Nuclear RNA for in vivo Correction of Myotonic Dystrophy," Nature, 2012, 488:111-117.

Wheeler et al., "Myotonic Dystrophy: RNA Mediated Muscle Disease," Curr Opin Neurol, 2007, 20:572-576.

Ionis Pharmaceuticals Press Release, Recently Published Preclinical Data Show Significant and Sustained Reduction of Muscle DMPK RNA with a Generation 2.5 Antisense Compound, Sep. 1, 2015, 1 page.

Ballantyne et al., "Locked nucleic acids in PCR primers increase sensitivity and performance" Genomics (2008) 91: 301-305.

Lebedev at el., "Oligonucleotides containing 2-aminoadenine and 5-methylcytosine are more effective as primers for PCR amplification than their nonmodified counterparts," Genetic Analysis: Biomolecular Engineering, Genetic.

Noronha et al., "Amplimers with 1-15 3'-terminal phosphorothioate linkages resist degradation by Vent polymersase and reduce Taq polymerase mispriming," PCR Methods & Applicatio, Cold Spring Harbor Laboratory Press (1992) 2: 131-136.

European Search Report for application EP 14834532.5 dated Feb. 20, 2017.

International Search Report for application PCT/US14/050481 dated Feb. 2, 2015.

* cited by examiner

MODULATION OF DYSTROPHIA MYOTONICA-PROTEIN KINASE (DMPK) EXPRESSION

STATEMENT OF GOVERNMENT SUPPORT

This invention was made with government support under NS072323 awarded by the National Institutes of Health. The government has certain rights in the invention.

SEQUENCE LISTING

The present application is being filed along with a Sequence Listing in electronic format. The Sequence Listing is provided as a file entitled BIOL0134USC1SEQ.txt created Jul. 28, 2015, which is approximately 220 Mb in size. The information in the electronic format of the sequence listing is incorporated herein by reference in its entirety.

FIELD

Provided herein are methods, compounds, and compositions for reducing expression of DMPK mRNA and protein in an animal. Also, provided herein are methods, compounds, and compositions comprising a DMPK inhibitor for preferentially reducing CUGexp DMPK RNA, reducing myotonia, or reducing spliceopathy in an animal. Such methods, compounds, and compositions are useful, for example, to treat, prevent, or ameliorate type 1 myotonic dystrophy (DM1) in an animal.

BACKGROUND

Myotonic dystrophy type 1 (DM1) is the most common form of muscular dystrophy in adults with an estimated frequency of 1 in 7,500 (Harper P S., Myotonic Dystrophy. London: W.B. Saunders Company; 2001). DM1 is an autosomal dominant disorder caused by expansion of a noncoding CTG repeat in DMPK1. DMPK1 is a gene encoding a cytosolic serine/threonine kinase (Brook J D, et al., Cell., 1992, 68(4):799-808). The physiologic functions and substrates of this kinase have not been fully determined. The expanded CTG repeat is located in the 3' untranslated region (UTR) of DMPK1. This mutation leads to RNA dominance, a process in which expression of RNA containing an expanded CUG repeat (CUGexp) induces cell dysfunction (Osborne R J and Thornton C A., Human Molecular Genetics., 2006, 15(2): R162-R169).

The DMPK gene normally has 5-37 CTG repeats in the 3' untranslated region. In myotonic dystrophy type I, this number is significantly expanded and is, for example, in the range of 50 to greater than 3,500 (Harper, Myotonic Dystrophy (Saunders, London, ed.3, 2001); Annu. Rev. Neurosci. 29: 259, 2006; EMBO J. 19: 4439, 2000; Curr Opin Neurol. 20: 572, 2007).

The CUGexp tract interacts with RNA binding proteins including muscleblind-like (MBNL) protein, a splicing factor, and causes the mutant transcript to be retained in nuclear foci. The toxicity of this RNA stems from sequestration of RNA binding proteins and activation of signaling pathways. Studies in animal models have shown that phenotypes of DM1 can be reversed if toxicity of CUGexp RNA is reduced (Wheeler T M, et al., Science., 2009, 325(5938):336-339; Mulders S A, et al., Proc Natl Acad Sci USA., 2009, 106(33):13915-13920).

In DM1, skeletal muscle is the most severely affected tissue, but the disease also has important effects on cardiac and smooth muscle, ocular lens, and brain. The cranial, distal limb, and diaphragm muscles are preferentially affected. Manual dexterity is compromised early, which causes several decades of severe disability. The median age at death is 55 years, usually from respiratory failure (de Die-Smulders C E, et al., Brain., 1998, 121(Pt 8):1557-1563).

Antisense technology is emerging as an effective means for modulating expression of certain gene products and may therefore prove to be uniquely useful in a number of therapeutic, diagnostic, and research applications for the modulation of DMPK1. Intramuscular injection of fully modified oligonucleotides targeting with the CAG-repeat were shown in mice to block formation of CUGexp-MBNL1 complexes, disperse nuclear foci of CUGexp transcripts, enhance the nucleocytoplasmic transport and translation of CUGexp transcripts, release MBNL proteins to the nucleoplasm, normalize alternative splicing of MBNL-dependent exons, and eliminate myotonia in CUGexp-expressing transgenic mice (Wheeler T M, et al., Science., 2009, 325(5938): 336-339; WO2008/036406).

Presently there is no treatment that can modify the course of DM1. The burden of disease, therefore, is significant. It is, therefore, an object herein to provide compounds, compositions, and methods for treating DM1

SUMMARY

Provided herein are methods, compounds, and compositions for inhibiting expression of DMPK and treating, preventing, delaying or ameliorating a DMPK related disease and or a symptom thereof. In certain embodiments, the compounds and compositions inhibit mutant DMPK or CUGexp DMPK.

Certain embodiments provide a method of reducing DMPK expression in an animal comprising administering to the animal a compound comprising a modified oligonucleotide as further described herein targeted to DMPK.

Certain embodiments provide a method of preferentially reducing CUGexp DMPK, reducing myotonia, or reducing spliceopathy in an animal comprising administering to the animal a compound comprising a modified oligonucleotide, as further described herein, targeted to CUGexp DMPK. CUGexp DMPK transcripts are believed to be particularly sensitive to antisense knockdown via nuclear ribonucleases, because of their longer residence time in the nucleus, and this sensitivity is thought to permit effective antisense inhibition of CUGexp DMPK transcripts in relevant tissues such as muscle despite the biodistribution barriers to tissue uptake of antisense oligonucleotides. Antisense mechanisms that do not elicit cleavage via nuclear ribonucleases, such as the CAG-repeat ASOs described in, for example, Wheeler T M, et al., Science., 2009, 325(5938):336-339 and WO2008/036406, do not provide the same therapeutic advantage.

Certain embodiments provide a method of treating an animal with type 1 myotonic dystrophy. In certain embodiments, the method includes administering to the animal a therapeutically effective amount of a compound comprising a modified oligonucleotide as further described herein targeted to DMPK. In certain embodiments, the method includes identifying an animal with type 1 myotonic dystrophy.

Certain embodiments provide a method of treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide a method of treating, preventing, delaying, or ameliorating symptoms and outcomes associated with development of DM1 in children, including, developmental delays, learning problems, language and speech issues, and personality development issues.

Certain embodiments provide a method of administering an antisense oligonucleotide to counteract RNA dominance by directing the cleavage of pathogenic transcripts.

In certain embodiments, the DMPK has a sequence as set forth in GenBank Accession No. NM_001081560.1 (incorporated herein as SEQ ID NO: 1). In certain embodiments, the DMPK has the sequence as set forth in GenBank Accession No. NT_011109.15 truncated from nucleotides 18540696 to Ser. No. 18/555,106 (incorporated herein as SEQ ID NO: 2). In certain embodiments, the DMPK has the sequence as set forth in GenBank Accession No. NT_039413.7 truncated from nucleotides 16666001 to Ser. No. 16/681,000 (incorporated herein as SEQ ID NO: 3). In certain embodiments, the DMPK has the sequence as set forth in GenBank Accession No. NM_032418.1 (incorporated herein as SEQ ID NO: 4). In certain embodiments, the DMPK has the sequence as set forth in GenBank Accession No. AI007148.1 (incorporated herein as SEQ ID NO: 5). In certain embodiments, the DMPK has the sequence as set forth in GenBank Accession No. AI304033.1 (incorporated herein as SEQ ID NO: 6). In certain embodiments, the DMPK has the sequence as set forth in GenBank Accession No. BC024150.1 (incorporated herein as SEQ ID NO: 7). In certain embodiments, the DMPK has the sequence as set forth in GenBank Accession No. BC056615.1 (incorporated herein as SEQ ID NO: 8). In certain embodiments, the DMPK has the sequence as set forth in GenBank Accession No. BC075715.1 (incorporated herein as SEQ ID NO: 793). In certain embodiments, the DMPK has the sequence as set forth in GenBank Accession No. BU519245.1 (incorporated herein as SEQ ID NO: 794). In certain embodiments, the DMPK has the sequence as set forth in GenBank Accession No. CB247909.1 (incorporated herein as SEQ ID NO: 795). In certain embodiments, the DMPK has the sequence as set forth in GenBank Accession No. CX208906.1 (incorporated herein as SEQ ID NO: 796). In certain embodiments, the DMPK has the sequence as set forth in GenBank Accession No. CX732022.1 (incorporated herein as SEQ ID NO: 797). In certain embodiments, the DMPK has the sequence as set forth in GenBank Accession No. 560315.1 (incorporated herein as SEQ ID NO: 798). In certain embodiments, the DMPK has the sequence as set forth in GenBank Accession No. 560316.1 (incorporated herein as SEQ ID NO: 799). In certain embodiments, the DMPK has the sequence as set forth in GenBank Accession No. NM_001081562.1 (incorporated herein as SEQ ID NO: 800). In certain embodiments, the DMPK has the sequence as set forth in GenBank Accession No. NM_001100.3 (incorporated herein as SEQ ID NO: 801).

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. Herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GEN-BANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'—O-methoxyethyl" (also 2'-MOE and 2'—O(CH$_2$)$_2$—OCH$_3$) refers to an O-methoxy-ethyl modification of the 2' position of a furanosyl ring. A 2'—O-methoxyethyl modified sugar is a modified sugar.

"2'—O-methoxyethyl nucleotide" means a nucleotide comprising a 2'—O-methoxyethyl modified sugar moiety.

"5-methylcytosine" means a cytosine modified with a methyl group attached to position 5. A 5-methylcytosine is a modified nucleobase.

"About" means within ±7% of a value. For example, if it is stated, "the compound affected at least 70% inhibition of DMPK", it is implied that the DMPK levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to DMPK is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound of the invention. For example, a first agent can be an antisense oligonucleotide targeting DMPK. "Second agent" means a second therapeutic compound of the invention (e.g. a second antisense oligonucleotide targeting DMPK) and/or a non-DMPK therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furanosyl ring modified by the bridging of two non-geminal carbon ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'—O-methoxyethyl nucleotides is chemically distinct from a region having nucleotides without 2'—O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"CUGexp DMPK" means mutant DMPK RNA containing an expanded CUG repeat (CUGexp). The wild-type DMPK gene has 5-37 CTG repeats in the 3' untranslated region. In a "CUGexp DMPK" (such as in a myotonic dystrophy type I patient) this number is significantly expanded and is, for example, in the range of 50 to greater than 3,500 (Harper, Myotonic Dystrophy (Saunders, London, ed.3, 2001); Annu Rev. Neurosci. 29: 259, 2006; EMBO J. 19: 4439, 2000; Curr Opin Neurol. 20: 572, 2007).

"Diluent" means an ingredient in a composition that lacks pharmacological activity, but is pharmaceutically necessary or desirable. For example, the diluent in an injected composition can be a liquid, e.g. saline solution.

"DMPK" means any nucleic acid or protein of DMPK. DMPK can be a mutant DMPK including CUGexp DMPK nucleic acid.

"DMPK expression" means the level of mRNA transcribed from the gene encoding DMPK or the level of protein translated from the mRNA. DMPK expression can be determined by art known methods such as a Northern or Western blot.

"DMPK nucleic acid" means any nucleic acid encoding DMPK. For example, in certain embodiments, a DMPK nucleic acid includes a DNA sequence encoding DMPK, an RNA sequence transcribed from DNA encoding DMPK (including genomic DNA comprising introns and exons), and an mRNA or pre-mRNA sequence encoding DMPK. "DMPK mRNA" means an mRNA encoding a DMPK protein.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal with type 1 myotonic dystrophy" means identifying an animal having been diagnosed with a type 1 myotonic dystrophy, disorder or condition or identifying an animal predisposed to develop a type 1 myotonic dystrophy, disorder or condition. For example, individuals with a familial history can be predisposed to type 1 myotonic dystrophy, disorder or condition. Such identification can be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded or linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar. "Motif" means the pattern of chemically distinct regions in an antisense compound. "Myotonia" means an abnormally slow relaxation of a muscle after voluntary contraction or electrical stimulation.

"Nuclear ribonuclease" means a ribonuclease found in the nucleus. Nuclear ribonucleases include, but are not limited to, RNase H including RNase H1 and RNase H2, the double stranded RNase drosha and other double stranded RNases.

"Naturally occurring internucleoside linkage" means a 3' to 5' phosphodiester linkage.

"Natural sugar moiety" means a sugar found in DNA (2'—H) or RNA (2'—OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition can comprise one or more active agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Preferentially reducing CUG exp DMPK RNA" refers to a preferential reduction of RNA transcripts from a CUGexp DMPK allele relative to RNA transcripts from a normal DMPK allele.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Spliceopathy" means a change in the alternative splicing of one or more RNAs that leads to the expression of altered splice products in a particular tissue.

"Subcutaneous administration" means administration just below the skin.

"Sugar surrogate" overlaps with the slightly broader term "nucleoside mimetic" but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Treat" refers to administering a pharmaceutical composition to effect an alteration or improvement of a disease, disorder, or condition.

"Type 1 myotonic dystrophy" or "DM1" means an autosomal dominant disorder caused by expansion of a noncoding CTG repeat in DMPK. This mutation leads to RNA dominance, a process in which expression of RNA containing an expanded CUG repeat (CUGexp) induced cell dysfunction. The CUGexp tract interacts with RNA binding proteins and causes the mutant transcript to be retained in nuclear foci. The toxicity of this RNA stems from sequestration of RNA binding proteins and activation of signaling pathways.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting DMPK expression.

Certain embodiments provide a method of reducing DMPK expression in an animal comprising administering to the animal a compound comprising a modified oligonucleotide targeting DMPK.

Certain embodiments provide a method of preferentially reducing CUGexp DMPK RNA, reducing myotonia or reducing spliceopathy in an animal comprising administering to the animal a compound comprising a modified oligonucleotide targeted to DMPK, wherein the modified oligonucleotide preferentially reduces CUGexp DMPK RNA, reduces myotonia or reduces spliceopathy in the animal.

Certain embodiments provide a method of administering an antisense oligonucleotide to counteract RNA dominance by directing the cleavage of pathogenic transcripts.

Certain embodiments provide a method of reducing spliceopathy of Serca1. In certain embodiments, methods provided herein result in exon 22 inclusion. In certain embodiments, the corrective splicing occurs in the tibialis anterior, gastrocnemius, and quadriceps muscles.

Certain embodiments provide a method of reducing spliceopathy of m-Titin. In certain embodiments, methods provided herein result in exon 5 inclusion. In certain embodiments, the corrective splicing occurs in the tibialis anterior, gastrocnemius, and quadriceps muscles.

Certain embodiments provide a method of reducing spliceopathy of Clcn1. In certain embodiments, methods provided herein result in exon 7a inclusion. In certain embodiments, the corrective splicing occurs in the tibialis anterior, gastrocnemius, and quadriceps muscles.

Certain embodiments provide a method of reducing spliceopathy of Zasp. In certain embodiments, methods provided herein result in exon 11 inclusion. In certain embodiments, the corrective splicing occurs in the tibialis anterior, gastrocnemius, and quadriceps muscles.

Certain embodiments provide a method for treating an animal with type 1 myotonic dystrophy comprising: a) identifying said animal with type 1 myotonic dystrophy, and b) administering to said animal a therapeutically effective amount of a compound comprising a modified oligonucleotide targeted to DMPK. In certain embodiments, the therapeutically effective amount of the compound administered to the animal preferentially reduces CUGexp DMPK RNA, reduces myotonia or reduces spliceopathy in the animal.

Certain embodiments provide a method of achieving a preferential reduction of CUGexp DMPK RNA, including administering to the subject suspected of having type 1 myotonic dystrophy or having a CUGexp DMPK RNA a modified antisense oligonucleotide complementary to a non-repeat region of said CUGexp DMPK RNA. The modified antisense oligonucleotide, when bound to said CUGexp DMPK RNA, achieves a preferential reduction of the CUGexp DMPK RNA.

Certain embodiments provide a method of achieving a preferential reduction of CUGexp DMPK RNA, including selecting a subject having type 1 myotonic dystrophy or having a CUGexp DMPK RNA and administering to said subject a modified antisense oligonucleotide complementary to a non-repeat region of said CUGexp DMPK RNA. The modified antisense oligonucleotide, when bound to the CUGexp DMPK RNA, activates a ribonuclease or nuclear ribonuclease, thereby achieving a preferential reduction of the CUGexp DMPK RNA in the nucleus.

Certain embodiments provide a method of achieving a preferential reduction of CUGexp DMPK RNA, including selecting a subject having type 1 myotonic dystrophy or having a mutant or CUGexp DMPK RNA and systemically administering to said subject a modified antisense oligonucleotide complementary to a non-repeat region of said CUGexp DMPK RNA. The modified antisense oligonucleotide, when bound to the mutant or CUGexp DMPK RNA, achieves a preferential reduction of the mutant or CUGexp DMPK RNA.

Certain embodiments provide a method of reducing myotonia in a subject in need thereof. The method includes administering to the subject a modified antisense oligonucleotide complementary to a non-repeat region of a DMPK RNA, wherein the modified antisense oligonucleotide, when bound to the DMPK RNA, activates a ribonuclease or nuclear ribonuclease, thereby reducing myotonia. In certain embodiments, the subject has or is suspected of having type 1 myotonic dystrophy or having a mutant DMPK RNA or CUGexp DMPK RNA. In certain embodiments, the DMPK RNA is nuclear retained.

Certain embodiments provide a method of reducing spliceopathy in a subject in need thereof. The method includes administering to the subject a modified antisense oligonucleotide complementary to a non-repeat region of a DMPK RNA, wherein the modified antisense oligonucleotide, when bound to the DMPK RNA, activates a ribonuclease or nuclear ribonuclease, thereby reducing spliceopathy. In certain embodiments, the subject has or is suspected of having type 1 myotonic dystrophy or having a nuclear retained CUGexp DMPK RNA. In certain embodiments, the DMPK RNA is nuclear retained. In certain embodiments, the spliceopathy is MBNL dependent spliceopathy.

In certain embodiments, the modified antisense oligonucleotide of the methods is chimeric. In certain embodiments, the modified antisense oligonucleotide of the methods is a gapmer.

In certain embodiments of the methods provided herein, the administering is subcutaneous. In certain embodiments, the administering is intravenous.

In certain embodiments, the modified antisense oligonucleotide of the methods targets a non-coding sequence within the non-repeat region of a DMPK RNA. In certain embodiments, the oligonucleotide targets a coding region, an intron, a 5'UTR, or a 3'UTR of the mutant DMPK RNA.

In certain embodiments of the methods provided herein, the nuclear ribonuclease is RNase H1.

In certain embodiments of the methods, the DMPK RNA is reduced in muscle tissue. In certain embodiments, the mutant DMPK RNA CUGexp DMPK RNA is preferentially reduced.

In certain embodiments, the DMPK has the sequence as set forth in GenBank Accession No. NM_001081560.1 (incorporated herein as SEQ ID NO: 1). In certain embodiments, the DMPK has the sequence as set forth in GenBank Accession No. NT_011109.15 truncated from nucleotides 18540696 to Ser. No. 18/555,106 (incorporated herein as SEQ ID NO: 2). In certain embodiments, the DMPK has the sequence as set forth in GenBank Accession No. NT_039413.7 truncated from nucleotides 16666001 to Ser. No. 16/681,000 (incorporated herein as SEQ ID NO: 3). In certain embodiments, the DMPK has the sequence as set forth in GenBank Accession No. NM_032418.1 (incorporated herein as SEQ ID NO: 4). In certain embodiments, the DMPK has the sequence as set forth in GenBank Accession No. AI007148.1 (incorporated herein as SEQ ID NO: 5). In certain embodiments, the DMPK has the sequence as set forth in GenBank Accession No. AI304033.1 (incorporated herein as SEQ ID NO: 6). In certain embodiments, the DMPK has the sequence as set forth in GenBank Accession No. BC024150.1 (incorporated herein as SEQ ID NO: 7). In certain embodiments, the DMPK has the sequence as set forth in GenBank Accession No. BC056615.1 (incorporated herein as SEQ ID NO: 8). In certain embodiments, the DMPK has the sequence as set forth in GenBank Accession No. BC075715.1 (incorporated herein as SEQ ID NO: 793). In certain embodiments, the DMPK has the sequence as set forth in GenBank Accession No. BU519245.1 (incorporated herein as SEQ ID NO: 794). In certain embodiments, the DMPK has the sequence as set forth in GenBank Accession No. CB247909.1 (incorporated herein as SEQ ID NO: 795). In certain embodiments, the DMPK has the sequence as set forth in GenBank Accession No. CX208906.1 (incorporated herein as SEQ ID NO: 796). In certain embodiments, the DMPK has the sequence as set forth in GenBank Accession No. CX732022.1 (incorporated herein as SEQ ID NO: 797). In certain embodiments, the DMPK has the sequence as set forth in GenBank Accession No. 560315.1 (incorporated herein as SEQ ID NO: 798). In certain embodiments, the DMPK has the sequence as set forth in GenBank Accession No. 560316.1 (incorporated herein as SEQ ID NO: 799). In certain embodiments, the DMPK has the sequence as set forth in GenBank Accession No. NM_001081562.1 (incorporated herein as SEQ ID NO: 800). In certain embodiments, the DMPK has the sequence as set forth in GenBank Accession No. NM_001100.3 (incorporated herein as SEQ ID NO: 801).

In certain embodiments, the modified oligonucleotide has a nucleobase sequence comprising at least 8 contiguous nucleobases of a nucleobase sequence recited in any one of SEQ ID NOs: 12-156, 160-770, and 774-792. In certain embodiments, the modified oligonucleotide has a nucleobase sequence comprising at least 9, at least 10, or at least 11, contiguous nucleobases of a nucleobase sequence recited in any one of SEQ ID NOs: 12-156, 160-770, and 774-792.

In certain embodiments, the modified oligonucleotide has a nucleobase sequence comprising at least 12 contiguous nucleobases of a nucleobase sequence recited in any one of SEQ ID NOs: 12-156, 160-770, and 774-792. In certain embodiments, the modified oligonucleotide has a nucleobase sequence comprising at least 13, or at least 14, contiguous nucleobases of a nucleobase sequence recited in any one of SEQ ID NOs: 12-156, 160-770, and 774-792.

In certain embodiments, the modified oligonucleotide has a nucleobase sequence comprising at least 15 contiguous nucleobases of a nucleobase sequence recited in any one of SEQ ID NOs: 12-156, 160-770, and 774-792. In certain embodiments, the modified oligonucleotide has a nucleobase sequence comprising at least 16, or at least 17, contiguous nucleobases of a nucleobase sequence recited in any one of SEQ ID NOs: 12-156, 160-770, and 774-792.

In certain embodiments, the modified oligonucleotide has a nucleobase sequence comprising at least 18 contiguous nucleobases of a nucleobase sequence recited in any one of SEQ ID NOs: 12-156, 160-770, and 774-792. In certain embodiments, the modified oligonucleotide has a nucleobase sequence comprising at least 19 contiguous nucleobases of a nucleobase sequence recited in any one of SEQ ID NOs: 12-156, 160-770, and 774-792.

In certain embodiments, the modified oligonucleotides provided herein are targeted to any one of the following regions of SEQ ID NO: 1: 1178-1206, 2159-2182, 2174-2196, 2426-2447, 2450-2518, 2679-2704, and 2697-2725.

In certain embodiments, the modified oligonucleotides provided herein are targeted to any one of the following regions of SEQ ID NO 1: 178-223, 232-253, 279-299, 366-399, 519-541, 923-975, 1073-1105, 1171-1196, 1215-1246, 1263-1324, 1706-1734, 1743-1763, 1932-1979, 1981-2003, 2077-2108, and 2152-2173.

In certain embodiments, the modified oligonucleotides provided herein are targeted to any one of the following regions of SEQ ID NO: 2: 1251-1303, 1305-1326, 1352-1372, 3762-3795, 4170-4192, 5800-5852, 6124-6149, 6168-6199, 6216-6277, 11979-12007, 12016-12036, 12993-13042, 13044-13066, 13140-13171, and 13215-13236.

In certain embodiments, the animal is a human.

In certain embodiments, the compounds or compositions of the invention are designated as a first agent and the methods of the invention further comprise administering a second agent. In certain embodiments, the first agent and the second agent are co-administered. In certain embodiments the first agent and the second agent are co-administered sequentially or concomitantly.

In certain embodiments, administration comprises parenteral administration.

In certain embodiments, the compound is a single-stranded modified oligonucleotide. In certain embodiments, the nucleobase sequence of the modified oligonucleotide is at least 95% complementary to any one of SEQ ID NOs: 1-8 and 793-801 as measured over the entirety of said modified oligonucleotide. In certain embodiments, the nucleobase sequence of the modified oligonucleotide is 100% complementary to any one of SEQ ID NOs: 1-8 and 793-801 as measured over the entirety of said modified oligonucleotide.

In certain embodiments, at least one internucleoside linkage of said modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified sugar. In certain embodiments, at least one modified sugar is a bicyclic sugar. In certain embodiments, at least one modified sugar comprises a 2'—O-methoxyethyl or a 4'—(CH$_2$)$_n$—O-2' bridge, wherein n is 1 or 2.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'—O-methoxyethyl sugar, each internucleoside linkage of said modified oligonucleotide is a phosphorothioate linkage, and each cytosine in said modified oligonucleotide is a 5'-methylcytosine.

In certain embodiments, the modified oligonucleotide consists of 20 linked nucleosides.

Certain embodiments provide a method of preferentially reducing CUGexp DMPK RNA, reducing myotonia or reducing spliceopathy in an animal comprising administering to the animal a compound comprising a modified oligonucleotide having a gap segment consisting of ten linked deoxynucleosides, a 5' wing segment consisting of five linked nucleosides and a 3' wing segment consisting of five linked nucleosides. The gap segment is positioned between the 5' wing segment and the 3' wing segment, each nucleoside of each wing segment comprises a 2'—O-methoxyethyl sugar, each internucleoside linkage of said modified oligonucleotide is a phosphorothioate linkage, each cytosine in said modified oligonucleotide is a 5'-methylcytosine.

Certain embodiments provide the use of any compound as described herein in the manufacture of a medicament for use in any of the therapeutic methods described herein. For example, certain embodiments provide the use of a compound as described herein in the manufacture of a medicament for treating, ameliorating, or preventing type 1 myotonic dystrophy. Certain embodiments provide the use of a compound as described herein in the manufacture of a medicament for inhibiting expression of DMPK and treating, preventing, delaying or ameliorating a DMPK related disease and or a symptom thereof. Certain embodiments provide the use of a compound as described herein in the manufacture of a medicament for reducing DMPK expression in an animal. Certain embodiments provide the use of a compound as described herein in the manufacture of a medicament for preferentially reducing CUGexp DMPK, reducing myotonia, or reducing spliceopathy in an animal. Certain embodiments provide the use of a compound as described herein in the manufacture of a medicament for treating an animal with type 1 myotonic dystrophy. Certain embodiments provide the use of a compound as described herein in the manufacture of a medicament for treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide the use of a compound as described herein in the manufacture of a medicament for counteracting RNA dominance by directing the cleavage of pathogenic transcripts.

Certain embodiments provide a kit for treating, preventing, or ameliorating type 1 myotonic dystrophy as described herein wherein the kit comprises: a) a compound as described herein; and optionally b) an additional agent or therapy as described herein. The kit can further include instructions or a label for using the kit to treat, prevent, or ameliorate type 1 myotonic dystrophy.

Certain embodiments provide any compound or composition as described herein, for use in any of the therapeutic methods described herein. For example, certain embodiments provide a compound or composition as described herein for inhibiting expression of DMPK and treating, preventing, delaying or ameliorating a DMPK related disease and or a symptom thereof. Certain embodiments provide a compound or composition as described herein for use in reducing DMPK expression in an animal. Certain embodiments provide a compound or composition as described herein for use in preferentially reducing CUGexp DMPK, reducing myotonia, or reducing spliceopathy in an animal. Certain embodiments provide a compound or composition as described herein for use in treating an animal with type 1 myotonic dystrophy. Certain embodiments provide a compound or composition as described herein for use in treating, preventing, delaying, or ameliorating symptoms and outcomes associated with development of DM1 including muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. Certain embodiments provide a compound or composition as described herein for use in counteracting RNA dominance by directing the cleavage of pathogenic transcripts. Certain embodiments provide compounds comprising a modified oligonucleotide consisting of 12 to 30 linked nucleosides having a nucleobase sequence comprising at least 12 contiguous nucleobases of any of the nucleobase sequences of SEQ ID NOs: 12-156, 160-770, and 774-792.

Other compounds which can be used in the methods described herein are also provided.

For example, certain embodiments provide compounds comprising a modified oligonucleotide consisting of 10 to 80, 12 to 50, 12 to 30, 15 to 30, 18 to 24, 19 to 22, or 20 linked nucleosides having a nucleobase sequence comprising at least 8, at least 9, at least 10, at least 11, at least 12, at least 13, at least 14, at least 15, at least 16, at least 17, at least 18, or at least 19, contiguous nucleobases of any of the nucleobase sequences of SEQ ID NOs: 41, 44, 76, 109, 153, 320, 321, 322, 325, 329, 335, and 657.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising at least 8, at least 9, at least 10, at least 11, at least 12, at least 13, at least 14, at least 15, at least 16, at least 17, at least 18, at least 19, contiguous nucleobases of any of the nucleobase sequences of SEQ ID NOs: 15, 73, 77, 79, 83, 85, 130, 602, 648, 655, 674, and 680.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising a portion of at least 8, at least 9, at least 10, at least 11, at least 12, at least 13, at least 14, at least 15, at least 16, at least 17, at least 18, or at least 19, or more, contiguous nucleobases complementary to an equal length portion of nucleobases 664-683, 773-792, 926-945, 927-946, 928-947, 931-950, 935-954, 941-960, 2089-2108, 2163-2182, 2490-2509, 2499-2518, 2676-2695, 2685-2704, 2676-2695, 2688-2707, 2697-2716, 2764-2783, and 2770-2789 of SEQ ID NO: 1, wherein the nucleobase sequence is complementary to SEQ ID NO: 1.

Certain embodiments provide compounds comprising a modified oligonucleotide consisting of 10 to 80, 12 to 50, 12 to 30, 15 to 30, 18 to 24, 19 to 22, or 20, linked nucleosides having a nucleobase sequence comprising a portion of at least 8, at least 9, at least 10, at least 11, at least 12, at least 13, at least 14, at least 15, at least 16, at least 17, at least 18, or at least 19, or more, contiguous nucleobases complementary to an equal length portion of nucleobases 812-831, 3629-3648, 4447-4466, 4613-4632, 5803-5822, 5804-5823, 5805-5824, 5808-5827, 5818-5837, 6794-6813, 12463-12482, 13152-13171, and 13553-13572 of SEQ ID NO: 2, wherein the nucleobase sequence is complementary to SEQ ID NO: 2.

In certain embodiments, the modified oligonucleotide is a single-stranded oligonucleotide.

In certain embodiments, the nucleobase sequence of the modified oligonucleotide is at least 70%, at least 75%, at least 80%, at least 85%, at least 90%, at least 95%, or 100%, complementary to any of SEQ ID NOs: 1-8 and 793-801.

In certain embodiments, at least one internucleoside linkage is a modified internucleoside linkage.

In certain embodiments, each internucleoside linkage is a phosphorothioate internucleoside linkage.

In certain embodiments, at least one nucleoside comprises a modified sugar.

In certain embodiments, at least one modified sugar is a bicyclic sugar.

In certain embodiments, at least one modified sugar comprises a 2'—O-methoxyethyl.

In certain embodiments, at least one nucleoside comprises a modified nucleobase.

In certain embodiments, the modified nucleobase is a 5-methylcytosine.

In certain embodiments, the modified oligonucleotide comprises:
 a gap segment consisting of linked deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar.

In certain embodiments, the modified oligonucleotide comprises:
 a gap segment consisting of ten linked deoxynucleosides;
 a 5' wing segment consisting of five linked nucleosides; and
 a 3' wing segment consisting of five linked nucleosides;
 wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide consists of 14 linked nucleosides.

In certain embodiments, the modified oligonucleotide consists of 16 linked nucleosides.

In certain embodiments, the modified oligonucleotide consists of 20 linked nucleosides.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to DMPK as described herein is 10 to 30 nucleotides in length. In other words, the antisense compounds are in some embodiments from 10 to 30 linked nucleobases. In other embodiments, the antisense compound comprises a modified oligonucleotide consisting of 8 to 80, 10 to 80, 12 to 30, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In certain embodiments, antisense compounds of any of these lengths contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 12-156, 160-770, and 774-792.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide can have two nucleosides deleted from the 5' end, or alternatively can have two subunits deleted from the 3' end. Alternatively, the deleted nucleosides can be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside can be located at the 5' or 3' end of the oligonucleotide. When two or more additional nucleosides are present, the added nucleosides can be adjacent to each other, for example, in an oligonucleotide having two nucleosides added to the 5' end (5' addition), or alternatively to the 3' end (3' addition), of the oligonucleotide. Alternatively, the added nucleoside can be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a DMPK nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound can optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer can in some embodiments include β-D-ribonucleosides, β-D-deoxyribonucleosides, 2'-modified nucleosides (such 2'-modified nucleosides can include 2'-MOE, and 2'—O—CH$_3$, among others), and bicyclic sugar modified nucleosides (such bicyclic sugar modified nucleosides can include those having a 4'—(CH$_2$)$_n$—O—2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 1-8-1, or 2-6-2.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a DMPK nucleic acid possess a 5-10-5 gapmer motif.

In certain embodiments, an antisense compound targeted to a DMPK nucleic acid has a gap-widened motif In certain embodiments, antisense compounds of any of these gapmer or wingmer motifs contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 12-156, 160-770, and 774-792.

Target Nucleic Acids, Target Regions and Nucleotide Sequences

Nucleotide sequences that encode DMPK include, without limitation, the following sequences as set forth in GenBank Accession No. NM_001081560.1 (incorporated herein as SEQ ID NO: 1), GenBank Accession No. NT_011109.15 truncated from nucleotides 18540696 to Ser. No. 18/555,106 (incorporated herein as SEQ ID NO: 2), GenBank Accession No. NT_039413.7 truncated from nucleotides 16666001 to Ser. No. 16/681,000 (incorporated herein as SEQ ID NO: 3), GenBank Accession No. NM_032418.1 (incorporated herein as SEQ ID NO: 4), GenBank Accession No. AI007148.1 (incorporated herein as SEQ ID NO: 5), GenBank Accession No. AI304033.1 (incorporated herein as SEQ ID NO: 6), GenBank Accession No. BC024150.1 (incorporated herein as SEQ ID NO: 7), GenBank Accession No. BC056615.1 (incorporated herein as SEQ ID NO: 8), GenBank Accession No. BC075715.1 (incorporated herein as SEQ ID NO: 793), GenBank Accession No. BU519245.1 (incorporated herein as SEQ ID NO: 794), GenBank Accession No. CB247909.1 (incorporated herein as SEQ ID NO: 795), GenBank Accession No. CX208906.1 (incorporated herein as SEQ ID NO: 796), GenBank Accession No. CX732022.1 (incorporated herein as SEQ ID NO: 797), GenBank Accession No. 560315.1 (incorporated herein as SEQ ID NO: 798), GenBank Accession No. 560316.1 (incorporated herein as SEQ ID NO: 799), GenBank Accession No. NM_001081562.1 (incorporated herein as SEQ ID NO: 800), and GenBank Accession No. NM_001100.3 (incorporated herein as SEQ ID NO: 801). It is understood that the sequence set forth in each SEQ ID NO in the Examples contained herein is independent of any modification to a sugar moiety, an internucleoside linkage, or a nucleobase. As such, antisense compounds defined by a SEQ ID NO can comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region can encompass a 3' UTR, a 5' UTR, an exon, an intron, an exon/intron junction, a coding region, a translation initiation region, translation termination region, or other defined nucleic acid region. The structurally defined regions for DMPK can be obtained by accession number from sequence databases such as NCBI and such information is incorporated herein by reference. In certain embodiments, a target region can encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in DMPK mRNA levels are indicative of inhibition of DMPK protein expression. Reductions in levels of a DMPK protein are also indicative of inhibition of target mRNA expression. Further, phenotypic changes, such as a reducing myotonia or reducing spliceopathy, can be indicative of inhibition of DMPK mRNA and/or protein expression.

Hybridization

In some embodiments, hybridization occurs between an antisense compound disclosed herein and a DMPK nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, $3^{rd}$ Ed., 2001). In certain embodiments, the antisense compounds provided herein are specifically hybridizable with a DMPK nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a DMPK nucleic acid).

An antisense compound can hybridize over one or more segments of a DMPK nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a DMPK nucleic acid, a target region, target segment, or specified portion thereof. In certain embodiments, the antisense compounds are at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to a DMPK nucleic acid, a target region, target segment, or specified portion thereof, and contain at least 8, at least 9, at least 10, at least 11, at least 12, at least 13, at least 14, at least 15, at least 16, at least 17, at least 18, or at least 19, contiguous nucleobases of the nucleobase sequence of any of the exemplary antisense compounds described herein (e.g., at least 8 contiguous nucleobases of a nucleobase sequence recited in any one of SEQ ID NOs: 12-156, 160-770, and 774-792). Percent complementarity of an antisense compound with a target nucleic acid can be determined using routine methods, and is measured over the entirety of the antisense compound.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound can be fully complementary to a DMPK nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound can be fully complementary to the target sequence, depending on whether the remaining 10 nucleobases of the antisense compound are also complementary to the target sequence.

The location of a non-complementary nucleobase can be at the 5' end or 3' end of the antisense compound. Alternatively, the non-complementary nucleobase or nucleobases can be at an internal position of the antisense compound. When two or more non-complementary nucleobases are present, they can be either contiguous (i.e. linked) or non-contiguous. In one embodiment, a non-complementary nucleobase is located in the wing segment of a gapmer antisense oligonucleotide.

In certain embodiments, antisense compounds that are, or are up to 10, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a DMPK nucleic acid, or specified portion thereof.

In certain embodiments, antisense compounds that are, or are up to 10, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a DMPK nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 10 nucleobase portion of a target segment. In certain embodiments, the antisense compounds are complementary to at least a 15 nucleobase portion of a target segment. Also contemplated are antisense compounds that are complementary to at least an 8, at least a 9, at least a 10, at least an 11, at least a 12, at least a 13, at least a 14, at least a 15, at least a 16, at least a 17, at least an 18, at least a 19, at least a 20, or more nucleobase portion of a target segment, or a range defined by any two of these values.

Identity

The antisense compounds provided herein can also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, at least 75%, at least 80%, at least 85%, at least 90%, at least 95%, at least 96%, at least 97%, at least 98%, at least 99% or 100% identical to one or more of the exemplary antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a DMPK nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'—S, 2'—F, 2'—$OCH_3$, 2'—$OCH_2CH_3$, 2'—$OCH_2CH_2F$ and 2'—$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_1)$—$(CH_2)_2$—$N(R_m)(R_n)$, where each $R_l$, $R_m$ and $R_n$ is, independently, H or substituted or unsubstituted $C_1$-$C_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-($CH_2$)—O—2' (LNA); 4'—($CH_2$)—S—2; 4'—($CH_2$)$_2$—O—2' (ENA); 4'—$CH(CH_3)$—O—2' and 4'-CH ($CH_2OCH_3$)—O—2' (and analogs thereof see U.S. Pat. No. 7,399,845, issued on Jul. 15, 2008); 4'—$C(CH_3)(CH_3)$—O—2' (and analogs thereof see PCT/US2008/068922 published as WO/2009/006478, published Jan. 8, 2009); 4'—$CH_2$—$N(OCH_3)$—2' (and analogs thereof see PCT/US2008/064591 published as WO/2008/150729, published Dec. 11, 2008); 4'—$CH_2$—O—$N(CH_3)$-2' (see published U.S. Patent Application US2004-0171570, published Sep. 2, 2004); 4'-$CH_2$—N(R)—O—2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C(=$CH_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al.,

*Nucleic Acids Research,* 2003, 21, 6365-6372; Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; Wahlestedt et al., *Proc. Natl. Acad. Sci. U.S.A,* 2000, 97, 5633-5638; Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups independently selected from $-[C(R_a)(R_b)]_n-$, $-C(R_a)=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl $(C(=O)-H)$, substituted acyl, CN, sulfonyl $(S(=O)_2-J_1)$, or sulfoxyl $(S(=O)-J_1)$; and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl $(C(=O)-H)$, substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, $-[C(R_a)(R_b)]_n-$, $-[C(R_a)(R_b)]_n-O-$, $-C(R_aR_b)-N(R)-O-$ or $-C(R_aR_b)-O-N(R)-$. In certain embodiments, the bridge is 4'$-CH_2-$2', 4'$-(CH_2)_2-$2', 4'$-(CH_2)_3-$2', 4'$-CH_2-O-$2', 4'$-(CH_2)_2-O-$2', 4'$-CH_2-O-N(R)-$2' and 4'$-CH_2-N(R)-O-$2'-wherein each R is, independently, H, a protecting group or $C_1-C_{12}$ alkyl.

In certain embodiments, bicyclic nucleosides are further defined by isomeric configuration. For example, a nucleoside comprising a 4'$-(CH_2)-O-$2' bridge, may be in the α-L configuration or in the β-D configuration. Previously, α-L-methyleneoxy (4'-$CH_2-O-$2') BNA's have been incorporated into antisense oligonucleotides that showed antisense activity (Frieden et al., *Nucleic Acids Research,* 2003, 21, 6365-6372).

In certain embodiments, bicyclic nucleosides include those having a 4' to 2' bridge wherein such bridges include without limitation, α-L-4'$-(CH_2)-O-$2', β-D-4'$-CH_2-O-$2', 4'$-(CH_2)_2-O-$2', 4'$-CH_2-O-N(R)-$2', 4'$-CH_2-N(R)-O-$2', 4'$-CH(CH_3)-O-$2', 4'$-CH_2-S-$2', 4'$-CH_2-N(R)-$2', 4'-$CH_2-CH(CH_3)$-2', and 4'$-(CH_2)_3-$2', wherein R is H, a protecting group or $C_1$-$C_{12}$ alkyl.

In certain embodiments, bicyclic nucleosides have the formula:

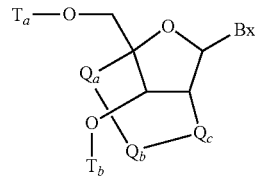

wherein:
Bx is a heterocyclic base moiety;
$-Q_a-Q_b-Q_c-$is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety or a covalent attachment to a support medium.

In certain embodiments, bicyclic nucleosides have the formula:

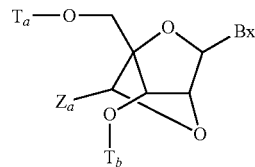

wherein:
Bx is a heterocyclic base moiety;
$T_a$ and $T_b$ are each, independently, H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

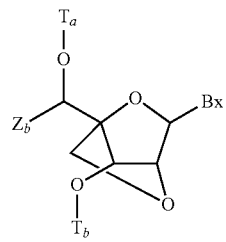

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

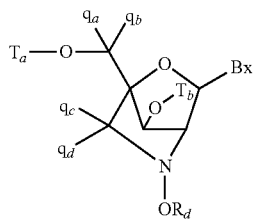

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

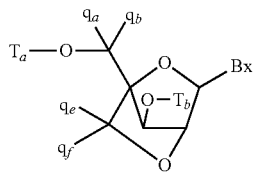

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'—$CH_2$—O—2' and 4'—$CH_2$—S—2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino-and 2'-methylamino-BNA's have been prepared and the thermal stability of their duplexes with complementary RNA and DNA strands has been previously reported.

In certain embodiments, bicyclic nucleosides have the formula:

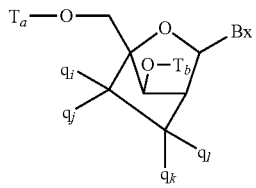

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'—$(CH_2)_3$-2' bridge and the alkenyl analog bridge 4'—CH=CH—$CH_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-$CH_2$—O—2') BNA (B) β-D-methyleneoxy (4'—$CH_2$—O—2') BNA (C) ethyleneoxy (4'—$(CH_2)_2$—O—2') BNA (D) aminooxy (4'—$CH_2$—O—N(R)—2') BNA, (E) oxyamino (4'—$CH_2$—N(R)—O—-2') BNA, (F) methyl(methyleneoxy) (4'—CH($CH_3$)—O—2') BNA (also referred to as constrained ethyl or cEt), (G) methylene-thio (4'—$CH_2$—S-2') BNA, (H) methylene-amino (4'—$CH_2$—N(R)—2') BNA, (I) methyl carbocyclic (4'—$CH_2$—CH($CH_3$)-2') BNA, (J) propylene carbocyclic (4'—$(CH_2)_3$-2') BNA, and (K) vinyl BNA as depicted below.

(A) 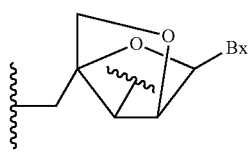

(B) 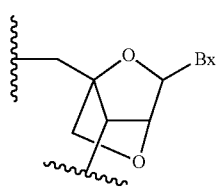

(C) 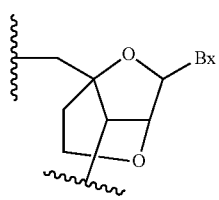

(D) 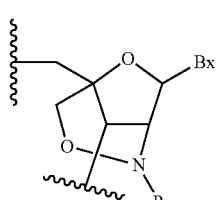

(E) 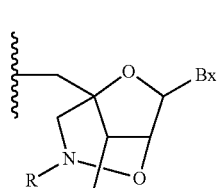

(F) 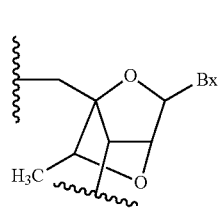

(G) 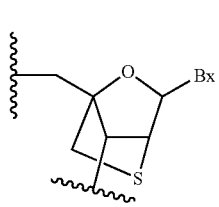

(H) 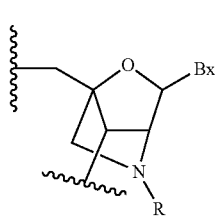

(I) 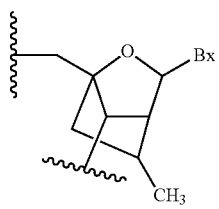

(J) 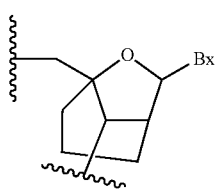

(K) 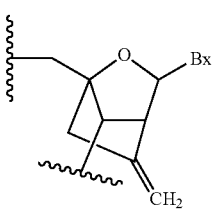

wherein Bx is the base moiety and R is, independently, H, a protecting group, $C_1$-$C_6$ alkyl or $C_1$-$C_6$ alkoxy.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

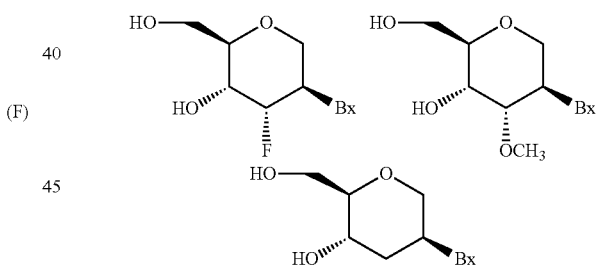

In certain embodiments, sugar surrogates are selected having the formula:

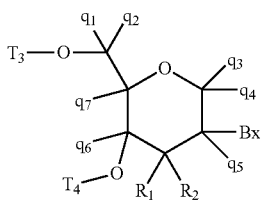

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group; $q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates include, but are not limited to, what is referred to in the art as hexitol nucleic acid (HNA), altritol nucleic acid (ANA), and mannitol nucleic acid (MNA) (see Leumann, C. J., *Bioorg. & Med. Chem.*, 2002, 10, 841-854).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have the formula:

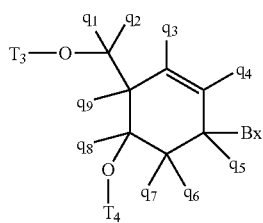

wherein:
Bx is a heterocyclic base moiety;
$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'-or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other bicyclic and tricyclic sugar surrogate ring systems are also known in the art that can be used to modify nucleosides for incorporation into antisense compounds (see for example review article: Leumann, Christian J., *Bioorg. & Med. Chem.*, 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds targeted to a DMPK nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a DMPK nucleic acid comprise one or more modified nucleobases. In certain embodiments, gap-widened antisense oligonucleotides targeted to a DMPK nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides can be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a DMPK nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a DMPK nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of DMPK nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a DMPK nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a DMPK nucleic acid. Methods for designing real-time PCR probes and primers are well known in the art, and can include the use of software such as PRIMER EXPRESS® Software (Applied Biosystems, Foster City, Calif.).

Analysis of Protein Levels

Antisense inhibition of DMPK nucleic acids can be assessed by measuring DMPK protein levels. Protein levels of DMPK can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of DMPK and produce phenotypic changes. Testing can be performed in normal animals, or in experimental disease models, for example, the $HSA^{LR}$ mouse model of myotonic dystrophy (DM1).

The $HSA^{LR}$ mouse model is an established model for DM1 (Mankodi, A. et al. Science. 289: 1769, 2000). The mice carry a human skeletal actin (hACTA1) transgene with 220 CTG repeats inserted in the 3' UTR of the gene. The hACTA1-$CUG^{exp}$ transcript accumulates in nuclear foci in skeletal muscles and results in myotonia similar to that in human DM1 (Mankodi, A. et al. Mol. Cell 10: 35, 2002; Lin, X. et al. Hum. Mol. Genet. 15: 2087, 2006). Hence, it is expected that amelioration of DM1 symptoms in the $HSA^{LR}$ mouse by antisense inhibition of the hACTA1 transgene would predict amelioration of similar symptoms in human patients by antisense inhibition of the DMPK transcript.

Expression of $CUG^{exp}$ RNA in mice causes extensive remodeling of the muscle transcriptome, much of which is reproduced by ablation of MBNL1. Hence, it is expected that normalization of the transcriptome in $HSA^{LR}$ mice would predict normalization of the human transcriptome in DM1 patients by antisense inhibition of the DMPK transcript.

For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in DMPK nucleic acid expression are measured. Changes in DMPK protein levels are also measured.

Splicing

Myotonic dystrophy (DM1) is caused by CTG repeat expansions in the 3' untranslated region of the DMPK gene (Brook, J. D. et al. Cell. 68: 799, 1992). This mutation leads to RNA dominance, a process in which expression of RNA containing an expanded CUG repeat (CUGexp) induces cell dysfunction (Osborne R J and Thornton C A., *Human Molecular Genetics.*, 2006, 15(2): R162-R169). Such CUG-exp are retained in the nuclear foci of skeletal muscles (Davis, B. M. et al. Proc. Natl. Acad. Sci. U.S.A. 94:7388, 1997). The accumulation of CUGexp in the nuclear foci leads to the sequestration of poly(CUG)-binding proteins, such as, Muscleblind-like 1 (MBLN1) (Miller, J. W. et al. EMBO J. 19: 4439, 2000). MBLN1 is a splicing factor and regulates the splicing of genes such as Serca1, ClC-1, Titin, and Zasp. Therefore, sequestration of MBLN1 by CUGexp triggers misregulated alternative splicing of the exons of genes that MBLN1 normally controls (Lin, X. et al. Hum. Mol. Genet. 15: 2087, 2006). Correction of alternative splicing in an animal displaying such disregulation, such as, for example, in a DM1 patient and the HSALR mouse model, is a useful indicator for the efficacy of a treatment, including treatment with an antisense oligonucleotide.

Certain Biomarkers

DM1 severity in mouse models is determined, at least in part, by the level of $CUG^{exp}$ transcript accumulation in the nucleus or nuclear foci. A useful physiological marker for DM1 severity is the development of high-frequency runs of involuntary action potentials (myotonia).

Certain Indications

In certain embodiments, provided herein are methods of treating an individual comprising administering one or more pharmaceutical compositions as described herein. In certain embodiments, the individual has type 1 myotonic dystrophy (DM1).

Accordingly, provided herein are methods for ameliorating a symptom associated with type 1 myotonic dystrophy in a subject in need thereof. In certain embodiments, provided is a method for reducing the rate of onset of a symptom associated with type 1 myotonic dystrophy. In certain embodiments, provided is a method for reducing the severity of a symptom associated with type 1 myotonic dystrophy. In certain embodiments, symptoms associated with DM1 include muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts. In children, the symptoms may also be developmental delays, learning problems, language and speech issues, and personality development issues.

In certain embodiments, the methods comprise administering to an individual in need thereof a therapeutically effective amount of a compound targeted to a DMPK nucleic acid.

In certain embodiments, administration of an antisense compound targeted to a DMPK nucleic acid results in reduction of DMPK expression by at least about 15%, by at least about 20%, by at least about 25%, by at least about 30%, by at least about 35%, by at least about 40%, by at least about 45%, by at least about 50%, by at least about 55%, by at least about 60%, by least about 65%, by least about 70%, by least about 75%, by least about 80%, by at least about 85%, by at least about 90%, by at least about 95% or by at least about 99%, or a range defined by any two of these values.

In certain embodiments, pharmaceutical compositions comprising an antisense compound targeted to DMPK are used for the preparation of a medicament for treating a patient suffering or susceptible to type 1 myotonic dystrophy.

In certain embodiments, the methods described herein include administering a compound comprising a modified oligonucleotide having a contiguous nucleobases portion as described herein of a sequence recited in SEQ ID NO: 12-156, 160-770, and 774-792.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection (e.g., bolus injection). The injection can be delivered with a syringe.

Parenteral administration includes subcutaneous administration, intravenous administration, intramuscular administration, intraarterial administration, intraperitoneal administration, or intracranial administration, e.g., intrathecal or intracerebroventricular administration. Administration can be continuous, or chronic, or short, or intermittent.

In certain embodiments, the administering is subcutaneous, intravenous, intracerebral, intracerebroventricular, intrathecal or another administration that results in a systemic effect of the oligonucleotide (systemic administration is characterized by a systemic effect, i.e., an effect in more than one tissue) or delivery to the CNS or to the CSF.

The duration of action as measured by inhibition of alpha 1 actin and reduction of myotonia in the $HSA^{LR}$ mouse model of DM1 is prolonged in muscle tissue including quadriceps, gastrocnemius, and the tibialis anterior (see Examples, below). Subcutaneous injections of antisense oligonucleotide for 4 weeks results in inhibition of alpha 1 actin by at least 70% in quadriceps, gastrocnemius, and the tibialis anterior in $HSA^{LR}$ mice for at least 11 weeks (77 days) after termination of dosing. Subcutaneous injections of antisense oligonucleotide for 4 weeks results in elimination of myotonia in quadriceps, gastrocnemius, and the tibialis anterior in $HSA^{LR}$ mice for at least 11 weeks (77 days) after termination of dosing.

In certain embodiments, delivery of a compound of composition, as described herein, results in at least 70% down-regulation of a target mRNA and/or target protein for at least 77 days. In certain embodiments, delivery of a compound or composition, as described herein, results in 50%, 55%, 60%, 65%, 70%, 75%, 80%, 85%, 90%, 95%, or 100% down-regulation of a target mRNA and/or target protein for at least 30 days, at least 35 days, at least 40 days, at least 45 days, at least 50 days, at least 55 days, at least 60 days, at least 65 days, at least 70 days, at least 75 days, at least 76 days, at least 77 days, at least 78 days, at least 79 days, at least 80 days, at least 85 days, at least 90 days, at least 95 days, at least 100 days, at least 105 days, at least 110 days, at least 115 days, at least 120 days, at least 1 year.

In certain embodiments, an antisense oligonucleotide is delivered by injection or infusion once every 77 days. In certain embodiments, an antisense oligonucleotide is delivered by injection or infusion once every month, every two months, every three months, every 6 months, twice a year or once a year.

Certain Combination Therapies

In certain embodiments, a first agent comprising the modified oligonucleotide of the invention is co-administered with one or more secondary agents. In certain embodiments, such second agents are designed to treat the same type 1 myotonic dystrophy as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human Dystrophia Myotonica Protein Kinase (DMPK) in Human Skeletal Muscle Cells (hSKMC)

Antisense oligonucleotides targeted to a human DMPK nucleic acid were tested for their effect on DMPK RNA transcript in vitro. Cultured hSKM cells at a density of 20,000 cells per well were transfected using electroporation with 100 nM antisense oligonucleotide. After approximately 24 hours, RNA was isolated from the cells and DMPK RNA transcript levels were measured by quantitative real-time PCR with human primer probe set RTS3164 (forward sequence AGCCTGAGCCGGGAGATG, designated herein as SEQ ID NO: 9; reverse sequence GCGTAGTTGACTGGCGAAGTT, designated herein as SEQ ID NO: 10; probe sequence AGGCCATCCGCACGGACAACCX, designated herein as SEQ ID NO: 11). DMPK RNA transcript levels were adjusted according to total RNA content, as measured by RIBOGREEN®. Results are presented as percent inhibition of hDMPK, relative to untreated control cells.

The antisense oligonucleotides in Tables 1 and 2 are 5-10-5 gapmers, where the gap segment comprises ten 2'-deoxynucleosides and each wing segment comprises five 2'-MOE nucleosides. The internucleoside linkages throughout each gapmer are phosphorothioate (P=S) linkages. All cytosine residues throughout each gapmer are 5-methylcytosines. 'Target start site' indicates the 5'-most nucleoside to which the antisense oligonucleotide is targeted. 'Target stop site' indicates the 3'-most nucleoside to which the antisense oligonucleotide is targeted. All the antisense oligonucleotides listed in Table 1 target SEQ ID NO: 1 (GENBANK Accession No. NM_001081560.1). All the antisense oligonucleotides listed in Table 2 target SEQ ID NO: 2 (the complement of GENBANK Accession No. NT_011109.15 truncated from nucleotides 18540696 to 18555106).

Several antisense oligonucleotides demonstrated significant inhibition of human DMPK mRNA levels under the conditions specified above.

TABLE 1

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 93 | 112 | 299476 | CTGGCTGCATGTCTGCCTGT | 81 | 12 |
| 277 | 296 | 299479 | CCAGGAGAAGGTCGAGCAGG | 57 | 13 |
| 737 | 756 | 299493 | TCTATGGCCATGACAATCTC | 57 | 14 |
| 773 | 792 | 299494 | ATGTCCCTGTGCACGTAGCC | 77 | 15 |
| 1194 | 1213 | 299501 | ATGTGTCCGGAAGTCGCCTG | 50 | 16 |
| 1628 | 1647 | 299511 | CTCAGGCTCTGCCGGGTGAG | 70 | 17 |
| 1855 | 1874 | 299517 | GGCACTGGCCCACAGCCACG | 78 | 18 |
| 2379 | 2398 | 299526 | CCTGGCCGAAAGAAAGAAAT | 31 | 19 |
| 2367 | 2386 | 444380 | AAAGAAATGGTCTGTGATCC | 56 | 20 |
| 2370 | 2389 | 444381 | AAGAAAGAAATGGTCTGTGA | 77 | 21 |
| 2376 | 2395 | 444382 | GGCCGAAAGAAAGAAATGGT | 61 | 22 |
| 2385 | 2404 | 444383 | CCTCAGCCTGGCCGAAAGAA | 57 | 23 |
| 2388 | 2407 | 444384 | GGGCCTCAGCCTGGCCGAAA | 65 | 24 |
| 2391 | 2410 | 444385 | TCAGGGCCTCAGCCTGGCCG | 61 | 25 |
| 2411 | 2430 | 444386 | CTGCAGTTTGCCCATCCACG | 68 | 26 |
| 2414 | 2433 | 444387 | GGCCTGCAGTTTGCCCATCC | 77 | 27 |
| 2417 | 2436 | 444388 | CCAGGCCTGCAGTTTGCCCA | 54 | 28 |
| 2423 | 2442 | 444389 | GCCTTCCCAGGCCTGCAGTT | 77 | 29 |
| 2426 | 2445 | 444390 | GCTGCCTTCCCAGGCCTGCA | 83 | 30 |
| 2429 | 2448 | 444391 | CTTGCTGCCTTCCCAGGCCT | 69 | 31 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 2435 | 2454 | 444392 | GCCCGGCTTGCTGCCTTCCC | 82 | 32 |
| 2438 | 2457 | 444393 | ACGGCCCGGCTTGCTGCCTT | 78 | 33 |
| 2441 | 2460 | 444394 | CGGACGGCCCGGCTTGCTGC | 57 | 34 |
| 2444 | 2463 | 444395 | ACACGGACGGCCCGGCTTGC | 73 | 35 |
| 2450 | 2469 | 444396 | GATGGAACACGGACGGCCCG | 80 | 36 |
| 2453 | 2472 | 444397 | GAGGATGGAACACGGACGGC | 86 | 37 |
| 2456 | 2475 | 444398 | GTGGAGGATGGAACACGGAC | 84 | 38 |
| 2481 | 2500 | 444399 | GCGAACCAACGATAGGTGGG | 80 | 39 |
| 2484 | 2503 | 444400 | TTTGCGAACCAACGATAGGT | 86 | 40 |
| 2490 | 2509 | 444401 | TTGCACTTTGCGAACCAACG | 89 | 41 |
| 2493 | 2512 | 444402 | GCTTTGCACTTTGCGAACCA | 89 | 42 |
| 2496 | 2515 | 444403 | AAAGCTTTGCACTTTGCGAA | 83 | 43 |
| 2499 | 2518 | 444404 | AAGAAAGCTTTGCACTTTGC | 91 | 44 |
| 2502 | 2521 | 444405 | CACAAGAAAGCTTTGCACTT | 70 | 45 |
| 2508 | 2527 | 444406 | GTCATGCACAAGAAAGCTTT | 34 | 46 |
| 2527 | 2546 | 444407 | ACGCTCCCCAGAGCAGGGCG | 39 | 47 |
| 2543 | 2562 | 444408 | GCAGAGATCGCGCCAGACGC | 85 | 48 |
| 2546 | 2565 | 444409 | CAGGCAGAGATCGCGCCAGA | 65 | 49 |
| 2549 | 2568 | 444410 | AAGCAGGCAGAGATCGCGCC | 84 | 50 |
| 2555 | 2574 | 444411 | CCGAGTAAGCAGGCAGAGAT | 58 | 51 |
| 2558 | 2577 | 444412 | TTCCCGAGTAAGCAGGCAGA | 70 | 52 |
| 2564 | 2583 | 444413 | GCAAATTTCCCGAGTAAGCA | 62 | 53 |
| 2567 | 2586 | 444414 | AAAGCAAATTTCCCGAGTAA | 53 | 54 |
| 2573 | 2592 | 444415 | TTGGCAAAAGCAAATTTCCC | 64 | 55 |
| 2576 | 2595 | 444416 | GGTTTGGCAAAAGCAAATTT | 23 | 56 |
| 2579 | 2598 | 444417 | GCGGGTTTGGCAAAAGCAAA | 70 | 57 |
| 2582 | 2601 | 444418 | AAAGCGGGTTTGGCAAAAGC | 43 | 58 |
| 2588 | 2607 | 444419 | CCCGAAAAGCGGGTTTGGC | 71 | 59 |
| 2591 | 2610 | 444420 | ATCCCCGAAAAGCGGGTTT | 53 | 60 |
| 2595 | 2614 | 444421 | CGGGATCCCCGAAAAGCGG | 45 | 61 |
| 2598 | 2617 | 444422 | GCGCGGGATCCCCGAAAAAG | 48 | 62 |
| 2623 | 2642 | 444423 | GAGAGCAGCGCAAGTGAGGA | 77 | 63 |
| 2626 | 2645 | 444424 | TCCGAGAGCAGCGCAAGTGA | 62 | 64 |
| 2629 | 2648 | 444425 | GGCTCCGAGAGCAGCGCAAG | 79 | 65 |
| 2649 | 2668 | 444426 | AAGCGGGCGGAGCCGGCTGG | 20 | 66 |
| 2652 | 2671 | 444427 | CCGAAGCGGGCGGAGCCGGC | 0 | 67 |
| 2658 | 2677 | 444428 | AAACCGCCGAAGCGGGCGGA | 0 | 68 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 2661 | 2680 | 444429 | TCCAAACCGCCGAAGCGGGC | 45 | 69 |
| 2664 | 2683 | 444430 | ATATCCAAACCGCCGAAGCG | 31 | 70 |
| 2667 | 2686 | 444431 | TAAATATCCAAACCGCCGAA | 42 | 71 |
| 2670 | 2689 | 444432 | CAATAAATATCCAAACCGCC | 53 | 72 |
| 2676 | 2695 | 444433 | CGAGGTCAATAAATATCCAA | 63 | 73 |
| 2679 | 2698 | 444434 | GGACGAGGTCAATAAATATC | 83 | 74 |
| 2682 | 2701 | 444435 | GGAGGACGAGGTCAATAAAT | 82 | 75 |
| 2685 | 2704 | 444436 | GTCGGAGGACGAGGTCAATA | 86 | 76 |
| 2688 | 2707 | 444437 | CGAGTCGGAGGACGAGGTCA | 73 | 77 |
| 2694 | 2713 | 444438 | TGTCAGCGAGTCGGAGGACG | 79 | 78 |
| 2697 | 2716 | 444439 | GCCTGTCAGCGAGTCGGAGG | 83 | 79 |
| 2700 | 2719 | 444440 | GTAGCCTGTCAGCGAGTCGG | 94 | 80 |
| 2703 | 2722 | 444441 | CCTGTAGCCTGTCAGCGAGT | 90 | 81 |
| 2706 | 2725 | 444442 | GGTCCTGTAGCCTGTCAGCG | 90 | 82 |
| 2764 | 2783 | 444443 | AAATACCGAGGAATGTCGGG | 82 | 83 |
| 2767 | 2786 | 444444 | AATAAATACCGAGGAATGTC | 66 | 84 |
| 2770 | 2789 | 444445 | GACAATAAATACCGAGGAAT | 67 | 85 |
| 2093 | 2112 | 445546 | CGGGGCCCCGGAGTCGAAGA | 0 | 86 |
| 2097 | 2116 | 445547 | CCAACGGGGCCCCGGAGTCG | 38 | 87 |
| 2099 | 2118 | 445548 | TTCCAACGGGGCCCCGGAGT | 22 | 88 |
| 2102 | 2121 | 445549 | GTCTTCCAACGGGGCCCCGG | 50 | 89 |
| 2104 | 2123 | 445550 | CAGTCTTCCAACGGGGCCCC | 27 | 90 |
| 2106 | 2125 | 445551 | CTCAGTCTTCCAACGGGGCC | 57 | 91 |
| 2109 | 2128 | 445552 | GCACTCAGTCTTCCAACGGG | 69 | 92 |
| 2115 | 2134 | 445553 | CCCCGGGCACTCAGTCTTCC | 76 | 93 |
| 2117 | 2136 | 445554 | TGCCCCGGGCACTCAGTCTT | 59 | 94 |
| 2119 | 2138 | 445555 | CGTGCCCCGGGCACTCAGTC | 61 | 95 |
| 2123 | 2142 | 445556 | GTGCCGTGCCCCGGGCACTC | 26 | 96 |
| 2126 | 2145 | 445557 | TCTGTGCCGTGCCCCGGGCA | 50 | 97 |
| 2129 | 2148 | 445558 | GCTTCTGTGCCGTGCCCCGG | 57 | 98 |
| 2132 | 2151 | 445559 | GCGGCTTCTGTGCCGTGCCC | 27 | 99 |
| 2134 | 2153 | 445560 | GCGCGGCTTCTGTGCCGTGC | 0 | 100 |
| 2136 | 2155 | 445561 | GGGCGCGGCTTCTGTGCCGT | 8 | 101 |
| 2142 | 2161 | 445562 | GGCGGTGGGCGCGGCTTCTG | 62 | 102 |
| 2146 | 2165 | 445563 | GGCAGGCGGTGGGCGCGGCT | 49 | 103 |
| 2148 | 2167 | 445564 | CTGGCAGGCGGTGGGCGCGG | 51 | 104 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 2150 | 2169 | 445565 | AACTGGCAGGCGGTGGGCGC | 38 | 105 |
| 2153 | 2172 | 445566 | GTGAACTGGCAGGCGGTGGG | 64 | 106 |
| 2157 | 2176 | 445567 | GGTTGTGAACTGGCAGGCGG | 66 | 107 |
| 2159 | 2178 | 445568 | GCGGTTGTGAACTGGCAGGC | 85 | 108 |
| 2163 | 2182 | 445569 | CGGAGCGGTTGTGAACTGGC | 92 | 109 |
| 2167 | 2186 | 445570 | CGCTCGGAGCGGTTGTGAAC | 51 | 110 |
| 2171 | 2190 | 445571 | CCCACGCTCGGAGCGGTTGT | 74 | 111 |
| 2174 | 2193 | 445572 | AGACCCACGCTCGGAGCGGT | 80 | 112 |
| 2177 | 2196 | 445573 | CGGAGACCCACGCTCGGAGC | 83 | 113 |
| 2180 | 2199 | 445574 | GGGCGGAGACCCACGCTCGG | 62 | 114 |
| 2183 | 2202 | 445575 | GCTGGGCGGAGACCCACGCT | 11 | 115 |
| 2186 | 2205 | 445576 | GGAGCTGGGCGGAGACCCAC | 42 | 116 |
| 2188 | 2207 | 445577 | CTGGAGCTGGGCGGAGACCC | 17 | 117 |
| 2191 | 2210 | 445578 | GGACTGGAGCTGGGCGGAGA | 53 | 118 |
| 2193 | 2212 | 445579 | CAGGACTGGAGCTGGGCGGA | 46 | 119 |
| 2197 | 2216 | 445580 | ATCACAGGACTGGAGCTGGG | 66 | 120 |
| 2209 | 2228 | 445581 | GGGCGGGCCCGGATCACAGG | 85 | 121 |
| 2211 | 2230 | 445582 | GGGGGCGGGCCCGGATCACA | 96 | 122 |
| 179 | 198 | 445583 | AGGCAGCACCATGGCCCCTC | 88 | 123 |
| 235 | 254 | 445584 | GGTCCAACACCAGCTGCTGG | 84 | 124 |
| 418 | 437 | 445585 | CGATCACCTTCAGAATCTCG | 11 | 125 |
| 498 | 517 | 445586 | CTTGTTCATGATCTTCATGG | 0 | 126 |
| 565 | 584 | 445587 | CCCCATTCACCAACACGTCC | 83 | 127 |
| 583 | 602 | 445588 | GCGTGATCCACCGCCGGTCC | 59 | 128 |
| 639 | 658 | 445589 | GTAATACTCCATGACCAGGT | 86 | 129 |
| 664 | 683 | 445590 | GCAGTGTCAGCAGGTCCCCG | 83 | 130 |
| 744 | 763 | 445591 | CACCGAGTCTATGGCCATGA | 60 | 131 |
| 761 | 780 | 445592 | ACGTAGCCAAGCCGGTGCAC | 68 | 132 |
| 812 | 831 | 445593 | ATGTGGCCACAGCGGTCCAG | 56 | 133 |
| 1099 | 1118 | 445594 | CTTCGTCCACCAGCGGCAGA | 32 | 134 |
| 1104 | 1123 | 445595 | GACCCCTTCGTCCACCAGCG | 83 | 135 |
| 1178 | 1197 | 445596 | CCTGCTCCACCCCGGCCCAG | 82 | 136 |
| 1187 | 1206 | 445597 | CGGAAGTCGCCTGCTCCACC | 81 | 137 |
| 1229 | 1248 | 445598 | CGGAGACCATCCCAGTCGAG | 67 | 138 |
| 1402 | 1421 | 445599 | TGAGGGCCATGCAGGAGTAG | 26 | 139 |
| 1443 | 1462 | 445600 | CTCCAGTTCCATGGGTGTGG | 80 | 140 |
| 1477 | 1496 | 445601 | GCGCTTGCACGTGTGGCTCA | 94 | 141 |

TABLE 1-continued

Inhibition of human DMPK RNA transcript in hSKMC by 5-10-5 gapmers targeting SEQ ID NO: 1

| Target Start Site | Target Stop Site | ISIS No | Sequence | % inhibition | SEQ ID NO. |
|---|---|---|---|---|---|
| 1526 | 1545 | 445602 | GCCACTTCAGCTGTTTCATC | 54 | 142 |
| 1562 | 1581 | 445603 | GCCTCAGCCTCTGCCGCAGG | 71 | 143 |
| 1576 | 1595 | 445604 | GCAGCGTCACCTCGGCCTCA | 31 | 144 |
| 1630 | 1649 | 445605 | GGCTCAGGCTCTGCCGGGTG | 86 | 145 |
| 1700 | 1719 | 445606 | TTCCGAGCCTCTGCCTCGCG | 73 | 146 |
| 1708 | 1727 | 445607 | GGTCCCGGTTCCGAGCCTCT | 76 | 147 |
| 1742 | 1761 | 445608 | ATCCGCTCCTGCAACTGCCG | 93 | 148 |
| 1750 | 1769 | 445609 | GCAACTCCATCCGCTCCTGC | 60 | 149 |
| 1812 | 1831 | 445610 | AGGTGGATCCGTGGCCCGGG | 48 | 150 |
| 2133 | 2152 | 445611 | CGCGGCTTCTGTGCCGTGCC | 24 | 151 |
| 2428 | 2447 | 445612 | TTGCTGCCTTCCCAGGCCTG | 80 | 152 |

TABLE 2

Inhibition of human DMPK RNA transcript in hSKMC by 5-10-5 gapmers targeting SEQ ID NO: 2

| Target Start Site | Target Stop Site | ISIS No | Sequence | % inhibition | SEQ ID NO. |
|---|---|---|---|---|---|
| 812 | 831 | 299471 | TGCTCCCGACAAGCTCCAGA | 95 | 153 |
| 876 | 895 | 299473 | AGAACCTGCCCATTGCTGAA | 68 | 154 |
| 2381 | 2400 | 299535 | CACTGAGGGCCAGACATATG | 68 | 155 |
| 3289 | 3308 | 299544 | CTCTAGATTCAGATGCAGGT | 88 | 156 |

The antisense oligonucleotides from Tables 1 and 2 were also tested in an assay with similar conditions as described above, and mRNA levels measured with the human primer probe RTS3162 (forward sequence CGGGCCGTCCGTGTT, designated herein as SEQ ID NO: 157; reverse sequence CTTTGCACTTTGCGAACCAA, designated herein as SEQ ID NO: 158; probe sequence CATCCTCCACGCACCCCACCX, designated herein as SEQ ID NO: 159). The results are presented in Table 3. DMPK mRNA expression was also assessed by RTS3162 which targets the DMPK gene near the 3'UTR. The use of a second primer probe was employed to confirm that the expression of the entire DMPK gene had been inhibited

TABLE 3

Inhibition of human DMPK RNA transcript in hSKMC by 5-10-5 gapmers measured using primer probe set RTS3162

| ISIS No | % inhibition |
|---|---|
| 299471 | 91 |
| 299473 | 65 |

TABLE 3-continued

Inhibition of human DMPK RNA transcript in hSKMC by 5-10-5 gapmers measured using primer probe set RTS3162

| ISIS No | % inhibition |
|---|---|
| 299476 | 76 |
| 299479 | 53 |
| 299493 | 60 |
| 299494 | 66 |
| 299501 | 44 |
| 299511 | 39 |
| 299517 | 71 |
| 299526 | 39 |
| 299535 | 75 |
| 299544 | 84 |
| 444380 | 72 |
| 444381 | 82 |
| 444382 | 67 |
| 444383 | 63 |
| 444384 | 66 |
| 444385 | 66 |
| 444386 | 74 |
| 444387 | 85 |
| 444388 | 60 |

TABLE 3-continued

Inhibition of human DMPK RNA transcript in hSKMC by 5-10-5 gapmers measured using primer probe set RTS3162

| ISIS No | % inhibition |
|---|---|
| 444389 | 81 |
| 444390 | 88 |
| 444391 | 79 |
| 444392 | 94 |
| 444393 | 88 |
| 444394 | 94 |
| 444395 | 96 |
| 444396 | 96 |
| 444397 | 95 |
| 444398 | 96 |
| 444399 | 95 |
| 444400 | 95 |
| 444401 | 95 |
| 444402 | 91 |
| 444403 | 84 |
| 444404 | 89 |
| 444405 | 71 |
| 444406 | 47 |
| 444407 | 42 |
| 444408 | 80 |
| 444409 | 56 |
| 444410 | 79 |
| 444411 | 66 |
| 444412 | 67 |
| 444413 | 55 |
| 444414 | 45 |
| 444415 | 57 |
| 444416 | 18 |
| 444417 | 64 |
| 444418 | 51 |
| 444419 | 66 |
| 444420 | 0 |
| 444421 | 46 |
| 444422 | 33 |
| 444423 | 74 |
| 444424 | 73 |
| 444425 | 78 |
| 444426 | 0 |
| 444427 | 0 |
| 444428 | 0 |
| 444429 | 75 |
| 444430 | 28 |
| 444431 | 58 |
| 444432 | 52 |
| 444433 | 60 |
| 444434 | 87 |
| 444435 | 76 |
| 444436 | 83 |
| 444437 | 71 |
| 444438 | 76 |
| 444439 | 73 |
| 444440 | 91 |
| 444441 | 87 |
| 444442 | 93 |
| 444443 | 77 |
| 444444 | 64 |
| 444445 | 67 |
| 445546 | 0 |
| 445547 | 59 |
| 445548 | 49 |
| 445549 | 77 |
| 445550 | 62 |
| 445551 | 74 |
| 445552 | 84 |
| 445553 | 70 |
| 445554 | 63 |
| 445555 | 75 |
| 445556 | 52 |
| 445557 | 78 |
| 445558 | 81 |
| 445559 | 58 |
| 445560 | 12 |
| 445561 | 42 |
| 445562 | 70 |
| 445563 | 76 |
| 445564 | 69 |
| 445565 | 60 |
| 445566 | 86 |
| 445567 | 84 |
| 445568 | 92 |
| 445569 | 93 |
| 445570 | 59 |
| 445571 | 84 |
| 445572 | 88 |
| 445573 | 84 |
| 445574 | 74 |
| 445575 | 26 |
| 445576 | 56 |
| 445577 | 38 |
| 445578 | 69 |
| 445579 | 70 |
| 445580 | 75 |
| 445581 | 85 |
| 445582 | 95 |
| 445583 | 88 |
| 445584 | 87 |
| 445585 | 34 |
| 445586 | 0 |
| 445587 | 82 |
| 445588 | 66 |
| 445589 | 87 |
| 445590 | 82 |
| 445591 | 68 |
| 445592 | 64 |
| 445593 | 54 |
| 445594 | 52 |
| 445595 | 77 |
| 445596 | 84 |
| 445597 | 78 |
| 445598 | 73 |
| 445599 | 29 |
| 445600 | 68 |
| 445601 | 92 |
| 445602 | 53 |
| 445603 | 70 |
| 445604 | 32 |
| 445605 | 61 |
| 445606 | 84 |
| 445607 | 80 |
| 445608 | 91 |
| 445609 | 68 |
| 445610 | 63 |
| 445611 | 44 |
| 445612 | 91 |

Example 2

Design of Antisense Oligonucleotides Targeting CUG Repeats

Antisense oligonucleotides were designed targeting mRNA transcripts that contain multiple CUG repeats. The chemistry of these oligonucleotides as well as their sequence is shown in Table 4. The symbols designated to the sugar type are shown after the base in subscript and are as follows: b=2'—O—N-[2-(dimethylamino)ethyl]acetamido ribose; d=2'-deoxyribose; e=2'—O-methoxyethyl ribose; f=2'-alpha-fluoro-2'-deoxyribose; g=2'—O—2[2-(2-methoxyethoxy]ethyl ribose; h=3'-fluoro-HNA; k=(S)-cEt; l=LNA (Locked Nucleic Acids); n=2'—O—(N-methylacetamide) ribose; o=2'—O—dimethylaminooxyethyl (DMAOE) ribose; p=PNA; r=propylribose; and x=amino acid core. The heterocycle names are defined with standard symbols for adenine, cytosine, thymine and guanine, 'mC' for 5-methylcytosine, and 'K' for Lysine Side Chain. Linkers are shown after the sugar type in subscript and designated with the following symbols: g=PNA-glycine full; a=amino acid; and s=thioate ester.

tested at various doses. Cells were plated at a density of 20,000 cells per well and transfected using electroporation with 1,250 nM, 2,500 nM, 5,000 nM, 10,000 nM and 20,000 nM concentrations of each antisense oligonucleotide. After approximately 16 hours, RNA was isolated from the cells and DMPK mRNA transcript levels were measured by quantitative real-time PCR using primer probe set RTS3164,

TABLE 4

Design of antisense oligonucleotides targeting CUG repeats

| ISIS No | Sequence | Chemistry | Backbone | SEQ ID NO |
|---|---|---|---|---|
| 431896 | $G_{ds}C_{ds}A_{ls}G_{ds}C_{ds}A_{ls}G_{ds}C_{ds}A_{ls}$ $G_{ds}C_{ds}A_{ls}G_{ds}C_{ds}A_{ls}G_{ds}C_{ds}A_{ls}G_d$ | Deoxy and LNA units | Phosphorothioate | 802 |
| 433804 | $K_{xa}G_{pg}C_{pg}A_{pg}G_{pg}C_{pg}A_{pg}G_{pg}C_{pg}A_{pg}G_{pg}C_{pg}A_{pg}G_{pg}$ $C_{pg}A_{pg}G_{pg}C_{pg}A_{pg}G_{pg}K_{xa}K_{xa}K_{xa}K_{xa}K_{xa}K_{xa}K_{xa}K_{xa}$ | PNA and Amino Acid Core units with a Carboxy-amide endcap | mixed | 803 |
| 444745 | $A_{es}G_{es}mC_{es}A_{es}G_{es}mC_{es}A_{es}G_{es}mC_{es}A_{es}G_{es}mC_{es}$ $A_{es}G_{es}mC_{es}A_{es}G_{es}mC_{es}A_{es}G_{es}mC_{es}A_{es}G_{es}mC_{es}A_e$ | Uniform MOE | Phosphorothioate | 789 |
| 444746 | $A_{es}G_{es}mC_{es}A_{es}G_{es}mC_{es}A_{es}G_{es}mC_{es}A_{es}$ $G_{es}mC_{es}A_{es}G_{es}mC_{es}A_{es}G_{es}mC_{es}A_{es}G_e$ | Uniform MOE | Phosphorothioate | 804 |
| 444747 | $G_{es}mC_{es}A_{es}G_{es}mC_{es}A_{es}G_{es}mC_{es}A_{es}$ $G_{es}mC_{es}A_{es}G_{es}mC_{es}A_{es}G_{es}mC_{es}A_{es}G_{es}$ | Uniform MOE | Phosphorothioate | 802 |
| 444748 | $G_{es}mC_{es}A_{es}G_{es}mC_{es}A_{es}G_{es}mC_{es}A_{es}$ $G_{es}mC_{es}A_{es}G_{es}mC_{es}A_{es}G_{es}mC_{es}A_e$ | Uniform MOE | Phosphorothioate | 805 |
| 444750 | $G_{ks}C_{ks}A_{ds}G_{ds}C_{ks}A_{ds}G_{ds}C_{ks}A_{ds}$ $G_{ds}C_{ks}A_{ds}G_{ds}C_{ks}A_{ds}G_{ds}C_{ks}A_k$ | Deoxy and (S)-cEt units | Phosphorothioate | 805 |
| 444752 | $G_{ks}C_{ks}A_{es}G_{es}C_{ks}A_{es}G_{es}C_{ks}A_{es}$ $G_{es}C_{ks}A_{es}G_{es}C_{ks}A_{es}G_{es}C_{ks}A_k$ | MOE and (S)-cEt units | Phosphorothioate | 805 |
| 444754 | $G_{es}mC_{es}A_{fs}G_{fs}C_{fs}A_{fs}G_{fs}C_{fs}A_{fs}$ $G_{fs}C_{fs}A_{fs}G_{fs}C_{fs}A_{fs}G_{fs}mC_{es}A_{es}$ | MOE and 2'-alpha-flouro units | Phosphorothioate | 805 |
| 444759 | $G_{hs}mC_{hs}A_{hs}G_{hs}mC_{hs}A_{hs}G_{hs}mC_{hs}A_{hs}$ $G_{hs}mC_{hs}A_{hs}G_{hs}mC_{hs}A_{hs}G_{hs}mC_{hs}A_h$ | Uniform 3'-fluoro-HNA | Phosphorothioate | 805 |
| 444761 | $G_{rs}mC_{rs}A_{rs}G_{rs}mC_{rs}A_{rs}G_{rs}mC_{rs}A_{rs}$ $G_{rs}mC_{rs}A_{rs}G_{rs}mC_{rs}A_{rs}G_{rs}mC_{rs}A_r$ | Uniform 2'-O-propylribose | Phosphorothioate | 805 |
| 444762 | $G_{ns}mC_{ns}A_{ns}G_{ns}mC_{ns}A_{ns}G_{ns}mC_{ns}A_{ns}$ $G_{ns}mC_{ns}A_{ns}G_{ns}mC_{ns}A_{ns}G_{ns}mC_{ns}A_n$ | Uniform 2'-O-(N-methylacetamide) ribose | Phosphorothioate | 805 |
| 444763 | $G_{os}mC_{es}A_{os}G_{os}mC_{es}A_{os}G_{os}mC_{es}A_{os}$ $G_{os}mC_{es}A_{os}G_{os}mC_{es}A_{os}G_{os}mC_{es}A_o$ | MOE and 2'-O-dimethylaminooxyethyl (DMAOE) ribose units | Phosphorothioate | 805 |
| 444764 | $G_{gs}mC_{es}A_{es}G_{gs}mC_{es}A_{es}G_{gs}mC_{es}A_{es}$ $G_{gs}mC_{es}A_{es}G_{gs}mC_{es}A_{es}G_{gs}mC_{es}A_{es}G_g$ | MOE and 2'-O-2[2-(2-methoxyethoxy)ethoxy]ethyl ribose units | Phosphorothioate | 802 |
| 444765 | $G_{bs}mC_{es}A_{es}G_{bs}mC_{es}A_{es}G_{bs}mC_{es}A_{es}$ $G_{bs}mC_{es}A_{es}G_{bs}mC_{es}A_{es}G_{bs}mC_{es}A_{es}G_b$ | MOE and 2'-O-N-[2-(dimethylamino)ethyl]acetamido ribose units | Phosphorothioate | 802 |
| 473810 | $A_{ks}G_{ds}mC_{ds}A_{ks}G_{ds}mC_{ds}A_{ks}G_{ds}mC_{ds}$ $A_{ks}G_{ds}mC_{ds}A_{ks}G_{ds}mC_{ds}A_{ks}G_{ds}mC_{ds}A_k$ | Deoxy and (S)-cEt units | Phosphorothioate | 806 |
| 473811 | $A_{ks}G_{ds}mC_{ds}A_{ks}G_{ds}mC_{ds}A_{ks}G_{ds}$ $mC_{ds}A_{ks}G_{ds}mC_{ds}A_{ks}G_{ds}mC_{ds}A_k$ | Deoxy and (S)-cEt units | Phosphorothioate | 807 |

Example 3

Dose-Dependent Antisense Inhibition of Human DMPK in Human Skeletal Muscle Cells Several of the antisense oligonucleotides exhibiting in vitro inhibition of DMPK in hSKMC (see Example 1) were described hereinabove. DMPK mRNA transcript levels were normalized to total RNA content, as measured by RIBOGREEN®. Results are presented in Table 5 as percent inhibition of DMPK, relative to untreated control cells.

The tested antisense oligonucleotides demonstrated dose-dependent inhibition of DMPK mRNA levels under the conditions specified above.

TABLE 5

Dose-dependent antisense inhibition of human DMPK in hSKMC tested with primer probe set RTS3164

| ISIS No. | 1,250 nM | 2,500 nM | 5,000 nM | 10,000 nM | 20,000 nM | IC$_{50}$ (μM) |
|---|---|---|---|---|---|---|
| 299471 | 34 | 65 | 87 | 91 | 94 | 1.60 |
| 299473 | 2 | 33 | 60 | 89 | 92 | 4.31 |
| 299476 | 15 | 17 | 49 | 81 | 91 | 4.89 |
| 299535 | 0 | 12 | 34 | 62 | 59 | 9.95 |
| 299535 | 20 | 33 | 47 | 67 | 80 | 5.11 |
| 299544 | 32 | 63 | 81 | 85 | 87 | 1.82 |
| 444397 | 10 | 30 | 58 | 85 | 82 | 4.51 |
| 444398 | 33 | 57 | 74 | 85 | 87 | 2.07 |
| 444400 | 52 | 46 | 63 | 82 | 88 | 1.76 |
| 444401 | 51 | 71 | 84 | 89 | 91 | 0.71 |
| 444402 | 53 | 79 | 83 | 87 | 84 | <1.25 |
| 444404 | 48 | 68 | 77 | 86 | 90 | 0.95 |
| 444408 | 26 | 47 | 70 | 87 | 87 | 2.80 |
| 444410 | 22 | 47 | 67 | 83 | 87 | 3.12 |
| 444436 | 28 | 67 | 76 | 89 | 92 | 1.94 |
| 444440 | 70 | 77 | 83 | 89 | 85 | <1.25 |
| 444441 | 33 | 55 | 81 | 87 | 86 | 1.99 |
| 444442 | 54 | 73 | 84 | 89 | 88 | <1.25 |
| 445568 | 65 | 83 | 85 | 84 | 76 | <1.25 |
| 445569 | 60 | 77 | 87 | 93 | 91 | <1.25 |
| 445581 | 16 | 44 | 78 | 86 | 94 | 3.13 |
| 445582 | 0 | 7 | 26 | 96 | 99 | 5.60 |
| 445583 | 39 | 53 | 73 | 89 | 94 | 2.00 |
| 445584 | 20 | 26 | 61 | 81 | 93 | 4.02 |
| 445589 | 42 | 61 | 81 | 91 | 87 | 1.36 |
| 445601 | 49 | 79 | 87 | 93 | 94 | 0.66 |
| 445608 | 26 | 59 | 71 | 85 | 97 | 2.41 |
| 445612 | 46 | 59 | 72 | 88 | 93 | 1.51 |

The antisense oligonucleotides from Table 5 were also tested with primer probe set RTS3162, described hereinabove. The results are presented in Table 6. DMPK mRNA expression was also assessed by RTS3162 which targets the DMPK gene near the 3'UTR. The use of a second primer probe was employed to confirm that the expression of the entire DMPK gene had been inhibited.

TABLE 6

Dose-dependent antisense inhibition of human DMPK in hSKMC tested with primer probe set RTS3164

| ISIS No. | 1,250 nM | 2,500 nM | 5,000 nM | 10,000 nM | 20,000 nM | IC$_{50}$ (μM) |
|---|---|---|---|---|---|---|
| 299471 | 40 | 72 | 86 | 91 | 93 | 1.17 |
| 299473 | 6 | 43 | 63 | 87 | 89 | 3.86 |
| 299476 | 3 | 21 | 48 | 74 | 86 | 5.58 |
| 299535 | 9 | 22 | 36 | 62 | 77 | 7.05 |
| 299535 | 6 | 19 | 49 | 68 | 70 | 6.70 |
| 299544 | 35 | 66 | 81 | 84 | 87 | 1.52 |
| 444397 | 88 | 90 | 95 | 97 | 96 | <1.25 |
| 444398 | 91 | 97 | 97 | 97 | 98 | <1.25 |
| 444400 | 72 | 87 | 93 | 96 | 96 | <1.25 |
| 444401 | 86 | 92 | 97 | 98 | 97 | <1.25 |
| 444402 | 83 | 91 | 94 | 95 | 95 | <1.25 |
| 444404 | 49 | 69 | 81 | 90 | 93 | 0.92 |
| 444408 | 21 | 46 | 70 | 84 | 86 | 3.10 |
| 444410 | 35 | 55 | 77 | 89 | 91 | 2.02 |
| 444436 | 37 | 66 | 81 | 89 | 92 | 1.50 |
| 444440 | 66 | 79 | 89 | 92 | 89 | <1.25 |
| 444441 | 40 | 62 | 85 | 89 | 89 | 1.40 |
| 444442 | 55 | 75 | 86 | 90 | 91 | <1.25 |
| 445568 | 74 | 92 | 91 | 92 | 91 | <1.25 |
| 445569 | 68 | 83 | 90 | 94 | 93 | <1.25 |
| 445581 | 8 | 48 | 77 | 85 | 92 | 3.33 |
| 445582 | 15 | 22 | 44 | 97 | 99 | 4.29 |
| 445583 | 36 | 58 | 71 | 87 | 92 | 1.96 |
| 445584 | 25 | 43 | 66 | 86 | 94 | 3.05 |
| 445589 | 38 | 56 | 77 | 85 | 81 | 1.74 |
| 445601 | 55 | 76 | 84 | 93 | 93 | <1.25 |

TABLE 6-continued

Dose-dependent antisense inhibition of human DMPK in hSKMC tested with primer probe set RTS3164

| ISIS No. | 1,250 nM | 2,500 nM | 5,000 nM | 10,000 nM | 20,000 nM | IC$_{50}$ (μM) |
|---|---|---|---|---|---|---|
| 445608 | 22 | 56 | 72 | 86 | 94 | 2.66 |
| 445612 | 61 | 75 | 85 | 91 | 94 | <1.25 |

Example 4

Dose-Dependent Antisense Inhibition of Human DMPK in Human Skeletal Muscle Cells Several of the antisense oligonucleotides exhibiting in vitro inhibition of DMPK in hSKMC (see Example 3) were tested at various doses. Cells were plated at a density of 20,000 cells per well and transfected using electroporation with 1,250 nM, 2,500 nM, 5,000 nM, 10,000 nM and 20,000 nM concentrations of each antisense oligonucleotide. After approximately 16 hours, RNA was isolated from the cells and DMPK mRNA transcript levels were measured by quantitative real-time PCR using primer probe set RTS3164, described hereinabove. DMPK mRNA transcript levels were normalized to total RNA content, as measured by RIBOGREEN®. Results are presented in Table 7 as percent inhibition of DMPK, relative to untreated control cells.

The majority of the tested antisense oligonucleotides demonstrated dose-dependent inhibition of DMPK mRNA levels under the conditions specified above.

TABLE 7

Dose-dependent antisense inhibition of human DMPK in hSKMC tested with primer probe set RTS3164

| ISIS No. | 1,250 nM | 2,500 nM | 5,000 nM | 10,000 nM | 20,000 nM | IC$_{50}$ (μM) |
|---|---|---|---|---|---|---|
| 299471 | 34 | 65 | 87 | 91 | 94 | 1.59 |
| 299473 | 2 | 33 | 60 | 89 | 92 | 4.31 |
| 299476 | 15 | 17 | 49 | 81 | 91 | 4.89 |
| 299535 | 0 | 12 | 34 | 62 | 59 | 9.95 |
| 299535 | 20 | 33 | 47 | 67 | 80 | 5.11 |
| 299544 | 32 | 63 | 81 | 85 | 87 | 1.82 |
| 444397 | 10 | 30 | 58 | 85 | 82 | 4.51 |
| 444398 | 33 | 57 | 74 | 85 | 87 | 2.07 |
| 444400 | 52 | 46 | 63 | 82 | 88 | 1.76 |
| 444401 | 51 | 71 | 84 | 89 | 91 | <1.25 |
| 444402 | 53 | 79 | 83 | 87 | 84 | <1.25 |
| 444404 | 48 | 68 | 77 | 86 | 90 | 0.95 |
| 444408 | 26 | 47 | 70 | 87 | 87 | 2.80 |
| 444410 | 22 | 47 | 67 | 83 | 87 | 3.12 |
| 444436 | 28 | 67 | 76 | 89 | 92 | 1.94 |
| 444440 | 66 | 77 | 83 | 89 | 85 | <1.25 |
| 444441 | 33 | 55 | 81 | 87 | 86 | 1.99 |
| 444442 | 54 | 73 | 84 | 89 | 88 | <1.25 |
| 445568 | 65 | 83 | 85 | 84 | 76 | <1.25 |
| 445569 | 60 | 77 | 87 | 93 | 91 | <1.25 |
| 445581 | 16 | 44 | 78 | 86 | 94 | 3.13 |
| 445582 | 0 | 7 | 26 | 96 | 99 | 5.62 |
| 445583 | 39 | 53 | 73 | 89 | 94 | 1.97 |
| 445584 | 20 | 26 | 61 | 81 | 93 | 4.20 |
| 445589 | 42 | 61 | 81 | 91 | 87 | 1.36 |
| 445601 | 49 | 79 | 87 | 93 | 94 | 0.66 |
| 445608 | 26 | 59 | 71 | 85 | 97 | 2.41 |
| 445612 | 46 | 59 | 72 | 88 | 93 | 1.51 |

Example 5

Dose-Dependent Antisense Inhibition of Human DMPK in Human Skeletal Muscle Cells Several antisense oligonucleotides were designed to target human DMPK mRNA and were tested in hSKMC at various doses. Several other antisense oligonucleotides were designed to target human actin mRNA and were also tested in hSKMC at various doses. The newly designed gapmers are 2-10-2 MOE or 3-10-3 MOE gapmers. The 2-10-2 MOE gapmers are 14 nucleosides in length and where the gap segment comprises ten 2'-deoxynucleosides and each wing segment comprises two 2'-MOE nucleosides. The 3-10-3 MOE gapmers are 16 nucleosides in length and where the gap segment comprises ten 2'-deoxynucleosides and each wing segment comprises three 2'-MOE nucleosides. The internucleoside linkages throughout each gapmer are phosphorothioate (P=S) linkages. All cytosine residues throughout each gapmer are 5-methylcytosines. 'Target start site' indicates the 5'-most nucleoside to which the antisense oligonucleotide is targeted. 'Target stop site' indicates the 3'-most nucleoside to which the antisense oligonucleotide is targeted. The antisense oligonucleotides listed in Table 8 target either the human DMPK genomic sequence, designated herein as SEQ ID NO: 2 (the complement of GEN-BANK Accession No. NT_011109.15 truncated from nucleotides 18540696 to Ser. No. 18/555,106) or the human actin sequence, designated herein as SEQ ID NO: 801 (GENBANK Accession No. NM_001100.3).

Cells were plated at a density of 20,000 cells per well and transfected using electroporation with 1,250 nM, 2,500 nM, 5,000 nM, 10,000 nM and 20,000 nM concentrations of each antisense oligonucleotide. After approximately 16 hours, RNA was isolated from the cells and DMPK mRNA transcript levels were measured by quantitative real-time PCR using primer probe set RTS3162, described hereinabove. DMPK mRNA transcript levels were normalized to total RNA content, as measured by RIBOGREEN®. Results are presented in Table 8 as percent inhibition of DMPK, relative to untreated control cells. The antisense oligonucleotides were also tested under similar conditions with RTS3164. The results are presented in Table 9.

Many of the tested antisense oligonucleotides demonstrated dose-dependent inhibition of DMPK mRNA levels under the conditions specified above.

TABLE 8

Dose-dependent antisense inhibition of human DMPK and human actin in hSKMC tested with primer probe set RTS3162

| ISIS No | Sequence | Motif | Target SEQ ID NO | Start Site | 1,250 nM | 2,500 nM | 5,000 nM | 10,000 nM | 20,000 nM | $IC_{50}$ (nM) | SEQ ID NO |
|---|---|---|---|---|---|---|---|---|---|---|---|
| 468787 | CTCCCGACAAGCTCCA | 3-10-3 | 2 | 814 | 28 | 47 | 51 | 84 | 88 | 3.27 | 808 |
| 468772 | TCCCGACAAGCTCC | 2-10-2 | 2 | 815 | 17 | 39 | 67 | 72 | 80 | 4.04 | 809 |
| 468795 | GCTTGCACGTGTGGCT | 3-10-3 | 2 | 10935 | 32 | 58 | 77 | 85 | 75 | 1.94 | 810 |
| 468780 | CTTGCACGTGTGGC | 2-10-2 | 2 | 10936 | 22 | 17 | 43 | 66 | 77 | 6.23 | 811 |
| 468793 | GGTTGTGAACTGGCAG | 3-10-3 | 2 | 13224 | 69 | 77 | 93 | 96 | 96 | <1.25 | 812 |
| 468778 | GTTGTGAACTGGCA | 2-10-2 | 2 | 13225 | 60 | 69 | 89 | 95 | 97 | <1.25 | 813 |
| 468794 | GAGCGGTTGTGAACTG | 3-10-3 | 2 | 13228 | 21 | 32 | 61 | 70 | 86 | 4.27 | 814 |
| 468779 | AGCGGTTGTGAACT | 2-10-2 | 2 | 13229 | 40 | 45 | 72 | 91 | 97 | 2.20 | 815 |
| 468796 | GCTGCCTTCCCAGGCC | 3-10-3 | 2 | 13493 | 73 | 79 | 91 | 96 | 95 | <1.25 | 816 |
| 468781 | CTGCCTTCCCAGGC | 2-10-2 | 2 | 13494 | 36 | 53 | 66 | 86 | 90 | 2.28 | 817 |
| 468788 | GCACTTTGCGAACCAA | 3-10-3 | 2 | 13555 | 55 | 80 | 84 | 94 | 96 | <1.25 | 818 |
| 468773 | CACTTTGCGAACCA | 2-10-2 | 2 | 13556 | 31 | 52 | 82 | 91 | 93 | 2.16 | 819 |
| 468789 | GAAAGCTTTGCACTTT | 3-10-3 | 2 | 13564 | 42 | 66 | 83 | 91 | 98 | 1.31 | 820 |
| 468774 | AAAGCTTTGCACTT | 2-10-2 | 2 | 13565 | 21 | 0 | 31 | 41 | 55 | 1.87 | 821 |
| 468790 | CGGAGGACGAGGTCAA | 3-10-3 | 2 | 13750 | 43 | 57 | 79 | 87 | 89 | 1.51 | 822 |
| 468775 | GGAGGACGAGGTCA | 2-10-2 | 2 | 13751 | 27 | 51 | 58 | 78 | 81 | 3.18 | 823 |
| 468791 | AGCCTGTCAGCGAGTC | 3-10-3 | 2 | 13765 | 49 | 63 | 85 | 62 | 95 | 1.04 | 824 |
| 468776 | GCCTGTCAGCGAGT | 2-10-2 | 2 | 13766 | 65 | 47 | 81 | 88 | 93 | <1.25 | 825 |
| 468792 | TCCTGTAGCCTGTCAG | 3-10-3 | 2 | 13771 | 38 | 57 | 73 | 85 | 93 | 1.91 | 826 |

TABLE 8-continued

Dose-dependent antisense inhibition of human DMPK and human actin in hSKMC tested with primer probe set RTS3162

| ISIS No | Sequence | Motif | Target SEQ ID NO | Start Site | 1,250 nM | 2,500 nM | 5,000 nM | 10,000 nM | 20,000 nM | IC$_{50}$ (nM) | SEQ ID NO |
|---|---|---|---|---|---|---|---|---|---|---|---|
| 468777 | CCTGTAGCCTGTCA | 2-10-2 | 2 | 13772 | 15 | 58 | 66 | 85 | 92 | 2.99 | 827 |
| 468783 | GAAGCGAGGCTTCACT | 3-10-3 | 801 | 22 | 0 | 20 | 5 | 0 | 0 | >20.00 | 828 |
| 468768 | AAGCGAGGCTTCAC | 2-10-2 | 801 | 23 | 25 | 22 | 5 | 17 | 0 | >20.00 | 829 |
| 468784 | ACCTGCCCGTCTGGCA | 3-10-3 | 801 | 836 | 15 | 25 | 32 | 18 | 25 | >20.00 | 830 |
| 468769 | CCTGCCCGTCTGGC | 2-10-2 | 801 | 837 | 32 | 11 | 11 | 20 | 32 | >20.00 | 831 |
| 468782 | GGTCAGCGATCCCAGG | 3-10-3 | 801 | 1030 | 0 | 0 | 0 | 0 | 0 | >20.00 | 832 |
| 468767 | GTCAGCGATCCCAG | 2-10-2 | 801 | 1031 | 15 | 0 | 11 | 0 | 0 | >20.00 | 833 |
| 468785 | ATTTTCTTCCACAGGG | 3-10-3 | 801 | 1432 | 12 | 0 | 0 | 0 | 0 | >20.00 | 834 |
| 468770 | TTTTCTTCCACAGG | 2-10-2 | 801 | 1433 | 36 | 2 | 0 | 0 | 28 | >20.00 | 835 |
| 468786 | GAATGACTTTAATGCT | 3-10-3 | 801 | 1462 | 0 | 0 | 0 | 4 | 0 | >20.00 | 836 |
| 468771 | AATGACTTTAATGC | 2-10-2 | 801 | 1463 | 8 | 16 | 0 | 5 | 0 | >20.00 | 837 |

TABLE 9

Dose-dependent antisense inhibition of human DMPK in hSKMC tested with primer probe set RTS3164

| ISIS No | 1,250 nM | 2,500 nM | 5,000 nM | 10,000 nM | 20,000 nM | IC$_{50}$ (µM) |
|---|---|---|---|---|---|---|
| 468777 | 20 | 66 | 72 | 87 | 96 | 2.41 |
| 468776 | 68 | 48 | 86 | 90 | 96 | <1.25 |
| 468794 | 18 | 23 | 58 | 65 | 86 | 4.97 |
| 468787 | 36 | 50 | 51 | 88 | 92 | 2.69 |
| 468772 | 12 | 47 | 69 | 80 | 86 | 3.57 |
| 468773 | 33 | 48 | 82 | 91 | 96 | 2.21 |
| 468774 | 21 | 0 | 30 | 42 | 59 | 1.60 |
| 468790 | 50 | 57 | 77 | 91 | 91 | 1.26 |
| 468780 | 23 | 22 | 55 | 73 | 85 | 4.69 |
| 468775 | 29 | 52 | 55 | 79 | 84 | 3.03 |
| 468782 | 9 | 0 | 0 | 0 | 0 | >20.00 |
| 468786 | 2 | 0 | 0 | 0 | 0 | >20.00 |
| 468785 | 15 | 0 | 1 | 0 | 5 | >20.00 |
| 468788 | 57 | 74 | 76 | 94 | 96 | <1.25 |
| 468791 | 45 | 66 | 88 | 61 | 97 | 1.10 |
| 468789 | 26 | 65 | 82 | 90 | 97 | 2.02 |
| 468781 | 28 | 46 | 59 | 82 | 84 | 3.08 |
| 468779 | 26 | 31 | 66 | 90 | 97 | 3.29 |
| 468784 | 7 | 23 | 26 | 7 | 18 | >20.00 |
| 468783 | 0 | 16 | 8 | 0 | 0 | >20.00 |
| 468792 | 26 | 49 | 73 | 84 | 92 | 2.72 |
| 468795 | 30 | 53 | 83 | 86 | 85 | 2.14 |
| 468793 | 49 | 66 | 90 | 96 | 95 | 0.93 |
| 468768 | 23 | 3 | 5 | 9 | 0 | >20.00 |
| 468767 | 0 | 0 | 14 | 0 | 0 | >20.00 |
| 468769 | 31 | 0 | 0 | 16 | 25 | >20.00 |
| 468771 | 4 | 0 | 0 | 0 | 0 | >20.00 |
| 468770 | 33 | 0 | 0 | 0 | 32 | >20.00 |
| 468796 | 62 | 72 | 84 | 96 | 95 | <1.25 |
| 468778 | 44 | 58 | 86 | 96 | 98 | 1.44 |

Example 6

Dose Response Studies with Antisense Oligonucleotides Targeting Human Dystrophia Myotonica-Protein Kinase (DMPK) in DM1 Fibroblast Cells The mutant form of the DMPK mRNA, harboring large CUG repeats, are fully transcribed and polyadenylated, but remain trapped in the nucleus (Davis et al, 1997, Proc. Natl. Acad. Sci. U.S.A 94, 7388-7393). These mutant nuclear-retained mRNAs are one of the most important pathological features of myotonic dystrophy 1 (DM1). Antisense inhibition of mutant DMPK mRNA in DM1 fibroblast cells was studied.

The DMPK gene normally has 5-37 CTG repeats in the 3' untranslated region. In myotonic dystrophy type I, this number is significantly expanded and may be in the range of 50 to greater than 3,500 (Harper, Myotonic Dystrophy (Saunders, London, ed.3, 2001); Annu. Rev. Neurosci. 29: 259, 2006; EMBO J. 19: 4439, 2000; Curr Opin Neurol. 20: 572, 2007). DM1 fibroblast cells were plated at a density of 4,500 cells per well and transfected using Cytofectin reagent with 9.4 nM, 18.8 nM, 37.5 nM, 75.0 nM, 150.0 nM, and 300.0 nM concentrations of each antisense oligonucleotide. After approximately 16 hours, RNA was isolated from the cells and DMPK RNA transcript levels were measured by quantitative real-time PCR using primer probe set RTS3164, described hereinabove. DMPK RNA transcript levels were normalized to total RNA content, as measured by RIBOGREEN®. Results are presented in Table 10 as percent inhibition of DMPK, relative to untreated control cells.

An assay with similar conditions was also performed with primer probe set RTS3162, described hereinabove, which targets the 3'-end of the DMPK transcript. Results are presented in Table 11 as percent inhibition of DMPK, relative to untreated control cells.

The tested antisense oligonucleotides demonstrated dose-dependent inhibition of DMPK mRNA levels under the conditions specified above.

TABLE 10

Dose-dependent antisense inhibition of DMPK mRNA in DM1 fibroblast cells with RTS3164

| ISIS No. | 9.4 nM | 18.8 nM | 37.5 nM | 75.0 nM | 150.0 nM | 300.0 nM | $IC_{50}$ (nM) |
|---|---|---|---|---|---|---|---|
| 299471 | 10 | 25 | 31 | 47 | 61 | 73 | 86.3 |
| 444401 | 8 | 27 | 41 | 60 | 67 | 74 | 64.3 |
| 444404 | 10 | 21 | 31 | 43 | 55 | 73 | 100.0 |
| 444436 | 7 | 17 | 36 | 64 | 68 | 70 | 72.3 |
| 445569 | 19 | 31 | 41 | 59 | 46 | 77 | 72.2 |

TABLE 11

Dose-dependent antisense inhibition of DMPK mRNA in DM1 fibroblast cells with RTS3162

| ISIS No | 9.4 nM | 18.8 nM | 37.5 nM | 75.0 nM | 150.0 nM | 300.0 nM | $IC_{50}$ (nM) |
|---|---|---|---|---|---|---|---|
| 299471 | 7 | 25 | 29 | 46 | 48 | 69 | 115.3 |
| 444401 | 20 | 34 | 52 | 72 | 83 | 89 | 35.8 |
| 444404 | 5 | 20 | 28 | 42 | 54 | 77 | 98.8 |
| 444436 | 12 | 15 | 27 | 61 | 68 | 75 | 74.3 |
| 445569 | 5 | 25 | 33 | 53 | 50 | 76 | 89.6 |

Example 7

Antisense Inhibition of Human DMPK in Human Skeletal Muscle Cells (hSKMc)

Antisense oligonucleotides targeted to a human DMPK nucleic acid were tested for their effect on DMPK RNA transcript in vitro. Cultured hSKMc at a density of 20,000 cells per well were transfected using electroporation with 10,000 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent inhibition of DMPK, relative to untreated control cells.

The antisense oligonucleotides in Tables 12 and 13 are 5-10-5 gapmers, where the gap segment comprises ten 2'-deoxynucleosides and each wing segment comprises five 2'-MOE nucleosides. The internucleoside linkages throughout each gapmer are phosphorothioate (P=S) linkages. All cytsoine residues throughout each gapmer are 5-methylcytosines. 'Target start site' indicates the 5'-most nucleoside to which the antisense oligonucleotide is targeted in the human genomic gene sequence. 'Target stop site' indicates the 3'-most nucleoside to which the antisense oligonucleotide is targeted in the human genomic sequence. All the antisense oligonucleotides listed in Table 12 target SEQ ID NO: 1 (GENBANK Accession No. NM_001081560.1). All the antisense oligonucleotides listed in Table 13 target SEQ ID NO: 2 (the complement of GENBANK Accession No. NT_011109.15 truncated from nucleotides 18540696 to Ser. No. 18/555,106).

Several of the antisense oligonucleotides demonstrated significant inhibition of DMPK mRNA levels under the conditions specified above.

TABLE 12

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 124 | 143 | 502369 | GCCTGGCAGCCCCTGTCCAG | 16 | 160 |
| 125 | 144 | 502370 | GGCCTGGCAGCCCCTGTCCA | 58 | 161 |
| 126 | 145 | 502371 | GGGCCTGGCAGCCCCTGTCC | 62 | 162 |
| 169 | 188 | 502372 | ATGGCCCCTCCCCGGGCCGG | 41 | 163 |
| 170 | 189 | 502373 | CATGGCCCCTCCCCGGGCCG | 29 | 164 |
| 171 | 190 | 502374 | CCATGGCCCCTCCCCGGGCC | 34 | 165 |
| 172 | 191 | 502375 | ACCATGGCCCCTCCCCGGGC | 60 | 166 |
| 173 | 192 | 502376 | CACCATGGCCCCTCCCCGGG | 68 | 167 |
| 174 | 193 | 502377 | GCACCATGGCCCCTCCCCGG | 75 | 168 |
| 175 | 194 | 502378 | AGCACCATGGCCCCTCCCCG | 65 | 169 |
| 176 | 195 | 502379 | CAGCACCATGGCCCCTCCCC | 63 | 170 |
| 177 | 196 | 502380 | GCAGCACCATGGCCCCTCCC | 73 | 171 |
| 178 | 197 | 502381 | GGCAGCACCATGGCCCCTCC | 80 | 172 |
| 180 | 199 | 502382 | CAGGCAGCACCATGGCCCCT | 82 | 173 |
| 181 | 200 | 502383 | ACAGGCAGCACCATGGCCCC | 72 | 174 |
| 183 | 202 | 502384 | GGACAGGCAGCACCATGGCC | 70 | 175 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 184 | 203 | 502385 | TGGACAGGCAGCACCATGGC | 71 | 176 |
| 185 | 204 | 502386 | TTGGACAGGCAGCACCATGG | 73 | 177 |
| 186 | 205 | 502387 | GTTGGACAGGCAGCACCATG | 73 | 178 |
| 187 | 206 | 502388 | TGTTGGACAGGCAGCACCAT | 60 | 179 |
| 188 | 207 | 502389 | ATGTTGGACAGGCAGCACCA | 75 | 180 |
| 189 | 208 | 502390 | CATGTTGGACAGGCAGCACC | 81 | 181 |
| 190 | 209 | 502391 | ACATGTTGGACAGGCAGCAC | 67 | 182 |
| 191 | 210 | 502392 | GACATGTTGGACAGGCAGCA | 71 | 183 |
| 192 | 211 | 502393 | TGACATGTTGGACAGGCAGC | 81 | 184 |
| 193 | 212 | 502394 | CTGACATGTTGGACAGGCAG | 76 | 185 |
| 194 | 213 | 502395 | GCTGACATGTTGGACAGGCA | 70 | 186 |
| 195 | 214 | 502396 | GGCTGACATGTTGGACAGGC | 77 | 187 |
| 196 | 215 | 502397 | CGGCTGACATGTTGGACAGG | 74 | 188 |
| 197 | 216 | 502398 | TCGGCTGACATGTTGGACAG | 63 | 189 |
| 198 | 217 | 502399 | CTCGGCTGACATGTTGGACA | 80 | 190 |
| 199 | 218 | 502400 | CCTCGGCTGACATGTTGGAC | 71 | 191 |
| 200 | 219 | 502401 | ACCTCGGCTGACATGTTGGA | 64 | 192 |
| 201 | 220 | 502402 | CACCTCGGCTGACATGTTGG | 71 | 193 |
| 202 | 221 | 502403 | GCACCTCGGCTGACATGTTG | 77 | 194 |
| 203 | 222 | 502404 | CGCACCTCGGCTGACATGTT | 80 | 195 |
| 204 | 223 | 502405 | CCGCACCTCGGCTGACATGT | 80 | 196 |
| 205 | 224 | 502406 | GCCGCACCTCGGCTGACATG | 79 | 197 |
| 206 | 225 | 502407 | AGCCGCACCTCGGCTGACAT | 74 | 198 |
| 207 | 226 | 502408 | CAGCCGCACCTCGGCTGACA | 66 | 199 |
| 208 | 227 | 502409 | TCAGCCGCACCTCGGCTGAC | 15 | 200 |
| 209 | 228 | 502410 | CTCAGCCGCACCTCGGCTGA | 32 | 201 |
| 210 | 229 | 502411 | CCTCAGCCGCACCTCGGCTG | 65 | 202 |
| 211 | 230 | 502412 | GCCTCAGCCGCACCTCGGCT | 81 | 203 |
| 232 | 251 | 502413 | CCAACACCAGCTGCTGGAGC | 90 | 204 |
| 233 | 252 | 502414 | TCCAACACCAGCTGCTGGAG | 78 | 205 |
| 234 | 253 | 502415 | GTCCAACACCAGCTGCTGGA | 84 | 206 |
| 236 | 255 | 502416 | GGGTCCAACACCAGCTGCTG | 69 | 207 |
| 257 | 276 | 502417 | GGCTCCAGCCCCAGGAAGCC | 46 | 208 |
| 258 | 277 | 502418 | GGGCTCCAGCCCCAGGAAGC | 28 | 209 |
| 276 | 295 | 502419 | CAGGAGAAGGTCGAGCAGGG | 41 | 210 |
| 278 | 297 | 502420 | CCCAGGAGAAGGTCGAGCAG | 71 | 211 |
| 279 | 298 | 502421 | GCCCAGGAGAAGGTCGAGCA | 85 | 212 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 280 | 299 | 451363 | CGCCCAGGAGAAGGTCGAGC | 84 | 213 |
| 281 | 300 | 502422 | ACGCCCAGGAGAAGGTCGAG | 67 | 214 |
| 317 | 336 | 502423 | TCCTGGGCCAGTTCGGAGGC | 58 | 215 |
| 318 | 337 | 502424 | GTCCTGGGCCAGTTCGGAGG | 71 | 216 |
| 319 | 338 | 502425 | TGTCCTGGGCCAGTTCGGAG | 69 | 217 |
| 320 | 339 | 502426 | TTGTCCTGGGCCAGTTCGGA | 71 | 218 |
| 321 | 340 | 502427 | CTTGTCCTGGGCCAGTTCGG | 66 | 219 |
| 322 | 341 | 502428 | ACTTGTCCTGGGCCAGTTCG | 59 | 220 |
| 323 | 342 | 502429 | TACTTGTCCTGGGCCAGTTC | 75 | 221 |
| 324 | 343 | 502430 | GTACTTGTCCTGGGCCAGTT | 78 | 222 |
| 325 | 344 | 502431 | CGTACTTGTCCTGGGCCAGT | 74 | 223 |
| 343 | 362 | 502432 | ACTGCAAGAAGTCGGCCACG | 73 | 224 |
| 345 | 364 | 502433 | CCACTGCAAGAAGTCGGCCA | 65 | 225 |
| 346 | 365 | 451364 | CCCACTGCAAGAAGTCGGCC | 32 | 226 |
| 347 | 366 | 502434 | GCCCACTGCAAGAAGTCGGC | 70 | 227 |
| 348 | 367 | 502435 | CGCCCACTGCAAGAAGTCGG | 61 | 228 |
| 349 | 368 | 502436 | CCGCCCACTGCAAGAAGTCG | 54 | 229 |
| 350 | 369 | 502437 | TCCGCCCACTGCAAGAAGTC | 40 | 230 |
| 351 | 370 | 502438 | CTCCGCCCACTGCAAGAAGT | 33 | 231 |
| 352 | 371 | 502439 | GCTCCGCCCACTGCAAGAAG | 23 | 232 |
| 353 | 372 | 502440 | GGCTCCGCCCACTGCAAGAA | 23 | 233 |
| 354 | 373 | 502441 | GGGCTCCGCCCACTGCAAGA | 17 | 234 |
| 355 | 374 | 502442 | TGGGCTCCGCCCACTGCAAG | 22 | 235 |
| 356 | 375 | 502443 | ATGGGCTCCGCCCACTGCAA | 14 | 236 |
| 357 | 376 | 502444 | GATGGGCTCCGCCCACTGCA | 43 | 237 |
| 358 | 377 | 502445 | CGATGGGCTCCGCCCACTGC | 37 | 238 |
| 359 | 378 | 502446 | ACGATGGGCTCCGCCCACTG | 0 | 239 |
| 360 | 379 | 502447 | CACGATGGGCTCCGCCCACT | 59 | 240 |
| 361 | 380 | 502448 | CCACGATGGGCTCCGCCCAC | 69 | 241 |
| 362 | 381 | 502449 | ACCACGATGGGCTCCGCCCA | 63 | 242 |
| 363 | 382 | 502450 | CACCACGATGGGCTCCGCCC | 73 | 243 |
| 364 | 383 | 502451 | TCACCACGATGGGCTCCGCC | 77 | 244 |
| 365 | 384 | 502452 | CTCACCACGATGGGCTCCGC | 66 | 245 |
| 366 | 385 | 502453 | CCTCACCACGATGGGCTCCG | 81 | 246 |
| 367 | 386 | 502454 | GCCTCACCACGATGGGCTCC | 77 | 247 |
| 368 | 387 | 502455 | AGCCTCACCACGATGGGCTC | 63 | 248 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 369 | 388 | 502456 | AAGCCTCACCACGATGGGCT | 70 | 249 |
| 370 | 389 | 502457 | TAAGCCTCACCACGATGGGC | 78 | 250 |
| 371 | 390 | 502458 | TTAAGCCTCACCACGATGGG | 76 | 251 |
| 372 | 391 | 502459 | CTTAAGCCTCACCACGATGG | 78 | 252 |
| 373 | 392 | 502460 | CCTTAAGCCTCACCACGATG | 68 | 253 |
| 374 | 393 | 502461 | TCCTTAAGCCTCACCACGAT | 67 | 254 |
| 375 | 394 | 502462 | CTCCTTAAGCCTCACCACGA | 84 | 255 |
| 376 | 395 | 502463 | CCTCCTTAAGCCTCACCACG | 76 | 256 |
| 377 | 396 | 502464 | ACCTCCTTAAGCCTCACCAC | 64 | 257 |
| 378 | 397 | 502465 | GACCTCCTTAAGCCTCACCA | 72 | 258 |
| 379 | 398 | 502466 | GGACCTCCTTAAGCCTCACC | 69 | 259 |
| 380 | 399 | 502467 | CGGACCTCCTTAAGCCTCAC | 81 | 260 |
| 381 | 400 | 502468 | TCGGACCTCCTTAAGCCTCA | 78 | 261 |
| 382 | 401 | 502469 | GTCGGACCTCCTTAAGCCTC | 57 | 262 |
| 384 | 403 | 502470 | CAGTCGGACCTCCTTAAGCC | 62 | 263 |
| 385 | 404 | 502471 | GCAGTCGGACCTCCTTAAGC | 45 | 264 |
| 386 | 405 | 502472 | TGCAGTCGGACCTCCTTAAG | 60 | 265 |
| 412 | 431 | 502473 | CCTTCAGAATCTCGAAGTCG | 67 | 266 |
| 413 | 432 | 502474 | ACCTTCAGAATCTCGAAGTC | 50 | 267 |
| 415 | 434 | 502475 | TCACCTTCAGAATCTCGAAG | 54 | 268 |
| 416 | 435 | 502476 | ATCACCTTCAGAATCTCGAA | 38 | 269 |
| 417 | 436 | 502477 | GATCACCTTCAGAATCTCGA | 35 | 270 |
| 419 | 438 | 502478 | CCGATCACCTTCAGAATCTC | 52 | 271 |
| 420 | 439 | 502479 | TCCGATCACCTTCAGAATCT | 50 | 272 |
| 421 | 440 | 502480 | GTCCGATCACCTTCAGAATC | 44 | 273 |
| 422 | 441 | 502481 | CGTCCGATCACCTTCAGAAT | 41 | 274 |
| 467 | 486 | 502482 | CCCGTCTGCTTCATCTTCAC | 67 | 275 |
| 468 | 487 | 502483 | GCCCGTCTGCTTCATCTTCA | 76 | 276 |
| 469 | 488 | 502484 | GGCCCGTCTGCTTCATCTTC | 57 | 277 |
| 470 | 489 | 502485 | TGGCCCGTCTGCTTCATCTT | 64 | 278 |
| 471 | 490 | 502486 | CTGGCCCGTCTGCTTCATCT | 64 | 279 |
| 472 | 491 | 502487 | CCTGGCCCGTCTGCTTCATC | 73 | 280 |
| 473 | 492 | 502488 | ACCTGGCCCGTCTGCTTCAT | 64 | 281 |
| 474 | 493 | 502489 | CACCTGGCCCGTCTGCTTCA | 80 | 282 |
| 475 | 494 | 502490 | ACACCTGGCCCGTCTGCTTC | 71 | 283 |
| 476 | 495 | 502491 | TACACCTGGCCCGTCTGCTT | 74 | 284 |
| 497 | 516 | 502492 | TTGTTCATGATCTTCATGGC | 56 | 285 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 499 | 518 | 502493 | ACTTGTTCATGATCTTCATG | 23 | 286 |
| 500 | 519 | 502494 | CACTTGTTCATGATCTTCAT | 43 | 287 |
| 501 | 520 | 502495 | CCACTTGTTCATGATCTTCA | 43 | 288 |
| 502 | 521 | 502496 | CCCACTTGTTCATGATCTTC | 47 | 289 |
| 503 | 522 | 502497 | TCCCACTTGTTCATGATCTT | 34 | 290 |
| 504 | 523 | 502498 | GTCCCACTTGTTCATGATCT | 34 | 291 |
| 505 | 524 | 502499 | TGTCCCACTTGTTCATGATC | 27 | 292 |
| 506 | 525 | 502500 | ATGTCCCACTTGTTCATGAT | 23 | 293 |
| 507 | 526 | 502501 | CATGTCCCACTTGTTCATGA | 51 | 294 |
| 508 | 527 | 502502 | GCATGTCCCACTTGTTCATG | 20 | 295 |
| 509 | 528 | 502503 | AGCATGTCCCACTTGTTCAT | 52 | 296 |
| 510 | 529 | 502504 | CAGCATGTCCCACTTGTTCA | 72 | 297 |
| 511 | 530 | 502505 | TCAGCATGTCCCACTTGTTC | 70 | 298 |
| 512 | 531 | 502506 | TTCAGCATGTCCCACTTGTT | 53 | 299 |
| 513 | 532 | 502507 | CTTCAGCATGTCCCACTTGT | 52 | 300 |
| 514 | 533 | 502508 | TCTTCAGCATGTCCCACTTG | 45 | 301 |
| 516 | 535 | 502509 | CCTCTTCAGCATGTCCCACT | 68 | 302 |
| 517 | 536 | 502510 | CCCTCTTCAGCATGTCCCAC | 68 | 303 |
| 518 | 537 | 502511 | CCCCTCTTCAGCATGTCCCA | 79 | 304 |
| 519 | 538 | 502512 | GCCCCTCTTCAGCATGTCCC | 85 | 305 |
| 520 | 539 | 502513 | CGCCCCTCTTCAGCATGTCC | 84 | 306 |
| 521 | 540 | 502514 | TCGCCCCTCTTCAGCATGTC | 80 | 307 |
| 522 | 541 | 502515 | CTCGCCCCTCTTCAGCATGT | 82 | 308 |
| 523 | 542 | 502516 | CCTCGCCCCTCTTCAGCATG | 78 | 309 |
| 524 | 543 | 502517 | ACCTCGCCCCTCTTCAGCAT | 73 | 310 |
| 525 | 544 | 502518 | CACCTCGCCCCTCTTCAGCA | 76 | 311 |
| 526 | 545 | 502519 | ACACCTCGCCCCTCTTCAGC | 79 | 312 |
| 527 | 546 | 502520 | GACACCTCGCCCCTCTTCAG | 73 | 313 |
| 821 | 840 | 502521 | GCCAGGCGGATGTGGCCACA | 57 | 314 |
| 868 | 887 | 502522 | ACCGCACCGTTCCATCTGCC | 62 | 315 |
| 869 | 888 | 502523 | GACCGCACCGTTCCATCTGC | 29 | 316 |
| 923 | 942 | 502524 | ACAGCCTGCAGGATCTCGGG | 86 | 317 |
| 924 | 943 | 502525 | CACAGCCTGCAGGATCTCGG | 81 | 318 |
| 925 | 944 | 502526 | CCACAGCCTGCAGGATCTCG | 83 | 319 |
| 926 | 945 | 502527 | CCCACAGCCTGCAGGATCTC | 84 | 320 |
| 927 | 946 | 502528 | GCCCACAGCCTGCAGGATCT | 91 | 321 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 928 | 947 | 502529 | CGCCCACAGCCTGCAGGATC | 90 | 322 |
| 929 | 948 | 502530 | CCGCCCACAGCCTGCAGGAT | 82 | 323 |
| 930 | 949 | 502531 | ACCGCCCACAGCCTGCAGGA | 83 | 324 |
| 931 | 950 | 502532 | CACCGCCCACAGCCTGCAGG | 85 | 325 |
| 932 | 951 | 502533 | CCACCGCCCACAGCCTGCAG | 84 | 326 |
| 933 | 952 | 502534 | CCCACCGCCCACAGCCTGCA | 80 | 327 |
| 934 | 953 | 502535 | GCCCACCGCCCACAGCCTGC | 90 | 328 |
| 935 | 954 | 502536 | GGCCCACCGCCCACAGCCTG | 94 | 329 |
| 936 | 955 | 502537 | AGGCCCACCGCCCACAGCCT | 88 | 330 |
| 937 | 956 | 502538 | CAGGCCCACCGCCCACAGCC | 91 | 331 |
| 938 | 957 | 502539 | CCAGGCCCACCGCCCACAGC | 73 | 332 |
| 939 | 958 | 502540 | CCCAGGCCCACCGCCCACAG | 86 | 333 |
| 940 | 959 | 502541 | TCCCAGGCCCACCGCCCACA | 88 | 334 |
| 941 | 960 | 502542 | GTCCCAGGCCCACCGCCCAC | 84 | 335 |
| 942 | 961 | 502543 | TGTCCCAGGCCCACCGCCCA | 85 | 336 |
| 943 | 962 | 502544 | CTGTCCCAGGCCCACCGCCC | 65 | 337 |
| 944 | 963 | 502545 | CCTGTCCCAGGCCCACCGCC | 81 | 338 |
| 945 | 964 | 502546 | GCCTGTCCCAGGCCCACCGC | 90 | 339 |
| 946 | 965 | 502547 | TGCCTGTCCCAGGCCCACCG | 85 | 340 |
| 947 | 966 | 502548 | CTGCCTGTCCCAGGCCCACC | 89 | 341 |
| 948 | 967 | 502549 | GCTGCCTGTCCCAGGCCCAC | 91 | 342 |
| 949 | 968 | 502550 | AGCTGCCTGTCCCAGGCCCA | 94 | 343 |
| 950 | 969 | 502551 | TAGCTGCCTGTCCCAGGCCC | 92 | 344 |
| 951 | 970 | 502552 | GTAGCTGCCTGTCCCAGGCC | 88 | 345 |
| 952 | 971 | 502553 | CGTAGCTGCCTGTCCCAGGC | 85 | 346 |
| 953 | 972 | 502554 | CCGTAGCTGCCTGTCCCAGG | 83 | 347 |
| 954 | 973 | 502555 | CCCGTAGCTGCCTGTCCCAG | 64 | 348 |
| 955 | 974 | 502556 | GCCCGTAGCTGCCTGTCCCA | 83 | 349 |
| 956 | 975 | 502557 | GGCCCGTAGCTGCCTGTCCC | 89 | 350 |
| 1004 | 1023 | 502558 | TAGAACATTTCATAGGCGAA | 68 | 351 |
| 1042 | 1061 | 502559 | TCTCCGCCGTGGAATCCGCG | 75 | 352 |
| 1043 | 1062 | 502560 | GTCTCCGCCGTGGAATCCGC | 79 | 353 |
| 1044 | 1063 | 502561 | GGTCTCCGCCGTGGAATCCG | 66 | 354 |
| 1045 | 1064 | 502562 | AGGTCTCCGCCGTGGAATCC | 50 | 355 |
| 1046 | 1065 | 502563 | TAGGTCTCCGCCGTGGAATC | 71 | 356 |
| 1067 | 1086 | 502564 | TTGTAGTGGACGATCTTGCC | 68 | 357 |
| 1068 | 1087 | 502565 | CTTGTAGTGGACGATCTTGC | 70 | 358 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1069 | 1088 | 502566 | CCTTGTAGTGGACGATCTTG | 61 | 359 |
| 1070 | 1089 | 502567 | TCCTTGTAGTGGACGATCTT | 72 | 360 |
| 1071 | 1090 | 502568 | CTCCTTGTAGTGGACGATCT | 75 | 361 |
| 1072 | 1091 | 502569 | GCTCCTTGTAGTGGACGATC | 75 | 362 |
| 1073 | 1092 | 502570 | TGCTCCTTGTAGTGGACGAT | 83 | 363 |
| 1074 | 1093 | 502571 | GTGCTCCTTGTAGTGGACGA | 72 | 364 |
| 1075 | 1094 | 502572 | GGTGCTCCTTGTAGTGGACG | 66 | 365 |
| 1076 | 1095 | 502573 | AGGTGCTCCTTGTAGTGGAC | 51 | 366 |
| 1077 | 1096 | 502574 | GAGGTGCTCCTTGTAGTGGA | 46 | 367 |
| 1078 | 1097 | 502575 | AGAGGTGCTCCTTGTAGTGG | 70 | 368 |
| 1079 | 1098 | 502576 | GAGAGGTGCTCCTTGTAGTG | 47 | 369 |
| 1080 | 1099 | 502577 | AGAGAGGTGCTCCTTGTAGT | 65 | 370 |
| 1081 | 1100 | 502578 | GAGAGAGGTGCTCCTTGTAG | 45 | 371 |
| 1082 | 1101 | 502579 | AGAGAGAGGTGCTCCTTGTA | 63 | 372 |
| 1083 | 1102 | 502580 | CAGAGAGAGGTGCTCCTTGT | 77 | 373 |
| 1085 | 1104 | 502581 | GGCAGAGAGAGGTGCTCCTT | 70 | 374 |
| 1086 | 1105 | 502582 | CGGCAGAGAGAGGTGCTCCT | 80 | 375 |
| 1087 | 1106 | 502583 | GCGGCAGAGAGAGGTGCTCC | 62 | 376 |
| 1088 | 1107 | 502584 | AGCGGCAGAGAGAGGTGCTC | 44 | 377 |
| 1089 | 1108 | 502585 | CAGCGGCAGAGAGAGGTGCT | 78 | 378 |
| 1090 | 1109 | 502586 | CCAGCGGCAGAGAGAGGTGC | 71 | 379 |
| 1165 | 1184 | 502587 | GGCCCAGCCGTGTCTCCGGG | 77 | 380 |
| 1166 | 1185 | 502588 | CGGCCCAGCCGTGTCTCCGG | 69 | 381 |
| 1167 | 1186 | 502589 | CCGGCCCAGCCGTGTCTCCG | 70 | 382 |
| 1168 | 1187 | 502590 | CCCGGCCCAGCCGTGTCTCC | 75 | 383 |
| 1169 | 1188 | 502591 | CCCCGGCCCAGCCGTGTCTC | 77 | 384 |
| 1170 | 1189 | 502592 | ACCCCGGCCCAGCCGTGTCT | 73 | 385 |
| 1171 | 1190 | 502593 | CACCCCGGCCCAGCCGTGTC | 84 | 386 |
| 1172 | 1191 | 502594 | CCACCCCGGCCCAGCCGTGT | 78 | 387 |
| 1173 | 1192 | 502595 | TCCACCCCGGCCCAGCCGTG | 71 | 388 |
| 1174 | 1193 | 502596 | CTCCACCCCGGCCCAGCCGT | 81 | 389 |
| 1175 | 1194 | 502597 | GCTCCACCCCGGCCCAGCCG | 86 | 390 |
| 1176 | 1195 | 502598 | TGCTCCACCCCGGCCCAGCC | 83 | 391 |
| 1177 | 1196 | 502599 | CTGCTCCACCCCGGCCCAGC | 88 | 392 |
| 1199 | 1218 | 502600 | AAGGGATGTGTCCGGAAGTC | 60 | 393 |
| 1200 | 1219 | 502601 | GAAGGGATGTGTCCGGAAGT | 58 | 394 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1201 | 1220 | 502602 | AGAAGGGATGTGTCCGGAAG | 63 | 395 |
| 1202 | 1221 | 502603 | AAGAAGGGATGTGTCCGGAA | 62 | 396 |
| 1203 | 1222 | 502604 | GAAGAAGGGATGTGTCCGGA | 61 | 397 |
| 1204 | 1223 | 502605 | AGAAGAAGGGATGTGTCCGG | 62 | 398 |
| 1205 | 1224 | 502606 | AAGAAGAAGGGATGTGTCCG | 56 | 399 |
| 1206 | 1225 | 502607 | AAAGAAGAAGGGATGTGTCC | 58 | 400 |
| 1207 | 1226 | 502608 | CAAAGAAGAAGGGATGTGTC | 50 | 401 |
| 1208 | 1227 | 502609 | CCAAAGAAGAAGGGATGTGT | 61 | 402 |
| 1210 | 1229 | 502610 | GGCCAAAGAAGAAGGGATGT | 73 | 403 |
| 1211 | 1230 | 502611 | AGGCCAAAGAAGAAGGGATG | 56 | 404 |
| 1212 | 1231 | 502612 | GAGGCCAAAGAAGAAGGGAT | 73 | 405 |
| 1213 | 1232 | 502613 | CGAGGCCAAAGAAGAAGGGA | 75 | 406 |
| 1214 | 1233 | 502614 | TCGAGGCCAAAGAAGAAGGG | 75 | 407 |
| 1215 | 1234 | 502615 | GTCGAGGCCAAAGAAGAAGG | 83 | 408 |
| 1216 | 1235 | 502616 | AGTCGAGGCCAAAGAAGAAG | 58 | 409 |
| 1217 | 1236 | 502617 | CAGTCGAGGCCAAAGAAGAA | 52 | 410 |
| 1218 | 1237 | 502618 | CCAGTCGAGGCCAAAGAAGA | 68 | 411 |
| 1219 | 1238 | 502619 | CCCAGTCGAGGCCAAAGAAG | 78 | 412 |
| 1220 | 1239 | 502620 | TCCCAGTCGAGGCCAAAGAA | 66 | 413 |
| 1221 | 1240 | 502621 | ATCCCAGTCGAGGCCAAAGA | 75 | 414 |
| 1222 | 1241 | 502622 | CATCCCAGTCGAGGCCAAAG | 70 | 415 |
| 1223 | 1242 | 502623 | CCATCCCAGTCGAGGCCAAA | 81 | 416 |
| 1224 | 1243 | 502624 | ACCATCCCAGTCGAGGCCAA | 82 | 417 |
| 1225 | 1244 | 502625 | GACCATCCCAGTCGAGGCCA | 88 | 418 |
| 1226 | 1245 | 502626 | AGACCATCCCAGTCGAGGCC | 79 | 419 |
| 1227 | 1246 | 502627 | GAGACCATCCCAGTCGAGGC | 82 | 420 |
| 1228 | 1247 | 502628 | GGAGACCATCCCAGTCGAGG | 60 | 421 |
| 1263 | 1282 | 502629 | TTCGAAATCCGGTGTAAAGG | 84 | 422 |
| 1264 | 1283 | 502630 | CTTCGAAATCCGGTGTAAAG | 57 | 423 |
| 1265 | 1284 | 502631 | CCTTCGAAATCCGGTGTAAA | 64 | 424 |
| 1266 | 1285 | 502632 | ACCTTCGAAATCCGGTGTAA | 73 | 425 |
| 1267 | 1286 | 502633 | CACCTTCGAAATCCGGTGTA | 77 | 426 |
| 1268 | 1287 | 502634 | GCACCTTCGAAATCCGGTGT | 59 | 427 |
| 1269 | 1288 | 502635 | GGCACCTTCGAAATCCGGTG | 85 | 428 |
| 1270 | 1289 | 502636 | TGGCACCTTCGAAATCCGGT | 86 | 429 |
| 1271 | 1290 | 502637 | GTGGCACCTTCGAAATCCGG | 74 | 430 |
| 1272 | 1291 | 502638 | GGTGGCACCTTCGAAATCCG | 79 | 431 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1273 | 1292 | 502639 | CGGTGGCACCTTCGAAATCC | 85 | 432 |
| 1274 | 1293 | 502640 | TCGGTGGCACCTTCGAAATC | 71 | 433 |
| 1275 | 1294 | 502641 | GTCGGTGGCACCTTCGAAAT | 88 | 434 |
| 1276 | 1295 | 502642 | TGTCGGTGGCACCTTCGAAA | 89 | 435 |
| 1277 | 1296 | 502643 | GTGTCGGTGGCACCTTCGAA | 88 | 436 |
| 1278 | 1297 | 502644 | TGTGTCGGTGGCACCTTCGA | 87 | 437 |
| 1279 | 1298 | 502645 | ATGTGTCGGTGGCACCTTCG | 88 | 438 |
| 1280 | 1299 | 502646 | CATGTGTCGGTGGCACCTTC | 88 | 439 |
| 1281 | 1300 | 502647 | GCATGTGTCGGTGGCACCTT | 91 | 440 |
| 1282 | 1301 | 502648 | TGCATGTGTCGGTGGCACCT | 87 | 441 |
| 1283 | 1302 | 502649 | TTGCATGTGTCGGTGGCACC | 86 | 442 |
| 1284 | 1303 | 502650 | GTTGCATGTGTCGGTGGCAC | 83 | 443 |
| 1285 | 1304 | 502651 | AGTTGCATGTGTCGGTGGCA | 81 | 444 |
| 1286 | 1305 | 502652 | AAGTTGCATGTGTCGGTGGC | 79 | 445 |
| 1287 | 1306 | 502653 | GAAGTTGCATGTGTCGGTGG | 58 | 446 |
| 1288 | 1307 | 502654 | CGAAGTTGCATGTGTCGGTG | 85 | 447 |
| 1290 | 1309 | 502655 | GTCGAAGTTGCATGTGTCGG | 77 | 448 |
| 1291 | 1310 | 502656 | AGTCGAAGTTGCATGTGTCG | 79 | 449 |
| 1292 | 1311 | 502657 | AAGTCGAAGTTGCATGTGTC | 74 | 450 |
| 1293 | 1312 | 502658 | CAAGTCGAAGTTGCATGTGT | 82 | 451 |
| 1294 | 1313 | 502659 | CCAAGTCGAAGTTGCATGTG | 82 | 452 |
| 1295 | 1314 | 502660 | ACCAAGTCGAAGTTGCATGT | 70 | 453 |
| 1296 | 1315 | 502661 | CACCAAGTCGAAGTTGCATG | 76 | 454 |
| 1297 | 1316 | 502662 | CCACCAAGTCGAAGTTGCAT | 79 | 455 |
| 1298 | 1317 | 502663 | TCCACCAAGTCGAAGTTGCA | 68 | 456 |
| 1299 | 1318 | 502664 | CTCCACCAAGTCGAAGTTGC | 71 | 457 |
| 1300 | 1319 | 502665 | CCTCCACCAAGTCGAAGTTG | 67 | 458 |
| 1301 | 1320 | 502666 | TCCTCCACCAAGTCGAAGTT | 70 | 459 |
| 1302 | 1321 | 502667 | GTCCTCCACCAAGTCGAAGT | 80 | 460 |
| 1303 | 1322 | 502668 | CGTCCTCCACCAAGTCGAAG | 76 | 461 |
| 1304 | 1323 | 502669 | CCGTCCTCCACCAAGTCGAA | 78 | 462 |
| 1305 | 1324 | 502670 | CCCGTCCTCCACCAAGTCGA | 83 | 463 |
| 1306 | 1325 | 502671 | GCCCGTCCTCCACCAAGTCG | 76 | 464 |
| 1307 | 1326 | 502672 | AGCCCGTCCTCCACCAAGTC | 72 | 465 |
| 1308 | 1327 | 502673 | GAGCCCGTCCTCCACCAAGT | 71 | 466 |
| 1309 | 1328 | 502674 | TGAGCCCGTCCTCCACCAAG | 60 | 467 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1702 | 1721 | 502675 | GGTTCCGAGCCTCTGCCTCG | 44 | 468 |
| 1703 | 1722 | 502676 | CGGTTCCGAGCCTCTGCCTC | 74 | 469 |
| 1704 | 1723 | 502677 | CCGGTTCCGAGCCTCTGCCT | 72 | 470 |
| 1705 | 1724 | 502678 | CCCGGTTCCGAGCCTCTGCC | 73 | 471 |
| 1706 | 1725 | 502679 | TCCCGGTTCCGAGCCTCTGC | 84 | 472 |
| 1707 | 1726 | 502680 | GTCCCGGTTCCGAGCCTCTG | 66 | 473 |
| 1709 | 1728 | 502681 | AGGTCCCGGTTCCGAGCCTC | 82 | 474 |
| 1710 | 1729 | 502682 | TAGGTCCCGGTTCCGAGCCT | 83 | 475 |
| 1711 | 1730 | 502683 | CTAGGTCCCGGTTCCGAGCC | 81 | 476 |
| 1712 | 1731 | 502684 | TCTAGGTCCCGGTTCCGAGC | 74 | 477 |
| 1713 | 1732 | 502685 | CTCTAGGTCCCGGTTCCGAG | 78 | 478 |
| 1714 | 1733 | 502686 | CCTCTAGGTCCCGGTTCCGA | 75 | 479 |
| 1715 | 1734 | 502687 | GCCTCTAGGTCCCGGTTCCG | 80 | 480 |
| 1743 | 1762 | 502688 | CATCCGCTCCTGCAACTGCC | 89 | 481 |
| 1744 | 1763 | 502689 | CCATCCGCTCCTGCAACTGC | 81 | 482 |
| 1745 | 1764 | 502690 | TCCATCCGCTCCTGCAACTG | 71 | 483 |
| 1746 | 1765 | 502691 | CTCCATCCGCTCCTGCAACT | 75 | 484 |
| 1747 | 1766 | 502692 | ACTCCATCCGCTCCTGCAAC | 64 | 485 |
| 1748 | 1767 | 502693 | AACTCCATCCGCTCCTGCAA | 52 | 486 |
| 1749 | 1768 | 502694 | CAACTCCATCCGCTCCTGCA | 45 | 487 |
| 1751 | 1770 | 502695 | AGCAACTCCATCCGCTCCTG | 78 | 488 |
| 1752 | 1771 | 502696 | CAGCAACTCCATCCGCTCCT | 64 | 489 |
| 1753 | 1772 | 502697 | GCAGCAACTCCATCCGCTCC | 56 | 490 |
| 1774 | 1793 | 502698 | CAGCTGTGGCTCCCTCTGCC | 60 | 491 |
| 1775 | 1794 | 502699 | ACAGCTGTGGCTCCCTCTGC | 45 | 492 |
| 1776 | 1795 | 502700 | GACAGCTGTGGCTCCCTCTG | 49 | 493 |
| 1777 | 1796 | 502701 | TGACAGCTGTGGCTCCCTCT | 26 | 494 |
| 1778 | 1797 | 502702 | GTGACAGCTGTGGCTCCCTC | 32 | 495 |
| 1779 | 1798 | 502703 | CGTGACAGCTGTGGCTCCCT | 28 | 496 |
| 1780 | 1799 | 502704 | CCGTGACAGCTGTGGCTCCC | 35 | 497 |
| 1781 | 1800 | 502705 | CCCGTGACAGCTGTGGCTCC | 33 | 498 |
| 1782 | 1801 | 502706 | CCCCGTGACAGCTGTGGCTC | 53 | 499 |
| 1783 | 1802 | 502707 | CCCCCGTGACAGCTGTGGCT | 39 | 500 |
| 1784 | 1803 | 502708 | ACCCCCGTGACAGCTGTGGC | 53 | 501 |
| 1785 | 1804 | 502709 | GACCCCCGTGACAGCTGTGG | 51 | 502 |
| 1786 | 1805 | 502710 | GGACCCCCGTGACAGCTGTG | 58 | 503 |
| 1787 | 1806 | 502711 | GGGACCCCCGTGACAGCTGT | 71 | 504 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1814 | 1833 | 502712 | GAAGGTGGATCCGTGGCCCG | 73 | 505 |
| 1815 | 1834 | 502713 | GGAAGGTGGATCCGTGGCCC | 70 | 506 |
| 1816 | 1835 | 502714 | GGGAAGGTGGATCCGTGGCC | 72 | 507 |
| 1817 | 1836 | 502715 | TGGGAAGGTGGATCCGTGGC | 50 | 508 |
| 1818 | 1837 | 502716 | ATGGGAAGGTGGATCCGTGG | 62 | 509 |
| 1819 | 1838 | 502717 | GATGGGAAGGTGGATCCGTG | 75 | 510 |
| 1821 | 1840 | 502718 | TAGATGGGAAGGTGGATCCG | 52 | 511 |
| 1822 | 1841 | 502719 | CTAGATGGGAAGGTGGATCC | 56 | 512 |
| 1823 | 1842 | 502720 | TCTAGATGGGAAGGTGGATC | 21 | 513 |
| 1824 | 1843 | 502721 | ATCTAGATGGGAAGGTGGAT | 34 | 514 |
| 1826 | 1845 | 502722 | CCATCTAGATGGGAAGGTGG | 43 | 515 |
| 1827 | 1846 | 502723 | GCCATCTAGATGGGAAGGTG | 17 | 516 |
| 1828 | 1847 | 451383 | GGCCATCTAGATGGGAAGGT | 0 | 517 |
| 1863 | 1882 | 502724 | CACCAGCGGGCACTGGCCCA | 51 | 518 |
| 1864 | 1883 | 502725 | CCACCAGCGGGCACTGGCCC | 55 | 519 |
| 1865 | 1884 | 502726 | CCCACCAGCGGGCACTGGCC | 61 | 520 |
| 1866 | 1885 | 502727 | CCCCACCAGCGGGCACTGGC | 43 | 521 |
| 1868 | 1887 | 502728 | GGCCCCACCAGCGGGCACTG | 16 | 522 |
| 1869 | 1888 | 502729 | TGGCCCCACCAGCGGGCACT | 43 | 523 |
| 1870 | 1889 | 502730 | CTGGCCCCACCAGCGGGCAC | 43 | 524 |
| 1871 | 1890 | 502731 | CCTGGCCCCACCAGCGGGCA | 41 | 525 |
| 1872 | 1891 | 502732 | GCCTGGCCCCACCAGCGGGC | 30 | 526 |
| 1874 | 1893 | 502733 | GGGCCTGGCCCCACCAGCGG | 66 | 527 |
| 1892 | 1911 | 502734 | AGGTGGCGGCGGTGCATGGG | 31 | 528 |
| 1893 | 1912 | 502735 | CAGGTGGCGGCGGTGCATGG | 23 | 529 |
| 1894 | 1913 | 502736 | GCAGGTGGCGGCGGTGCATG | 57 | 530 |
| 1895 | 1914 | 502737 | AGCAGGTGGCGGCGGTGCAT | 54 | 531 |
| 1896 | 1915 | 502738 | CAGCAGGTGGCGGCGGTGCA | 61 | 532 |
| 1897 | 1916 | 502739 | GCAGCAGGTGGCGGCGGTGC | 57 | 533 |
| 1898 | 1917 | 502740 | AGCAGCAGGTGGCGGCGGTG | 36 | 534 |
| 1899 | 1918 | 502741 | GAGCAGCAGGTGGCGGCGGT | 53 | 535 |
| 1900 | 1919 | 502742 | GGAGCAGCAGGTGGCGGCGG | 39 | 536 |
| 1901 | 1920 | 502743 | GGGAGCAGCAGGTGGCGGCG | 36 | 537 |
| 1902 | 1921 | 502744 | AGGGAGCAGCAGGTGGCGGC | 62 | 538 |
| 1903 | 1922 | 502745 | CAGGGAGCAGCAGGTGGCGG | 56 | 539 |
| 1904 | 1923 | 502746 | GCAGGGAGCAGCAGGTGGCG | 58 | 540 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1905 | 1924 | 502747 | GGCAGGGAGCAGCAGGTGGC | 65 | 541 |
| 1906 | 1925 | 502748 | TGGCAGGGAGCAGCAGGTGG | 47 | 542 |
| 1907 | 1926 | 502749 | CTGGCAGGGAGCAGCAGGTG | 41 | 543 |
| 1909 | 1928 | 451432 | CCCTGGCAGGGAGCAGCAGG | 53 | 544 |
| 1910 | 1929 | 502750 | ACCCTGGCAGGGAGCAGCAG | 52 | 545 |
| 1911 | 1930 | 502751 | GACCCTGGCAGGGAGCAGCA | 77 | 546 |
| 1912 | 1931 | 502752 | GGACCCTGGCAGGGAGCAGC | 0 | 547 |
| 1919 | 1938 | 502753 | GGCCTAGGGACCCTGGCAGG | 39 | 548 |
| 1920 | 1939 | 502754 | AGGCCTAGGGACCCTGGCAG | 35 | 549 |
| 1922 | 1941 | 502755 | CCAGGCCTAGGGACCCTGGC | 44 | 550 |
| 1923 | 1942 | 502756 | GCCAGGCCTAGGGACCCTGG | 60 | 551 |
| 1924 | 1943 | 502757 | GGCCAGGCCTAGGGACCCTG | 58 | 552 |
| 1925 | 1944 | 502758 | AGGCCAGGCCTAGGGACCCT | 57 | 553 |
| 1926 | 1945 | 502759 | TAGGCCAGGCCTAGGGACCC | 52 | 554 |
| 1927 | 1946 | 502760 | ATAGGCCAGGCCTAGGGACC | 51 | 555 |
| 1928 | 1947 | 502761 | GATAGGCCAGGCCTAGGGAC | 41 | 556 |
| 1929 | 1948 | 502762 | CGATAGGCCAGGCCTAGGGA | 69 | 557 |
| 1930 | 1949 | 502763 | CCGATAGGCCAGGCCTAGGG | 80 | 558 |
| 1931 | 1950 | 502764 | TCCGATAGGCCAGGCCTAGG | 78 | 559 |
| 1932 | 1951 | 502765 | CTCCGATAGGCCAGGCCTAG | 89 | 560 |
| 1933 | 1952 | 502766 | CCTCCGATAGGCCAGGCCTA | 79 | 561 |
| 1934 | 1953 | 502767 | GCCTCCGATAGGCCAGGCCT | 73 | 562 |
| 1936 | 1955 | 502768 | GCGCCTCCGATAGGCCAGGC | 83 | 563 |
| 1952 | 1971 | 502769 | AACAGGAGCAGGGAAAGCGC | 83 | 564 |
| 1953 | 1972 | 502770 | GAACAGGAGCAGGGAAAGCG | 70 | 565 |
| 1954 | 1973 | 502771 | CGAACAGGAGCAGGGAAAGC | 43 | 566 |
| 1955 | 1974 | 502772 | GCGAACAGGAGCAGGGAAAG | 47 | 567 |
| 1956 | 1975 | 502773 | GGCGAACAGGAGCAGGGAAA | 61 | 568 |
| 1957 | 1976 | 502774 | CGGCGAACAGGAGCAGGGAA | 74 | 569 |
| 1958 | 1977 | 502775 | ACGGCGAACAGGAGCAGGGA | 60 | 570 |
| 1959 | 1978 | 502776 | AACGGCGAACAGGAGCAGGG | 86 | 571 |
| 1960 | 1979 | 502777 | CAACGGCGAACAGGAGCAGG | 84 | 572 |
| 1981 | 2000 | 502778 | GGGCGGCGGCACGAGACAGA | 80 | 573 |
| 1982 | 2001 | 502779 | AGGGCGGCGGCACGAGACAG | 76 | 574 |
| 1983 | 2002 | 502780 | CAGGGCGGCGGCACGAGACA | 58 | 575 |
| 1984 | 2003 | 502781 | CCAGGGCGGCGGCACGAGAC | 80 | 576 |
| 1985 | 2004 | 502782 | CCCAGGGCGGCGGCACGAGA | 59 | 577 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 1986 | 2005 | 502783 | GCCCAGGGCGGCGGCACGAG | 68 | 578 |
| 1987 | 2006 | 502784 | AGCCCAGGGCGGCGGCACGA | 75 | 579 |
| 1988 | 2007 | 502785 | CAGCCCAGGGCGGCGGCACG | 76 | 580 |
| 1989 | 2008 | 502786 | GCAGCCCAGGGCGGCGGCAC | 70 | 581 |
| 2026 | 2045 | 502787 | CTGCGGTGAGTTGGCCGGCG | 68 | 582 |
| 2027 | 2046 | 502788 | ACTGCGGTGAGTTGGCCGGC | 67 | 583 |
| 2028 | 2047 | 502789 | GACTGCGGTGAGTTGGCCGG | 58 | 584 |
| 2029 | 2048 | 502790 | AGACTGCGGTGAGTTGGCCG | 71 | 585 |
| 2030 | 2049 | 502791 | CAGACTGCGGTGAGTTGGCC | 70 | 586 |
| 2031 | 2050 | 502792 | CCAGACTGCGGTGAGTTGGC | 79 | 587 |
| 2032 | 2051 | 502793 | GCCAGACTGCGGTGAGTTGG | 76 | 588 |
| 2033 | 2052 | 502794 | CGCCAGACTGCGGTGAGTTG | 66 | 589 |
| 2077 | 2096 | 502795 | AAGACAGTTCTAGGGTTCAG | 87 | 590 |
| 2078 | 2097 | 502796 | GAAGACAGTTCTAGGGTTCA | 78 | 591 |
| 2079 | 2098 | 502797 | CGAAGACAGTTCTAGGGTTC | 85 | 592 |
| 2080 | 2099 | 502798 | TCGAAGACAGTTCTAGGGTT | 78 | 593 |
| 2081 | 2100 | 502799 | GTCGAAGACAGTTCTAGGGT | 92 | 594 |
| 2082 | 2101 | 502800 | AGTCGAAGACAGTTCTAGGG | 85 | 595 |
| 2083 | 2102 | 502801 | GAGTCGAAGACAGTTCTAGG | 83 | 596 |
| 2084 | 2103 | 502802 | GGAGTCGAAGACAGTTCTAG | 86 | 597 |
| 2085 | 2104 | 502803 | CGGAGTCGAAGACAGTTCTA | 91 | 598 |
| 2086 | 2105 | 502804 | CCGGAGTCGAAGACAGTTCT | 76 | 599 |
| 2087 | 2106 | 502805 | CCCGGAGTCGAAGACAGTTC | 90 | 600 |
| 2088 | 2107 | 502806 | CCCCGGAGTCGAAGACAGTT | 83 | 601 |
| 2089 | 2108 | 502807 | GCCCCGGAGTCGAAGACAGT | 82 | 602 |
| 2090 | 2109 | 502808 | GGCCCCGGAGTCGAAGACAG | 73 | 603 |
| 2091 | 2110 | 502809 | GGGCCCCGGAGTCGAAGACA | 67 | 604 |
| 2143 | 2162 | 502810 | AGGCGGTGGGCGCGGCTTCT | 73 | 605 |
| 2144 | 2163 | 502811 | CAGGCGGTGGGCGCGGCTTC | 57 | 606 |
| 2145 | 2164 | 502812 | GCAGGCGGTGGGCGCGGCTT | 69 | 607 |
| 2147 | 2166 | 502813 | TGGCAGGCGGTGGGCGCGGC | 73 | 608 |
| 2149 | 2168 | 502814 | ACTGGCAGGCGGTGGGCGCG | 56 | 609 |
| 2151 | 2170 | 502815 | GAACTGGCAGGCGGTGGGCG | 71 | 610 |
| 2152 | 2171 | 502816 | TGAACTGGCAGGCGGTGGGC | 80 | 611 |
| 2154 | 2173 | 502817 | TGTGAACTGGCAGGCGGTGG | 85 | 612 |
| 2187 | 2206 | 502818 | TGGAGCTGGGCGGAGACCCA | 55 | 613 |

TABLE 12-continued

Inhibition of human DMPK RNA transcript in hSKMc by 5-10-5 gapmers targeting SEQ ID NO: 1

| Target Start Site | Target Stop Site | ISIS No | Sequence | % inhibition | SEQ ID NO. |
|---|---|---|---|---|---|
| 2189 | 2208 | 502819 | ACTGGAGCTGGGCGGAGACC | 53 | 614 |
| 2190 | 2209 | 502820 | GACTGGAGCTGGGCGGAGAC | 55 | 615 |
| 2192 | 2211 | 502821 | AGGACTGGAGCTGGGCGGAG | 76 | 616 |
| 2194 | 2213 | 502822 | ACAGGACTGGAGCTGGGCGG | 77 | 617 |
| 2195 | 2214 | 502823 | CACAGGACTGGAGCTGGGCG | 74 | 618 |
| 2196 | 2215 | 502824 | TCACAGGACTGGAGCTGGGC | 90 | 619 |
| 2386 | 2405 | 502825 | GCCTCAGCCTGGCCGAAAGA | 80 | 620 |
| 2387 | 2406 | 502826 | GGCCTCAGCCTGGCCGAAAG | 72 | 621 |
| 2490 | 2509 | 444401 | TTGCACTTTGCGAACCAACG | 97 | 41 |

TABLE 13

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 503 | 522 | 502983 | TGGTGGAGCCAAGCCCTCCC | 83 | 622 |
| 561 | 580 | 502984 | GGGCACCCTCAGAGCCTGAA | 82 | 623 |
| 1197 | 1216 | 502369 | GCCTGGCAGCCCCTGTCCAG | 16 | 160 |
| 1198 | 1217 | 502370 | GGCCTGGCAGCCCCTGTCCA | 58 | 161 |
| 1199 | 1218 | 502371 | GGGCCTGGCAGCCCCTGTCC | 62 | 162 |
| 1242 | 1261 | 502372 | ATGGCCCCTCCCCGGGCCGG | 41 | 163 |
| 1243 | 1262 | 502373 | CATGGCCCCTCCCCGGGCCG | 29 | 164 |
| 1244 | 1263 | 502374 | CCATGGCCCCTCCCCGGGCC | 34 | 165 |
| 1245 | 1264 | 502375 | ACCATGGCCCCTCCCCGGGC | 60 | 166 |
| 1246 | 1265 | 502376 | CACCATGGCCCCTCCCCGGG | 68 | 167 |
| 1247 | 1266 | 502377 | GCACCATGGCCCCTCCCCGG | 75 | 168 |
| 1248 | 1267 | 502378 | AGCACCATGGCCCCTCCCCG | 65 | 169 |
| 1249 | 1268 | 502379 | CAGCACCATGGCCCCTCCCC | 63 | 170 |
| 1250 | 1269 | 502380 | GCAGCACCATGGCCCCTCCC | 73 | 171 |
| 1251 | 1270 | 502381 | GGCAGCACCATGGCCCCTCC | 80 | 172 |
| 1253 | 1272 | 502382 | CAGGCAGCACCATGGCCCCT | 82 | 173 |
| 1254 | 1273 | 502383 | ACAGGCAGCACCATGGCCCC | 72 | 174 |
| 1256 | 1275 | 502384 | GGACAGGCAGCACCATGGCC | 70 | 175 |
| 1257 | 1276 | 502385 | TGGACAGGCAGCACCATGGC | 71 | 176 |
| 1258 | 1277 | 502386 | TTGGACAGGCAGCACCATGG | 73 | 177 |
| 1259 | 1278 | 502387 | GTTGGACAGGCAGCACCATG | 73 | 178 |
| 1260 | 1279 | 502388 | TGTTGGACAGGCAGCACCAT | 60 | 179 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 1261 | 1280 | 502389 | ATGTTGGACAGGCAGCACCA | 75 | 180 |
| 1262 | 1281 | 502390 | CATGTTGGACAGGCAGCACC | 81 | 181 |
| 1263 | 1282 | 502391 | ACATGTTGGACAGGCAGCAC | 67 | 182 |
| 1264 | 1283 | 502392 | GACATGTTGGACAGGCAGCA | 71 | 183 |
| 1265 | 1284 | 502393 | TGACATGTTGGACAGGCAGC | 81 | 184 |
| 1266 | 1285 | 502394 | CTGACATGTTGGACAGGCAG | 76 | 185 |
| 1267 | 1286 | 502395 | GCTGACATGTTGGACAGGCA | 70 | 186 |
| 1268 | 1287 | 502396 | GGCTGACATGTTGGACAGGC | 77 | 187 |
| 1269 | 1288 | 502397 | CGGCTGACATGTTGGACAGG | 74 | 188 |
| 1270 | 1289 | 502398 | TCGGCTGACATGTTGGACAG | 63 | 189 |
| 1271 | 1290 | 502399 | CTCGGCTGACATGTTGGACA | 80 | 190 |
| 1272 | 1291 | 502400 | CCTCGGCTGACATGTTGGAC | 71 | 191 |
| 1273 | 1292 | 502401 | ACCTCGGCTGACATGTTGGA | 64 | 192 |
| 1274 | 1293 | 502402 | CACCTCGGCTGACATGTTGG | 71 | 193 |
| 1275 | 1294 | 502403 | GCACCTCGGCTGACATGTTG | 77 | 194 |
| 1276 | 1295 | 502404 | CGCACCTCGGCTGACATGTT | 80 | 195 |
| 1277 | 1296 | 502405 | CCGCACCTCGGCTGACATGT | 80 | 196 |
| 1278 | 1297 | 502406 | GCCGCACCTCGGCTGACATG | 79 | 197 |
| 1279 | 1298 | 502407 | AGCCGCACCTCGGCTGACAT | 74 | 198 |
| 1280 | 1299 | 502408 | CAGCCGCACCTCGGCTGACA | 66 | 199 |
| 1281 | 1300 | 502409 | TCAGCCGCACCTCGGCTGAC | 15 | 200 |
| 1282 | 1301 | 502410 | CTCAGCCGCACCTCGGCTGA | 32 | 201 |
| 1283 | 1302 | 502411 | CCTCAGCCGCACCTCGGCTG | 65 | 202 |
| 1284 | 1303 | 502412 | GCCTCAGCCGCACCTCGGCT | 81 | 203 |
| 1305 | 1324 | 502413 | CCAACACCAGCTGCTGGAGC | 90 | 204 |
| 1306 | 1325 | 502414 | TCCAACACCAGCTGCTGGAG | 78 | 205 |
| 1307 | 1326 | 502415 | GTCCAACACCAGCTGCTGGA | 84 | 206 |
| 1309 | 1328 | 502416 | GGGTCCAACACCAGCTGCTG | 69 | 207 |
| 1330 | 1349 | 502417 | GGCTCCAGCCCCAGGAAGCC | 46 | 208 |
| 1331 | 1350 | 502418 | GGGCTCCAGCCCCAGGAAGC | 28 | 209 |
| 1349 | 1368 | 502419 | CAGGAGAAGGTCGAGCAGGG | 41 | 210 |
| 1351 | 1370 | 502420 | CCCAGGAGAAGGTCGAGCAG | 71 | 211 |
| 1352 | 1371 | 502421 | GCCCAGGAGAAGGTCGAGCA | 85 | 212 |
| 1353 | 1372 | 451363 | CGCCCAGGAGAAGGTCGAGC | 84 | 213 |
| 1354 | 1373 | 502422 | ACGCCCAGGAGAAGGTCGAG | 67 | 214 |
| 1390 | 1409 | 502423 | TCCTGGGCCAGTTCGGAGGC | 58 | 215 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 1391 | 1410 | 502424 | GTCCTGGGCCAGTTCGGAGG | 71 | 216 |
| 1392 | 1411 | 502425 | TGTCCTGGGCCAGTTCGGAG | 69 | 217 |
| 1393 | 1412 | 502426 | TTGTCCTGGGCCAGTTCGGA | 71 | 218 |
| 1394 | 1413 | 502427 | CTTGTCCTGGGCCAGTTCGG | 66 | 219 |
| 1395 | 1414 | 502428 | ACTTGTCCTGGGCCAGTTCG | 59 | 220 |
| 1396 | 1415 | 502429 | TACTTGTCCTGGGCCAGTTC | 75 | 221 |
| 1397 | 1416 | 502430 | GTACTTGTCCTGGGCCAGTT | 78 | 222 |
| 1398 | 1417 | 502431 | CGTACTTGTCCTGGGCCAGT | 74 | 223 |
| 1416 | 1435 | 502432 | ACTGCAAGAAGTCGGCCACG | 73 | 224 |
| 1418 | 1437 | 502433 | CCACTGCAAGAAGTCGGCCA | 65 | 225 |
| 1419 | 1438 | 451364 | CCCACTGCAAGAAGTCGGCC | 32 | 226 |
| 1421 | 1440 | 502985 | ACCCCACTGCAAGAAGTCGG | 60 | 624 |
| 1551 | 1570 | 502986 | GCCCCAGGATGGGAGGATCT | 58 | 625 |
| 1597 | 1616 | 502987 | CATAGGACAGAGAAATGTTG | 70 | 626 |
| 1630 | 1649 | 502988 | TGCTGACCTTACTCTGCCCC | 86 | 627 |
| 1666 | 1685 | 502989 | TAAGCCATGGCTCTGAGTCA | 51 | 628 |
| 1712 | 1731 | 502990 | AGAGAGGCCATGGGAGGCTG | 42 | 629 |
| 1841 | 1860 | 502991 | CTGGCCCTCCTGGCTTGCCC | 72 | 630 |
| 1853 | 1872 | 502992 | AGCTGCCCCATGCTGGCCCT | 76 | 631 |
| 1862 | 1881 | 502993 | GCCCCTGGCAGCTGCCCCAT | 70 | 632 |
| 1873 | 1892 | 502994 | CTGTCGGCTGCGCCCCTGGC | 78 | 633 |
| 1887 | 1906 | 502995 | CGCCGAACACCTGCCTGTCG | 68 | 634 |
| 1931 | 1950 | 502996 | CCTCCCAGTGCCTGGGCACC | 52 | 635 |
| 1981 | 2000 | 502998 | GCGCCTGTCTGCAAAGCTGG | 84 | 636 |
| 2025 | 2044 | 502999 | CCCAAAGTTGTCCCTCCTGG | 83 | 637 |
| 2038 | 2057 | 503000 | ACACCCAGAAGAACCCAAAG | 75 | 638 |
| 2117 | 2136 | 503001 | CTGACCCACACGGCTCATAG | 65 | 639 |
| 2235 | 2254 | 503002 | TGGCCCCAGGCCCTGGAAAG | 67 | 640 |
| 2278 | 2297 | 503003 | GACAAGGCAGCTGGCAGAAG | 79 | 641 |
| 2331 | 2350 | 503004 | AAGAAACCAGTGACCAGTGA | 85 | 642 |
| 2523 | 2542 | 503005 | CTGTGAAATGGGAGGAGGAG | 0 | 643 |
| 2578 | 2597 | 503006 | GAAGGTTTTTCCAGAGGCTG | 88 | 644 |
| 2615 | 2634 | 503007 | GGCCAGGAGAGTCATTAGGG | 84 | 645 |
| 2710 | 2729 | 503008 | CCACAAAAGGAGTGCTCCTC | 79 | 646 |
| 2789 | 2808 | 503009 | CCTTTTAAGGCAGCAGGAAC | 78 | 647 |
| 3629 | 3648 | 503010 | CTAGGACTGTCTGCTTCCCA | 88 | 648 |
| 3761 | 3780 | 502452 | CTCACCACGATGGGCTCCGC | 66 | 245 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 3762 | 3781 | 502453 | CCTCACCACGATGGGCTCCG | 81 | 246 |
| 3763 | 3782 | 502454 | GCCTCACCACGATGGGCTCC | 77 | 247 |
| 3764 | 3783 | 502455 | AGCCTCACCACGATGGGCTC | 63 | 248 |
| 3765 | 3784 | 502456 | AAGCCTCACCACGATGGGCT | 70 | 249 |
| 3766 | 3785 | 502457 | TAAGCCTCACCACGATGGGC | 78 | 250 |
| 3767 | 3786 | 502458 | TTAAGCCTCACCACGATGGG | 76 | 251 |
| 3768 | 3787 | 502459 | CTTAAGCCTCACCACGATGG | 78 | 252 |
| 3769 | 3788 | 502460 | CCTTAAGCCTCACCACGATG | 68 | 253 |
| 3770 | 3789 | 502461 | TCCTTAAGCCTCACCACGAT | 67 | 254 |
| 3771 | 3790 | 502462 | CTCCTTAAGCCTCACCACGA | 84 | 255 |
| 3772 | 3791 | 502463 | CCTCCTTAAGCCTCACCACG | 76 | 256 |
| 3773 | 3792 | 502464 | ACCTCCTTAAGCCTCACCAC | 64 | 257 |
| 3774 | 3793 | 502465 | GACCTCCTTAAGCCTCACCA | 72 | 258 |
| 3775 | 3794 | 502466 | GGACCTCCTTAAGCCTCACC | 69 | 259 |
| 3776 | 3795 | 502467 | CGGACCTCCTTAAGCCTCAC | 81 | 260 |
| 3777 | 3796 | 502468 | TCGGACCTCCTTAAGCCTCA | 78 | 261 |
| 3778 | 3797 | 502469 | GTCGGACCTCCTTAAGCCTC | 57 | 262 |
| 3780 | 3799 | 502470 | CAGTCGGACCTCCTTAAGCC | 62 | 263 |
| 3781 | 3800 | 502471 | GCAGTCGGACCTCCTTAAGC | 45 | 264 |
| 3782 | 3801 | 502472 | TGCAGTCGGACCTCCTTAAG | 60 | 265 |
| 3808 | 3827 | 502473 | CCTTCAGAATCTCGAAGTCG | 67 | 266 |
| 3809 | 3828 | 502474 | ACCTTCAGAATCTCGAAGTC | 50 | 267 |
| 3811 | 3830 | 502475 | TCACCTTCAGAATCTCGAAG | 54 | 268 |
| 3812 | 3831 | 502476 | ATCACCTTCAGAATCTCGAA | 38 | 269 |
| 3813 | 3832 | 502477 | GATCACCTTCAGAATCTCGA | 35 | 270 |
| 3815 | 3834 | 502478 | CCGATCACCTTCAGAATCTC | 52 | 271 |
| 3816 | 3835 | 502479 | TCCGATCACCTTCAGAATCT | 50 | 272 |
| 3817 | 3836 | 502480 | GTCCGATCACCTTCAGAATC | 44 | 273 |
| 3818 | 3837 | 502481 | CGTCCGATCACCTTCAGAAT | 41 | 274 |
| 3921 | 3940 | 503011 | GTCATTCATCAATTTCTAAG | 44 | 649 |
| 4118 | 4137 | 502482 | CCCGTCTGCTTCATCTTCAC | 67 | 275 |
| 4119 | 4138 | 502483 | GCCCGTCTGCTTCATCTTCA | 76 | 276 |
| 4120 | 4139 | 502484 | GGCCCGTCTGCTTCATCTTC | 57 | 277 |
| 4121 | 4140 | 502485 | TGGCCCGTCTGCTTCATCTT | 64 | 278 |
| 4122 | 4141 | 502486 | CTGGCCCGTCTGCTTCATCT | 64 | 279 |
| 4123 | 4142 | 502487 | CCTGGCCCGTCTGCTTCATC | 73 | 280 |

TABLE 13-continued

Inhibition of human DMPK RNA transcript in hSKMc by
5-10-5 gapmers targeting SEQ ID NO: 2

| Target Start Site | Target Stop Site | ISIS No | Sequence | % inhibition | SEQ ID NO. |
|---|---|---|---|---|---|
| 4124 | 4143 | 502488 | ACCTGGCCCGTCTGCTTCAT | 64 | 281 |
| 4125 | 4144 | 502489 | CACCTGGCCCGTCTGCTTCA | 80 | 282 |
| 4126 | 4145 | 502490 | ACACCTGGCCCGTCTGCTTC | 71 | 283 |
| 4127 | 4146 | 502491 | TACACCTGGCCCGTCTGCTT | 74 | 284 |
| 4148 | 4167 | 502492 | TTGTTCATGATCTTCATGGC | 56 | 285 |
| 4150 | 4169 | 502493 | ACTTGTTCATGATCTTCATG | 23 | 286 |
| 4151 | 4170 | 502494 | CACTTGTTCATGATCTTCAT | 43 | 287 |
| 4152 | 4171 | 502495 | CCACTTGTTCATGATCTTCA | 43 | 288 |
| 4153 | 4172 | 502496 | CCCACTTGTTCATGATCTTC | 47 | 289 |
| 4154 | 4173 | 502497 | TCCCACTTGTTCATGATCTT | 34 | 290 |
| 4155 | 4174 | 502498 | GTCCCACTTGTTCATGATCT | 34 | 291 |
| 4156 | 4175 | 502499 | TGTCCCACTTGTTCATGATC | 27 | 292 |
| 4157 | 4176 | 502500 | ATGTCCCACTTGTTCATGAT | 23 | 293 |
| 4158 | 4177 | 502501 | CATGTCCCACTTGTTCATGA | 51 | 294 |
| 4159 | 4178 | 502502 | GCATGTCCCACTTGTTCATG | 20 | 295 |
| 4160 | 4179 | 502503 | AGCATGTCCCACTTGTTCAT | 52 | 296 |
| 4161 | 4180 | 502504 | CAGCATGTCCCACTTGTTCA | 72 | 297 |
| 4162 | 4181 | 502505 | TCAGCATGTCCCACTTGTTC | 70 | 298 |
| 4163 | 4182 | 502506 | TTCAGCATGTCCCACTTGTT | 53 | 299 |
| 4164 | 4183 | 502507 | CTTCAGCATGTCCCACTTGT | 52 | 300 |
| 4165 | 4184 | 502508 | TCTTCAGCATGTCCCACTTG | 45 | 301 |
| 4167 | 4186 | 502509 | CCTCTTCAGCATGTCCCACT | 68 | 302 |
| 4168 | 4187 | 502510 | CCCTCTTCAGCATGTCCCAC | 68 | 303 |
| 4169 | 4188 | 502511 | CCCCTCTTCAGCATGTCCCA | 79 | 304 |
| 4170 | 4189 | 502512 | GCCCCTCTTCAGCATGTCCC | 85 | 305 |
| 4171 | 4190 | 502513 | CGCCCCTCTTCAGCATGTCC | 84 | 306 |
| 4172 | 4191 | 502514 | TCGCCCCTCTTCAGCATGTC | 80 | 307 |
| 4173 | 4192 | 502515 | CTCGCCCCTCTTCAGCATGT | 82 | 308 |
| 4174 | 4193 | 502516 | CCTCGCCCCTCTTCAGCATG | 78 | 309 |
| 4175 | 4194 | 502517 | ACCTCGCCCCTCTTCAGCAT | 73 | 310 |
| 4176 | 4195 | 502518 | CACCTCGCCCCTCTTCAGCA | 76 | 311 |
| 4239 | 4258 | 503012 | GGAGGAGCTGCAGCCGGAGA | 7 | 650 |
| 4245 | 4264 | 503013 | GCACCCGGAGGAGCTGCAGC | 0 | 651 |
| 4261 | 4280 | 503014 | GCACGACACCTGCAGGGCAC | 23 | 652 |
| 4355 | 4374 | 503015 | AGCTCACCAGGTAGTTCTCA | 49 | 653 |
| 4427 | 4446 | 503016 | GCTTCCTCTCCCCACCTCCT | 65 | 654 |
| 4447 | 4466 | 503017 | GCAGCACCCCCAATCCTAGA | 67 | 655 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 4508 | 4527 | 503018 | GCCCCTCATCCACCTGACAC | 62 | 656 |
| 4613 | 4632 | 503019 | TTCCAGGTAAGAGACCCCCC | 87 | 657 |
| 4679 | 4698 | 503020 | AGAATAGGTCCCAGACACTC | 81 | 658 |
| 4731 | 4750 | 503021 | CTCCCCCTGAGATGTTCTGG | 53 | 659 |
| 4858 | 4877 | 503022 | CCCCAGCCCAGAGATAACCA | 74 | 660 |
| 4927 | 4946 | 503023 | CCTGATCCATCACGGATGGC | 69 | 661 |
| 4987 | 5006 | 503024 | TACTCCATGACCAGGTACTG | 81 | 662 |
| 5185 | 5204 | 503025 | GCTCTGACCTTCCAAGAACC | 56 | 663 |
| 5354 | 5373 | 503026 | CTCCCTTCTGTGGTCCCACC | 0 | 664 |
| 5407 | 5426 | 503027 | GTCGGGTTTGATGTCCCTGC | 75 | 665 |
| 5445 | 5464 | 502521 | GCCAGGCGGATGTGGCCACA | 57 | 314 |
| 5500 | 5519 | 503028 | AGGGCACTGGCTCACCGTTC | 45 | 666 |
| 5681 | 5700 | 503029 | GGGCCCTCCTTCCAACCACT | 28 | 667 |
| 5708 | 5727 | 503030 | GCCCACCCCTCTGGGCCCAC | 45 | 668 |
| 5728 | 5747 | 503031 | AGGAGCAGAGCGAGGCTTGG | 38 | 669 |
| 5800 | 5819 | 502524 | ACAGCCTGCAGGATCTCGGG | 86 | 317 |
| 5801 | 5820 | 502525 | CACAGCCTGCAGGATCTCGG | 81 | 318 |
| 5802 | 5821 | 502526 | CCACAGCCTGCAGGATCTCG | 83 | 319 |
| 5803 | 5822 | 502527 | CCCACAGCCTGCAGGATCTC | 84 | 320 |
| 5804 | 5823 | 502528 | GCCCACAGCCTGCAGGATCT | 91 | 321 |
| 5805 | 5824 | 502529 | CGCCCACAGCCTGCAGGATC | 90 | 322 |
| 5806 | 5825 | 502530 | CCGCCCACAGCCTGCAGGAT | 82 | 323 |
| 5807 | 5826 | 502531 | ACCGCCCACAGCCTGCAGGA | 83 | 324 |
| 5808 | 5827 | 502532 | CACCGCCCACAGCCTGCAGG | 85 | 325 |
| 5809 | 5828 | 502533 | CCACCGCCCACAGCCTGCAG | 84 | 326 |
| 5810 | 5829 | 502534 | CCCACCGCCCACAGCCTGCA | 80 | 327 |
| 5811 | 5830 | 502535 | GCCCACCGCCCACAGCCTGC | 90 | 328 |
| 5812 | 5831 | 502536 | GGCCCACCGCCCACAGCCTG | 94 | 329 |
| 5813 | 5832 | 502537 | AGGCCCACCGCCCACAGCCT | 88 | 330 |
| 5814 | 5833 | 502538 | CAGGCCCACCGCCCACAGCC | 91 | 331 |
| 5815 | 5834 | 502539 | CCAGGCCCACCGCCCACAGC | 73 | 332 |
| 5816 | 5835 | 502540 | CCCAGGCCCACCGCCCACAG | 86 | 333 |
| 5817 | 5836 | 502541 | TCCCAGGCCCACCGCCCACA | 88 | 334 |
| 5818 | 5837 | 502542 | GTCCCAGGCCCACCGCCCAC | 84 | 335 |
| 5819 | 5838 | 502543 | TGTCCCAGGCCCACCGCCCA | 85 | 336 |
| 5820 | 5839 | 502544 | CTGTCCCAGGCCCACCGCCC | 65 | 337 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 5821 | 5840 | 502545 | CCTGTCCCAGGCCCACCGCC | 81 | 338 |
| 5822 | 5841 | 502546 | GCCTGTCCCAGGCCCACCGC | 90 | 339 |
| 5823 | 5842 | 502547 | TGCCTGTCCCAGGCCCACCG | 85 | 340 |
| 5824 | 5843 | 502548 | CTGCCTGTCCCAGGCCCACC | 89 | 341 |
| 5825 | 5844 | 502549 | GCTGCCTGTCCCAGGCCCAC | 91 | 342 |
| 5826 | 5845 | 502550 | AGCTGCCTGTCCCAGGCCCA | 94 | 343 |
| 5827 | 5846 | 502551 | TAGCTGCCTGTCCCAGGCCC | 92 | 344 |
| 5828 | 5847 | 502552 | GTAGCTGCCTGTCCCAGGCC | 88 | 345 |
| 5829 | 5848 | 502553 | CGTAGCTGCCTGTCCCAGGC | 85 | 346 |
| 5830 | 5849 | 502554 | CCGTAGCTGCCTGTCCCAGG | 83 | 347 |
| 5831 | 5850 | 502555 | CCCGTAGCTGCCTGTCCCAG | 64 | 348 |
| 5832 | 5851 | 502556 | GCCCGTAGCTGCCTGTCCCA | 83 | 349 |
| 5833 | 5852 | 502557 | GGCCCGTAGCTGCCTGTCCC | 89 | 350 |
| 5881 | 5900 | 502558 | TAGAACATTTCATAGGCGAA | 68 | 351 |
| 5919 | 5938 | 502559 | TCTCCGCCGTGGAATCCGCG | 75 | 352 |
| 5920 | 5939 | 502560 | GTCTCCGCCGTGGAATCCGC | 79 | 353 |
| 5921 | 5940 | 502561 | GGTCTCCGCCGTGGAATCCG | 66 | 354 |
| 5922 | 5941 | 502562 | AGGTCTCCGCCGTGGAATCC | 50 | 355 |
| 5923 | 5942 | 502563 | TAGGTCTCCGCCGTGGAATC | 71 | 356 |
| 5944 | 5963 | 502564 | TTGTAGTGGACGATCTTGCC | 68 | 357 |
| 5945 | 5964 | 502565 | CTTGTAGTGGACGATCTTGC | 70 | 358 |
| 5946 | 5965 | 502566 | CCTTGTAGTGGACGATCTTG | 61 | 359 |
| 5948 | 5967 | 503032 | CACCTTGTAGTGGACGATCT | 62 | 670 |
| 6039 | 6058 | 502582 | CGGCAGAGAGAGGTGCTCCT | 80 | 375 |
| 6040 | 6059 | 502583 | GCGGCAGAGAGAGGTGCTCC | 62 | 376 |
| 6041 | 6060 | 502584 | AGCGGCAGAGAGAGGTGCTC | 44 | 377 |
| 6042 | 6061 | 502585 | CAGCGGCAGAGAGAGGTGCT | 78 | 378 |
| 6043 | 6062 | 502586 | CCAGCGGCAGAGAGAGGTGC | 71 | 379 |
| 6118 | 6137 | 502587 | GGCCCAGCCGTGTCTCCGGG | 77 | 380 |
| 6119 | 6138 | 502588 | CGGCCCAGCCGTGTCTCCGG | 69 | 381 |
| 6120 | 6139 | 502589 | CCGGCCCAGCCGTGTCTCCG | 70 | 382 |
| 6121 | 6140 | 502590 | CCCGGCCCAGCCGTGTCTCC | 75 | 383 |
| 6122 | 6141 | 502591 | CCCCGGCCCAGCCGTGTCTC | 77 | 384 |
| 6123 | 6142 | 502592 | ACCCCGGCCCAGCCGTGTCT | 73 | 385 |
| 6124 | 6143 | 502593 | CACCCCGGCCCAGCCGTGTC | 84 | 386 |
| 6125 | 6144 | 502594 | CCACCCCGGCCCAGCCGTGT | 78 | 387 |
| 6126 | 6145 | 502595 | TCCACCCCGGCCCAGCCGTG | 71 | 388 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 6127 | 6146 | 502596 | CTCCACCCCGGCCCAGCCGT | 81 | 389 |
| 6128 | 6147 | 502597 | GCTCCACCCCGGCCCAGCCG | 86 | 390 |
| 6129 | 6148 | 502598 | TGCTCCACCCCGGCCCAGCC | 83 | 391 |
| 6130 | 6149 | 502599 | CTGCTCCACCCCGGCCCAGC | 88 | 392 |
| 6152 | 6171 | 502600 | AAGGGATGTGTCCGGAAGTC | 60 | 393 |
| 6153 | 6172 | 502601 | GAAGGGATGTGTCCGGAAGT | 58 | 394 |
| 6154 | 6173 | 502602 | AGAAGGGATGTGTCCGGAAG | 63 | 395 |
| 6155 | 6174 | 502603 | AAGAAGGGATGTGTCCGGAA | 62 | 396 |
| 6156 | 6175 | 502604 | GAAGAAGGGATGTGTCCGGA | 61 | 397 |
| 6157 | 6176 | 502605 | AGAAGAAGGGATGTGTCCGG | 62 | 398 |
| 6158 | 6177 | 502606 | AAGAAGAAGGGATGTGTCCG | 56 | 399 |
| 6159 | 6178 | 502607 | AAAGAAGAAGGGATGTGTCC | 58 | 400 |
| 6160 | 6179 | 502608 | CAAAGAAGAAGGGATGTGTC | 50 | 401 |
| 6161 | 6180 | 502609 | CCAAAGAAGAAGGGATGTGT | 61 | 402 |
| 6163 | 6182 | 502610 | GGCCAAAGAAGAAGGGATGT | 73 | 403 |
| 6164 | 6183 | 502611 | AGGCCAAAGAAGAAGGGATG | 56 | 404 |
| 6165 | 6184 | 502612 | GAGGCCAAAGAAGAAGGGAT | 73 | 405 |
| 6166 | 6185 | 502613 | CGAGGCCAAAGAAGAAGGGA | 75 | 406 |
| 6167 | 6186 | 502614 | TCGAGGCCAAAGAAGAAGGG | 75 | 407 |
| 6168 | 6187 | 502615 | GTCGAGGCCAAAGAAGAAGG | 83 | 408 |
| 6169 | 6188 | 502616 | AGTCGAGGCCAAAGAAGAAG | 58 | 409 |
| 6170 | 6189 | 502617 | CAGTCGAGGCCAAAGAAGAA | 52 | 410 |
| 6171 | 6190 | 502618 | CCAGTCGAGGCCAAAGAAGA | 68 | 411 |
| 6172 | 6191 | 502619 | CCCAGTCGAGGCCAAAGAAG | 78 | 412 |
| 6173 | 6192 | 502620 | TCCCAGTCGAGGCCAAAGAA | 66 | 413 |
| 6174 | 6193 | 502621 | ATCCCAGTCGAGGCCAAAGA | 75 | 414 |
| 6175 | 6194 | 502622 | CATCCCAGTCGAGGCCAAAG | 70 | 415 |
| 6176 | 6195 | 502623 | CCATCCCAGTCGAGGCCAAA | 81 | 416 |
| 6177 | 6196 | 502624 | ACCATCCCAGTCGAGGCCAA | 82 | 417 |
| 6178 | 6197 | 502625 | GACCATCCCAGTCGAGGCCA | 88 | 418 |
| 6179 | 6198 | 502626 | AGACCATCCCAGTCGAGGCC | 79 | 419 |
| 6180 | 6199 | 502627 | GAGACCATCCCAGTCGAGGC | 82 | 420 |
| 6181 | 6200 | 502628 | GGAGACCATCCCAGTCGAGG | 60 | 421 |
| 6216 | 6235 | 502629 | TTCGAAATCCGGTGTAAAGG | 84 | 422 |
| 6217 | 6236 | 502630 | CTTCGAAATCCGGTGTAAAG | 57 | 423 |
| 6218 | 6237 | 502631 | CCTTCGAAATCCGGTGTAAA | 64 | 424 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 6219 | 6238 | 502632 | ACCTTCGAAATCCGGTGTAA | 73 | 425 |
| 6220 | 6239 | 502633 | CACCTTCGAAATCCGGTGTA | 77 | 426 |
| 6221 | 6240 | 502634 | GCACCTTCGAAATCCGGTGT | 59 | 427 |
| 6222 | 6241 | 502635 | GGCACCTTCGAAATCCGGTG | 85 | 428 |
| 6223 | 6242 | 502636 | TGGCACCTTCGAAATCCGGT | 86 | 429 |
| 6224 | 6243 | 502637 | GTGGCACCTTCGAAATCCGG | 74 | 430 |
| 6225 | 6244 | 502638 | GGTGGCACCTTCGAAATCCG | 79 | 431 |
| 6226 | 6245 | 502639 | CGGTGGCACCTTCGAAATCC | 85 | 432 |
| 6227 | 6246 | 502640 | TCGGTGGCACCTTCGAAATC | 71 | 433 |
| 6228 | 6247 | 502641 | GTCGGTGGCACCTTCGAAAT | 88 | 434 |
| 6229 | 6248 | 502642 | TGTCGGTGGCACCTTCGAAA | 89 | 435 |
| 6230 | 6249 | 502643 | GTGTCGGTGGCACCTTCGAA | 88 | 436 |
| 6231 | 6250 | 502644 | TGTGTCGGTGGCACCTTCGA | 87 | 437 |
| 6232 | 6251 | 502645 | ATGTGTCGGTGGCACCTTCG | 88 | 438 |
| 6233 | 6252 | 502646 | CATGTGTCGGTGGCACCTTC | 88 | 439 |
| 6234 | 6253 | 502647 | GCATGTGTCGGTGGCACCTT | 91 | 440 |
| 6235 | 6254 | 502648 | TGCATGTGTCGGTGGCACCT | 87 | 441 |
| 6236 | 6255 | 502649 | TTGCATGTGTCGGTGGCACC | 86 | 442 |
| 6237 | 6256 | 502650 | GTTGCATGTGTCGGTGGCAC | 83 | 443 |
| 6238 | 6257 | 502651 | AGTTGCATGTGTCGGTGGCA | 81 | 444 |
| 6239 | 6258 | 502652 | AAGTTGCATGTGTCGGTGGC | 79 | 445 |
| 6240 | 6259 | 502653 | GAAGTTGCATGTGTCGGTGG | 58 | 446 |
| 6241 | 6260 | 502654 | CGAAGTTGCATGTGTCGGTG | 85 | 447 |
| 6243 | 6262 | 502655 | GTCGAAGTTGCATGTGTCGG | 77 | 448 |
| 6244 | 6263 | 502656 | AGTCGAAGTTGCATGTGTCG | 79 | 449 |
| 6245 | 6264 | 502657 | AAGTCGAAGTTGCATGTGTC | 74 | 450 |
| 6246 | 6265 | 502658 | CAAGTCGAAGTTGCATGTGT | 82 | 451 |
| 6247 | 6266 | 502659 | CCAAGTCGAAGTTGCATGTG | 82 | 452 |
| 6248 | 6267 | 502660 | ACCAAGTCGAAGTTGCATGT | 70 | 453 |
| 6249 | 6268 | 502661 | CACCAAGTCGAAGTTGCATG | 76 | 454 |
| 6250 | 6269 | 502662 | CCACCAAGTCGAAGTTGCAT | 79 | 455 |
| 6251 | 6270 | 502663 | TCCACCAAGTCGAAGTTGCA | 68 | 456 |
| 6252 | 6271 | 502664 | CTCCACCAAGTCGAAGTTGC | 71 | 457 |
| 6253 | 6272 | 502665 | CCTCCACCAAGTCGAAGTTG | 67 | 458 |
| 6254 | 6273 | 502666 | TCCTCCACCAAGTCGAAGTT | 70 | 459 |
| 6255 | 6274 | 502667 | GTCCTCCACCAAGTCGAAGT | 80 | 460 |
| 6256 | 6275 | 502668 | CGTCCTCCACCAAGTCGAAG | 76 | 461 |

TABLE 13-continued

Inhibition of human DMPK RNA transcript in hSKMc by
5-10-5 gapmers targeting SEQ ID NO: 2

| Target Start Site | Target Stop Site | ISIS No | Sequence | % inhibition | SEQ ID NO. |
|---|---|---|---|---|---|
| 6257 | 6276 | 502669 | CCGTCCTCCACCAAGTCGAA | 78 | 462 |
| 6258 | 6277 | 502670 | CCCGTCCTCCACCAAGTCGA | 83 | 463 |
| 6259 | 6278 | 502671 | GCCCGTCCTCCACCAAGTCG | 76 | 464 |
| 6260 | 6279 | 502672 | AGCCCGTCCTCCACCAAGTC | 72 | 465 |
| 6261 | 6280 | 502673 | GAGCCCGTCCTCCACCAAGT | 71 | 466 |
| 6262 | 6281 | 502674 | TGAGCCCGTCCTCCACCAAG | 60 | 467 |
| 6289 | 6308 | 503033 | CTACCCCGCCCCCGCTCACC | 60 | 671 |
| 6445 | 6464 | 503034 | CTAGGTCACTGCTGGGTCCT | 86 | 672 |
| 6596 | 6615 | 503035 | CTCAGATAGCTCCCCACTCC | 55 | 673 |
| 6794 | 6813 | 503036 | AATTCTCTAATTCTCTAGAC | 19 | 674 |
| 8666 | 8685 | 503037 | TACCTGAGGGCCATGCAGGA | 51 | 675 |
| 8765 | 8784 | 503038 | GTTCCAAGACTGATCCTGCA | 69 | 676 |
| 11975 | 11994 | 502675 | GGTTCCGAGCCTCTGCCTCG | 44 | 468 |
| 11976 | 11995 | 502676 | CGGTTCCGAGCCTCTGCCTC | 74 | 469 |
| 11977 | 11996 | 502677 | CCGGTTCCGAGCCTCTGCCT | 72 | 470 |
| 11978 | 11997 | 502678 | CCCGGTTCCGAGCCTCTGCC | 73 | 471 |
| 11979 | 11998 | 502679 | TCCCGGTTCCGAGCCTCTGC | 84 | 472 |
| 11980 | 11999 | 502680 | GTCCCGGTTCCGAGCCTCTG | 66 | 473 |
| 11982 | 12001 | 502681 | AGGTCCCGGTTCCGAGCCTC | 82 | 474 |
| 11983 | 12002 | 502682 | TAGGTCCCGGTTCCGAGCCT | 83 | 475 |
| 11984 | 12003 | 502683 | CTAGGTCCCGGTTCCGAGCC | 81 | 476 |
| 11985 | 12004 | 502684 | TCTAGGTCCCGGTTCCGAGC | 74 | 477 |
| 11986 | 12005 | 502685 | CTCTAGGTCCCGGTTCCGAG | 78 | 478 |
| 11987 | 12006 | 502686 | CCTCTAGGTCCCGGTTCCGA | 75 | 479 |
| 11988 | 12007 | 502687 | GCCTCTAGGTCCCGGTTCCG | 80 | 480 |
| 12016 | 12035 | 502688 | CATCCGCTCCTGCAACTGCC | 89 | 481 |
| 12017 | 12036 | 502689 | CCATCCGCTCCTGCAACTGC | 81 | 482 |
| 12018 | 12037 | 502690 | TCCATCCGCTCCTGCAACTG | 71 | 483 |
| 12019 | 12038 | 502691 | CTCCATCCGCTCCTGCAACT | 75 | 484 |
| 12020 | 12039 | 502692 | ACTCCATCCGCTCCTGCAAC | 64 | 485 |
| 12021 | 12040 | 502693 | AACTCCATCCGCTCCTGCAA | 52 | 486 |
| 12022 | 12041 | 502694 | CAACTCCATCCGCTCCTGCA | 45 | 487 |
| 12024 | 12043 | 502695 | AGCAACTCCATCCGCTCCTG | 78 | 488 |
| 12025 | 12044 | 502696 | CAGCAACTCCATCCGCTCCT | 64 | 489 |
| 12026 | 12045 | 502697 | GCAGCAACTCCATCCGCTCC | 56 | 490 |
| 12173 | 12192 | 503039 | AGGAGGGCGGTGGCGCGGCG | 0 | 677 |

TABLE 13-continued

Inhibition of human DMPK RNA transcript in hSKMc by
5-10-5 gapmers targeting SEQ ID NO: 2

| Target Start Site | Target Stop Site | ISIS No | Sequence | % inhibition | SEQ ID NO. |
|---|---|---|---|---|---|
| 12221 | 12240 | 503040 | TGACAGCTGGAAGGAGAAGA | 41 | 678 |
| 12258 | 12277 | 502712 | GAAGGTGGATCCGTGGCCCG | 73 | 505 |
| 12259 | 12278 | 502713 | GGAAGGTGGATCCGTGGCCC | 70 | 506 |
| 12260 | 12279 | 502714 | GGGAAGGTGGATCCGTGGCC | 72 | 507 |
| 12261 | 12280 | 502715 | TGGGAAGGTGGATCCGTGGC | 50 | 508 |
| 12262 | 12281 | 502716 | ATGGGAAGGTGGATCCGTGG | 62 | 509 |
| 12263 | 12282 | 451417 | CATGGGAAGGTGGATCCGTG | 77 | 679 |
| 12463 | 12482 | 503041 | GGAGGTTATCTAGGGAGATC | 42 | 680 |
| 12542 | 12561 | 503042 | GAAGGGACAGGTGACCCGAT | 69 | 681 |
| 12596 | 12615 | 502724 | CACCAGCGGGCACTGGCCCA | 51 | 518 |
| 12597 | 12616 | 502725 | CCACCAGCGGGCACTGGCCC | 55 | 519 |
| 12598 | 12617 | 502726 | CCCACCAGCGGGCACTGGCC | 61 | 520 |
| 12599 | 12618 | 502727 | CCCCACCAGCGGGCACTGGC | 43 | 521 |
| 12601 | 12620 | 502728 | GGCCCCACCAGCGGGCACTG | 16 | 522 |
| 12602 | 12621 | 502729 | TGGCCCCACCAGCGGGCACT | 43 | 523 |
| 12603 | 12622 | 502730 | CTGGCCCCACCAGCGGGCAC | 43 | 524 |
| 12604 | 12623 | 502731 | CCTGGCCCCACCAGCGGGCA | 41 | 525 |
| 12605 | 12624 | 502732 | GCCTGGCCCCACCAGCGGGC | 30 | 526 |
| 12607 | 12626 | 502733 | GGGCCTGGCCCCACCAGCGG | 66 | 527 |
| 12625 | 12644 | 502734 | AGGTGGCGGCGGTGCATGGG | 31 | 528 |
| 12626 | 12645 | 502735 | CAGGTGGCGGCGGTGCATGG | 23 | 529 |
| 12627 | 12646 | 502736 | GCAGGTGGCGGCGGTGCATG | 57 | 530 |
| 12628 | 12647 | 502737 | AGCAGGTGGCGGCGGTGCAT | 54 | 531 |
| 12629 | 12648 | 502738 | CAGCAGGTGGCGGCGGTGCA | 61 | 532 |
| 12630 | 12649 | 502739 | GCAGCAGGTGGCGGCGGTGC | 57 | 533 |
| 12631 | 12650 | 502740 | AGCAGCAGGTGGCGGCGGTG | 36 | 534 |
| 12632 | 12651 | 502741 | GAGCAGCAGGTGGCGGCGGT | 53 | 535 |
| 12633 | 12652 | 502742 | GGAGCAGCAGGTGGCGGCGG | 39 | 536 |
| 12634 | 12653 | 502743 | GGGAGCAGCAGGTGGCGGCG | 36 | 537 |
| 12635 | 12654 | 502744 | AGGGAGCAGCAGGTGGCGGC | 62 | 538 |
| 12636 | 12655 | 502745 | CAGGGAGCAGCAGGTGGCGG | 56 | 539 |
| 12637 | 12656 | 502746 | GCAGGGAGCAGCAGGTGGCG | 58 | 540 |
| 12638 | 12657 | 502747 | GGCAGGGAGCAGCAGGTGGC | 65 | 541 |
| 12639 | 12658 | 502748 | TGGCAGGGAGCAGCAGGTGG | 47 | 542 |
| 12640 | 12659 | 502749 | CTGGCAGGGAGCAGCAGGTG | 41 | 543 |
| 12642 | 12661 | 451432 | CCCTGGCAGGGAGCAGCAGG | 53 | 544 |
| 12643 | 12662 | 502750 | ACCCTGGCAGGGAGCAGCAG | 52 | 545 |

TABLE 13-continued

Inhibition of human DMPK RNA transcript in hSKMc by
5-10-5 gapmers targeting SEQ ID NO: 2

| Target Start Site | Target Stop Site | ISIS No | Sequence | % inhibition | SEQ ID NO. |
|---|---|---|---|---|---|
| 12646 | 12665 | 503043 | CGTACCCTGGCAGGGAGCAG | 59 | 682 |
| 12918 | 12937 | 502977 | GGACTCGCCCCGCCTACGCC | 71 | 683 |
| 12924 | 12943 | 502978 | CTCCTGGGACTCGCCCCGCC | 67 | 684 |
| 12925 | 12944 | 503044 | GCTCCTGGGACTCGCCCCGC | 66 | 685 |
| 12929 | 12948 | 503045 | ATTGGCTCCTGGGACTCGCC | 77 | 686 |
| 12930 | 12949 | 502979 | GATTGGCTCCTGGGACTCGC | 70 | 687 |
| 12936 | 12955 | 502980 | GCCTCTGATTGGCTCCTGGG | 56 | 688 |
| 12942 | 12961 | 502981 | GCATGGGCCTCTGATTGGCT | 20 | 689 |
| 12948 | 12967 | 502982 | CACCCGGCATGGGCCTCTGA | 20 | 690 |
| 12986 | 13005 | 503046 | GCCAGGCCTAGGGACCTGCG | 58 | 691 |
| 12990 | 13009 | 502760 | ATAGGCCAGGCCTAGGGACC | 51 | 555 |
| 12991 | 13010 | 502761 | GATAGGCCAGGCCTAGGGAC | 41 | 556 |
| 12992 | 13011 | 502762 | CGATAGGCCAGGCCTAGGGA | 69 | 557 |
| 12993 | 13012 | 502763 | CCGATAGGCCAGGCCTAGGG | 80 | 558 |
| 12994 | 13013 | 502764 | TCCGATAGGCCAGGCCTAGG | 78 | 559 |
| 12995 | 13014 | 502765 | CTCCGATAGGCCAGGCCTAG | 89 | 560 |
| 12996 | 13015 | 502766 | CCTCCGATAGGCCAGGCCTA | 79 | 561 |
| 12997 | 13016 | 502767 | GCCTCCGATAGGCCAGGCCT | 73 | 562 |
| 12999 | 13018 | 502768 | GCGCCTCCGATAGGCCAGGC | 83 | 563 |
| 13015 | 13034 | 502769 | AACAGGAGCAGGGAAAGCGC | 83 | 564 |
| 13016 | 13035 | 502770 | GAACAGGAGCAGGGAAAGCG | 70 | 565 |
| 13017 | 13036 | 502771 | CGAACAGGAGCAGGGAAAGC | 43 | 566 |
| 13018 | 13037 | 502772 | GCGAACAGGAGCAGGGAAAG | 47 | 567 |
| 13019 | 13038 | 502773 | GGCGAACAGGAGCAGGGAAA | 61 | 568 |
| 13020 | 13039 | 502774 | CGGCGAACAGGAGCAGGGAA | 74 | 569 |
| 13021 | 13040 | 502775 | ACGGCGAACAGGAGCAGGGA | 60 | 570 |
| 13022 | 13041 | 502776 | AACGGCGAACAGGAGCAGGG | 86 | 571 |
| 13023 | 13042 | 502777 | CAACGGCGAACAGGAGCAGG | 84 | 572 |
| 13044 | 13063 | 502778 | GGGCGGCGGCACGAGACAGA | 80 | 573 |
| 13045 | 13064 | 502779 | AGGGCGGCGGCACGAGACAG | 76 | 574 |
| 13046 | 13065 | 502780 | CAGGGCGGCGGCACGAGACA | 58 | 575 |
| 13047 | 13066 | 502781 | CCAGGGCGGCGGCACGAGAC | 80 | 576 |
| 13048 | 13067 | 502782 | CCCAGGGCGGCGGCACGAGA | 59 | 577 |
| 13049 | 13068 | 502783 | GCCCAGGGCGGCGGCACGAG | 68 | 578 |
| 13050 | 13069 | 502784 | AGCCCAGGGCGGCGGCACGA | 75 | 579 |
| 13051 | 13070 | 502785 | CAGCCCAGGGCGGCGGCACG | 76 | 580 |

TABLE 13-continued

Inhibition of human DMPK RNA transcript in hSKMc by
5-10-5 gapmers targeting SEQ ID NO: 2

| Target Start Site | Target Stop Site | ISIS No | Sequence | % inhibition | SEQ ID NO. |
|---|---|---|---|---|---|
| 13052 | 13071 | 502786 | GCAGCCCAGGGCGGCGGCAC | 70 | 581 |
| 13089 | 13108 | 502787 | CTGCGGTGAGTTGGCCGGCG | 68 | 582 |
| 13090 | 13109 | 502788 | ACTGCGGTGAGTTGGCCGGC | 67 | 583 |
| 13091 | 13110 | 502789 | GACTGCGGTGAGTTGGCCGG | 58 | 584 |
| 13092 | 13111 | 502790 | AGACTGCGGTGAGTTGGCCG | 71 | 585 |
| 13093 | 13112 | 502791 | CAGACTGCGGTGAGTTGGCC | 70 | 586 |
| 13094 | 13113 | 502792 | CCAGACTGCGGTGAGTTGGC | 79 | 587 |
| 13095 | 13114 | 502793 | GCCAGACTGCGGTGAGTTGG | 76 | 588 |
| 13096 | 13115 | 502794 | CGCCAGACTGCGGTGAGTTG | 66 | 589 |
| 13140 | 13159 | 502795 | AAGACAGTTCTAGGGTTCAG | 87 | 590 |
| 13141 | 13160 | 502796 | GAAGACAGTTCTAGGGTTCA | 78 | 591 |
| 13142 | 13161 | 502797 | CGAAGACAGTTCTAGGGTTC | 85 | 592 |
| 13143 | 13162 | 502798 | TCGAAGACAGTTCTAGGGTT | 78 | 593 |
| 13144 | 13163 | 502799 | GTCGAAGACAGTTCTAGGGT | 92 | 594 |
| 13145 | 13164 | 502800 | AGTCGAAGACAGTTCTAGGG | 85 | 595 |
| 13146 | 13165 | 502801 | GAGTCGAAGACAGTTCTAGG | 83 | 596 |
| 13147 | 13166 | 502802 | GGAGTCGAAGACAGTTCTAG | 86 | 597 |
| 13148 | 13167 | 502803 | CGGAGTCGAAGACAGTTCTA | 91 | 598 |
| 13149 | 13168 | 502804 | CCGGAGTCGAAGACAGTTCT | 76 | 599 |
| 13150 | 13169 | 502805 | CCCGGAGTCGAAGACAGTTC | 90 | 600 |
| 13151 | 13170 | 502806 | CCCCGGAGTCGAAGACAGTT | 83 | 601 |
| 13152 | 13171 | 502807 | GCCCCGGAGTCGAAGACAGT | 82 | 602 |
| 13153 | 13172 | 502808 | GGCCCCGGAGTCGAAGACAG | 73 | 603 |
| 13154 | 13173 | 502809 | GGGCCCCGGAGTCGAAGACA | 67 | 604 |
| 13206 | 13225 | 502810 | AGGCGGTGGGCGCGGCTTCT | 73 | 605 |
| 13207 | 13226 | 502811 | CAGGCGGTGGGCGCGGCTTC | 57 | 606 |
| 13208 | 13227 | 502812 | GCAGGCGGTGGGCGCGGCTT | 69 | 607 |
| 13210 | 13229 | 502813 | TGGCAGGCGGTGGGCGCGGC | 73 | 608 |
| 13212 | 13231 | 502814 | ACTGGCAGGCGGTGGGCGCG | 56 | 609 |
| 13214 | 13233 | 502815 | GAACTGGCAGGCGGTGGGCG | 71 | 610 |
| 13215 | 13234 | 502816 | TGAACTGGCAGGCGGTGGGC | 80 | 611 |
| 13217 | 13236 | 502817 | TGTGAACTGGCAGGCGGTGG | 85 | 612 |
| 13250 | 13269 | 502818 | TGGAGCTGGGCGGAGACCCA | 55 | 613 |
| 13252 | 13271 | 502819 | ACTGGAGCTGGGCGGAGACC | 53 | 614 |
| 13253 | 13272 | 502820 | GACTGGAGCTGGGCGGAGAC | 55 | 615 |
| 13255 | 13274 | 502821 | AGGACTGGAGCTGGGCGGAG | 76 | 616 |
| 13257 | 13276 | 502822 | ACAGGACTGGAGCTGGGCGG | 77 | 617 |

TABLE 13-continued

Inhibition of human DMPK RNA transcript in hSKMc by 5-10-5 gapmers targeting SEQ ID NO: 2

| Target Start Site | Target Stop Site | ISIS No | Sequence | % inhibition | SEQ ID NO. |
|---|---|---|---|---|---|
| 13258 | 13277 | 502823 | CACAGGACTGGAGCTGGGCG | 74 | 618 |
| 13259 | 13278 | 502824 | TCACAGGACTGGAGCTGGGC | 90 | 619 |
| 13449 | 13468 | 502825 | GCCTCAGCCTGGCCGAAAGA | 80 | 620 |
| 13450 | 13469 | 502826 | GGCCTCAGCCTGGCCGAAAG | 72 | 621 |
| 13553 | 13572 | 444401 | TTGCACTTTGCGAACCAACG | 97 | 41 |
| 14037 | 14056 | 503047 | TTCCTCCCCCAACCCTGATT | 34 | 692 |
| 14255 | 14274 | 503048 | AAGTTTGCAGCAACTTTTCT | 0 | 693 |
| 14325 | 14344 | 503049 | GCCCCTCGGAATTCCCGGCT | 0 | 694 |
| 14343 | 14362 | 503050 | CATCTCGGCCTGCGCTCCGC | 39 | 695 |
| 14361 | 14380 | 503051 | GCAGGCCCCCACATTCCCCA | 0 | 696 |
| 14392 | 14411 | 503052 | CTTCTGCACGCCTCCGTCTC | 30 | 697 |

Example 8

Antisense Inhibition of Murine DMPK in Mouse Primary Hepatocytes

Antisense oligonucleotides targeted to a murine DMPK nucleic acid were tested for their effect on DMPK RNA transcript in vitro. Cultured mouse primary hepatocytes at a density of 35,000 cells per well were transfected using electroporation with 8,000 nM antisense oligonucleotide. After approximately 24 hours, RNA was isolated from the cells and DMPK transcript levels were measured by quantitative real-time PCR. DMPK RNA transcript levels were adjusted according to total RNA content, as measured by RIBOGREEN®. Results are presented as percent inhibition of DMPK, relative to untreated control cells.

The antisense oligonucleotides in Tables 14, 15, and 16 are 5-10-5 gapmers, where the gap segment comprises ten 2'-deoxynucleosides and each wing segment comprises five 2'-MOE nucleosides. The internucleoside linkages throughout each gapmer are phosphorothioate (P=S) linkages. All cytosine residues throughout each gapmer are 5-methylcytosines. 'Murine Target start site' indicates the 5'-most nucleoside to which the antisense oligonucleotide is targeted in the murine gene sequence. 'Murine Target stop site' indicates the 3'-most nucleoside to which the antisense oligonucleotide is targeted in the murine gene sequence. All the antisense oligonucleotides listed in Table 12 target SEQ ID NO: 3 (GENBANK Accession No. NT_039413.7 truncated from nucleotides 16666001 to Ser. No. 16/681,000). All the antisense oligonucleotides listed in Table 13 target SEQ ID NO: 4 (GENBANK Accession No. NM_032418.1). The antisense oligonucleotides of Table 14 target SEQ ID NO: 5 (GENBANK Accession No. AI007148.1), SEQ ID NO: 6 (GENBANK Accession No. AI304033.1), SEQ ID NO: 7 (GENBANK Accession No. BC024150.1), SEQ ID NO: 8 (GENBANK Accession No. BC056615.1), SEQ ID NO: 793 (GENBANK Accession No. BC075715.1), SEQ ID NO: 794 (GENBANK Accession No. BU519245.1), SEQ ID NO: 795 (GENBANK Accession No. CB247909.1), SEQ ID NO: 796 (GENBANK Accession No. CX208906.1), SEQ ID NO: 797 (GENBANK Accession No. CX732022.1), SEQ ID NO: 798 (GENBANK Accession No. S60315.1), or SEQ ID NO: 799 (GENBANK Accession No. S60316.1). In addition, the human antisense oligonucleotide ISIS 451421 targeting SEQ ID NO: 800(GENBANK Accession No. NM_001081562.1) was also included in this assay and is listed in Table 14.

The murine oligonucleotides of Tables 14, 15, and 16 may also be cross-reactive with human gene sequences. 'Mismatches' indicate the number of nucleobases by which the murine oligonucleotide is mismatched with a human gene sequence. The greater the complementarity between the murine oligonucleotide and the human sequence, the more likely the murine oligonucleotide can cross-react with the human sequence. The murine oligonucleotides in Tables 14, 15, and 16 were compared to SEQ ID NO: 800 (GENBANK Accession No. NM_001081562.1). "Human Target start site" indicates the 5'-most nucleoside to which the gapmer is targeted in the human gene sequence. "Human Target stop site" indicates the 3'-most nucleoside to which the gapmer is targeted human gene sequence.

Several of the tested antisense oligonucleotides demonstrated significant inhibition of DMPK mRNA levels under the conditions specified above. Certain of the tested antisense oligonucleotides are cross-reactive with human gene sequences.

TABLE 14

Inhibition of murine DMPK RNA transcript in mouse primary hepatocytes by 5-10-5 gapmers targeting SEQ ID NO: 800

| Murine Target Start Site | Murine Target Stop Site | ISIS No | Sequence | % inhibition | SEQ ID NO. | Human Target Start Site | Human Target Stop Site | Mismatches |
|---|---|---|---|---|---|---|---|---|
| 11904 | 11923 | 299516 | TGGCCCACAGCCACGGCCGG | 47 | 698 | 1850 | 1869 | 0 |
| 11927 | 11946 | 299520 | GGCCTGGCCCCACCAGCGGG | 58 | 699 | 1873 | 1892 | 0 |
| 11962 | 11981 | 299521 | CCTGGCAGGGAGCAGCAGGT | 44 | 700 | 1908 | 1927 | 0 |
| 3345 | 3364 | 451360 | CAGCCGCACTTCGGCTGACA | 29 | 701 | 207 | 226 | 1 |
| 3378 | 3397 | 451361 | GCCTGGGTCCAGCACCAGCT | 67 | 702 | 240 | 259 | 2 |
| 3388 | 3407 | 451362 | GTCCCAGGAAGCCTGGGTCC | 62 | 703 | 250 | 269 | 2 |
| 3418 | 3437 | 451363 | CGCCCAGGAGAAGGTCGAGC | 69 | 213 | 280 | 299 | 0 |
| 3484 | 3503 | 451364 | CCCACTGCAAGAAGTCGGCC | 69 | 226 | 346 | 365 | 0 |
| 6264 | 6283 | 451366 | CGTTAGCAGGTCCCCGCCCA | 73 | 704 | 660 | 679 | 2 |
| 6342 | 6361 | 451367 | GTCTATGGCCATGACAATCT | 61 | 705 | 738 | 757 | 0 |
| 6363 | 6382 | 451368 | GTAGCCCAGCCGGTGCACGG | 54 | 706 | 759 | 778 | 2 |
| 6851 | 6870 | 451370 | GGGTGCCCACAGCCACCAGC | 72 | 707 | 889 | 908 | 0 |
| 6919 | 6938 | 451371 | TGGCCCGTAGCTGCCTGCCC | 80 | 708 | 957 | 976 | 2 |
| 7448 | 7467 | 451373 | GGAAATCACCTGCCCCACCT | 80 | 709 | n/a | n/a | n/a |
| 7458 | 7477 | 451374 | GGATGTTTCTGGAAATCACC | 84 | 710 | n/a | n/a | n/a |
| 7533 | 7552 | 451375 | GTGGCACCCTCGAAGTCTGG | 77 | 711 | 1271 | 1290 | 3 |
| 7589 | 7608 | 451376 | CCCCGCTCACCATGGCAGTG | 31 | 712 | n/a | n/a | n/a |
| 10278 | 10297 | 451378 | GGTCCGGGACCTGATTGTCT | 85 | 713 | n/a | n/a | n/a |
| 3229 | 3248 | 451385 | GCTGCATGTCTGCCCGTCCC | 74 | 714 | 90 | 109 | 1 |
| 3244 | 3263 | 451386 | GGCCCCAGAACCCTAGCTGC | 73 | 715 | n/a | n/a | n/a |
| 3270 | 3289 | 451387 | TCACAGGGCCTGGCTGCCCC | 62 | 716 | 131 | 150 | 1 |
| 3333 | 3352 | 451388 | GGCTGACATGTTGGGCAGGC | 60 | 717 | 195 | 214 | 1 |
| 3250 | 3269 | 451389 | TGTCCAGGCCCCAGAACCCT | 68 | 718 | 111 | 130 | 3 |
| 12295 | 12314 | 451391 | GGCCAGGCCTAGGGATCTGC | 51 | 719 | n/a | n/a | n/a |
| 12306 | 12325 | 451392 | CGCCTCGGATAGGCCAGGCC | 52 | 720 | 1935 | 1954 | 1 |
| 12450 | 12469 | 451393 | GGCTTGGAGTCTTAGGGTTC | 85 | 721 | n/a | n/a | n/a |
| 12623 | 12642 | 451394 | TCCCCGGCCGCCAGGTGGCA | 43 | 722 | 2224 | 2243 | 3 |
| 12651 | 12670 | 451395 | GGTGCTGGGCACGAGCCCTG | 62 | 723 | n/a | n/a | n/a |
| 12698 | 12717 | 451396 | GCCCAGCTGCTGCAGCAGCG | 66 | 724 | n/a | n/a | n/a |
| 12876 | 12895 | 451397 | CCGTGTGTGCTGGCAGAGGT | 76 | 725 | n/a | n/a | n/a |
| 13084 | 13103 | 451398 | ATAAATACCGAGGAATGTCG | 77 | 726 | 2766 | 2785 | 0 |
| 13094 | 13113 | 451399 | GGGACAGACAATAAATACCG | 80 | 727 | 2776 | 2795 | 0 |
| 12362 | 12381 | 451405 | GTGCAGCCCAGTGTGGCGGC | 69 | 728 | 1991 | 2010 | 3 |
| 11175 | 11194 | 451415 | CCTGGAGAAGTTCTGGTTGG | 48 | 729 | 1674 | 1693 | 3 |
| 11585 | 11604 | 451417 | CATGGGAAGGTGGATCCGTG | 65 | 679 | 1819 | 1838 | 1 |
| 11854 | 11873 | 451419 | GGTGACCCGATCGGAGCCCA | 11 | 730 | n/a | n/a | n/a |

TABLE 14-continued

Inhibition of murine DMPK RNA transcript in mouse primary hepatocytes by 5-10-5 gapmers targeting SEQ ID NO: 800

| Murine Target Start Site | Murine Target Stop Site | ISIS No | Sequence | % inhibition | SEQ ID NO. | Human Target Start Site | Human Target Stop Site | Mismatches |
|---|---|---|---|---|---|---|---|---|
| 11874 | 11893 | 451420 | AGCTGGAGAGAGAAGGGACA | 37 | 731 | n/a | n/a | n/a |
| 11379 | 11398 | 451422 | GTGAGGGACTCGCCTGCGGC | 36 | 732 | n/a | n/a | n/a |
| 11479 | 11498 | 451423 | GCGGCTGCGGTGCCCCAGCC | 50 | 733 | n/a | n/a | n/a |
| 11883 | 11902 | 451424 | GGGCCATCTAGCTGGAGAGA | 45 | 734 | n/a | n/a | n/a |
| 3485 | 3504 | 451427 | CCCCACTGCAAGAAGTCGGC | 57 | 735 | 347 | 366 | 1 |
| 4621 | 4640 | 451428 | TTGAGCCCTTTTAAGGCAGC | 43 | 736 | n/a | n/a | n/a |
| 6232 | 6251 | 451429 | TGACCAGGTACTGGGAGCGG | 47 | 737 | n/a | n/a | n/a |
| 10985 | 11004 | 451430 | CCTGGAGCTGGATCAGTCCC | 6 | 738 | n/a | n/a | n/a |
| 11586 | 11605 | 451431 | ACATGGGAAGGTGGATCCGT | 70 | 739 | 1820 | 1839 | 1 |
| 11963 | 11982 | 451432 | CCCTGGCAGGGAGCAGCAGG | 42 | 544 | 1909 | 1928 | 0 |
| 11973 | 11992 | 451433 | GTGGGACATACCCTGGCAGG | 34 | 740 | n/a | n/a | n/a |
| 12294 | 12313 | 451434 | GCCAGGCCTAGGGATCTGCA | 35 | 741 | n/a | n/a | n/a |

TABLE 15

Inhibition of murine DMPK RNA transcript in mouse primary hepatocytes by 5-10-5 gapmers targeting SEQ ID NO: 800

| Murine Target Start Site | Murine Target Stop Site | ISIS No | Sequence | % inhibition | SEQ ID NO. | Human Target Start Site | Human Target Stop Site | Mismatches |
|---|---|---|---|---|---|---|---|---|
| 330 | 349 | 451365 | GGAAGCACGACACCTCGCCT | 67 | 742 | 535 | 554 | 1 |
| 662 | 681 | 451369 | CCTCACCATTCCATCAGGCT | 81 | 743 | n/a | n/a | n/a |
| 881 | 900 | 451372 | CGGCAGCGACAAGTGTTCCC | 90 | 744 | n/a | n/a | n/a |
| 1217 | 1236 | 451377 | GTCTCTGAAGGCCATGCAGC | 69 | 745 | 1407 | 1426 | 3 |
| 1329 | 1348 | 451379 | CAGCCACTTGATCCGGTGGG | 62 | 746 | n/a | n/a | n/a |
| 1342 | 1361 | 451380 | AGGTCGGCCTCTTCAGCCAC | 74 | 747 | n/a | n/a | n/a |
| 1494 | 1513 | 451381 | GTTGGCTGGAGAAGTTCTGG | 39 | 748 | 1678 | 1697 | 2 |
| 1598 | 1617 | 451382 | CCCCGTGATGGCTGCGGCTC | 54 | 749 | 1782 | 1801 | 3 |
| 1644 | 1663 | 451383 | GGCCATCTAGATGGGAAGGT | 21 | 517 | 1828 | 1847 | 0 |
| 1741 | 1760 | 451384 | AGGCCAGGCCTAGGGATCCT | 39 | 750 | 1925 | 1944 | 1 |

TABLE 16

Inhibition of murine DMPK RNA transcript in mouse primary hepatocytes by 5-10-5 gapmers targeting SEQ ID NOs: 5-8 and 793-799

| Murine Target Start Site | Murine Target Stop Site | Murine SEQ ID NO | ISIS No | Sequence | % inhibition | SEQ ID NO. | Human Target Start Site | Human Target Stop Site | Mismatches |
|---|---|---|---|---|---|---|---|---|---|
| 324 | 343 | 5 | 451410 | GGCGCGGTGCCCCAGCCTGG | 67 | 751 | n/a | n/a | n/a |
| 485 | 504 | 5 | 451411 | GTCCTGGCCCCACCAGCGGG | 66 | 752 | 1873 | 1892 | 1 |

TABLE 16-continued

Inhibition of murine DMPK RNA transcript in mouse primary hepatocytes by 5-10-5 gapmers targeting SEQ ID NOs: 5-8 and 793-799

| Murine Target Start Site | Murine Target Stop Site | Murine Target SEQ ID NO | ISIS No | Sequence | % inhibition | Human SEQ ID NO. | Human Target Start Site | Human Target Stop Site | Mismatches |
|---|---|---|---|---|---|---|---|---|---|
| 534 | 553 | 5 | 451412 | CCAGGCCTAGGAATCCTGGC | 17 | 753 | 1922 | 1941 | 2 |
| 547 | 566 | 5 | 451413 | GCGCCTCGGATAGCCAGGCC | 51 | 754 | n/a | n/a | n/a |
| 594 | 613 | 5 | 451414 | CCCAGTGTGGCGCAGCAGCC | 65 | 755 | n/a | n/a | n/a |
| 393 | 412 | 6 | 451402 | GTGTTTCATCTTCACCACCG | 80 | 756 | 462 | 481 | 3 |
| 1475 | 1494 | 7 | 451390 | AGGTCAGCCTCTTCAGCCAC | 60 | 757 | n/a | n/a | n/a |
| n/a | n/a | n/a | 451425 | GGCCATATGGGAAGGTGGAT | 48 | 758 | 1824 | 1843 | 0 |
| 1763 | 1782 | 8 | 451418 | GGAGGATTTGGCGAGAAGCA | 48 | 759 | n/a | n/a | n/a |
| 1032 | 1051 | 793 | 451403 | CGAAGTCTGCCCCACCTCGA | 58 | 760 | n/a | n/a | n/a |
| 1042 | 1061 | 793 | 451404 | GTGGCACCCTCGAAGTCTGC | 72 | 761 | n/a | n/a | n/a |
| 217 | 236 | 794 | 451400 | GGGTCCATTGTAAGGAAGCT | 4 | 762 | n/a | n/a | n/a |
| 754 | 773 | 794 | 451401 | GGTGCCCACAGCCACCAGGG | 82 | 763 | 888 | 907 | 1 |
| 322 | 341 | 795 | 451406 | TCCATGGCAGTGAGCCGGTC | 55 | 764 | 1319 | 1338 | 1 |
| 523 | 542 | 795 | 451407 | GGGACCACTTGATCCGGTGG | 63 | 765 | n/a | n/a | n/a |
| 534 | 553 | 795 | 451408 | GGATCAGAGTTGGGACCACT | 0 | 766 | n/a | n/a | n/a |
| 492 | 511 | 796 | 451416 | CCCCGTGATGGCTGCGGTTC | 49 | 767 | n/a | n/a | n/a |
| 469 | 488 | 797 | 451409 | GTGTGTCCTCATACCCCGCC | 60 | 768 | n/a | n/a | n/a |
| 629 | 648 | 798 | 451421 | GCACCCTCGAAGTCTCGACC | 72 | 769 | n/a | n/a | n/a |
| 854 | 873 | 799 | 451426 | GCTCTGAAGGCCATGCAGCA | 52 | 770 | n/a | n/a | n/a |

Example 9

Dose-Dependent Antisense Inhibition of Murine DMPK in Mouse Primary Hepatocytes

Several of the antisense oligonucleotides exhibiting in vitro inhibition of DMPK in mouse primary hepatocytes (see Example 8) were tested at various doses. Cells were plated at a density of 35,000 cells per well and transfected using electroporation with 1,000 nM, 2,000 nM, 4,000 nM, 8,000 nM, and 16,000 nM concentrations of each antisense oligonucleotide. After approximately 16 hours, RNA was isolated from the cells and DMPK transcript levels were measured by quantitative real-time PCR using primer probe set RTS3181 (forward sequence GACATATGCCAAGATTGT-GCACTAC, designated herein as SEQ ID NO: 771; reverse sequence CACGAATGAGGTCCTGAGCTT, designated herein as SEQ ID NO: 772; probe sequence AACACTT-GTCGCTGCCGCTGGCX, designated herein as SEQ ID NO: 773). DMPK transcript levels were normalized to total RNA content, as measured by RIBOGREEN®. Results are presented in Table 17 as percent inhibition of DMPK, relative to untreated control cells.

The majority of the tested antisense oligonucleotides demonstrated dose-dependent inhibition of DMPK mRNA levels under the conditions specified above.

TABLE 17

Dose-dependent antisense inhibition of murine DMPK in mouse primary hepatocytes

| ISIS No | 1,000 nM | 2,000 nM | 4,000 nM | 8,000 nM | 16,000 nM | $IC_{50}$ (μM) |
|---|---|---|---|---|---|---|
| 451369 | 33 | 59 | 78 | 87 | 94 | 1.57 |
| 451371 | 60 | 77 | 84 | 90 | 91 | 0.24 |
| 451373 | 53 | 62 | 82 | 89 | 92 | 0.74 |
| 451374 | 33 | 42 | 76 | 88 | 94 | 2.00 |
| 451375 | 43 | 62 | 81 | 89 | 88 | 1.05 |
| 451378 | 39 | 79 | 80 | 87 | 94 | 0.87 |
| 451385 | 22 | 57 | 80 | 78 | 93 | 2.01 |
| 451393 | 49 | 63 | 86 | 80 | 80 | 0.59 |
| 451397 | 63 | 75 | 74 | 81 | 92 | 0.22 |
| 451398 | 29 | 72 | 84 | 83 | 90 | 1.29 |
| 451399 | 27 | 53 | 81 | 68 | 80 | 2.07 |
| 451401 | 34 | 71 | 87 | 86 | 92 | 1.12 |
| 451402 | 34 | 69 | 75 | 86 | 74 | 1.14 |

Example 10

Antisense Inhibition of Human Alpha1 Skeletal Actin in HepG2 Cells

Antisense oligonucleotides targeted to a human alpha1 skeletal actin nucleic acid, a gene which may carry an expanded CTG repeat capable of causing symptoms of DM1 when inserted into mouse models, were tested for their effect on alpha1 actin RNA transcript in vitro. Cultured HepG2 cells at a density of 20,000 cells per well were transfected using electroporation with 10,000 nM antisense oligonucleotide. After approximately 24 hours, RNA was isolated from the cells and alpha1 actin RNA transcript levels were measured by quantitative real-time PCR. Alpha1 actin RNA transcript levels were adjusted according to total RNA content, as measured by RIBOGREEN®. Results are presented as percent inhibition of alpha1 actin, relative to untreated control cells.

The antisense oligonucleotides in Table 18 are 5-10-5 gapmers, where the gap segment comprises ten 2'-deoxynucleosides and each wing segment comprises five 2'-MOE nucleosides. The internucleoside linkages throughout each gapmer are phosphorothioate (P=S) linkages. All cytosine residues throughout each gapmer are 5-methylcytosines. 'Target start site' indicates the 5'-most nucleoside to which the antisense oligonucleotide is targeted. 'Target stop site' indicates the 3'-most nucleoside to which the antisense oligonucleotide is targeted. All the antisense oligonucleotides listed in Table 18 target SEQ ID NO: 801 (GENBANK Accession No. NM_001100.3).

The tested antisense oligonucleotide sequences demonstrated dose-dependent inhibition of alpha 1 actin mRNA levels under the conditions specified above.

set RTS3154 (forward sequence CCACCGCAAATGCTTCTAGAC, designated herein as SEQ ID NO: 785; reverse sequence CCCCCCCATTGAGAAGATTC, designated herein as SEQ ID NO: 786; probe sequence CTCCACCTCCAGCACGCGACTTCTX, designated herein as SEQ ID NO: 787). Alpha1 actin RNA transcript levels were normalized to total RNA content, as measured by RIBOGREEN®. Results are presented in Table 19 as percent inhibition of alpha1 actin, relative to untreated control cells.

Several of the antisense oligonucleotides demonstrated dose-dependent inhibition of alpha 1 actin mRNA levels under the conditions specified above.

TABLE 19

Dose-dependent antisense inhibition of human alpha1 actin in HepG2 cells

| ISIS No. | 625 nM | 1,250 nM | 2,500 nM | 5,000 nM | 10,000 nM | 20,000 nM | IC$_{50}$ (µM) |
|---|---|---|---|---|---|---|---|
| 445233 | 21 | 72 | 63 | 82 | 96 | 83 | 1.1 |
| 445236 | 26 | 68 | 82 | 91 | 90 | 91 | 0.8 |
| 445237 | 36 | 59 | 76 | 84 | 83 | 90 | 0.8 |
| 445232 | 14 | 42 | 54 | 59 | 80 | 91 | 2.6 |
| 445238 | 27 | 43 | 54 | 73 | 76 | 90 | 2.0 |
| 445235 | 26 | 52 | 29 | 58 | 59 | 24 | 0.7 |
| 190403 | 25 | 29 | 36 | 25 | 61 | 54 | 11.9 |
| 190401 | 17 | 14 | 40 | 68 | 76 | 72 | 3.9 |

TABLE 18

Inhibition of human alpha 1 actin RNA transcript in HepG2 cells by 5-10-5 gapmers targeting SEQ ID NO: 801

| Target Start Site | Target Stop Site | ISIS No | Sequence | % inhibition | SEQ ID NO. |
|---|---|---|---|---|---|
| 16 | 35 | 445205 | AGCGAGGCTTCACTTGGCGC | 74 | 774 |
| 20 | 39 | 190403 | GGGAAGCGAGGCTTCACTTG | 75 | 775 |
| 1028 | 1047 | 190401 | GCGGTCAGCGATCCCAGGGT | 78 | 776 |
| 1058 | 1077 | 445225 | GGGTGCCAGCGCGGTGATCT | 73 | 777 |
| 1320 | 1339 | 445231 | TGTTACAAAGAAAGTGACTG | 74 | 778 |
| 1339 | 1358 | 445232 | CGATGGCAGCAACGGAAGTT | 96 | 779 |
| 1348 | 1367 | 445233 | GTCAGTTTACGATGGCAGCA | 100 | 780 |
| 1417 | 1436 | 445235 | CAGGGCTTTGTTTCGAAAAA | 91 | 781 |
| 1430 | 1449 | 445236 | CCATTTTCTTCCACAGGGCT | 99 | 782 |
| 1447 | 1466 | 445237 | ATGCTTCTTCAAGTTTTCCA | 97 | 783 |
| 1460 | 1479 | 445238 | CAGAATGACTTTAATGCTTC | 95 | 784 |

Example 11

Dose-Dependent Antisense Inhibition of Human Alpha1 Actin in HepG2 Cells

Several of the antisense oligonucleotides exhibiting in vitro inhibition of alpha1 actin in HepG2 cells (see Example 8) were tested at various doses. Cells were plated at a density of 20,000 cells per well and transfected using electroporation with 625 nM, 1,250 nM, 2,500 nM, 5,000 nM, 10,000 nM and 20,000 nM concentrations of each antisense oligonucleotide. After approximately 16 hours, RNA was isolated from the cells and alpha1 actin RNA transcript levels were measured by quantitative real-time PCR using primer probe TABLE 19-continued Dose-dependent antisense inhibition of human alpha1 actin in HepG2 cells

| ISIS No. | 625 nM | 1,250 nM | 2,500 nM | 5,000 nM | 10,000 nM | 20,000 nM | IC$_{50}$ (µM) |
|---|---|---|---|---|---|---|---|
| 445225 | 25 | 23 | 49 | 28 | 52 | 50 | 15.8 |
| 445205 | 26 | 31 | 34 | 28 | 55 | 36 | 7.6 |
| 445231 | 30 | 25 | 39 | 26 | 42 | 36 | >20.0 |

Example 12

In vivo Antisense Inhibition of Human Alpha1 Actin by Intramuscular Administration in Transgenic Mice To test the effect of antisense inhibition for the treatment of myotonic dystrophy, an appropriate mouse model was required. The HSA$^{LR}$ mouse model is an established model for DM1 (Mankodi, A. et al. Science. 289: 1769, 2000). The mice carry a human skeletal actin (hACTA1) transgene with 220 CTG repeats inserted in the 3' UTR of the gene. The hACTA1-CUGexp transcript accumulates in nuclear foci in skeletal muscles and results in myotonia similar to that in human DM1 (Mankodi, A. et al. Mol. Cell 10: 35, 2002; Lin, X. et al. Hum. Mol. Genet. 15: 2087, 2006). Hence, it was expected that amelioration of DM1 symptoms in the HSA$^{LR}$ mouse by antisense inhibition of the hACTA1 transgene would predict amelioration of similar symptoms in human patients by antisense inhibition of the DMPK transcript.

HSA (human skeletal actin)$^{LR}$ (long repeat) DM1 mice were generated by insertion in FVB/N mice of a transgene with 250 CUG repeats in the 3' UTR of human skeletal actin. The transgene is expressed in the mice as a CUG repeat RNA, which is retained in the nucleus, forming nuclear inclusions or foci, similar to that seen in human tissue samples of patients with myotonic dystrophy (DM1).

ISIS 190403 and ISIS 445238, which demonstrated statistically significant dose-dependent inhibition in vitro (see Example 11), were evaluated for their ability to reduce human alpha1 actin RNA transcript in vivo.

Treatment

HSA$^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into two treatment groups. The two groups received direct intramuscular injections of ISIS 190403 or ISIS 445238 at a dose of 0.8 nM into the tibialis anterior muscle on one side. The contralateral tibialis anterior muscle in each mouse received a single dose intramuscular injection of PBS. The PBS-injected muscle acted as the control.

Inhibition of Alpha1 Actin RNA

Twenty four hours after the final dose, the animals were sacrificed and tissue from the tibialis anterior muscles of both sides was isolated. RNA was isolated for real-time PCR analysis of alpha1 actin and normalized to 18s RNA. As presented in Table 20, treatment with antisense oligonucleotides reduced human alpha1 actin RNA transcript expression. The results are expressed as percent inhibition of alpha1 actin transcript, relative to the PBS control.

The results indicate that treatment with ISIS 190403 and ISIS 445238 resulted in inhibition of alpha 1 actin RNA levels in the mice.

TABLE 20

Percent inhibition of human alpha1 actin RNA transcript in HSA$^{LR}$ mice

| ISIS No. | % inhibition |
|---|---|
| 190403 | 38 |
| 445238 | 40 |

Example 13

Dose Dependent Antisense Inhibition of Human Alpha1 Actin by Intramuscular Administration in Transgenic Mice ISIS 445236, which demonstrated statistically significant dose-dependent inhibition in vitro (see Example 11), was evaluated for its ability to reduce human alpha1 actin RNA transcript in vivo.

Treatment

HSA$^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into three treatment groups. The groups received direct intramuscular injections of ISIS 445236 at doses of 0.2 nM, 0.4 nM or 0.8 nM into the tibialis anterior muscle of one side. The contralateral tibialis anterior muscle in each mouse received a single dose intramuscular injection of PBS. The PBS-injected muscle acted as the control.

Inhibition of Alpha1 Actin RNA

Twenty four hours after the final dose, the animals were sacrificed and tissue from the tibialis anterior muscles of both sides was isolated. RNA was isolated for real-time PCR analysis of alpha1 actin and normalized to 18s RNA. As presented in Table 21, treatment with ISIS 445236 reduced human alpha1 actin RNA transcript expression at all dosages. The results are expressed as percent inhibition of alpha1 actin transcript, relative to the control.

The results indicate that treatment with ISIS 445236 resulted in significant inhibition of alpha 1 actin mRNA levels under the conditions specified above.

TABLE 21

Inhibition of human alpha1 actin RNA transcript by ISIS 445236 in HSA$^{LR}$ mice

| Dose (nM) | % inhibition |
|---|---|
| 0.2 | 70 |
| 0.4 | 54 |
| 0.8 | 78 |

Assessment of Myotonia by Electromyography

Myotonia refers to repetitive action potential that is due to delayed relaxation of muscle fibers. This phenomenon is observed in patients of myotonic dystrophy as well as in the HSA$^{LR}$ mice. When the EMG needle is inserted into a myotonic muscle, the electrical activity is prolonged for up to several seconds past when the insertional activity should normally cease. The frequency of myotonic discharges ranges from 50 to 100 impulses per second.

Myotonia was measured via electromyography and graded in the following manner: grade 0 refers to no myotonia elicited by any needle insertion (0%); grade 1 refers to myotonia elicited by less than 50% needle insertions; grade 2 refers to myotonia elicited by more than 50% needle insertions; and grade 3 refers to mytonia elicited by 100% needle insertions.

Before electromyography, mice were anesthetized by using i.p. a cocktail of 100 mg/kg ketamine, 10 mg/kg xylazine, and 3 mg/kg acepromazine. Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 22 as the average myotonia grade observed in four mice of each group and demonstrates significant reduction of myotonia in mice treated with ISIS 445236.

TABLE 22

Average reduction of myotonia in various muscles of antisense oligonucleotide-treated $HSA^{LR}$ mice

| Treatment | Dose (nM) | Myotonia grade |
|---|---|---|
| PBS |  | 2.7 |
| ISIS 455236 | 0.2 | 1.3 |
|  | 0.4 | 1.0 |
|  | 0.8 | 1.0 |

Correction of Alternative Splicing

In DM1/$HSA^{LR}$ mouse model, the accumulation of expanded CUG RNA in the nucleus leads to the sequestration of poly(CUG)-binding proteins, such as Muscleblind-like 1 (MBLN1) (Miller, J. W. et al. EMBO J. 19: 4439, 2000). The splicing factor MBNL1, which controls alternative splicing of the Serca1 gene is sequestered in expanded CUG foci. This triggers dysregulation of the alternative splicing of this gene. To evaluate the effect of antisense inhibition of human alpha 1 actin on such alternative splicing, total RNA was purified from the tibialis anterior, gastrocnemius, and quadriceps muscle using RNeasy Lipid Tissue Mini Kit (Qiagen), according to the manufacturer's instructions. RT-PCR was performed with the SuperScript III One-Step RT-PCR System and Platinum Taq Polymerase (Invitrogen), using gene-specific primers for cDNA synthesis and PCR amplification. The forward and reverse primers for Serca-1 have been described in Bennett and Swayze (Annu Rev. Pharmacol. 2010; 50: 259-93). PCR products were separated on agarose gels, stained with SybrGreen I Nucleic Acid Gel Stain (Invitrogen), and imaged using a Fujifilm LAS-3000 Intelligent Dark Box.

The PCR products of Serca1 splicing in the PBS control demonstrated exon 22 exclusion as a result of dysregulation of MBLN1. Treatment with ISIS 445236 resulted in exon 22 inclusion and normalization of alternative splicing of the Serca1 gene in the tibialis anterior, gastrocnemius, and quadriceps muscles.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci corrects MBLN1 sequestration thereby allowing normal splicing to occur.

Example 14

In vivo Antisense Inhibition of Human Alpha1 Actin by Subcutaneous Administration in Transgenic Mice ISIS 190403, ISIS 445236 and ISIS 445238 were evaluated for their ability to reduce human alpha1 actin RNA transcript in vivo.

Treatment $HSA^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into four treatment groups. The first three groups received subcutaneous injections of ISIS 190403, ISIS 445236 or ISIS 445238 at a dose of 25 mg/kg twice per week for 4 weeks. The fourth group received subcutaneous injections of PBS twice weekly for 4 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles (left and right), gastrocnemius muscles (left and right), and tibialis anterior muscles (left and right) was isolated. RNA was isolated for real-time PCR analysis of alpha1 actin and normalized to 18s RNA. As presented in Table 23, treatment with antisense oligonucleotides reduced human alpha1 actin RNA transcript expression. The results are expressed as percent inhibition of alpha1 actin transcript, relative to the control.

Both ISIS 445236 and ISIS 445238 demonstrated significant inhibition of alpha1 actin mRNA levels under the conditions specified above.

TABLE 23

Percent inhibition of human alpha1 actin RNA transcript in $HSA^{LR}$ mice

| Muscle Type | ISIS 190403 | ISIS 445236 | ISIS 445238 |
|---|---|---|---|
| Quadriceps | 16 | 83 | 72 |
| Gastrocnemius | 0 | 85 | 73 |
| Tibialis anterior | 2 | 81 | 71 |

Fluorescence In Situ Hybridization of Alpha1 Actin in Muscles

Frozen muscle tissue sections were fixed in fresh 3% paraformaldehyde in PBS solution for 15-20 minutes, after which they were rinsed twice with PBS for 5 minutes. The nuclei were permeabilized with 0.5% Triton X-100 for 5 minutes after which the tissue was blocked with normal goat serum for 30 minutes. The sections were incubated a 2'-O-methyl RNA targeted to alpha1 actin that is 5'-labeled with Texas Red (Integrated DNA Technologies). The sections were counter-stained with DAPI to label the nuclei. The sections were mounted and viewed with a standard fluorescence microscope. Image acquisition was by Metavue software and deconvolution was achieved by Autoquant software.

All muscle tissue sections from mice treated with ISIS 445236 and ISIS 445238 displayed reduced fluorescent intensity of alpha1 actin signal at the ribonuclear foci, indicating antisense inhibition of human alpha1 actin mRNA and reduction of the RNA in the nuclear foci.

Assessment of Myotonia by Electromyography

Myotonia refers to repetitive action potential that is due to delayed relaxation of muscle fibers. This phenomenon is observed in patients of myotonic dystrophy as well as in the $HSA^{LR}$ mice. When the EMG needle is inserted into a myotonic muscle, the electrical activity is prolonged for up to several seconds past when the insertional activity should normally cease. The frequency of myotonic discharges ranges from 50 to 100 impulses per second.

Myotonia may be measured via electromyography and is graded in the following manner: grade 0 refers to no myotonia elicited by any needle insertion (0%); grade 1 refers to myotonia elicited by less than 50% needle insertions; grade 2 refers to myotonia elicited by more than 50% needle insertions; and grade 3 refers to mytonia elicited by 100% needle insertions.

Before electromyography, mice were anesthetized by using i.p. 100 mg/kg ketamine, 10 mg/kg xylazine, and 3 mg/kg acepromazine or 250 mg/kg 2,2,2-tribromoethanol. Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 24 as the average myotonia grade observed in four mice of each group and demonstrates significant reduction of myotonia in mice treated with ISIS 445236 and ISIS 445238.

TABLE 24

Average reduction of myotonia in various muscles of antisense oligonucleotide-treated $HSA^{LR}$ mice

| | PBS | ISIS 190403 | ISIS 445236 | ISIS 445238 |
| --- | --- | --- | --- | --- |
| Left quadriceps | 3.00 | 3.00 | 0.00 | 0.25 |
| Right quadriceps | 3.00 | 3.00 | 0.00 | 0.00 |
| Left gastrocnemius | 3.00 | 3.00 | 0.00 | 0.25 |
| Right gastrocnemius | 3.00 | 3.00 | 0.00 | 0.25 |
| Left Tibialis anterior | 2.75 | 2.50 | 0.00 | 0.00 |
| Right Tibialis anterior | 2.75 | 2.50 | 0.00 | 0.00 |
| Lumbar paraspinals | 3.00 | 3.00 | 0.00 | 0.75 |

Correction of Alternative Splicing

The splicing factor MBNL1, which controls Serca1 splicing, m-Titin splicing, ClC-1 chloride channel gene (Clcn1) splicing, and Zasp splicing, is sequestered in expanded CUG foci. MBNL1 sequestration triggers dysregulated splicing in each of these genes. To evaluate the effect of antisense inhibition of human alpha 1 actin on splicing, total RNA was purified from the tibialis anterior, gastrocnemius, and quadriceps muscle and RT-PCR was performed, as described in Example 13. The forward and reverse primers for Serca-1, m-Titin, Clcn1, and ZASP have been described in Bennett and Swayze, Annu Rev. Pharmacol. 2010; 50: 259-93.

In PBS treated $HSA^{LR}$ mice, Serca1 splicing is dysregulated as demonstrated by exon 22 exclusion. Treatment with each of ISIS 445236 and ISIS 445238 resulted in exon 22 inclusion and normalization of alternative splicing of the Serca1 gene in the tibialis anterior, gastrocnemius, and quadriceps muscles.

In PBS treated $HSA^{LR}$ mice, m-Titin splicing is dysregulated as demonstrated by exon 5 inclusion. Treatment with each of ISIS 445236 and ISIS 445238 resulted in skipping of exon 5 and normalization of alternative splicing of the m-Titin gene in the tibialis anterior, gastrocnemius, and quadriceps muscles.

In PBS treated $HSA^{LR}$ mice, Clcn1 splicing is dysregulated as demonstrated by exon 7a inclusion. Treatment with each of ISIS 445236 and ISIS 445238 resulted in skipping of exon 7a and normalization of alternative splicing of the Clcn1 gene in the tibialis anterior, gastrocnemius, and quadriceps muscles.

In PBS treated $HSA^{LR}$ mice, Zasp splicing is dysregulated as demonstrated by exon 11 inclusion. Treatment with each of ISIS 445236 and ISIS 445238 resulted in skipping of exon 11 and normalization of alternative splicing of the Zasp gene in the tibialis anterior, gastrocnemius, and quadriceps muscles.

Therefore, antisense inhibition of alpha1 actin corrected Serca1, m-Titin, Clcn1, and Zasp splicing dysregulation, which indicates that treatment with antisense oligonucleotide reduced accumulation of CUGexp in the nuclear foci. Reduced accumulation of CUGexp in the nuclear foci correct MBLN1 sequestration thereby allowing normal splicing to occur.

Example 15

In vivo Antisense Inhibition of Human Alpha1 Actin in Transgenic Mice

Antisense inhibition of human alpha1 actin RNA transcript by ISIS 445236 and ISIS 445238 on myotonia in $HSA^{LR}$ mice was further evaluated.

Treatment $HSA^{LR}$ mice were divided into three treatment groups. The first two groups received subcutaneous injections of ISIS 445236 or ISIS 445238 at a dose of 25 mg/kg twice per week for 2 weeks. The third group received subcutaneous injections of PBS twice per week for 2 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 25, treatment with antisense oligonucleotides reduced human alpha1 actin RNA transcript expression. The results are expressed as percent inhibition of alpha1 actin transcript, relative to the PBS control.

Both ISIS 445236 and ISIS 445238 demonstrated significant inhibition of alpha1 actin mRNA levels under the conditions specified above.

TABLE 25

Percent inhibition of human alpha1 actin RNA transcriptin $HSA^{LR}$ mice

| Muscle Type | ISIS 445236 | ISIS 445238 |
| --- | --- | --- |
| Quadriceps | 61 | 64 |
| Gastrocnemius | 68 | 37 |
| Tibialis anterior | 68 | 41 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 26 as the average myotonia grade observed in four mice of each group and demonstrates significant reduction of myotonia in mice treated with ISIS 445236 and ISIS 445238.

TABLE 26

Average reduction of myotonia in various muscles of antisense oligonucleotide-treated HSA$^{LR}$ mice

|  | PBS | ISIS 445236 | ISIS 445238 |
|---|---|---|---|
| Left quadriceps | 3.00 | 0.00 | 1.75 |
| Right quadriceps | 3.00 | 0.00 | 1.75 |
| Left gastrocnemius | 3.00 | 0.25 | 1.5 |
| Right gastrocnemius | 3.00 | 0.25 | 1.00 |
| Left Tibialis anterior | 2.75 | 0.00 | 0.00 |
| Right Tibialis anterior | 2.75 | 0.00 | 0.00 |
| Lumbar paraspinals | 3.00 | 0.50 | 2.00 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated HSA$^{LR}$ mice, Serca1 splicing is dysregulated as demonstrated by exon 22 exclusion, as a result of MBLN1 dysregulation. Treatment with each of ISIS 445236 and ISIS 445238 resulted in near-complete inclusion and normalization of alternative splicing of exon 22 of the Serca1 gene in the tibialis anterior and quadriceps muscles.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci correct MBLN1 sequestration thereby allowing normal splicing to occur.

Example 16

Dose-Dependent Antisense Inhibition of Human Alpha1 Actin in Transgenic Mice

Dose-dependent inhibition of human alpha1 actin RNA transcript by ISIS 445236 and ISIS 445238 on myotonia in HSA$^{LR}$ mice was evaluated.

Treatment

HSA$^{LR}$ mice were subcutaneously injected with ISIS 445236 or ISIS 445238 at doses of 2.5 mg/kg, 8.5 mg/kg or 25.0 mg/kg twice per week for 4 weeks. The control group received subcutaneous injections of PBS twice per week for 4 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles (Quad), gastrocnemius muscles (Gastroc), and tibialis anterior muscles (TA) was isolated. RNA was isolated for real-time PCR analysis of alpha1 actin and normalized to 18s RNA. As presented in Table 27, treatment with antisense oligonucleotides reduced human alpha1 actin RNA transcript expression. The results are expressed as percent inhibition of alpha1 actin transcript, relative to the PBS control.

Both the antisense oligonucleotides demonstrated dose-dependent inhibition of alpha1 actin mRNA levels in quadriceps muscles, gastrocnemius muscles, and tibialis anterior muscles under the conditions specified above.

TABLE 27

Dose-dependent inhibition of human alpha1 actin RNA transcript in HSA$^{LR}$ mice

|  | mg/kg/wk | Quad | Gastroc | TA |
|---|---|---|---|---|
| ISIS 445236 | 5 | 24 | 36 | 46 |
|  | 17 | 53 | 57 | 59 |
|  | 50 | 86 | 86 | 90 |
| ISIS 445238 | 5 | 21 | 37 | 3 |
|  | 17 | 30 | 39 | 60 |
|  | 50 | 59 | 81 | 70 |

Assessment of Myotonia by Electromyography

Electromyography on left and right quadriceps (Quad), left and right gastrocnemius muscles (Gastroc), left and right tibialis anterior (TA) muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 28 as the average myotonia grade observed in four mice of each group and demonstrates significant dose-dependent reduction of myotonia in mice treated with ISIS 445236 and ISIS 445238.

TABLE 28

Average reduction of myotonia in various muscles of antisense oligonucleotide-treated HSA$^{LR}$ mice

|  | mg/kg/wk | Left Quad | Right Quad | Left Gastroc | Right Gastroc | Left TA | Right TA | Lumbar paraspinals |
|---|---|---|---|---|---|---|---|---|
| PBS | — | 3.00 | 3.00 | 3.00 | 3.00 | 2.75 | 2.75 | 3.00 |
| ISIS 445236 | 5 | 3.00 | 3.00 | 3.00 | 3.00 | 2.25 | 2.25 | 3.00 |
|  | 17 | 0.75 | 0.75 | 0.75 | 1.00 | 0.00 | 0.00 | 1.75 |
|  | 50 | 0.00 | 0.00 | 0.00 | 0.00 | 0.00 | 0.00 | 0.00 |
| ISIS 445238 | 5 | 2.75 | 2.75 | 2.50 | 2.50 | 2.00 | 1.75 | 2.75 |
|  | 17 | 3.00 | 3.00 | 2.00 | 2.25 | 0.00 | 0.00 | 2.75 |
|  | 50 | 0.75 | 0.75 | 0.25 | 0.25 | 0.00 | 0.00 | 1.00 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated HSA$^{LR}$ mice, Serca1 splicing is dysregulated as demonstrated by exon 22 exclusion, as a result of MBLN1 dysregulation. Treatment with either ISIS 445236 or ISIS 445238 at doses of 8.5 mg/kg or 25.0 mg/kg twice a week (or 17.0 mg/kg/week and 50.0 mg/kg/week) resulted in complete inclusion and normalization of alternative splicing of exon 22 of the Serca1 gene in all three muscle types.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci correct MBLN1 sequestration thereby allowing normal splicing to occur.

Example 17

In vivo Antisense Inhibition by an Oligonucleotide Targeting the HSA Coding Region of Human Alpha1 Actin in Transgenic Mice Antisense inhibition of human alpha1 actin RNA transcript by ISIS 190401 (5'-GCGGTCAGCGATCCCA-GGGT-3' (SEQ ID NO: 788), target start site 1028 of SEQ ID NO: 1) on myotonia in HSA$^{LR}$ mice was evaluated.

Treatment

HSA$^{LR}$ mice received subcutaneous injections of ISIS 190401 at a dose of 25 mg/kg twice per week for 4 weeks. A control group received subcutaneous injections of PBS twice per week for 2 weeks. The PBS-injected group served as the control group to which the oligonucleotide-treated group was compared.

Inhibition of Alpha1 Actin RNA

Twenty four hours after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 29, treatment with antisense oligonucleotides reduced human alpha1 actin RNA transcript expression. The results are expressed as percent inhibition of alpha1 actin transcript, relative to the PBS control.

Treatment with ISIS 190401 resulted in significant inhibition of alpha1 actin mRNA levels in quadriceps muscle, gastrocnemius muscle, and tibialis anterior muscle under the conditions specified above.

TABLE 29

Antisense inhibition of human alpha1 actin RNA transcript in HSA$^{LR}$ mice

| Muscle Type | % inhibition |
|---|---|
| Quadriceps | 85 |
| Gastrocnemius | 86 |
| Tibialis anterior | 89 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 30 as the average myotonia grade observed in four mice of each group and demonstrates significant reduction of myotonia in mice treated with ISIS 190401.

TABLE 30

Average reduction of myotonia in various muscles of antisense oligonucleotide-treated HSA$^{LR}$ mice

|  | PBS | ISIS 190401 |
|---|---|---|
| Left quadriceps | 3.00 | 0.00 |
| Right quadriceps | 3.00 | 0.00 |
| Left gastrocnemius | 3.00 | 0.00 |
| Right gastrocnemius | 3.00 | 0.00 |
| Left Tibialis anterior | 2.50 | 0.00 |
| Right Tibialis anterior | 2.50 | 0.00 |
| Lumbar paraspinals | 3.00 | 0.50 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated HSA$^{LR}$ mice, Serca1 splicing is dysregulated as demonstrated by exon 22 exclusion, as a result of MBLN1 dysregulation. Treatment with ISIS 190401 resulted in complete inclusion and normalization of alternative splicing of exon 22 of the Serca1 gene in all three muscle types.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci corrects MBLN1 sequestration thereby allowing normal splicing to occur.

Example 18

Duration of Action of Antisense Inhibition by an Oligonucleotide Targeting Human Alpha1 Actin in Transgenic Mice The duration of action of antisense inhibition of human alpha1 actin RNA transcript by ISIS 445236 in HSA$^{LR}$ mice was evaluated.

Treatment

HSA$^{LR}$ mice received subcutaneous injections of ISIS 445236 at a dose of 25 mg/kg twice per week for 4 weeks. A control group received subcutaneous injections of PBS twice per week for 2 weeks. The PBS-injected group served as the control group to which the oligonucleotide-treated group was compared. The mice were analyzed 6 weeks after administration of the last dose.

Inhibition of Alpha1 Actin RNA

Six weeks after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 31, treatment with ISIS 445236 reduced human alpha1 actin RNA transcript expression, and this effect was sustained at least for 6 weeks. The results are expressed as percent inhibition of alpha1 actin transcript, relative to the PBS control.

Treatment with ISIS 445236 resulted in significant inhibition of alpha1 actin mRNA levels in quadriceps muscle, gastrocnemius muscle, and tibialis anterior muscle under the conditions specified above.

TABLE 31

Antisense inhibition of human alpha1 actin RNA transcript in HSA$^{LR}$ mice

| Muscle Type | % inhibition |
|---|---|
| Quadriceps | 88 |
| Gastrocnemius | 76 |
| Tibialis anterior | 67 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 32 as the average myotonia grade observed in four mice of each group and demonstrates significant reduction of myotonia in mice treated with ISIS 445236. Therefore, the effect of antisense inhibition of alpha actin by ISIS 445236 was sustained at least for 6 weeks.

TABLE 32

Average reduction of myotonia in various muscles of antisense oligonucleotide-treated HSA$^{LR}$ mice

| | PBS | ISIS 445236 |
|---|---|---|
| Left quadriceps | 3.00 | 0.00 |
| Right quadriceps | 3.00 | 0.00 |
| Left gastrocnemius | 3.00 | 0.00 |
| Right gastrocnemius | 3.00 | 0.00 |
| Left Tibialis anterior | 2.50 | 0.00 |
| Right Tibialis anterior | 2.50 | 0.00 |
| Lumbar paraspinals | 3.00 | 0.00 |

Example 19

In vivo Effect of Antisense Inhibition of mRNA with CUG Repeats by Intramuscular Administration in Transgenic Mice The effect of antisense inhibition of mRNA transcripts containing multiple CUG repeats on myotonia in HSA$^{LR}$ mice was evaluated. Three antisense oligonucleotides targeting the CUG repeats and with varying lengths were assayed for their effectiveness in inhibiting myotonia in the mice. ISIS 444745 (AGCAGCAGCAGCAGCAGCAGCA (SEQ ID NO: 789) is a uniform 2'—O-methoxyethyl oligonucleotide, 25 nucleotides in length and with a phosphorothioate backbone. ISIS 444746 (AGCAGCAGCAGCAGCAGCAG (SEQ ID NO: 790) is a uniform 2'—O-methoxyethyl oligonucleotide, 20 nucleotides in length and with a phosphorothioate backbone. ISIS 444749 (GCAGCAGCAGCAGCA (SEQ ID NO: 791) is a uniform 2'—O-methoxyethyl oligonucleotide, 15 nucleotides in length and with a phosphorothioate backbone. ISIS 445236 was included in the assay as a positive control.

Treatment

HSA$^{LR}$ mice were divided into three treatment groups. The groups received direct intramuscular injections of ISIS 444745, ISIS 444746 or ISIS 444749 at a dose of 0.4 nM into the tibialis anterior muscle. The contralateral tibialis anterior muscle in each mouse received a single dose intramuscular injection of PBS. The PBS-injected muscle acted as the control.

Inhibition of Alpha1 Actin RNA

Twenty four hours after the final dose, the animals were sacrificed and tissue from the tibialis anterior (left and right) was isolated. RNA was isolated for real-time PCR analysis of alpha1 actin and normalized to 18s RNA. As presented in Table 33, only treatment with ISIS 444745 reduced human alpha1 actin RNA transcript expression. The results are expressed as percent inhibition of alpha1 actin transcript, relative to the PBS control.

TABLE 33

Percent inhibition of human alpha1 actin RNA transcript in HSA$^{LR}$ mice

| ISIS No. | % inhibition |
|---|---|
| 444745 | 51 |
| 444746 | 0 |
| 444749 | 12 |

Example 20

In vivo Dose Dependent Inhibition of mRNA with CUG Repeats by Intramuscular Administration in Transgenic Mice ISIS 444745 and ISIS 444746 were further evaluated for their ability to reduce human alpha 1 actin mRNA in vivo.

Treatment

HSA$^{LR}$ mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into 6 treatment groups. Three of the groups received direct intramuscular injections of ISIS 444745 at doses of 0.2 nM, 0.5 nM, or 1.0 nM into the tibialis anterior muscle on one side. Another three groups direct intramuscular injections of ISIS 444746 at doses of 0.2 nM, 0.5 nM, or 1.0 nM into the tibialis anterior muscle on one side. The contralateral tibialis anterior muscle in each mouse received a single dose intramuscular injection of PBS. The PBS-injected muscle acted as the control for the corresponding muscle treated with ISIS oligonucleotide.

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 34 as the average myotonia grade observed in four mice of each group and demonstrates significant reduction of myotonia in mice treated with either ISIS 444745 or ISIS 444746. The effect of antisense inhibition of alpha actin by ISIS 444745 and 444746 was sustained at least for 6 weeks.

TABLE 34

Dose-dependent reduction of myotonia in muscles of antisense oligonucleotide-treated HSA$^{LR}$ mice

|  | 0.2 nM | 0.5 nM | 1.0 nM |
|---|---|---|---|
| PBS | 3.00 | 3.00 | 2.33 |
| ISIS 444745 | 1.67 | 1.00 | 0.33 |
| PBS | 2.50 | 2.00 | 3.00 |
| ISIS 444746 | 2.00 | 0.00 | 1.00 |

Example 21

In vivo Effect of Antisense Inhibition of mRNA with CUG Repeats by Subcutaneous Administration in Transgenic Mice The effect of antisense inhibition of mRNA transcripts containing multiple CUG repeats on myotonia in HSA$^{LR}$ mice was evaluated. ISIS 445236 was included in the assay as a positive control.

Treatment

HSA$^{LR}$ mice were divided into five treatment groups. The first three groups received subcutaneous injections of ISIS 444745, ISIS 444746 or ISIS 444749 at a dose of 25 mg/kg twice per week for 4 weeks. The fourth group received subcutaneous injections of PBS twice per week for 4 weeks. The fifth group received subcutaneous injections of ISIS 445236 at a dose of 25 mg/kg twice per week for 4 weeks. The PBS-injected group served as the control group to which the oligonucleotide-treated group was compared.

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 35 as the average myotonia grade observed in four mice of each group.

Treatment with ISIS 445236 led to significant reduction in myotonia. Treatment with ISIS 444745 and ISIS 444746 also resulted in reduced myotonia in some of the tissues tested.

TABLE 35

Average reduction of myotonia in various muscles of antisense oligonucleotide-treated HSA$^{LR}$ mice

|  | PBS | ISIS 444745 | ISIS 444746 | ISIS 444749 | ISIS 445236 |
|---|---|---|---|---|---|
| Left quadriceps | 3.00 | 3.00 | 3.00 | 3.00 | 0.00 |
| Right quadriceps | 3.00 | 3.00 | 3.00 | 3.00 | 0.00 |
| Left gastrocnemius | 3.00 | 2.75 | 3.00 | 3.00 | 0.00 |
| Right gastrocnemius | 3.00 | 2.75 | 2.75 | 3.00 | 0.00 |
| Left Tibialis anterior | 3.00 | 2.25 | 2.75 | 2.75 | 0.00 |
| Right Tibialis anterior | 3.00 | 2.25 | 2.50 | 2.75 | 0.00 |
| Lumbar paraspinals | 3.00 | 3.00 | 3.00 | 3.00 | 0.00 |

Example 22

Dose-Dependent Inhibition of Long CUG Repeat mRNA (HSA$^{LR}$ Mice) and a Short CUG Repeat (HSA$^{SR}$ Mice) by Subcutaneous Administration in Transgenic Mice Dose-dependent inhibition of mRNA transcripts containing a long CUG repeat (HSA$^{LR}$ mice) and a short CUG repeat (HSA$^{SR}$ mice), was evaluated. HSA-short repeat (HSA$^{SR}$) mice express the identical transgene as the HSA$^{LR}$ mice, except that 5 instead of 250 CUG repeats are inserted in the 3' UTR. HSA$^{SR}$ mice do not have myotonia, splicing changes, or any other observable myotonia phenotype. ISIS 445236 was used in this assay.

Treatment

HSA$^{LR}$ mice were divided into four treatment groups. The first three groups received subcutaneous injections of ISIS 445236 at doses of 2.5 mg/kg, 8.5 mg/kg or 25.0 mg/kg twice per week for 4 weeks. The fourth group received subcutaneous injections of PBS twice per week for 4 weeks. The PBS-injected group served as the control group to which the oligonucleotide-treated group was compared. HSA$^{SR}$ mice were also divided into four groups and similarly treated.

Inhibition of Alpha1 Actin RNA

Twenty four hours after the final dose, the animals were sacrificed and tissue from the quadriceps muscles (left and right), gastrocnemius muscles (left and right), and tibialis anterior muscles (left and right) was isolated. RNA was isolated for real-time PCR analysis of alpha1 actin and normalized to 18s RNA. The results are presented in Tables 36 and 37 and are expressed as percent inhibition of alpha1 actin transcript, relative to the control. Greater inhibition of the nuclear-retained long repeat in the muscle of HSA$^{LR}$ mice was achieved compared with the non-nuclear-retained short repeat in the muscle of HSA$^{SR}$ mice.

TABLE 36

Percent inhibition of human alpha1 actin RNA transcript in HSA$^{LR}$ mice

| Dose (mg/kg) | Quadriceps | Gastrocnemius | Tibialis anterior |
|---|---|---|---|
| 2.5 | 24 | 36 | 46 |
| 8.5 | 53 | 66 | 59 |
| 25 | 86 | 86 | 90 |

TABLE 37

Percent inhibition of human alpha1 actin RNA transcript in HSA$^{SR}$ mice

| Dose (mg/kg) | Quadriceps | Gastrocnemius | Tibialis anterior |
|---|---|---|---|
| 2.5 | 15 | 14 | 0 |
| 8.5 | 30 | 11 | 0 |
| 25 | 59 | 48 | 54 |

Example 23

In vivo Antisense Inhibition of Human DMPK in Transgenic Mice

LC15 mice, Line A, are transgenic mice containing the entire human DMPK 3'UTR (developed by Wheeler et al, University of Rochester). The mice are the second generation of mice backcrossed to an FVB background. The transgene is expressed in the mice as a CUG repeat RNA, which is retained in the nucleus, forming nuclear inclusions or foci, similar to that seen in human tissue samples of patients with myotonic dystrophy (DM1). There are 350-400 CUG repeats in the DMPK transgene. These mice display early signs of DM1 and do not display any myotonia in their muscle tissues.

ISIS 445569, ISIS 444404, ISIS 444436 and ISIS 473810, which demonstrated statistically significant dose-dependent inhibition in vitro (see Example 5), were evaluated for their ability to reduce human DMPK RNA transcript in vivo.

Treatment

LC15, Line A mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into five treatment groups. The first three groups received subcutaneous injections of ISIS 445569, ISIS 444404 or ISIS 444436 at a dose of 25 mg/kg twice per week for 4 weeks. The fourth group received subcutaneous injections of ISIS 473810 at a dose of 12.5 mg/kg twice per week for 4 weeks. The fifth group received subcutaneous injections of PBS twice weekly for 4 weeks. The PBS-injected group served as the control group to which the oligonucleotide-treated group was compared.

Inhibition of DMPK RNA

Twenty four hours after the final dose, the animals were sacrificed and tissue from the quadriceps muscles was isolated. RNA was isolated for real-time PCR analysis of DMPK and normalized to 18s RNA. As presented in Table 38, treatment with antisense oligonucleotides reduced human DMPK RNA transcript expression. The results are expressed as percent inhibition of DMPK transcript, relative to the PBS control.

TABLE 38

Antisense inhibition of human DMPK RNA transcript in LC15 mice

| ISIS No | mg/kg/wk | % inhibition |
|---|---|---|
| 444404 | 50 | 20 |
| 444404 | 50 | 55 |
| 444436 | 50 | 41 |
| 473810 | 25 | 56 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. Since LC15 mice do not have myotonia, neither the control group nor the treatment groups displayed any myotonia in any muscle tested.

Example 24

In vivo Antisense Inhibition of Human DMPK in Transgenic Mice

LC15 mice, Line D, are transgenic mice containing the entire human DMPK 3'UTR (developed by Wheeler et al, University of Rochester). The mice are the third generation of mice backcrossed to an FVB background. The transgene is expressed in the mice as a CUG repeat RNA, which is retained in the nucleus, forming nuclear inclusions or foci, similar to that seen in human tissue samples of patients with myotonic dystrophy (DM1). There are 350-400 CUG repeats in the DMPK transgene. These mice display early signs of DM1 and do not display any myotonia in their muscle tissues.

ISIS 445569, ISIS 444404, ISIS 444436 and ISIS 473810 were further evaluated for their ability to reduce human DMPK RNA transcript in vivo.

Treatment

LC15, Line D mice were maintained on a 12-hour light/dark cycle and fed ad libitum normal Purina mouse chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

The mice were divided into six treatment groups. The first three groups received subcutaneous injections of ISIS 445569, ISIS 444404 or ISIS 444436 at a dose of 25.00 mg/kg twice per week for 4 weeks. The fourth group received subcutaneous injections of ISIS 473810 at a dose of 12.50 mg/kg twice per week for 4 weeks. The fifth group received subcutaneous injections of ISIS 473810 at a dose of 6.25 mg/kg twice per week for 4 weeks. The sixth group received subcutaneous injections of PBS twice weekly for 4 weeks. The PBS-injected group served as the control group to which the oligonucleotide-treated group was compared.

Inhibition of DMPK RNA

Twenty four hours after the final dose, the animals were sacrificed and tissue from the quadriceps muscles was isolated. RNA was isolated for real-time PCR analysis of DMPK and normalized to 18s RNA. As presented in Table 39, treatment with antisense oligonucleotides reduced human DMPK RNA transcript expression. The results are expressed as percent inhibition of DMPK transcript, relative to the PBS control.

The results indicate that treatment with the antisense oligonucleotides resulted in inhibition of DMPK mRNA in the mice.

TABLE 39

Antisense inhibition of human DMPK RNA transcript in LC15 mice

| ISIS No | mg/kg/wk | % inhibition |
|---|---|---|
| 444404 | 50.00 | 24 |
| 444404 | 50.00 | 30 |
| 444436 | 50.00 | 17 |
| 473810 | 25.00 | 7 |
| 473810 | 12.50 | 18 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. Since LC15 mice do not have myotonia, neither the control group nor the treatment groups displayed any myotonia in any muscle tested.

Example 25

In vivo Antisense Inhibition of Human DMPK in SXL Transgenic Mouse Model

Using hDMPK-targeting ASOs 444401 and 299471 target knockdown in soleus muscle was measured in SXL mice.

The SXL mouse is transgenic for the entire DMPK gene and promoter and contains a 1000 CUG repeat sequence in the 3'UTR of DMPK gene. Mice were dosed 50 mg/kg twice weekly for 4 weeks (n=3 mice per group, except n=2 for saline-injected controls). Results of Taqman assays demonstrated that treatment with either ISISI 444401 or ISIS 299471 significantly reduced mut-hDMPK mRNA levels but had negligible effect on endogenous mouse Dmpk mRNA levels.

Therefore, ISIS 444401 and ISIS 299471 selectively target human DMPK mRNA transcript.

Example 26

Duration of Action of Antisense Inhibition by an Oligonucleotide Targeting Human Alpha1 Actin in Transgenic Mice The duration of action of antisense inhibition of human alpha1 actin RNA transcript by ISIS 190401 in HSA$^{LR}$ mice was evaluated.

Treatment

HSA$^{LR}$ mice received subcutaneous injections of ISIS 190401 at a dose of 25 mg/kg twice per week for 4 weeks. A control group received subcutaneous injections of PBS twice per week for 4 weeks. The PBS-injected group served as the control group to which the oligonucleotide-treated group was compared. The mice were analyzed 15 weeks after administration of the last dose.

Inhibition of Alpha1 Actin RNA

Fifteen weeks after the final dose, the animals were sacrificed and tissue from the quadriceps muscles, gastrocnemius muscles, and tibialis anterior muscles was isolated. RNA was isolated for real-time PCR analysis of alpha1 actin and normalized to 18s RNA. As presented in Table 40, treatment with ISIS 190401 reduced human alpha1 actin RNA transcript expression, and this effect was sustained at least for 15 weeks. The results are expressed as percent inhibition of alpha1 actin transcript, relative to the PBS control.

Treatment with ISIS 190401 resulted in significant inhibition of alpha1 actin mRNA levels under the conditions specified above.

TABLE 40

Antisense inhibition of human alpha1 actin
RNA transcript in HSA$^{LR}$ mice

| Muscle Type | % inhibition |
| --- | --- |
| Quadriceps | 74 |
| Gastrocnemius | 81 |
| Tibialis anterior | 75 |

Assessment of Myotonia by Electromyography

Electromyography on left and right quadriceps, left and right gastrocnemius muscles, left and right tibialis anterior muscles and lumbar paraspinals muscles was performed as previously described (Kanadia et al, 2003, Science, 302: 1978-1980) by using 30 gauge concentric needle electrodes and a minimum of 10 needle insertions for each muscle. The data is presented in Table 41 as the average myotonia grade observed in four mice of each group and demonstrates significant reduction of myotonia in mice treated with ISIS 190401. Therefore, the effect of antisense inhibition of alpha actin by ISIS 190401 was sustained at least for 15 weeks.

TABLE 41

Average reduction of myotonia in various muscles
of antisense oligonucleotide-treated HSA$^{LR}$ mice

| | PBS | ISIS 190401 |
| --- | --- | --- |
| Left quadriceps | 3.0 | 0.0 |
| Right quadriceps | 3.0 | 0.0 |
| Left gastrocnemius | 2.5 | 0.0 |
| Right gastrocnemius | 2.5 | 0.0 |
| Left Tibialis anterior | 2.5 | 0.0 |
| Right Tibialis anterior | 2.5 | 0.0 |
| Lumbar paraspinals | 2.5 | 0.0 |

Correction of Alternative Splicing

To evaluate the effect of ISIS 190401 on alternative splicing of Serca1, total RNA purified from the tibialis anterior gastrocnemius, and quadriceps muscle was analyzed in a procedure similar to that described in Example 13.

In PBS treated HSA$^{LR}$ mice, Serca1 splicing is dysregulated as demonstrated by exon 22 exclusion. Treatment with ISIS 190401 resulted in complete inclusion and normalization of alternative splicing of exon 22 of the Serca1 gene in all three muscle types, which was sustained even after 15 weeks.

Therefore, antisense inhibition of alpha1 actin corrected Serca1 splicing dysregulation, which indicates that treatment with antisense oligonucleotide reduced accumulation of CUGexp in the nuclear foci. Reduced accumulation of CUGexp in the nuclear foci corrects MBLN1 sequestration thereby allowing normal splicing to occur.

Example 27

Microarray Analysis of Transcriptomic Effect of Antisense Inhibition of Human Actin Expression of actin mRNA with expanded CUG repeats causes extensive remodeling of the muscle transcriptome. To evaluate the overall transcriptomic effects of ISIS 190401 and ISIS 445236, microarray analyses was utilized in HSA$^{LR}$ mice.

Treatment

HSA$^{LR}$ mice received subcutaneous injections of ISIS 190401 or ISIS 445236 at a dose of 25 mg/kg twice per week for 4 weeks. A control group received subcutaneous injections of PBS twice per week for 4 weeks. The PBS-injected group served as the control group to which the oligonucleotide-treated group was compared.

Transcriptome Analysis by Microarray

RNA was isolated from the quadriceps muscle of wild-type or HSA$^{LR}$ mice. RNA integrity was verified using an Agilent Bioanalyzer (RNA integrity number >7.5). RNA was processed to complementary RNA (cRNA) and hybridized on microbeads using MouseRef-8 v2.0 Expression BeadChip Kits (Illumina, San Diego), according to the manufacturer's recommendations. Image data were quantified using BeadStudio software (Illumina). Signal intensities were quantile normalized. Row-specific offsets were used to avoid any values of less than 2 prior to normalization. Data from all probe sets with 6 or more nucleotides of CUG, UGC, or GCU repeats was suppressed to eliminate the possibility that expanded repeats in the hybridization mixture (CAG repeats in cRNA originating from CUG repeats in the mRNA) could cross-hybridize with repeat sequences in the probes. To eliminate genes whose expression was not readily quantified on the arrays, probes showing a P value for detection probability of <0.1 were suppressed in all samples. Comparisons between groups were summarized and rank-ordered by fold-changes of mean expression level and t tests. The software package R (Butler et al. *Diabetes*. 2002; 51: 1028-34) was used to perform principal components analysis (Levin et al. In *Antisense Drug Technology: Principles, Strategies, and Applications*, S. T. Crooke, Ed. (CRC Press, Boca Raton, 2008), pp 183-215; Geary et al. *Drug Metab. Dispos.* 2003; 31: 1419-28) on wild-type, ISIS oligonucleotide-treated, and PBS-treated microarray samples. The principle components allowed the capture of the majority of the expression variation in each sample within 3 dimensions. The first three principal components of each sample were plotted.

The principle component analysis of untreated wild-type and HSA$^{LR}$ mice demonstrated segregation of HSA$^{LR}$ away from wild-type mice, in widely separated clusters. In contrast, antisense oligonucleotide-treated HSA$^{LR}$ mice clustered more closely to wild-type mice, suggesting an overall trend for transcriptome normalization. Comparisons of HSA$^{LR}$ transgenic mice with wild-type mice identified 93 transcripts whose expression levels were altered more than two-fold (P<0.0001), as presented in Table 42, below. The extent of dysregulation for these transcripts was reduced or normalized for antisense oligonucleotides (88% dysregulated transcripts responded to ISIS 445236, P<0.05 for ISIS 445236 vs. PBS control, whereas 90% responded to ISIS 190401).

In order to consider transcripts that have off-target knockdown, all transcripts whose expression was reduced in antisense oligonucleotide-treated HSA$^{LR}$ mice were identified (>two-fold reduction by either oligonucleotide, P<0.0001, n=41 transcripts). All transcripts that were down-regulated by these criteria demonstrated upregulation in HSA$^{LR}$ mice. The only exception, collagen 6 alpha2, is unlikely to result from off-target cleavage because it was down-regulated by the two antisense oligonucleotides with non-overlapping sequences.

These results indicate that treatment with antisense oligonucleotides for 4 weeks resulted in a general improvement of the muscle transcriptome without any evidence for off-target effects.

TABLE 42

Comparisons of HSA$^{LR}$ transgenic mice with wild-type mice identified 93 transcripts

| Transcript | Fold-change HSALR-saline vs. WT | t test HSALR-Saline vs. WT | Fold-change HSALR-190104 vs. HSALR-saline | t test HASLR 190401 vs. HSALR-saline | Fold-change HSALR-190401 vs. WT | t test HSALR-190401 vs. WT | Fold-change HSALR-445236 vs. HSALR-saline | t test HSALR-445236 vs. HSALR-saline | Fold-change HSALR-445236 vs. WT | t test HSALR-445236 vs. WT |
|---|---|---|---|---|---|---|---|---|---|---|
| OSBPL10 | 15.11 | 0.0000 | 0.46 | 0.0023 | 6.95 | 0.0008 | 0.39 | 0.0007 | 5.92 | 0.0002 |
| FBXL13 | 12.12 | 0.0000 | 0.49 | 0.0159 | 5.91 | 0.0385 | 0.65 | 0.0255 | 7.93 | 0.0026 |
| NGFR | 11.57 | 0.0000 | 0.23 | 0.0001 | 2.66 | 0.0314 | 0.16 | 0.0000 | 1.84 | 0.0133 |
| SLC1A1 | 9.39 | 0.0000 | 0.39 | 0.0001 | 3.66 | 0.0001 | 0.30 | 0.0001 | 2.85 | 0.0116 |
| CXADR | 9.13 | 0.0000 | 0.14 | 0.0000 | 1.30 | 0.6119 | 0.21 | 0.0001 | 1.94 | 0.2244 |
| NFATC2 | 8.48 | 0.0000 | 0.32 | 0.0002 | 2.67 | 0.0043 | 0.22 | 0.0001 | 1.84 | 0.0394 |
| ATP1B4 | 7.02 | 0.0000 | 0.24 | 0.0000 | 1.68 | 0.0021 | 0.24 | 0.0000 | 1.70 | 0.0091 |
| UCHL1 | 6.80 | 0.0000 | 0.71 | 0.0168 | 4.86 | 0.0005 | 0.72 | 0.1187 | 4.91 | 0.0090 |
| TEAD4 | 6.76 | 0.0000 | 0.50 | 0.0030 | 3.39 | 0.0085 | 0.30 | 0.0004 | 2.06 | 0.1213 |
| TAS1R1 | 6.72 | 0.0000 | 0.28 | 0.0003 | 1.91 | 0.1857 | 0.43 | 0.0002 | 2.88 | 0.0047 |
| MUSTN1 | 6.52 | 0.0000 | 0.31 | 0.0000 | 2.01 | 0.0006 | 0.33 | 0.0000 | 2.15 | 0.0115 |
| IRF5 | 6.01 | 0.0000 | 0.21 | 0.0000 | 1.28 | 0.0556 | 0.33 | 0.0001 | 1.96 | 0.0035 |
| CRIP3 | 5.82 | 0.0000 | 0.33 | 0.0000 | 1.92 | 0.0151 | 0.29 | 0.0001 | 1.67 | 0.1470 |
| TAL2 | 5.75 | 0.0000 | 0.20 | 0.0001 | 1.13 | 0.7717 | 0.36 | 0.0002 | 2.08 | 0.0274 |
| ORF63 | 5.39 | 0.0000 | 0.27 | 0.0001 | 1.45 | 0.0206 | 0.47 | 0.0018 | 2.51 | 0.0066 |
| COPG | 5.05 | 0.0000 | 0.30 | 0.0000 | 1.53 | 0.0218 | 0.25 | 0.0001 | 1.25 | 0.3617 |
| CAMK1D | 4.92 | 0.0000 | 0.23 | 0.0002 | 1.12 | 0.8157 | 0.27 | 0.0000 | 1.32 | 0.2449 |
| HSPA2 | 4.76 | 0.0000 | 0.43 | 0.0000 | 2.02 | 0.0079 | 0.42 | 0.0000 | 2.02 | 0.0197 |
| CAMK2D | 4.70 | 0.0000 | 0.36 | 0.0001 | 1.70 | 0.0493 | 0.45 | 0.0004 | 2.12 | 0.0095 |
| CNTNAP2 | 4.49 | 0.0000 | 0.58 | 0.0001 | 2.59 | 0.0000 | 0.67 | 0.0007 | 3.02 | 0.0000 |
| TTC7 | 4.33 | 0.0000 | 0.38 | 0.0000 | 1.63 | 0.0085 | 0.68 | 0.0468 | 2.96 | 0.0126 |
| CD276 | 4.08 | 0.0001 | 0.36 | 0.0001 | 1.47 | 0.1613 | 0.59 | 0.0029 | 2.39 | 0.0072 |
| USH1C | 4.07 | 0.0000 | 0.50 | 0.0011 | 2.04 | 0.0077 | 0.38 | 0.0029 | 1.55 | 0.2881 |
| LRP11 | 4.03 | 0.0000 | 0.55 | 0.0017 | 2.24 | 0.0011 | 0.55 | 0.0006 | 2.23 | 0.0000 |
| PHLDA3 | 3.96 | 0.0000 | 0.40 | 0.0001 | 1.60 | 0.0019 | 0.36 | 0.0001 | 1.42 | 0.0609 |
| HSPB7 | 3.80 | 0.0000 | 0.30 | 0.0000 | 1.14 | 0.5358 | 0.30 | 0.0000 | 1.15 | 0.4474 |
| TRIT1 | 3.74 | 0.0000 | 0.43 | 0.0000 | 1.62 | 0.0003 | 0.31 | 0.0000 | 1.16 | 0.1043 |
| PCNX | 3.66 | 0.0000 | 0.37 | 0.0002 | 1.34 | 0.1628 | 0.42 | 0.0001 | 1.53 | 0.0105 |
| 3632451O06RIK | 3.51 | 0.0000 | 0.81 | 0.1094 | 2.83 | 0.0025 | 0.71 | 0.0015 | 2.51 | 0.0002 |
| AMHR2 | 3.46 | 0.0000 | 0.45 | 0.0001 | 1.56 | 0.0037 | 0.52 | 0.0003 | 1.79 | 0.0016 |
| SNX13 | 3.27 | 0.0000 | 0.47 | 0.0000 | 1.55 | 0.0007 | 0.44 | 0.0000 | 1.42 | 0.0003 |
| ATP9A | 3.26 | 0.0000 | 0.60 | 0.0001 | 1.96 | 0.0024 | 0.42 | 0.0002 | 1.38 | 0.2009 |
| D030028O16RIK | 3.22 | 0.0000 | 0.53 | 0.0011 | 1.70 | 0.0104 | 0.48 | 0.0001 | 1.56 | 0.0007 |
| RPS6KA3 | 3.09 | 0.0000 | 0.38 | 0.0000 | 1.17 | 0.1845 | 0.44 | 0.0001 | 1.37 | 0.0321 |
| GCA | 3.00 | 0.0000 | 0.70 | 0.0031 | 2.09 | 0.0005 | 0.74 | 0.0103 | 2.22 | 0.0006 |
| PACRG | 2.89 | 0.0001 | 0.51 | 0.0002 | 1.46 | 0.0063 | 0.46 | 0.0001 | 1.34 | 0.0229 |
| SPSB2 | 2.88 | 0.0001 | 0.33 | 0.0000 | 0.95 | 0.6599 | 0.37 | 0.0000 | 1.07 | 0.6216 |
| POU4F1 | 2.83 | 0.0000 | 0.42 | 0.0000 | 1.19 | 0.2046 | 0.60 | 0.0007 | 1.68 | 0.0074 |
| STRN4 | 2.72 | 0.0000 | 0.38 | 0.0000 | 1.03 | 0.8900 | 0.46 | 0.0000 | 1.25 | 0.2128 |
| NCAM1 | 2.67 | 0.0001 | 0.70 | 0.0259 | 1.87 | 0.0135 | 0.54 | 0.0006 | 1.43 | 0.0343 |
| A930018M24Rik | 2.65 | 0.0001 | 0.58 | 0.0058 | 1.53 | 0.0727 | 0.43 | 0.0002 | 1.13 | 0.3919 |
| TUBA4A | 2.60 | 0.0000 | 0.42 | 0.0000 | 1.09 | 0.1806 | 0.50 | 0.0000 | 1.31 | 0.0041 |
| 1AP | 2.57 | 0.0000 | 0.57 | 0.0002 | 1.46 | 0.0108 | 0.59 | 0.0016 | 1.52 | 0.0333 |
| ANKRD40 | 2.56 | 0.0000 | 0.63 | 0.0155 | 1.60 | 0.0683 | 0.57 | 0.0002 | 1.46 | 0.0047 |

TABLE 42-continued

Comparisons of HSA$^{LR}$ transgenic mice with wild-type mice identified 93 transcripts

| Transcript | Fold-change HSALR-saline vs. WT | t test HSALR-Saline vs. WT | Fold-change HSALR-190104 vs. HSALR-saline | t test HASLR 190401 vs. HSALR-saline | Fold-change HSALR-190401 vs. HSALR-saline | t test HSALR-190401 vs. WT | Fold-change HSALR-445236 vs. HSALR-saline | t test HSALR-445236 vs. HSALR-saline | Fold-change HSALR-445236 vs. WT | t test HSALR-445236 vs. WT |
|---|---|---|---|---|---|---|---|---|---|---|
| UVRAG | 2.48 | 0.0000 | 0.59 | 0.0000 | 1.48 | 0.0005 | 0.52 | 0.0000 | 1.28 | 0.0165 |
| HIST1H4H | 2.46 | 0.0001 | 0.55 | 0.0001 | 1.34 | 0.0474 | 0.65 | 0.0014 | 1.60 | 0.0125 |
| EPS15 | 2.44 | 0.0000 | 0.61 | 0.0001 | 1.50 | 0.0057 | 0.77 | 0.0043 | 1.87 | 0.0007 |
| PANX1 | 2.41 | 0.0001 | 0.46 | 0.0004 | 1.11 | 0.4311 | 0.36 | 0.0000 | 0.87 | 0.0561 |
| CALML4 | 2.41 | 0.0001 | 0.45 | 0.0008 | 1.10 | 0.6994 | 0.67 | 0.0154 | 1.62 | 0.0538 |
| ASPH | 2.40 | 0.0000 | 0.40 | 0.0000 | 0.95 | 0.6969 | 0.44 | 0.0000 | 1.05 | 0.7267 |
| CREB3L2 | 2.37 | 0.0001 | 0.71 | 0.0287 | 1.67 | 0.0416 | 0.65 | 0.0051 | 1.54 | 0.0410 |
| TRAF3 | 2.32 | 0.0001 | 0.50 | 0.0001 | 1.16 | 0.2851 | 0.57 | 0.0001 | 1.32 | 0.0481 |
| CMYA1 | 2.30 | 0.0000 | 0.44 | 0.0007 | 1.02 | 0.9450 | 0.44 | 0.0000 | 1.01 | 0.9265 |
| ADAMTSL5 | 2.30 | 0.0001 | 0.48 | 0.0000 | 1.11 | 0.3365 | 0.53 | 0.0004 | 1.22 | 0.1827 |
| HS2ST1 | 2.27 | 0.0001 | 0.64 | 0.0002 | 1.44 | 0.0223 | 0.74 | 0.0041 | 1.68 | 0.0062 |
| HIST1H4J | 2.21 | 0.0000 | 0.59 | 0.0000 | 1.31 | 0.0283 | 0.72 | 0.0002 | 1.60 | 0.0023 |
| SPSB1 | 2.20 | 0.0000 | 0.53 | 0.0005 | 1.16 | 0.2409 | 0.48 | 0.0000 | 1.05 | 0.3088 |
| LANCL1 | 2.20 | 0.0000 | 0.63 | 0.0002 | 1.39 | 0.0002 | 0.66 | 0.0006 | 1.46 | 0.0005 |
| KCNC4 | 2.16 | 0.0000 | 0.91 | 0.3892 | 1.96 | 0.0036 | 0.98 | 0.8712 | 2.12 | 0.0029 |
| PRRC1 | 2.16 | 0.0000 | 0.57 | 0.0001 | 1.23 | 0.0324 | 0.59 | 0.0000 | 1.26 | 0.0070 |
| MID1IP1 | 2.13 | 0.0001 | 1.27 | 0.0161 | 2.70 | 0.0001 | 1.09 | 0.4336 | 2.32 | 0.0014 |
| DICER1 | 2.13 | 0.0000 | 0.65 | 0.0006 | 1.39 | 0.0051 | 0.69 | 0.0018 | 1.47 | 0.0035 |
| IKBKB | 2.10 | 0.0001 | 0.74 | 0.0240 | 1.56 | 0.0262 | 0.78 | 0.0039 | 1.64 | 0.0015 |
| D5WSU178E | 2.10 | 0.0000 | 0.86 | 0.1447 | 1.80 | 0.0049 | 0.88 | 0.0352 | 1.84 | 0.0002 |
| ZFP106 | 2.08 | 0.0000 | 0.53 | 0.0000 | 1.11 | 0.1324 | 0.58 | 0.0002 | 1.20 | 0.0706 |
| B930041F14RIK | 2.06 | 0.0000 | 0.71 | 0.0002 | 1.47 | 0.0000 | 0.72 | 0.0030 | 1.49 | 0.0025 |
| FHL1 | 2.04 | 0.0000 | 0.58 | 0.0000 | 1.17 | 0.1332 | 0.40 | 0.0000 | 0.81 | 0.0815 |
| UHRF1BP1L | 2.04 | 0.0001 | 0.78 | 0.0315 | 1.59 | 0.0071 | 0.68 | 0.0024 | 1.38 | 0.0151 |
| PHCA | 2.02 | 0.0000 | 0.64 | 0.0001 | 1.29 | 0.0354 | 0.74 | 0.0070 | 1.50 | 0.0145 |
| B230312A22RIK | 2.02 | 0.0000 | 0.79 | 0.0022 | 1.59 | 0.0004 | 0.77 | 0.0019 | 1.56 | 0.0007 |
| PPP2R5C | 2.01 | 0.0000 | 0.59 | 0.0001 | 1.16 | 0.0161 | 0.66 | 0.0017 | 1.32 | 0.0177 |
| UCK2 | 2.01 | 0.0001 | 0.70 | 0.0004 | 1.41 | 0.0129 | 0.64 | 0.0001 | 1.28 | 0.0510 |
| LEPROTL1 | 0.50 | 0.0000 | 1.45 | 0.0013 | 0.72 | 0.0004 | 1.47 | 0.0011 | 0.73 | 0.0005 |
| COPS7A | 0.49 | 0.0000 | 1.35 | 0.0645 | 0.66 | 0.0039 | 1.49 | 0.0026 | 0.73 | 0.0016 |
| PRM17 | 0.48 | 0.0001 | 1.51 | 0.2023 | 0.73 | 0.1585 | 1.34 | 0.0445 | 0.65 | 0.0002 |
| LDB3 | 0.47 | 0.0000 | 1.55 | 0.0550 | 0.73 | 0.0607 | 1.57 | 0.0010 | 0.74 | 0.0055 |
| LOC100046120 | 0.47 | 0.0000 | 1.31 | 0.0077 | 0.61 | 0.0000 | 1.27 | 0.0381 | 0.60 | 0.0002 |
| LOC677317 | 0.45 | 0.0001 | 1.49 | 0.0004 | 0.68 | 0.0012 | 1.93 | 0.0011 | 0.88 | 0.2082 |
| LDB2 | 0.45 | 0.0000 | 1.73 | 0.0424 | 0.78 | 0.1234 | 1.23 | 0.0817 | 0.56 | 0.0000 |
| SUM03 | 0.44 | 0.0000 | 1.70 | 0.0123 | 0.74 | 0.0223 | 1.37 | 0.0960 | 0.60 | 0.0023 |
| LRRC24 | 0.43 | 0.0001 | 1.89 | 0.0009 | 0.82 | 0.0212 | 1.42 | 0.0898 | 0.61 | 0.0041 |
| HNRPH1 | 0.42 | 0.0000 | 1.64 | 0.0077 | 0.69 | 0.0094 | 1.70 | 0.0057 | 0.71 | 0.0144 |
| ARMETL1 | 0.38 | 0.0000 | 2.58 | 0.0000 | 0.98 | 0.7666 | 2.70 | 0.0000 | 1.02 | 0.7109 |
| LOC100041504 | 0.37 | 0.0000 | 2.02 | 0.0001 | 0.75 | 0.0061 | 1.84 | 0.0040 | 0.68 | 0.0094 |
| MMP9 | 0.32 | 0.0000 | 2.40 | 0.0006 | 0.77 | 0.0340 | 1.37 | 0.1834 | 0.44 | 0.0009 |
| CBFB | 0.28 | 0.0000 | 2.66 | 0.0304 | 0.75 | 0.1852 | 1.94 | 0.0056 | 0.55 | 0.0004 |
| MDH2 | 0.24 | 0.0000 | 1.20 | 0.0473 | 0.29 | 0.0000 | 1.12 | 0.1037 | 0.27 | 0.0000 |
| APCDD1 | 0.20 | 0.0000 | 1.98 | 0.2157 | 0.39 | 0.0059 | 4.55 | 0.0001 | 0.90 | 0.2873 |
| LOC654842 | 0.19 | 0.0000 | 1.28 | 0.1712 | 0.24 | 0.0000 | 1.07 | 0.8807 | 0.20 | 0.0001 |
| F2RL3 | 0.15 | 0.0000 | 5.78 | 0.0001 | 0.86 | 0.1901 | 4.92 | 0.0004 | 0.73 | 0.0310 |
| EIF3H | 0.13 | 0.0000 | 1.99 | 0.2185 | 0.26 | 0.0001 | 1.86 | 0.1997 | 0.24 | 0.0000 |
| AVIL | 0.12 | 0.0000 | 4.22 | 0.0156 | 0.52 | 0.0081 | 1.88 | 0.2270 | 0.23 | 0.0001 |
| ACTC1 | 0.08 | 0.0000 | 1.42 | 0.0346 | 0.11 | 0.0000 | 6.07 | 0.0098 | 0.48 | 0.0087 |

What is claimed is:

1. A method of treating an animal having type 1 myotonic dystrophy comprising administering to the animal a therapeutically effective amount of a compound comprising an oligonucleotide consisting of 10 to 30 linked nucleosides targeted to a DMPK nucleic acid, wherein the oligonucleotide has a nucleobase sequence that is at least 90% complementary to a non-CUG repeat region of SEQ ID NO: 1 or SEQ ID NO: 2 as measured over the entirety of the oligonucleotide, wherein the compound reduces myotonia or reduces spliceopathy in the animal.

2. The method of claim 1, wherein the animal is a human.

3. The method of claim 2, wherein myotonia is reduced by at least 25%.

4. The method of claim 3, wherein myotonia is reduced in any of the quadriceps muscle, the gastrocnemius muscle, or the tibialis anterior muscle.

5. The method of claim 2, wherein the oligonucleotide has a nucleobase sequence that is 100% complementary to SEQ ID NO: 1 or SEQ ID NO: 2.

6. The method of claim 1, wherein the oligonucleotide is a modified oligonucleotide.

7. The method of claim 6, wherein the modified oligonucleotide is a single-stranded oligonucleotide.

8. The method of claim 7, wherein the single-stranded modified oligonucleotide is a gapmer.

9. The method of claim 7, wherein at least one internucleoside linkage of the modified oligonucleotide is a modified linkage.

10. The method of claim 9, wherein the modified internucleoside linkage is a phosphorothioate internucleoside linkage.

11. The method of claim 9, wherein each internucleoside linkage of the modified oligonucleotide is a modified internucleoside linkage.

12. The method of claim 11, wherein the modified internucleoside linkage is a phosphorothioate internucleoside linkage.

13. The method of claim 9, wherein at least one internucleoside linkage of the modified oligonucleotide is a phosphorothioate internucleoside linkage and at least one internucleoside linkage of the modified oligonucleotide is a phosphodiester internucleoside linkage.

14. The method of claim 7, wherein at least one nucleobase of the modified oligonucleotide is a modified nucleobase.

15. The method of claim 14, wherein the modified nucleobase is a 5-methylcytosine.

16. The method of claim 7, wherein at least one nucleoside of the modified oligonucleotide comprises a modified sugar.

17. The method of claim 16, wherein the modified sugar is a bicyclic sugar.

18. The method of claim 17, wherein the bicyclic sugar comprises a chemical bridge between the 4' and 2' positions of the sugar, wherein the chemical bridge is selected from: 4'—CH(R)—O—2' and 4'—(CH$_2$)$_2$—O—2', wherein R is independently H, C$_1$-C$_6$ alkyl, and C$_1$-C$_6$ alkoxy.

19. The method of claim 18, wherein the chemical bridge is 4'—CH(R)—O—2' and wherein R is methyl.

20. The method of claim 18, wherein the chemical bridge is 4'—CH(R)—O—2' and wherein R is H.

21. The method of claim 18, wherein the chemical bridge is 4'—CH(R)—O—2' and wherein R is —CH$_2$—O—CH$_3$.

22. The method of claim 16, wherein the modified sugar comprises a 2'—O-methoxyethyl group.

23. The method of claim 1, wherein the compound comprises the oligonucleotide covalently linked to a conjugate group.

24. The method of claim 1, wherein the oligonucleotide is a salt.

* * * * *

UNITED STATES PATENT AND TRADEMARK OFFICE
CERTIFICATE OF CORRECTION

PATENT NO. : 9,765,338 B2
APPLICATION NO. : 14/814174
DATED : September 19, 2017
INVENTOR(S) : C. Frank Bennett et al.

It is certified that error appears in the above-identified patent and that said Letters Patent is hereby corrected as shown below:

On the Title Page

Item [73], add "University Of Rochester, Rochester, NY (US)"

Signed and Sealed this
Eighteenth Day of October, 2022

Katherine Kelly Vidal
*Director of the United States Patent and Trademark Office*

SEQUENCE LISTING

<160> NUMBER OF SEQ ID NOS: 837

<210> SEQ ID NO 1
<211> LENGTH: 2877
<212> TYPE: DNA
<213> ORGANISM: Homo sapiens

<400> SEQUENCE: 1

```
agggggctg gaccaagggg tggggagaag gggaggaggc ctcggccggc cgcagagaga    60
agtggccaga gaggcccagg ggacagccag ggacaggcag acatgcagcc agggctccag   120
ggcctggaca ggggctgcca ggccctgtga caggaggacc ccgagccccc ggcccgggga   180
```

```
ggggccatgg tgctgcctgt ccaacatgtc agccgaggtg cggctgaggc ggctccagca    240
gctggtgttg gacccgggct tcctggggct ggagcccctg ctcgaccttc tcctgggcgt    300
ccaccaggag ctgggcgcct ccgaactggc ccaggacaag tacgtggccg acttcttgca    360
gtgggcggag cccatcgtgg tgaggcttaa ggaggtccga ctgcagaggg acgacttcga    420
gattctgaag gtgatcggac gcggggcgtt cagcgaggta gcggtagtga agatgaagca    480
gacgggccag gtgtatgcca tgaagatcat gaacaagtgg gacatgctga gaggggcga    540 ggtgtcgtgc ttccgtgagg agagggacgt gttggtgaat ggggaccggc ggtggatcac    600
gcagctgcac ttcgccttcc aggatgagaa ctacctgtac ctggtcatgg agtattacgt    660
gggcggggac ctgctgacac tgctgagcaa gtttggggag cggattccgg ccgagatggc    720
gcgcttctac ctggcggaga ttgtcatggc catagactcg gtgcaccggc ttggctacgt    780
gcacagggac atcaaacccg acaacatcct gctggaccgc tgtggccaca tccgcctggc    840
cgacttcggc tcttgcctca gctgcgggc agatggaacg gtgcggtcgc tggtggctgt    900 gggcaccca gactacctgt ccccgagat cctgcaggct gtgggcggtg ggcctgggac    960
aggcagctac gggcccgagt gtgactggtg ggcgctgggt gtattcgcct atgaaatgtt   1020
ctatgggcag acgcccttct acgcggattc cacggcggag acctatggca agatcgtcca   1080
ctacaaggag cacctctctc tgccgctggt ggacgaaggg gtccctgagg aggctcgaga   1140
cttcattcag cggttgctgt gtcccccgga gacacggctg ggccggggtg gagcaggcga   1200
cttccggaca catcccttct tctttggcct cgactgggat ggtctccggg acagcgtgcc   1260
cccctttaca ccggatttcg aaggtgccac cgacacatgc aacttcgact tggtggagga   1320
cgggctcact gccatggaga cactgtcgga cattcgggaa ggtgcgccgc taggggtcca   1380
cctgcctttt gtgggctact cctactcctg catggccctc agggacagtg aggtcccagg   1440
ccccacaccc atggaactgg aggccgagca gctgcttgag ccacacgtgc aagcgcccag   1500
cctggagccc tcggtgtccc cacaggatga aacagctgaa gtggcagttc cagcggctgt   1560
ccctgcggca gaggctgagg ccgaggtgac gctgcgggag ctccaggaag ccctggagga   1620
ggaggtgctc acccggcaga gcctgagccg ggagatggag gccatccgca cggacaacca   1680
gaacttcgcc agtcaactac gcgaggcaga ggctcggaac cgggacctag aggcacacgt   1740
ccggcagttg caggagcgga tggagttgct gcaggcagag ggagccacag ctgtcacggg   1800
ggtccccagt ccccgggcca cggatccacc ttcccatcta gatggccccc cggccgtggc   1860
tgtgggccag tgcccgctgg tggggccagg cccatgcac cgccgccacc tgctgctccc   1920
tgccagggtc cctaggcctg cctatcggga ggcgctttcc ctgctcctgt tcgccgttgt   1980
tctgtctcgt gccgccgccc tgggctgcat tgggttggtg gccacgccg ccaactcac    2040 cgcagtctgg cgccgcccag gagccgcccg cgctccctga accctagaac tgtcttcgac   2100
tccggggccc cgttggaaga ctgagtgccc ggggcacggc acagaagccg cgcccaccgc   2160
ctgccagttc acaaccgctc cgagcgtggg tctccgccca gctccagtcc tgtgatccgg   2220
gcccgccccc tagcggccgg ggagggaggg gccgggtccg cggccggcga acggggctcg   2280
aagggtcctt gtagccggga atgctgctgc tgctgctgct gctgctgctg ctgctgctgc   2340
tgctgctgct gctgctgctg ctggggggat cacagaccat ttctttcttt cggccaggct   2400
gaggccctga cgtggatggg caaactgcag gcctgggaag gcagcaagcc gggccgtccg   2460
tgttccatcc tccacgcacc cccacctatc gttggttcgc aaagtgcaaa gctttcttgt   2520
```

```
gcatgacgcc ctgctctggg gagcgtctgg cgcgatctct gcctgcttac tcgggaaatt      2580
tgcttttgcc aaacccgctt tttcggggat cccgcgcccc cctcctcact tgcgctgctc      2640
tcggagcccc agccggctcc gcccgcttcg gcggtttgga tatttattga cctcgtcctc      2700
cgactcgctg acaggctaca ggaccccccaa caaccccaat ccacgttttg gatgcactga     2760
gaccccgaca ttcctcggta tttattgtct gtccccacct aggaccccca ccccgaccc      2820 tcgcgaataa aaggccctcc atctgcccaa aaaaaaaaa aaaaaaaaaa aaaaaaa         2877
```

```
<210> SEQ ID NO 2
<211> LENGTH: 14411
<212> TYPE: DNA
<213> ORGANISM: Homo sapiens

<400> SEQUENCE: 2
```

```
ctcccagccc agcgcctccc acccctttc atagcaggaa aagccggagc ccagggaggg        60
aacggacctg cgagtcacac aactggtgac ccacaccagc ggctggagca ggaccctctt      120
ggggagaaga gcatcctgcc cgcagccagg gcccctcatc aaagtcctcg gtgtttttta     180
aattatcaga actgcccagg accacgtttc ccaggccctg cccagctggg actcctcggt     240
ccttgcctcc tagtttctca ggcctggccc tctcaaggcc caggcacccc aggccggttg     300
gaggccccga cttccactct ggagaaccgt ccaccctgga agaagagct cagattcctc      360 ttggctctcg gagccgcagg gagtgtgtct tcccgcgcca ccctccaccc ccgaaatgt      420 ttctgtttct aatcccagcc tgggcaggaa tgtggctccc cggccagggg ccaaggagct     480 attttgggt ctcgtttgcc cagggaggc ttggctccac cactttcctc ccccagcctt       540
tgggcagcag gtcacccctg ttcaggctct gagggtgccc cctcctggtc ctgtcctcac     600
caccccttcc ccacctcctg ggaaaaaaaa aaaaaaaaaa aaaaaagct ggtataaagc       660 agagagcctg agggctaaat ttaactgtcc gagtcggaat ccatctctga gtcacccaag      720
aagctgccct ggcctcccgt ccccttccca ggcctcaacc cctttctccc acccagcccc     780 aaccccccagc cctcacccc tagccccag ttctggagct tgtcgggagc aaggggggtgg    840 ttgctactgg gtcactcagc ctcaattggc cctgttttcag caatgggcag gttcttcttg    900
aaattcatca cacctgtggc ttcctctgtg ctctaccttt ttattggggt gacagtgtga     960
cagctgagat tctccatgca ttcccccctac tctagcactg aagggttctg aagggccctg   1020
gaaggaggga gcttgggggg ctggcttgtg agggggttaag gctgggaggc gggaggggggg   1080 ctggaccaag gggtgggggag aagggggagga ggcctcggcc ggccgcagag agaagtggcc   1140
agagaggccc aggggacagc cagggacagg cagacatgca gccagggctc cagggcctgg    1200
acaggggctg ccaggccctg tgacaggagg accccgagcc cccggccgg ggaggggccca     1260 tggtgctgcc tgtccaacat gtcagccgag gtgcggctga ggcggctcca gcagctggtg    1320
ttggacccgg gcttcctggg gctggagccc ctgctcgacc ttctcctggg cgtccaccag    1380
gagctgggcg cctccgaact ggcccaggac aagtacgtgg ccgacttctt gcagtggggt    1440
gagtgcctac cctcggggct cctgcagatg gggtgggggt ggggcaggag acaggtctgg    1500
gcacagaggc ctggctgttg ggggggcagg atggcaggat gggcatgggg agatcctccc    1560 atcctgggc tcagagtgtg gacctggcc ctggggcaac atttctctgt cctatgccac      1620
cactctggag gggcagagta aggtcagcag aggctagggt ggctgtgact cagagccatg    1680
gcttaggagt cacagcaggc taggctgcca acagcctccc atggcctctc tgcacccgc     1740 ctcagggtca gggtcagggt catgctggga gctccctctc ctaggaccct ccccccaaaa    1800
```

```
gtgggctcta tggccctctc ccctggtttc ctgtggcctg gggcaagcca ggagggccag    1860
catggggcag ctgccagggg cgcagccgac aggcaggtgt tcggcgccag cctctccagc    1920
tgccccaaca ggtgcccagg cactgggagg gcggtgactc acgcgggccc tgtgggagaa    1980
ccagctttgc agacaggcgc caccagtgcc cctcctctg cgatccagga gggacaactt    2040
tgggttcttc tgggtgtgtc tccttctttt gtaggttctg cacccacccc caccccagc    2100 cccaaagtct cggttcctat gagccgtgtg ggtcagccac cattcccgcc accccgggtc    2160
cctgcgtcct ttagttctcc tggcccaggg cctccaacct tccagctgtc ccacaaaacc    2220
ccttcttgca agggctttcc agggcctggg gccaggctg gaaggaggat gcttccgctt     2280
ctgccagctg ccttgtctgc ccacctcctc cccaagccca ggactcgggc tcactggtca    2340
ctggtttctt tcattcccag caccctgccc ctctggccct catatgtctg gcccagtg     2400 actggtgttt ggttttggc ctgtgtgtaa caaactgtgt gtgacacttg ttcctgttt     2460 ctccgccttc ccctgcttcc tcttgtgtcc atctcttct gacccaggcc tggttccttt    2520
ccctcctcct cccatttcac agatgggaag gtggaggcca agaagggcca ggccattcag    2580
cctctggaaa aaccttctcc caacctccca cagcccctaa tgactctcct ggcctccctt    2640
tagtagagga tgaagttggg ttggcagggt aaactgagac cgggtggggt aggggtctgg    2700
cgctcccggg aggagcactc cttttgtggc ccgagctgca tctcgcggcc cctcccctgc    2760
caggcctggg gcggggagg gggccagggt tcctgctgcc ttaaaagggc tcaatgtctt     2820
ggctctctcc tccctccccc gtcctcagcc ctggctggtt cgtccctgct ggcccactct    2880
cccggaaccc cccggaaccc ctctctttcc tccagaaccc actgtctcct ctccttccct    2940
cccctcccat acccatccct ctctccatcc tgcctccact tcttccaccc ccggagtcc    3000 aggcctccct gtccccacag tccctgagcc acaagcctcc accccagctg gtcccccacc    3060
caggctgccc agtttaacat tcctagtcat aggaccttga cttctgagag gcctgattgt    3120
catctgtaaa taaggggtag gactaaagca ctcctcctgg aggactgaga gatgggctgg    3180
accggagcac ttgagtctgg gatatgtgac catgctacct ttgtctccct gtcctgttcc    3240
ttcccccagc cccaaatcca gggttttcca aagtgtggtt caagaaccac ctgcatctga    3300
atctagaggt actggataca accccacgtc tgggccgtta cccaggacat tctacatgag    3360
aacgtggggg tggggccctg gctgcacctg aactgtcacc tggagtcagg gtggaaggtg    3420
gaagaactgg gtcttatttc cttctcccct tgttctttag ggtctgtcct tctgcagact    3480
ccgttacccc accctaacca tcctgcacac ccttggagcc ctctgggcca atgccctgtc    3540
ccgcaaaggg cttctcaggc atctcacctc tatgggaggg cattttggc ccccagaacc     3600 ttacacggtg tttatgtggg gaagccctg ggaagcagac agtcctaggg tgaagctgag     3660
aggcagagag aagggagac agacagaggg tggggctttc ccccttgtct ccagtgccct     3720
ttctggtgac cctcggttct tttccccac caccccccca gcggagccca tcgtggtgag     3780
gcttaaggag gtccgactgc agagggacga cttcgagatt ctgaaggtga tcggacgcgg    3840
ggcgttcagc gaggtaagcc gaaccggcg ggagcctgac ttgactcgtg gtgggcgggg     3900 catagggggtt ggggcgggc cttagaaatt gatgaatgac cgagccttag aacctagggc    3960
tgggctggag gcggggcttg ggaccaatgg gcgtggtgtg gcaggtgggg cggggccacg    4020
gctgggtgca gaagcgggtg gagttgggtc tgggcgagcc ctttttgtttt cccgccgtct   4080 ccactctgtc tcactatctc gacctcaggt agcggtagtg aagatgaagc agacgggcca    4140
```

-continued

```
ggtgtatgcc atgaagatca tgaacaagtg ggacatgctg aagaggggcg aggtgagggg      4200
ctgggcggac gtgggggggct ttgaggatcc gcgccccgtc tccggctgca gctcctccgg      4260
gtgccctgca ggtgtcgtgc ttccgtgagg agagggacgt gttggtgaat ggggaccggc      4320
ggtggatcac gcagctgcac ttcgccttcc aggatgagaa ctacctggtg agctccgggc      4380
cggggtgact aggaagaggg acaagagccc gtgctgtcac tggacgagga ggtggggaga      4440
ggaagctcta ggattggggg tgctgcccgg aaacgtctgt gggaaagtct gtgtgcggta      4500
agagggtgtg tcaggtggat gagggggcctt ccctatctga gacggggatg gtgtccttca      4560
ctgcccgttt ctgggtgat ctgggggact cttataaaga tgtctctgtt gcgggggggtc      4620 tcttacctgg aatgggatag gtcttcagga attctaacgg ggccactgcc tagggaagga      4680
gtgtctggga cctattctct gggtgttggg tggcctctgg gttctctttc ccagaacatc      4740 tcaggggggag tgaatctgcc cagtgacatc ccaggaaagt ttttttgttt gtgttttttt      4800
ttgaggggcg ggggcggggg ccgcaggtgg tctctgattt ggcccggcag atctctatgg      4860
ttatctctgg gctgggggctg caggtctctg cccaaggatg gggtgtctct ggggaggggtt      4920 gtcccagcca tccgtgatgg atcagggcct caggggacta ccaaccaccc atgacgaacc      4980
ccttctcagt acctggtcat ggagtattac gtgggcgggg acctgctgac actgctgagc      5040
aagtttgggg agcggattcc ggccgagatg gcgcgcttct acctggcgga gattgtcatg      5100
gccatagact cggtgcaccg gcttggctac gtgcacaggt gggtgcagca tggccgaggg      5160
gatagcaagc ttgttccctg gccgggttct tggaaggtca gagcccagag aggccagggc      5220
ctggagaggg accttcttgg ttggggccca ccggggggtg cctgggagta ggggtcagaa      5280
ctgtagaagc cctacagggg cggaacccga ggaagtgggg tcccaggtgg cactgcccgg      5340
aggggcggag cctggtggga ccacagaagg gaggttcatt tatcccaccc ttctcttttc      5400
ctccgtgcag ggacatcaaa cccgacaaca tcctgctgga ccgctgtggc cacatccgcc      5460
tggccgactt cggctcttgc ctcaagctgc gggcagatgg aacggtgagc cagtgccctg      5520
gccacagagc aactggggct gctgatgagg gatggaaggc acagagtgtg ggagcgggac      5580
tggatttgga ggggaaaaga ggtggtgtga cccaggctta agtgtgcatc tgtgtggcgg      5640
agtattagac caggcagagg gagggggctaa gcatttgggg agtggttgga aggagggccc      5700
agagctggtg ggcccagagg ggtgggccca agcctcgctc tgctccttttt ggtccaggtg      5760 cggtcgctgg tggctgtggg caccccagac tacctgtccc ccgagatcct gcaggctgtg      5820
ggcggtgggc ctgggacagg cagctacggg cccgagtgtg actggtgggc gctgggtgta      5880
ttcgcctatg aaatgttcta tgggcagacg cccttctacg cggattccac ggcggagacc      5940
tatggcaaga tcgtccacta caaggtgagc acggccgcag ggagacctgg cctctcccgg      6000
taggcgctcc caggctatcg cctcctctcc ctctgagcag gagcacctct ctctgccgct      6060 ggtgacgaa ggggtccctg aggaggctcg agacttcatt cagcggttgc tgtgtccccc      6120
ggagacacgg ctgggccggg gtggagcagg cgacttccgg acacatccct tcttctttgg      6180
cctcgactgg gatggtctcc gggacagcgt gccccctttt acaccggatt tcgaaggtgc      6240
caccgacaca tgcaacttcg acttggtgga ggacgggctc actgccatgg tgagcggggg      6300
cggggtaggt acctgtggcc cctgctcggc tgcgggaacc tccccatgct ccctccataa      6360
agttggagta aggacagtgc ctaccttctg gggtcctgaa tcactcattc cccagagcac      6420
ctgctctgtg cccatctact actgaggacc cagcagtgac ctagacttac agtccagtgg      6480
gggaacacag agcagtcttc agacagtaag gccccagagt gatcagggct gagacaatgg      6540
```

-continued

```
agtgcagggg gtgggggact cctgactcag caaggaaggt cctggagggc tttctggagt      6600
ggggagctat ctgagctgag acttggaggg atgagaagca ggagaggact cctcctccct      6660
taggccgtct ctcttcaccg tgtaacaagc tgtcatggca tgcttgctcg gctctgggtg      6720
cccttttgct gaacaatact ggggatccag cacggaccag atgagctctg gtccctgccc      6780
tcatccagtt gcagtctaga gaattagaga attatggaga gtgtggcagg tgccctgaag      6840
ggaagcaaca ggatacaaga aaaaatgatg gggccaggca cggtggctca cgcctgtaac      6900
cccagcaatt tggcaggccg aagtgggtgg attgcttgag cccaggagtt cgagaccagc      6960
ctgggcaatg tggtgagacc cccgtctcta caaaaatgtt ttaaaaattg gttgggcgtg      7020
gtggcgcatg cctgtatact cagctactag ggtggccgac gtgggcttga gcccaggagg      7080
tcaaggctgc agtgagctgt gattgtgcca ctgcactcca gcctgggcaa cggagagaga      7140
ctctgtctca aaataagat aaactgaaat taaaaaatag gctgggctgg ccgggcgtgg       7200
tggctcacgc ctgtaatctc agcactttgg gaggccgagg cgggtggatc acgaggtcag      7260
gagatcgaga ccatcttggc taacacggtg aaaccccatc tctcctaaaa atacaaaaaa      7320
ttagccaggc gtggtggcgg gcgcctgtag tcccagctac tcaggaggct gaggcaggag      7380
aatggcgtga acccgggagg cagagtttgc agtgagccga gatcgtgcca ctgcactcca      7440
gcctgggcga cagagcgaga ctctgtctca gaaaaaaaaa aaaaaaaaaa aaaaaatagg      7500
ctggaccgcg gccgggcgct gtggctcatg cctgtaatcc cagcactttg ggagtccaag      7560
gccggtgggt catgagatca ggagttttga gactaggctg gccaacacgg tgaaaccccg      7620
tctctactaa aaatacaaga aaattagctg ggtgtggtct cgggtgcctg taattccagt      7680
tactggggaa gctgaggcag gagaattgct tgaacctggg aggcagagtt tgcagtgagc      7740
caagatcatg ccactacact ccagtctggg tgacagagtg agactctgtc tcaaaaaaaa      7800
aaaaaaaaaa aagggttggg caaggtggtt cacgcctgta atcccagaac tttgggaggc      7860
tgaggcaggc agatcactgg aagtcaggag ttcaagacca gcctggccaa catggtgaaa      7920
ccctgtgtct actaaaaata caaaatttag ccaggcttgg tggcgtatgc ctgtaatgcc      7980
agctactcag gaggctgagg caggagaatc gcttgattga acctgggagg cagagtttgc      8040
agtgggctgg ggttgtgcca ctgcactcta ggctgggaga cagcaagact ccatctaaaa      8100
aaaaaaaaca gaactgggct gggcacagtg gcttatattt gtaatcccag cactttggga      8160
ggctgaggtt ggaggactgc ttgagcccag agtttgggac tacaacagct gaggtaggcg      8220
gatcacttga ggtcagaaga tggagaccag cctggccagc gtggcgaaac cccgtctcta      8280
ccaaaaatat aaaaaattag ccaggcgtgg tagagggcgc ctgtaatctc agctactcag      8340
gacgctgagg caggagaatc gcctgaacct gggaggcgga ggttgcagtg agctgagatt      8400
gcaccactgc actccagcct gggtaacaga gcgagactcc gtatcaaaga aaagaaaaa      8460 agaaaaaatg ctggagggggc cactttagat aagccctgag ttgggctgg tttgggggaa     8520 acatgtaagc caagatcaaa aagcagtgag gggcccgccc tgacgactgc tgctcacatc      8580
tgtgtgtctt gcgcaggaga cactgtcgga cattcgggaa ggtgcgccgc taggggtcca      8640
cctgcctttt gtgggctact cctactcctg catggccctc aggtaagcac tgccctggac      8700
ggcctccagg ggccacgagg ctgcttgagc ttcctgggtc ctgctccttg gcagccaatg      8760
gagttgcagg atcagtcttg gaaccttact gttttgggcc caaagactcc taagaggcca      8820
gagttggagg accttaaatt ttcagatcta tgtacttcaa aatgttagat tgaattttaa      8880
```

```
aacctcagag tcacagactg ggcttcccag aatcttgtaa ccattaactt ttacgtctgt   8940
agtacacaga gccacaggac ttcagaactt ggaaaatatg aagtttagac ttttacaatc   9000
agttgtaaaa gaatgcaaat tctttgaatc agccatataa caataaggcc atttaaaagt   9060
attaatttag gcgggccgcg gtggctcacg cctgtaatcc tagcactttg ggaggccaag   9120
gcaggtggat catgaggtca ggagatcgag accatcctgg ctaacacggt gaaaccccgt   9180
ctctactaaa aatacaaaaa aattagccgg gcatggtggc gggcgcttgc ggtcccagct   9240
acttgggagg cgaggcagga gaatggcatg aacccgggag gcggagcttg cagtgagccg   9300
agatcatgcc actgcactcc agcctgggcg acagagcaag actccgtctc aaaaaaaaaa   9360
aaaaaaaagt atttatttag gccgggtgtg gtggctcacg cctgtaattc cagtgctttg   9420
ggaggatgag gtgggtggat cacctgaggt caggagttcg agaccagcct gaccaacgtg   9480
gagaaacctc atctctacta aaaaacaaaa ttagccaggc gtggtggcat atacctgtaa   9540
tcccagctac tcaggaggct gaggcaggag aatcagaacc caggaggggg aggttgtggt   9600
gagctgagat cgtgccattg cattccagcc tgggcaacaa gagtgaaact tcatctcaaa   9660
aaaaaaaaaa aaaagtact aatttacagg ctgggcatgg tggctcacgc ttggaatccc   9720
agcactttgg gaggctgaag tggacggatt gcttcagccc aggagttcaa gaccagcctg   9780
agcaacataa tgagaccctg tctctacaaa aaattgaaaa aatcgtgcca ggcatggtgg   9840
tctgtgcctg cagtcctagc tactcaggag tctgaagtag gagaatcact tgagcctgga   9900
gtttgaggct tcagtgagcc atgatagatt ccagcctagg caacaaagtg agacctggtc   9960
tcaacaaaag tattaattac acaaataatg cattgcttat cacaagtaaa ttagaaaata  10020
cagataagga aaaggaagtt gatatctcgt gagctcacca gatggcagtg gtccctggct  10080
cacacgtgta ctgacacatg tttaaatagt ggagaacagg tgtttttttg gtttgttttt  10140
ttccccttcc tcatgctact ttgtctaaga gaacagttgg ttttctagtc agcttttatt  10200
actggacaac attacacata ctatacctta tcattaatga actccagctt gattctgaac  10260
cgctgcgggg cctgaacggt gggtcaggat tgaacccatc ctctattaga acccaggcgc  10320
atgtccagga tagctaggtc ctgagccgtg ttcccacagg agggactgct gggttggagg  10380
ggacagccac ttcataccccc agggaggagc tgtcccctt ccacagctga gtggggtgtg  10440
ctgacctcaa gttgccatct tggggtccca tgcccagtct taggaccaca tctgtggagg  10500
tggccagagc caagcagtct ccccatcagg tcggcctccc tgtcctgagg ccctgagaag  10560
aggggtctgc agcggtcaca tgtcaaggga ggagatgagc tgaccctaga acatgggggt  10620
ctggacccca agtccctgca gaaggtttag aaagagcagc tcccaggggc ccaaggccag  10680
gagaggggca gggcttttcc taagcagagg aggggctatt ggcctacctg ggactctgtt  10740
ctcttcgctc tgctgctccc cttcctcaaa tcaggaggtc ttggaagcag ctgcccctac  10800
ccacaggcca gaagttctgg ttctccacca gagaatcagc attctgtctc cctccccact  10860
ccctcctcct ctccccaggg acagtgaggt cccaggcccc acacccatgg aactggaggc  10920
cgagcagctg cttgagccac acgtgcaagc gcccagcctg gagccctcgg tgtccccaca  10980
ggatgaaaca gtaagttggt ggaggggagg gggtccgtca gggacaattg ggagagaaaa  11040
ggtgagggct tcccgggtgg cgtgcactgt agagccctct agggacttcc tgaacagaag  11100
cagacagaaa ccacggagag acgaggttac ttcagacatg ggacggtctc tgtagttaca  11160
gtggggcatt aagtaagggt gtgtgtgttg ctggggatct gagaagtcga tctttgagct  11220
gagcgctggt gaaggagaaa caagccatgg aaggaaaggt gccaagtggt caggcgagag  11280
```

```
cctccagggc aaaggccttg ggcaggtggg aatcctgatt tgttcctgaa aggtagtttg    11340
gctgaatcat tcctgagaag gctggagagg ccagcaggaa acaaaaccca gcaaggcctt    11400
ttgtcgtgag ggcattaggg agctggaggg attttgagca gcagagggac ataggttgtg    11460
ttagtgtttg agcaccagcc ctctggtccc tgtgtagatt tagaggacca gactcaggga    11520
tggggctgag ggaggtaggg aagggagggg gcttggatca ttgcaggagc tatggggatt    11580
ccagaaatgt tgaggggacg gaggagtagg ggataaacaa ggattcctag cctggaacca    11640
gtgcccaagt cctgagtctt ccaggagcca caggcagcct taagcctggt ccccatacac    11700
aggctgaagt ggcagttcca gcggctgtcc ctgcggcaga ggctgaggcc gaggtgacgc    11760
tgcgggagct ccaggaagcc ctggaggagg aggtgctcac ccggcagagc ctgagccggg    11820
agatggaggc catccgcacg gacaaccaga acttcgccag gtcgggatcg gggccggggc    11880
cggggccggg atgcgggccg gtggcaaccc ttggcatccc ctctcgtccg gcccggacgg    11940
actcaccgtc cttacctccc cacagtcaac tacgcgaggc agaggctcgg aaccgggacc    12000
tagaggcaca cgtccggcag ttgcaggagc ggatggagtt gctgcaggca gagggagcca    12060
caggtgagtc cctcatgtgt ccccttcccc ggaggaccgg gaggaggtgg gccgtctgct    12120
ccgcggggcg tgtatagaca cctggaggag ggaagggacc cacgctgggg cacgccgcgc    12180
caccgccctc cttcgcccct ccacgcgccc tatgcctctt tcttctcctt ccagctgtca    12240
cgggggtccc cagtccccgg gccacggatc caccttccca tgtaagaccc ctctctttcc    12300
cctgcctcag acctgctgcc cattctgcag atcccctccc tggctcctgg tctcccgtc     12360 cagatatagg gctcacccta cgtctttgcg actttagagg gcagaagccc tttattcagc    12420
cccagatctc cctccgttca ggcctcacca gattccctcc gggatctccc tagataacct    12480
ccccaacctc gattcccctc gctgtctctc gccccaccgc tgagggctgg gctgggctcc    12540
gatcgggtca cctgtccctt ctctctccag ctagatggcc cccggccgt ggctgtgggc      12600 cagtgcccgc tggtggggcc aggccccatg caccgccgcc acctgctgct ccctgccagg    12660
gtacgtccgg ctgcccacgc ccccctccgc cgtcgcgccc cgcgctccac ccgcccttg     12720 ccaccgcctt agctgcgcat ttgcggggct gggcccacgg caggagggcg gatcttcggg    12780
cagccaatca acacaggccg ctaggaagca gccaatgacg agttcggacg ggattcgagg    12840
cgtgcgagtg gactaacaac agctgtaggc tgttggggcg ggggcggggc gcagggaaga    12900
gtgcgggccc acctatgggc gtaggcgggg cgagtcccag gagccaatca gaggcccatg    12960
ccgggtgttg acctcgccct ctccccgcag gtccctaggc ctggcctatc ggaggcgctt    13020
tccctgctcc tgttcgccgt tgttctgtct cgtgccgccg ccctgggctg cattgggttg    13080
gtggcccacg ccgccaact caccgcagtc tggcgccgcc caggagccgc ccgcgctccc     13140
tgaaccctag aactgtcttc gactccgggg ccccgttgga agactgagtg cccggggcac    13200
ggcacagaag ccgcgcccac cgcctgccag ttcacaaccg ctccgagcgt gggtctccgc    13260
ccagctccag tcctgtgatc cgggcccgcc ccctagcggc cggggaggga ggggccgggt    13320
ccgcggccgg cgaacggggc tcgaagggtc cttgtagccg ggaatgctgc tgctgctgct    13380
gctgctgctg ctgctgctgc tgctgctgct gctgctgctg ctgctggggg gatcacagac    13440
catttctttc tttcggccag gctgaggccc tgacgtggat gggcaaactg caggcctggg    13500
aaggcagcaa gccgggccgt ccgtgttcca tcctccacgc accccacct atcgttggtt      13560 cgcaaagtgc aaagctttct tgtgcatgac gccctgctct ggggagcgtc tggcgcgatc    13620
```

| | |
|---|---|
| tctgcctgct tactcgggaa atttgctttt gccaaacccg cttttcgggg gatcccgcgc | 13680 |
| ccccctcctc acttgcgctg ctctcggagc cccagccggc tccgcccgct tcggcggttt | 13740 |
| ggatatttat tgacctcgtc ctccgactcg ctgacaggct acaggacccc caacaacccc | 13800 |
| aatccacgtt ttggatgcac tgagaccccg acattcctcg gtatttattg tctgtcccca | 13860 |
| cctaggaccc ccaccccga ccctcgcgaa taaaaggccc tccatctgcc caaagctctg | 13920 |
| gactccacag tgtccgcggt ttgcgttgtg ggcggaggc tccgcagcgg gccaatccgg | 13980 |
| aggcgtgtgg aggcggccga aggtctggga ggagctagcg ggatgcgaag cggccgaatc | 14040 |
| agggttgggg gaggaaaagc cacggggcgg ggctttggcg tccggccaat aggagggcga | 14100 |
| gcgggccacc cggaggcacc gccccgccc agctgtggcc cagctgtgcc accgagcgtc | 14160 |
| gagaagaggg ggctgggctg gcagcgcgcg cggccatcct ccttccactg cgcctgcgca | 14220 |
| cgccacgcgc atccgctcct gggacgcaag ctcgagaaaa gttgctgcaa actttctagc | 14280 |
| ccgttccccg cccctcctcc cggccagacc cgccccccct gcggagccgg gaattccgag | 14340 |
| gggcggagcg caggccgaga tgggaatgt ggggcctgc agaggaccct ggagacggag | 14400 |
| gcgtgcagaa g | 14411 |

<210> SEQ ID NO 3
<211> LENGTH: 15000
<212> TYPE: DNA
<213> ORGANISM: Mus musculus

<400> SEQUENCE: 3

| | |
|---|---|
| cagtgtcccc actgcccaag gctggctcca tcacgtaccg ctttggctca gctggccagg | 60 |
| acacacagtt ctgcctgtgg gacctcacag aagatgtgct ctcccctcat ccgtctctgg | 120 |
| cccgtacccg cacccttccg ggcacacctg gtgccacccc accagcttct ggtagttctc | 180 |
| gggccggaga gacaggtgca ggccccctgc cccgctccct gtctcgttcc aacagtctcc | 240 |
| cacacccagc tggtggtggc aaggctggtg ggcctagtgc atcgatggag cctggcatac | 300 |
| cattcagcat tggccgcttt gccacactga ccctgcagga gcggcgggac cggggagctg | 360 |
| agaaggaaca caaacgctac catagcctgg gaaacatcag ccgcgtggc agtgggggca | 420 |
| atagcagcaa tgacaagctc agtggtcctg ccccccgaag ccgattggac ccagctaagg | 480 |
| tgctgggcac ggcactgtgc cctcggatcc atgaggtgcc actgctggag cctctcgtgt | 540 |
| gcaagaagat tgctcaggaa cgcctgaccg tgctactgtt cctggaggat tgtatcatca | 600 |
| ctgcctgcca agagggcctc atctgcacct gggcccggcc aggcaaggcg gtgagtccgc | 660 |
| acctgcccaa gcgctgaggg gcaccagttc tgtccctacc ggatgccagt tatccgtcag | 720 |
| cagaaaggtc aggtatagga gacagaatgg ggggaaccac agctaacgtc tttagagcct | 780 |
| ctgctggccc atatggctca tccttagtac ttcacactca aggcagaacc tgtgtttata | 840 |
| ggaaatctga agtgtagatg gtgaaacttt attcaggtct agggatgtga ttgagctggg | 900 |
| ggcccacttc tggcctgcct cttagacact gtttctgagc cagctgctga aggcctggat | 960 |
| gggaattagc cagggtccag gcctgcactt cctcttgctg ctgtgtggtc ctggtcattg | 1020 |
| ggtctcacag atgggctgtg cagtggctgt gctcttagtt ggtgaggtgc aggcctgtca | 1080 |
| cctggtcagg cttgagcatg tggtctcagt gtctaggacc ctactctgcc ctcagtcctt | 1140 |
| cagtcccttg ctttggaagg ctagagtcca gaagccttag aacgtcaggc agttgcagag | 1200 |
| ccactgccag gctagtaggg ctgcgggagt tgactgagtt ctcacagaca ccctctgtc | 1260 |
| tccctagttc acagacgagg agaccgaggc ccaggcaggg caagcaagtt ggcccaggtc | 1320 |

```
acccagcaag tcagttgtag aggtaggaca acccctgaag ctgcaagtgg acccccagttt    1380 cttttctctc cactgtcgtc ccctgtatgc ccaggacacc tggggccaca ttactgtgga    1440
agtgctactc tgggtcagtg gagacggccg agctgtttgt tcctagctag gacagcagct    1500
ttaggcctgg ggggcagatc ccagctgggg cagcagctcc aaggcctttg ggtggctcct    1560
tctccgggtt ctggcagaag cccaggtgct gtctaatcca cctttctcct cttgttctcc    1620
ccagggcatc tcctcccaac caggcagctc ccccagtggc actgtggtgt gaaatgtgga    1680
tgtcccatgt tcccggcctc ctagccataa ccctccccgc tgacctcaag aatcactgta    1740
ttaacaagac taatcatgat ggaaggactg ctccaagccc cacgctgcac acatactggg    1800
ggtcccctag gttggcccag ccatggggat gtagtgtcct gtgtggcctt ggccctgtcc    1860
tccacccact gccaagtaca atgacctgtt ctctgaaaca tcagtgttaa ccatatccct    1920
gtcccagcat gtgactgttc actcctggga gagacttagc ccacagtacc cctgggtgag    1980
agggcagggc aggggccatc cccactcctg cccaaactcc accccttgct atggtctgtg    2040
attttgaaag tgttaaatta tggaagccct gagggccctc cttgttcccc tggacctctt    2100
atttatacta aagtccttgt ttgcacagtg tttctgttcc ctggggcagg gtagggtggg    2160
ggttgcagta cttggcctcc aagctgtgct ctgaccaaag gaagcccaat cttagctgtt    2220
tccccatccc tagccccgag cagagagccc tctgaaagat gagtctcgac ccccaaagtc    2280
aagaggctga gatggccttc ctactaggtc cttggagatg tttgaaactt gttttaaaca    2340
ccaggactat ccaagcatgc tctccttggg gagaggagga tgctggaatt gactgcactc    2400
cctgcctcct ctgaacatgc cttttgcagtc tgctgcccct ggcccatttta tgactggcca    2460 tctagtgcca gctggaggtc atgatttcct ccccagagaa ctggccaccc tagaaagaag    2520
ctaacttgtc gcctggcttg ctgtccaggc agctccgccc tcaaccccta aaatgtttct    2580
gtctctaatc ctagcccagg caggaatgtg gctgccccgg cctgtggcca aggagctatt    2640 ttgggggttct cttttgctta aggagggcct ggatccacca cttgcctccc ccaggctggg    2700
gccagcaggt cacccctggc cctgcggct gagcaaactc tctcctgatc ttccttctac    2760
ctcctgccaa aaaatggggg ggcgggtaat acagcaggca caggggctaa atttaactgt    2820
cccaaagtcg gaatccattg ctgagtcacg aagaagctgc ccctggcctt tgccccccc    2880 actacccct caccccctgt tgcccaggca tcagccctttt cccccaaccc ctcccagctc    2940
tgagtctata gactggctct cctgggcact gacacctccc acctgtaact ccctgtgctc    3000
tctttatggg tgggtagagt caatgggggg gggcaaccct ggagtattac tctgtccccct    3060 gacattgggc tctgaagagt tttgaggggc cctggaagaa gggagttggg gtgttggctc    3120 aggagggggtt aaaaactggg aggcgggagg ggggctgggc caaggggtgg agaaaagagg    3180
aggaggcctt aagcatagaa ctggccagag agacccaagg gatagtcagg gacgggcaga    3240
catgcagcta gggttctggg gcctggacag gggcagccag gccctgtgac gggaagaccc    3300
cgagctccgg cccggggagg ggccatggtg ttgcctgccc aacatgtcag ccgaagtgcg    3360
gctgaggcag ctccagcagc tggtgctgga cccaggcttc ctgggactgg agccctgct    3420 cgaccttctc ctgggcgtcc accaggagct gggtgcctct cacctagccc aggacaagta    3480
tgtggccgac ttcttgcagt ggggtgagta tggataggaa gcctgggggtt gggtgcaagg    3540 cagaggtggg tctacagggc aagaatgggc tatggagggg caggagggcc tggaaagggc    3600 ttttttgtaag ggagccaagc agagctcatg acctgacccc aagctcccct ggtgaggcac    3660
```

```
cagggtcagt gaggccacct atgactcagc cagtgcaggc tggggtgggc atagcctcct    3720
gctatctcag cacccacact aggacctggc agctttctct tttaggaccc ttggctcctc    3780
aaactggctt catagccctc cccagtttcc cagagtgtgg ggagggacag cgtggggcag    3840
ctgccagggt gtggcccata ggcaggtgtt tggcgtctgc ctccccagct gccctgacag    3900
gtgtccagga gctatgaggg cactgtgact cacagaggcc ctgggggaga accagcccgg    3960
cagacaggcg ccaccgagca ccctttctgt tccccaaatt aagaggaagg aacaacttca    4020
gcttctgagt gtgcccatcc ctagcactct gatcccgccc agcctttgtg ggccagattg    4080
gtcatccctc ctggcttctc atctgctttt gtggttctag ctcaagacct ctaattcctc    4140
tgctgactta aatgcccttc cccagaggtc ttctcaggcc tagtggacaa gcttggagcc    4200
ttatctgctc ctgcccaaca ttgagccaaa gctccagctt ccccagctt ccttacaagt     4260
aacgacctgt tttgttgctc tgtgcctatt attaagggtc caggtcttga ttcttggctg    4320
tctgcccatg tgtgtgaccc tagtgcattc tcccctcctc cccgtttca cagatggaaa     4380
ggttgaggcc atcggttaga ctgctaagcc tgtgaaagac ttttctcct ctccagtctt     4440
tagtgtctcc ctcaacccttt cttttgaagg atggggtttg gctggcagg gtaaactgag    4500
aactggggtg ggggcagggg gtctgaccct ctgggaagga gcagtccttt tgtggcctga    4560
gcagcatcct gtgggcccct cccctgccag gcctgggcgg gggaggggc ctgggttccc     4620
gctgccttaa aagggctcaa cgccttggct ctctcctcct ccccaccccc cagccttggc    4680
cctagctgta tcttccccgg ctgcccactt tcccaaaccc cttcttctc tgtgaccca     4740
tctcccgct tccccacacg tccctcctcc atccttactc cccggcctta gaacttccct    4800
aagggagatc tgacctccct ctgcccaccc cgcaccccca gtcgccagcc tcagacctag    4860
ctgctctccc ctctggctga accacccag cacaggacct tataccctgg agctttggtt      4920
ataagaagac tctccttcac cctttggaaa ccagaaagc cttccaaca gtgtccagga      4980
tgctggaggg cagtgaccct cccccacttc ttcttcgtgc tggctgtgct gacacagctc    5040
cagttcgagg ttgtggcccg agacattaag tgagagcccc gggtgacctg acttagcacc    5100
ctgatcatca catgggagtg aaaggcctga tcgccagct tctcccactg cctcccttc      5160
tgccctgcaa ccctgtggaa acaggcagtt ctgggtccca caaacatcac agaggttttg    5220
aaagcagaat cctaaagccg atttaagggg cagaaggaag gaggctataa agtcactacc    5280
cttaccgcta gtgttctgat gacccttggt tcttcttccc ccaccccgc ccagtggagc     5340
ccattgcagc aaggcttaag gaggtccgac tgcagaggga tgattttgag attttgaagg    5400
tgatcgggcg tggggcgttc agcgaggtga gtcttcagtg gcctgggaat ggaactttac    5460
ttgatgtggg tggggcataa cagctggggc agagccttaa aaattgatga atgagcttga    5520
atttaaggct ggaggggtgg gggcggagct tgtggtcagt gggcggtgtg cacgtgaggg    5580
cggggctaag gttgggtgga gataagggtg gagtcctgtc tgggtgagcc ttgctggttt    5640
tccctgccac ctcttgctgt catctcggtt ccgtatttag gtagcggtgg tgaagatgaa    5700
acagacgggc caagtgtatg ccatgaagat tatgaataag tgggacatgc tgaagagagg    5760
cgaggtgagg gccagggatt agggcagcgc cctcatctct ccaactcacc tcctgtagct    5820
tctctcctac ctcacaggtg tcgtgcttcc gggaagaaag ggatgtatta gtgaaagggg    5880
accggcgctg gatcacacag ctgcactttg ccttccagga tgagaactac ctggtaagct    5940
ccgggttcag gtgactagga aagagtgaca gttacatcgc cccaagtcaa gaaggctgga    6000
gaagggagaa gctgctgtag atcgggggg tggggtggg gggacacac acaggggatg      6060
```

```
ggggacgggg gtaggattgt gtctcaagta taggagagac cttccttgag acaggagtga    6120
tatctggttt ggcctttgga tggggcgctc tctcactgtg cggggtcct ctgtgcttgg     6180 gaacggggtg tctttgggag tcttgggggc taccaaaccc ctgtgacaca cccgctccca    6240
gtacctggtc atggaatact acgtgggcgg ggacctgcta acgctgctga gcaagtttgg    6300
ggagcggatc cccgccgaga tggctcgctt ctacctggcc gagattgtca tggccataga    6360
ctccgtgcac cggctgggct acgtgcacag gtgggcgtgg cggggcccctt ggagggttag   6420 cagaatttgt gtgggaagga agggtacctg aaggtcagat cccattgggg acagaatcgg   6480
ggtctagaat tgtagaatcc tgggtggggt ggaagtggat cgagctgacg ggccctaaga   6540
gggaaggttt tcaagaaagc acactttccc tcttctctct atgcacaggg acatcaaacc   6600
agataacatt ctgctggacc gatgtgggca cattcgcctg gcagacttcg gctcctgcct   6660
caaactgcag cctgatggaa tggtaagaag agcctggcga aactctcctc attggtgaag   6720
gaccggatta gggggcgggg ctgggttgag gagcaggagg ggagcttggt ctgggatgtc   6780
ctgcgcacca tatttggaca gtcaagggaa aggttttaag cattcaggtc tgattggcac   6840
aggtgaggtc gctggtggct gtgggcaccc cggactacct gtctcctgag attctgcagg   6900
ccgttggtgg agggcctggg gcaggcagct acgggccaga gtgtgactgg tgggcactgg   6960
gcgtgttcgc ctatgagatg ttctatgggc agaccccctt ctacgcggac tccacagccg   7020
agacatatgc caagattgtg cactacaggg tgagcacaag caccatgcag ggggggctgac  7080 ttagtggctt gtgctcccag actgtctttt taaaagata tttatttata tgtgtgtgtt    7140
ttctgtgtat gtatatctgt gcactgagta ggtgtgcgaa ggtcagaggg catgggatcc   7200
cctggaactg gagtcacaga ctattgtgtg ctgccatgct gagtgctggg aaacagaacc   7260
ttgatcactc tgcaagagca gccagtgcac tgaaacgaca gagccagctc tgcagcccag   7320
ggctaactgt tgcttttctt tctaaatagg aacacttgtc gctgccgctg cagacacag    7380 ttgtccccga ggaagctcag gacctcattc gtgggctgct gtgtcctgct gagataaggc   7440
taggtcgagg tggggcaggt gatttccaga aacatccttt cttctttggc cttgattggg    7500
agggtctccg agacagtgta cccccctta caccagactt cgagggtgcc acggacacat    7560
gcaatttcga tgtggtggag accggctca ctgccatggt gagcggggc ggggtacgta     7620 cctgcagttc ctgatccgtt gaggggactt ccctagcctc ttccataaaa ttggggtgat   7680
tggccaggtg tggtggtgca tacctttaat cgtagaactt cataggcaga ggcaggtggc   7740
tctctggtaa atcaaggcca tcttggtcta catagtgact tctaggccag tcaggagtga   7800
gatcctccct tgaaaaataa aaagggggt gttgaccttc ctgggtccca aattattatc    7860
ctagagcact gctatgtatc cactcaggta tgaggacaca caggtgacca gtcccaagaa   7920
cagtgagtga ggcctcactc ttggcagtac taaaattgat tgtaggggc tgggctcttg    7980 acccagcctg gaaagtgctg gagggcttcc tggaggagga gactagctga gcccagaagg   8040
atgcaggaga tcctttctcg ggtgagtgct ctcagcattt taacaagctc taggccctgc   8100
agagagaagt ctggtgtggg cagagcccca atagaaagca acaagataga agagaaaatg   8160
gtggagtttg ttagtggggg cagttatgcc gtgaacatag aggggcgaag gccatctcg    8220 gataactgct agccacaaga gccctgtctg tcttcctagg agacgctgtc agacatgcag   8280
gaagacatgc cccttgggt gcgcctgccc ttcgtgggct actcctactg ctgcatggcc    8340
ttcaggtgag cacgactgcc ccctgctggg gcctgtgtgc aggcccacca cagccactca   8400
```

```
attgaaggct cagtcttcaa accaagtatt cctaggagct gtctaagtta ggctttctgc    8460
tgctgcgatg aaccctgact aaaagcaagc tggggaggaa aaggcttatc gggcttacgt    8520
ttccacatgg gagcccatca ctgaaggaag ccaggacagg aactcacagc ggggcaggaa    8580
cgtggagctg atgcagaggc aatggagggg agctgcttac tgacttgatc cttatgtctt    8640
cctcagcctg tttccttgta gagcccagga ccaccaggcc agtgagggct ccactcacaa    8700
tgggctgagc tctcatctat gatcactagt tatgaaaatg cccgataggc ttgcctgcag    8760
cttcagtttt tgaggcactt tccttccttc cttccttcct tccttccttc cttccttcct    8820
ttctttcttt ctttctttct ttctttcttt ctttctttct ttcttttcttt ctttctttct    8880
tagtctttta gagacagggt ctttctatgt agctctggct gtcttggaat tcattctgta    8940
gaccaggctg gtcttattta tttattttat gtatgtgagt ccactatcac tgtcctcaga    9000
cacaccagaa gagggcatca gatcccatta cagatggctg tgagccacca tgtggttgct    9060
gggaattgaa ctcaggacct ctggaagagc agccagtgct cctgccctgt agaggcattt    9120
tcttcatgaa ggctgtctcc tctctgatga cttgatgact ctagcttgtt gtgtcaagtg    9180
gacataagac taggaaagca gctacacatg cactttgttt attttttgttt tgcttttttga    9240
gactgggtct ctccatctca tagctctggc catcctgcct ggtgacattc cagtccagtt    9300
gtataaccta agaatctgag actcagcctt gcagaatcct gctattaacg ggtctaggac    9360
actccataga atccaggatc ttagaaaaac aaacctgaag tgtgacagtt tattttaaga    9420
acacaattgg agcacataac aataatacaa cttttcagtt ttaaaaagtt ttctgtcttg    9480
ttttttgagg caggagctcc ttaatatagt ctaagccgcc ctgcgagtgc tgtgattgat    9540
gggcatgtac caccatgcct agtcaataaa gcctttaaaa agcatccgtt atgctggctg    9600
tggtgccaca aacctgtaat cccagcactt agaaggtaga ggcaagatta tcagaaaattc    9660
aaggccatcc tgggctatac agtaatctaa ggctagcctg gtctacaaga gactctgtct    9720
aaagaaacaa aagataaata gcacccacta ttgctaggca atataaccct ataaccccac    9780
cattgaggag gctgaggctg gagcatcact gcaaatttga ggccaggatg gtcaacaaat    9840
aagtcccaga gctggcatag aggaactctg tctcaacaat aaagagaact tatctagcat    9900
ttatgagggt aaataaaaat ttaccattgc cacaaaaaat gtaaatgaag agactgcttt    9960
taggagtgaa ctgggaagca gggaacactt agaggatgct cactcacaca ggtatccacc    10020
atcaggcatg cctcaggcct gcacagggaa ggacaacttg tttcatgatt tgcaagcagc    10080
atcccatgct ccttagagcg ggttgggccc agcccaccct ctgtggagtt atcgctcagc    10140
caggcagcaa ggcagccaag gtgctgaggc cctggcagtc tgctctcttc tctgctctga    10200
acctccttta gctttagcct aggagcctgg cctggtgccc acaggctagg gagtccctag    10260
cctcttcctc ttctcagaga caatcaggtc ccggacccca cccctatgga actagaggcc    10320
ctgcagttgc ctgtgtcaga cttgcaaggg cttgacttgc agccccagt gtccccaccg    10380
gatcaagtgg tgagtagact gagaggtggg caaagcttcc tgggtgggtg tacctgcagt    10440
gccaactgcc aggctgttaa ttcagtagga cactgtcccc aactggccca actgcacatc    10500
ctgtagtcag gaggcacagg cagaaaaatc ccaaattcaa ggcttgctcc cgttatgtaa    10560
tgagatcctg tcttggagta aaaacaaag aagagaacta gggatagctc agaggtagat    10620
gctctcctgg catggggggtg gggtcagaaa gcaacaccaa ccgggcctg ggagggaggg    10680
actgccaacc acctgagga gtctgggta gacttggtga acaaagttca gaggccatca    10740
ggtgggatgc tggtttctta aaagccacag ataggtgggt agcattggaa agaggagtgg    10800
```

```
ggggttgcag aaagtgacaa gacacaaact ggggaggcct aagggtaaag ccagggttgt   10860
ctgaagcact gtggagctgg gaggaacacg ctaaacttct gacttcagcc cttcagttcc   10920
cctgttgact acactgtccc cagggaccca gggatgggga gaggtggacg ggggagggaa   10980
gtacgggact gatccagctc caggtcccaa ctctgatccc caccgacagg ctgaagaggc   11040
tgacctagtg gctgtccctg cccctgtggc tgaggcagag accacggtaa cgctgcagca   11100
gctccaggaa gccctggaag aagaggttct cacccggcag agcctgagcc gcgagctgga   11160
ggccatccgg accgccaacc agaacttctc caggtcaggg tcacagtgct ggggtgaggg   11220
gagaggagag cagcaaccct cgcagtctcc tcaccgatag gtcggctcac tcccctatct   11280
ttcccagcca actacaggag gccgaggtcc gaaaccgaga cctggaggcg catgttcggc   11340
agctacagga acgatggag atgctgcagg ccccaggagc cgcaggcgag tccctcacct   11400
gcttccagcc aaggggcac tgggtggaga tggggggcat gttgggtgtg tgaaccctcg   11460
gggcagggga ggagtccagg ctggggcacc gcagccgcgc cactgccttt ctcctccatc   11520
ctccacactc catacacctc tctcttctcc ttccagccat cacggggtc cccagtcccc   11580 gggcacgga tccaccttcc catgtaagac ccctctctcc cctccccgat ccccatctta   11640
gatatgctac ccacagccct tctcccgtcc acgtttaggg tccattctcc ttgggggttc   11700
cagaagaaag ctgcccttca ctcatccatt cagcatgcac tatctaccag ctctccctcg   11760
tttcaggctt ctcgccaaat cctccccaag ggaactccct atactcccgt tctggcctcg   11820
actagattcc cgcactgcct ctcgccctgc tgctgggctc cgatcgggtc acctgtccct   11880
tctctctcca gctagatggc cccccggccg tggctgtggg ccagtgcccg ctggtggggc   11940
caggccccat gcaccgccgt cacctgctgc tccctgccag ggtatgtccc acgtccgccc   12000
accacgggcc tctgcctagc tctgcccact gagtgtcacc actgcttgct gtgcctctgt   12060
ggagctcggc ccaccgcagg gagggggggt attcgggcgg ccaatcaaca caggctgctg   12120
ctaagtagcc aatgacgagt tccaacagga gctctttctt gcgagcagac caactttagc   12180
tgcgggctgt ggggaccaga gatgcgctca gaggcccatc tatgggtata ggctgggcgg   12240
ctcccaggag ccagtgggcc cctgtagcct agtgctaatc caaccttctc tcctgcagat   12300
ccctaggcct ggcctatccg aggcgcgttg cctgctcctg ttcgccgctg ctctggctgc   12360
tgccgccaca ctgggctgca ctgggttggt ggcctatacc ggcggtctca ccccagtctg   12420
gtgtttcccg ggagccacct tcgcccctg aaccctaaga ctccaagcca tctttcattt   12480
aggcctccta ggaaggtcga gcgaccaggg agcgacccaa agcgtctctg tgcccatcgc   12540
gccccccccc ccccccacc gctccgctcc acacttctgt gagcctgggt ccccacccag   12600
ctccgctcct gtgatccagg cctgccacct ggcggccggg gagggaggaa cagggctcgt   12660
gcccagcacc cctggttcct gcagagctgg tagccaccgc tgctgcagca gctgggcatt   12720
cgccgacctt gctttactca gccccgacgt ggatgggcaa actgctcagc tcatccgatt   12780 tcacttttc actctcccag ccatcagtta caagccataa gcatgagccc cctatttcca   12840
gggacatccc attcccatag tgatggatca gcaagacctc tgccagcaca cacggagtct   12900
ttggcttcgg acagcctcac tcctgggggt tgctgcaact ccttccccgt gtacacgtct   12960
gcactctaac aacggagcca cagctgcact ccccctccc ccaaagcagt gtgggtattt   13020
attgatcttg ttatctgact cactgacaga ctccgggacc cacgttttag atgcattgag   13080
actcgacatt cctcggtatt tattgtctgt ccccacctac gacctccact cccgacccctt   13140
```

```
gcgaataaaa tacttctggt ctgccctaaa tcccgcgcaa tatctctgtt gtggaaagga   13200
aaccgccccg caggccaatg gagagtccaa tagagacaac caatggcttg agtgggagct   13260
agaggggagg caaagcgcac gaatcaggtt gaagggtggg gcttaggcat ccagccagta   13320
ggagagaagc aacaagccac cagagacacc accgccccccc acccctccccc ccagctgtga   13380 cccagctgtg ccactcaagt ttggaaaaaa gtaggggggtt gggccagcag cgggcacacc   13440
atcttcccac tgcgcctgcg caagccacgc gcatccgctt tttggaccga cactccagaa   13500
aagttgctgc aaactttcta gcgcgattcc ccgcccctcc tcccagctag atccaccgcc   13560
tacccgcggg gccgggaatt ccgaggggcg gagcacggcg cggagatggg aagggagggg   13620
gcccttcaag ggacccggga gatgggagcg gcttcgcgcc cttaaccctc cggacggccc   13680
attaccttct ccgttgctct gatagggaaa ctgaggccct gagtcagagg cacacaaggg   13740
gggaaggcca aaagcgcggc cagagacgga gggaaaacaa agaatcctga cagcccggga   13800
ggggggcgga cacacaggga caaggacaga cccgagtgca gagctgggtc tagtctttgg   13860
gagggggcca gaagactgca aggggaccgg ggggggggc ggcgaggagg actgggcgga   13920 ggaggggct gggggaagccc gcgggaggcg gcaaaggagg gaggaacttt ccaaagttgc   13980
caaacatggc tacctcgcct gcggagccga gcgcggggcc cgcggctcgg ggggaggcgg   14040
cggcggcgac cgaggagcag gaggaggaag cgcgccagct tctgcagact ctgcaggcag   14100
ccgaggggga ggcggcggcg gcggggcgg gagatgcggc ggcggcggcg gactctgggt   14160
ccccgagtgg cccggggtct ccccgggaga ccgtgaccga ggtgcccact ggccttcgct   14220
tctcgcccga acaggtggca tgcgtgtgcg aggcgctgct gcaggcgggc cacgccggcc   14280
gcttgagccg cttcctgggc gcgctgcccc cggccgagcg cctacgtggc agcgatccgg   14340
tgctgcgcgc gcgggcccta gtggccttcc agcggggtga atacgccgag ctctaccaac   14400
ttctcgagag ccgcccttc cccgccgccc accacgcctt cctgcaggac ctctacctgc   14460
gcgcgcgcta ccacgaggcc gagcgggccc gtggccgtgc gctgggcgct gtggacaaat   14520
accggctgcg caagaagttc cctctgccca agaccatctg ggatggcgag gagaccgtct   14580
attgcttcaa ggagcgctcg cgagcggcgc tcaaggcctg ctaccgcggc aaccgctatc   14640
ccacgcctga cgagaagcgc cgcctggcca cgctcaccgg cctctcgctt acacaggtca   14700
gcaactggtt caagaaccgg cgacagcgcg accgcactgg gaccggcggt ggagcgcctt   14760
gcaaaaggtg agggggggaac cgaccctcct tcctcggtgg ccgctggagt ctgcgcaagt   14820
gacccttcac atcctcttc ggtggcgtcg gcgagtgcat aggctgagcg tggagagacc   14880
aggcacaccc tgggttctct gggcatcact gcctcagggg cagaggttgt tccagctact   14940
tctaagctgg gaacgcagtg ccaggaatgg gggggggggc ggggcggga cggcagtga    15000
```

<210> SEQ ID NO 4
<211> LENGTH: 1896
<212> TYPE: DNA
<213> ORGANISM: Mus musculus

<400> SEQUENCE: 4

```
atgtcagccg aagtgcggct gaggcagctc cagcagctgg tgctggaccc aggcttcctg     60
ggactggagc ccctgctcga ccttctcctg ggcgtccacc aggagctggg tgcctctcac    120
ctagcccagg acaagtatgt ggccgacttc ttgcagtggg tggagcccat tgcagcaagg    180
cttaaggagt ccgactgca gagggatgat tttgagattt tgaaggtgat cgggcgtggg    240
gcgttcagcg aggtagcggt ggtgaagatg aaacagacgg gccaagtgta tgccatgaag    300
```

```
attatgaata agtgggacat gctgaagaga ggcgaggtgt cgtgcttccg ggaagaaagg      360
gatgtattag tgaaagggga ccggcgctgg atcacacagc tgcactttgc cttccaggat      420
gagaactacc tgtacctggt catggaatac tacgtgggcg gggacctgct aacgctgctg      480
agcaagtttg gggagcggat ccccgccgag atggctcgct tctacctggc cgagattgtc      540
atggccatag actccgtgca ccggctgggc tacgtgcaca gggacatcaa accagataac      600
attctgctgg accgatgtgg gcacattcgc ctggcagact cggctcctg cctcaaactg       660
cagcctgatg aatggtgag gtcgctggtg ctgtgggca ccccggacta cctgtctcct       720
gagattctgc aggccgttgg tggagggcct ggggcaggca gctacgggcc agagtgtgac      780
tggtgggcac tgggcgtgtt cgcctatgag atgttctatg gcagacccc cttctacgcg       840
gactccacag ccgagacata tgccaagatt gtgcactaca gggaacactt gtcgctgccg      900
ctggcagaca cagttgtccc cgaggaagct caggacctca ttcgtgggct gctgtgtcct      960
gctgagataa ggctaggtcg aggtggggca ggtgatttcc agaaacatcc tttcttcttt     1020
ggccttgatt gggagggtct ccgagacagt gtaccccct ttacaccaga cttcgagggt      1080
gccacggaca catgcaattt cgatgtggtg gaggaccggc tcactgccat ggtgagcggg     1140
ggcggggaga cgctgtcaga catgcaggaa gacatgcccc ttggggtgcg cctgcccttc     1200
gtgggctact cctactgctg catggccttc agagacaatc aggtcccgga ccccaccccct    1260
atggaactag aggccctgca gttgcctgtg tcagacttgc aagggcttga cttgcagccc     1320
ccagtgtccc caccggatca agtggctgaa gaggccgacc tagtggctgt ccctgccct     1380
gtggctgagg cagagaccac ggtaacgctg cagcagctcc aggaagccct ggaagaagag     1440
gttctcaccc ggcagagcct gagccgcgag ctggaggcca tccggaccgc caaccagaac     1500
ttctccagcc aactacagga ggccgaggtc cgaaaccgag acctggaggc gcatgttcgg     1560
cagctacagg aacggatgga gatgctgcag gccccaggag ccgcagccat cacggggtc      1620
cccagtcccc gggccacgga tccaccttcc catctagatg gccccccggc cgtggctgtg     1680
ggccagtgcc cgctggtggg gccaggcccc atgcaccgcc gtcacctgct gctccctgcc     1740
aggatcccta ggcctggcct atccgaggcg cgttgcctgc tcctgttcgc cgctgctctg     1800
gctgctgccg ccacactggg ctgcactggg ttggtggcct ataccggcgg tctcacccca     1860
gtctggtgtt tcccgggagc caccttcgcc ccctga                              1896
```

<210> SEQ ID NO 5
<211> LENGTH: 771
<212> TYPE: DNA
<213> ORGANISM: Mus musculus
<220> FEATURE:
<221> NAME/KEY: misc_feature
<222> LOCATION: 89, 238, 506
<223> OTHER INFORMATION: n = A,T,C or G

<400> SEQUENCE: 5

```
cctgcccctg tggctgaggc agagaccacg gtaacgctgc agcagctcca ggaagccctg       60
gaagaagagg ttctcacccg gcagagctng agccgcgagc tggaggccat ccggaccgcc      120
aaccagaact tctccagcca actacaggag gccgaggtcc gaaaccgaga cctggaggcg      180
catgttcggc agctacagga acggatggag atgctgcagg ccccaggagc cgccggantc     240
cctcacctgc ttccagccaa gggggcactg gtggagatg ggggcatgt tgggtgtgtg       300
aaccctcggg gcaggggagg agtccaggct ggggcaccgc gccgcgccac tgcctttctc      360
```

```
ctccatcctc cacactccat acacctctct cttctccttc cagccatcac gggggtccca    420
gtccccgggc cacggatcca ccttcccatc tagatggccc cccggcggtg gctgtgggcc    480
agtgcccgct ggtggggcca ggacantgtc accgccgtca cctgctgctc cctgccagga    540
ttcctaggcc tggctatccg aggcgcgttg ctgctcctgt tcgccgctgc tctggctgct    600
gcgccacact gggctgcact gggttggttg gctataccgg cggtcttcac ccagtctggt    660
gtttcccgtg agcacccttc gcccctgaaa cctaagactt caagccatct ttcatttagg    720
ccttctagga aggtcgagcg acagggagc gacccaaagc gtctctgtgc c              771

<210> SEQ ID NO 6
<211> LENGTH: 434
<212> TYPE: DNA
<213> ORGANISM: Mus musculus

<400> SEQUENCE: 6
gagagaccca aggggtagtc agggacgggc agacatgcag ctagggttct ggggcctgga     60
caggggcagc caggccctgt gacgggaaga ccccgagctc cggcccgggg aggggccatg    120
gtgttgcctg cccaacatgt cagccgaagt gcggctgagg cagctccagc agctggtgct    180
ggacccaggc ttcctgggac tggagcccct gctcgacctt ctcctgggcg tccaccagga    240
gctgggtgcc tctcacctag cccaggacaa gtatgtggcc gacttcttgc agtgggtgga    300
gcccattgca gcaaggctta aggaggtccg actgcagagg gatgattttg agattttgaa    360
ggtgatcggg cgtggggcgt tcagcgaggt agcggtggtg aagatgaaac acacggagtc    420
tttggcttcg gaca                                                      434

<210> SEQ ID NO 7
<211> LENGTH: 2688
<212> TYPE: DNA
<213> ORGANISM: Mus musculus

<400> SEQUENCE: 7
ccacgcgtcc gcccacgcgt ccggggcaga catgcagcta gggttctggg gcctggacag     60
gggcagccag gccctgtgac gggaagaccc cgagctccgg cccggggagg ggccatggtg    120
ttgcctgccc aacatgtcag ccgaagtgcg gctgaggcag ctccagcagc tggtgctgga    180
cccaggcttc ctgggactgg agcccctgct cgaccttctc ctgggcgtcc accaggagct    240
gggtgcctct cacctagccc aggacaagta tgtggccgac ttcttgcagt gggtggagcc    300
cattgcagca aggcttaagg aggtccgact gcagagggat gattttgaga ttttgaaggt    360
gatcgggcgt ggggcgttca gcgaggtagc ggtggtgaag atgaaacaga cgggccaagt    420
gtatgccatg aagattatga ataagtggga catgctgaag agaggcgagg tgtcgtgctt    480
ccgggaagaa agggatgtat tagtgaaagg ggaccggcgc tggatcacac agctgcactt    540
tgccttccag gatgagaact acctgtacct ggtcatggaa tactacgtgg gcggggacct    600
gctaacgctg ctgagcaagt tggggagcg gatccccgcc gagatggctc gcttctacct    660
ggccgagatt gtcatggcca tagactccgt gcaccggctg gctacgtgc acaggggacat    720
caaaccagat aacattctgc tggaccgatg tgggcacatt cgcctggcag acttcggctc    780
ctgcctcaaa ctgcagcctg atggaatggt gaggtcgctg gtggctgtgg caccccggga    840
ctacctgtct cctgagattc tgcaggccgt tggtggaggg cctggggcag gcagctacgg    900
gccagagtgt gactggtggg cactgggcgt gttcacctat gagatgttct atgggcagac    960
ccccttctac gcggactcca cagccgagac atatgccaag attgtgcact acagggaaca    1020
```

-continued

| | | |
|---|---|---|
| cttgtcgctg ccgctggcag acacagttgt ccccgaggaa gctcaggacc tcattcgtgg | 1080 |
| gctgctgtgt cctgctgaga taaggctagg tcgaggtggg gcaggtgatt ccagaaaca | 1140 |
| tcctttcttc tttggccttg attgggaggg tctccgagac agtgtacccc cctttacacc | 1200 |
| agacttcgag ggtgccacgg acacatgcaa tttcgatgtg gtggaggacc ggctcactgc | 1260 |
| catggtgagc gggggcgggg agacgctgtc agacatgcag gaagacatgc cccttggggt | 1320 |
| gcgcctgccc ttcgtgggct actcctactg ctgcatggcc ttcagagaca atcaggtccc | 1380 |
| ggaccccacc cctatggaac tagaggccct gcagttgcct gtgtcagact gcaagggct | 1440 |
| tgacttgcag cccccagtgt ccccaccgga tcaagtggct gaagaggctg acctagtggc | 1500 |
| tgtccctgcc cctgtggctg aggcagagac cacggtaacg ctgcagcagc tccaggaagc | 1560 |
| cctggaagaa gaggttctca cccggcagag cctgagccgc gagctggagg ccatccggac | 1620 |
| cgccaaccag aacttctcca gccaactaca ggaggccgag gtccgaaacc gagacctgga | 1680 |
| ggcgcatgtt cggcagctac aggaacggat ggagatgctg caggcccag agccgcaga | 1740 |
| tccctaggcc tggcctatcc gaggcgcgtt gcctgctcct gttcgccgct gctctggctg | 1800 |
| ctgccgccac actgggctgc actgggttgg tggcctatac cggcggtctc accccagtct | 1860 |
| ggtgtttccc gggagccacc ttcgccccct gaaccctaag actccaagcc atctttcatt | 1920 |
| taggcctcct aggaaggtcg agcgaccagg gagcgaccca aagcgtctct gtgcccatcg | 1980 |
| ccccccccc cccccccacc gctccgctcc acacttctgt gagcctgggt ccccacccag | 2040 |
| ctccgctcct gtgatccagg cctgccacct ggcggccggg gagggaggaa cagggctcgt | 2100 |
| gcccagcacc cctggttcct gcagagctgg tagccaccgc tgctgcagca gctgggcatt | 2160 |
| cgccgacctt gctttactca gccccgacgt ggatgggcaa actgctcagc tcatccgatt | 2220 |
| tcactttttc actctcccag ccatcagtta caagccataa gcatgagccc ctatttcca | 2280 |
| gggacatccc attcccatag tgatggatca gcaagacctc tgccagcaca cacggagtct | 2340 |
| ttggcttcgg acagcctcac tcctgggggt tgctgcaact ccttcccgt gtacacgtct | 2400 |
| gcactctaac aacggagcca cagctgcact ccccctccc caaagcagt gtgggtattt | 2460 |
| attgatcttg ttatctgact cactgacaga ctccgggacc cacgttttag atgcattgag | 2520 |
| actcgacatt cctcggtatt tattgtctgt ccccacctac gacctccact cccgacctt | 2580 |
| gcgaataaaa tacttctggt ctgccctaaa aaaaaaaaaa aaaaaaaaaa aaaaaaaaa | 2640 |
| aaaaaaaaa aaaaaaaaa aaaaaaaaa aaaaaaaaa aaaaaaa | 2688 |

<210> SEQ ID NO 8
<211> LENGTH: 2862
<212> TYPE: DNA
<213> ORGANISM: Mus musculus

<400> SEQUENCE: 8

| | | |
|---|---|---|
| gggatagtca gggacgggca gacatgcagc tagggttctg ggcctggac aggggcagcc | 60 |
| aggccctgtg acgggaagac cccgagctcc ggcccgggga ggggccatgg tgttgcctgc | 120 |
| ccaacatgtc agccgaagtg cggctgaggc agctccagca gctggtgctg gacccaggct | 180 |
| tcctgggact ggagcccctg ctcgaccttc tcctgggcgt ccaccaggag ctgggtgcct | 240 |
| ctcacctagc ccaggacaag tatgtggccg acttcttgca gtgggtggag cccattgcag | 300 |
| caaggcttaa ggaggtccga ctgcagaggg atgattttga dattttgaag gtgatcgggc | 360 |
| gtggggcgtt cagcgaggta gcggtggtga agatgaaaca gacgggccaa gtgtatgcca | 420 |

```
tgaagattac gaataagtgg gacatgctga agagaggcga ggtgtcgtgc ttccgggaag    480
aaagggatgt attagtgaaa ggggaccggc gctggatcac acagctgcac tttgccttcc    540
aggatgagaa ctacctgtac ctggtcatgg aatactacgt gggcggggac ctgctaacgc    600
tgctgagcaa gtttggggag cggatccccg ccgagatggc tcgcttctac ctggccgaga    660
ttgtcatggc catagactcc gtgcaccggc tgggctacgt gcacagggac atcaaaccag    720
ataacattct gctggaccga tgtgggcaca ttcgcctggc agacttcggc tcctgcctca    780
aactgcagcc tgatggaatg tgtgaggtcg ctggtggctgt gggcacccccg gactacctgt    840 ctcctgagat tctgcaggcc gttggtggag ggcctgggc aggcagctac gggccagagt    900
gtgactggtg ggcactgggc gtgttcacct atgagatgtt ctatgggcag accccttct    960 acgcggactc cacagccgag acatatgcca agattgtgca ctacagggaa cacttgtcgc    1020
tgccgctggc agacacagtt gtccccgagg aagctcagga cctcattcgt gggctgctgt    1080
gtcctgctga gataaggcta ggtcgaggtg gggcaggtga tttccagaaa catccttct    1140 tctttggcct tgattgggag ggtctccgag acagtgtacc cccctttaca ccagacttcg    1200
agggtgccac ggacacatgc aatttcgatg tggtggagga ccggctcact gccatggaga    1260
cgctgtcaga catgcaggaa gacatgcccc ttggggtgcg cctgcccttc gtgggctact    1320
cctactgctg catggccttc agagacaatc aggtcccgga ccccacccct atggaactag    1380
aggccctgca gttgcctgtg tcagacttgc aagggcttga cttgcagccc ccagtgtccc    1440
caccggatca agtggctgaa gaggctgacc tagtggctgt ccctgcccct gtggctgagg    1500
cagagaccac ggtaacgctg cagcagctcc aggaagccct ggaagaagag gttctcaccc    1560
ggcagagcct gagccgcgag ctggaggcca tccggaccgc caaccagaac ttctccagcc    1620
aactacagga ggccgaggtc cgaaaccgag acctggaggc gcatgttcgg cagctacagg    1680
aacggatgga gatgctgcag gccccaggag ccgcagccat cacgggggtc cccagtcccc    1740
gggccacgga tccaccttcc catgcttctc gccaaatcct ccccaaggga actccctaga    1800
ctcccgttct ggcctcgact agattcccgc actgcctctc gccctgctgc tgggctccga    1860
tcgggtcacc tgtcccttct ctctccagct agatggcccc ccggccgtgg ctgtgggcca    1920
gtgcccgctg gtggggccag gccccatgca ccgccgtcac ctgctgctcc ctgccaggat    1980
ccctaggcct ggcctatccg aggcgcgttg cctgctcctg ttcgccgctg ctctggctgc    2040
tgccgccaca ctgggctgca ctgggttggt ggcctatacc ggcggtctca ccccagtctg    2100
gtgtttcccg ggagccacct tcgcccctg aaccctaaga ctccaagcca tctttcattt    2160
aggcctccta ggaaggtcga gcgaccaggg agcgacccaa agcgtctctg tgcccatcgc    2220 ccccccccc ccccaccg ctccgctcca cacttctgtg agcctgggtc cccacccagc    2280
tccgctcctg tgatccaggc ctgccacctg gcggccgggg agggaggaac agggctcgtg    2340
cccagcaccc ctggttcctg cagagctggt agccaccgct gctgcagcag ctgggcattc    2400
gccgaccttg ctttactcag cccgacgtg gatgggcaaa ctgctcagct catccgattt    2460 cacttttca ctctcccagc catcagttac aagccataag catgagcccc ctatttccag    2520
ggacatccca ttcccatagt gatggatcag caagacctct gccagcacac acggagtctt    2580
tggcttcgga cagcctcact cctgggggtt gctgcaactc cttccccgtg tacacgtctg    2640
cactctaaca acggagccac agctgcactc ccccctcccc caaagcagtg tgggtattta    2700
ttgatcttgt tatctgactc actgacagac tccgggaccc acgttttaga tgcattgaga    2760
ctcgacattc ctcggtattt attgtctgtc cccacctacg acctccactc ccgacccttg    2820
```
cgaataaaat acttctggtc tgccctaaaa aaaaaaaaa aa                              2862

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
agcctgagcc gggagatg                                                        18

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gcgtagttga ctggcgaagt t                                                    21

<210> SEQ ID NO 11
<211> LENGTH: 21
<212> TYPE: DNA
<213> ORGANISM: Artificial Sequence
<220> FEATURE:
<223> OTHER INFORMATION: Probe

<400> SEQUENCE: 11
aggccatccg cacggacaac c                                                    21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ctggctgcat gtctgcctgt                                                      20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
ccaggagaag gtcgagcagg                                                      20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tctatggcca tgacaatctc                                                      20

<210> SEQ ID NO 15
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 15
atgtccctgt gcacgtagcc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
atgtgtccgg aagtcgcctg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
ctcaggctct gccgggtgag                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ggcactggcc cacagccacg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
cctggccgaa agaaagaaat                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
aaagaaatgg tctgtgatcc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
aagaaagaaa tggtctgtga                                              20
```

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ggccgaaaga aagaaatggt                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
cctcagcctg gccgaaagaa                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gggcctcagc ctggccgaaa                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tcagggcctc agcctggccg                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
ctgcagtttg cccatccacg                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
ggcctgcagt tgcccatcc                                                20

<210> SEQ ID NO 28
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 28
ccaggcctgc agtttgccca                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
gccttcccag gcctgcagtt                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
gctgccttcc caggcctgca                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
cttgctgcct tcccaggcct                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
gcccggcttg ctgccttccc                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
acggcccggc ttgctgcctt                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
cggacggccc ggcttgctgc                                          20

```
<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
acacggacgg cccggcttgc                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gatggaacac ggacggcccg                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gaggatggaa cacggacggc                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
gtggaggatg gaacacggac                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gcgaaccaac gataggtggg                                                    20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tttgcgaacc aacgataggt                                                    20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 41
ttgcactttg cgaaccaacg                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
gctttgcact ttgcgaacca                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
aaagctttgc actttgcgaa                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
aagaaagctt tgcactttgc                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cacaagaaag ctttgcactt                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gtcatgcaca agaaagcttt                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
acgctcccca gagcagggcg                                               20

<210> SEQ ID NO 48
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 48
gcagagatcg cgccagacgc                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
caggcagaga tcgcgccaga                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
aagcaggcag agatcgcgcc                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
ccgagtaagc aggcagagat                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
ttcccgagta agcaggcaga                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
gcaaatttcc cgagtaagca                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
```
aaagcaaatt tcccgagtaa                                          20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
ttggcaaaag caaatttccc                                          20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ggtttggcaa aagcaaattt                                          20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gcgggtttgg caaaagcaaa                                          20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
aaagcgggtt tggcaaaagc                                          20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
cccgaaaaag cgggtttggc                                          20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
atccccgaaa aagcgggttt                                          20

<210> SEQ ID NO 61
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 61
cgggatcccc gaaaaagcgg                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
gcgcgggatc cccgaaaaag                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
gagagcagcg caagtgagga                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
tccgagagca gcgcaagtga                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
ggctccgaga gcagcgcaag                                               20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
aagcgggcgg agccggctgg                                               20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
ccgaagcggg cggagccggc                                               20
```

```
<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
aaaccgccga agcgggcgga                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
tccaaaccgc cgaagcgggc                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
atatccaaac cgccgaagcg                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
taaatatcca aaccgccgaa                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
caataaatat ccaaaccgcc                                               20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
cgaggtcaat aaatatccaa                                               20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 74
ggacgaggtc aataaatatc                                                    20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
ggaggacgag gtcaataaat                                                    20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
gtcggaggac gaggtcaata                                                    20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
cgagtcggag gacgaggtca                                                    20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
tgtcagcgag tcggaggacg                                                    20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
gcctgtcagc gagtcggagg                                                    20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
gtagcctgtc agcgagtcgg                                                    20

<210> SEQ ID NO 81
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
cctgtagcct gtcagcgagt                                          20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
ggtcctgtag cctgtcagcg                                          20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
aaataccgag gaatgtcggg                                          20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
aataaatacc gaggaatgtc                                          20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
gacaataaat accgaggaat                                          20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
cggggccccg gagtcgaaga                                          20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
```
ccaacggggc cccggagtcg					20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
ttccaacggg gccccggagt					20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
gtcttccaac ggggccccgg					20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
cagtcttcca acggggcccc					20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
ctcagtcttc caacggggcc					20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
gcactcagtc ttccaacggg					20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
ccccgggcac tcagtcttcc					20

<210> SEQ ID NO 94
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 94
tgccccgggc actcagtctt                                                    20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
cgtgccccgg gcactcagtc                                                    20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
gtgccgtgcc ccgggcactc                                                    20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
tctgtgccgt gccccgggca                                                    20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
gcttctgtgc cgtgccccgg                                                    20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
gcggcttctg tgccgtgccc                                                    20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
gcgcggcttc tgtgccgtgc                                                    20
```

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gggcgcggct tctgtgccgt                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
ggcggtgggc gcggcttctg                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
ggcaggcggt gggcgcggct                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
ctggcaggcg gtgggcgcgg                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
aactggcagg cggtgggcgc                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
gtgaactggc aggcggtggg                                               20

<210> SEQ ID NO 107
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 107
ggttgtgaac tggcaggcgg					20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gcggttgtga actggcaggc					20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
cggagcggtt gtgaactggc					20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
cgctcggagc ggttgtgaac					20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
cccacgctcg gagcggttgt					20

<210> SEQ ID NO 112
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 112
agacccacgc tcggagcggt					20

<210> SEQ ID NO 113
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 113
cggagaccca cgctcggagc					20

```
<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 114
gggcggagac ccacgctcgg                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 115
gctgggcgga gacccacgct                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 116
ggagctgggc ggagacccac                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 117
ctggagctgg gcggagaccc                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 118
ggactggagc tgggcggaga                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 119
caggactgga gctgggcgga                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 120
atcacaggac tggagctggg                                                    20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
gggcgggccc ggatcacagg                                                    20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
gggggcgggc ccggatcaca                                                    20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
aggcagcacc atggcccctc                                                    20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 124
ggtccaacac cagctgctgg                                                    20

<210> SEQ ID NO 125
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 125
cgatcacctt cagaatctcg                                                    20

<210> SEQ ID NO 126
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 126
cttgttcatg atcttcatgg                                                    20

<210> SEQ ID NO 127
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 127
ccccattcac caacacgtcc                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 128
gcgtgatcca ccgccggtcc                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 129
gtaatactcc atgaccaggt                                               20

<210> SEQ ID NO 130
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 130
gcagtgtcag caggtccccg                                               20

<210> SEQ ID NO 131
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 131
caccgagtct atggccatga                                               20

<210> SEQ ID NO 132
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 132
acgtagccaa gccggtgcac                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
```
atgtggccac agcggtccag    20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
cttcgtccac cagcggcaga    20

<210> SEQ ID NO 135
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 135
gaccccttcg tccaccagcg    20

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 136
cctgctccac cccggcccag    20

<210> SEQ ID NO 137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 137
cggaagtcgc ctgctccacc    20

<210> SEQ ID NO 138
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 138
cggagaccat cccagtcgag    20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 139
tgagggccat gcaggagtag    20

<210> SEQ ID NO 140
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 140
ctccagttcc atgggtgtgg                                               20

<210> SEQ ID NO 141
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 141
gcgcttgcac gtgtggctca                                               20

<210> SEQ ID NO 142
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 142
gccacttcag ctgtttcatc                                               20

<210> SEQ ID NO 143
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 143
gcctcagcct ctgccgcagg                                               20

<210> SEQ ID NO 144
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 144
gcagcgtcac ctcggcctca                                               20

<210> SEQ ID NO 145
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 145
ggctcaggct ctgccgggtg                                               20

<210> SEQ ID NO 146
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 146
ttccgagcct ctgcctcgcg                                               20
```

<210> SEQ ID NO 147
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 147
ggtcccggtt ccgagcctct                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 148
atccgctcct gcaactgccg                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 149
gcaactccat ccgctcctgc                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 150
aggtggatcc gtggcccggg                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 151
cgcggcttct gtgccgtgcc                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 152
ttgctgcctt cccaggcctg                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 153
tgctcccgac aagctccaga                                           20

<210> SEQ ID NO 154
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 154
agaacctgcc cattgctgaa                                           20

<210> SEQ ID NO 155
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 155
cactgagggc cagacatatg                                           20

<210> SEQ ID NO 156
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 156
ctctagattc agatgcaggt                                           20

<210> SEQ ID NO 157
<211> LENGTH: 15
<212> TYPE: DNA
<213> ORGANISM: Artificial Sequence
<220> FEATURE:
<223> OTHER INFORMATION: Primer

<400> SEQUENCE: 157
cgggccgtcc gtgtt                                                15

<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
ctttgcactt tgcgaaccaa                                           20

<210> SEQ ID NO 159
<211> LENGTH: 21
<212> TYPE: DNA
<213> ORGANISM: Artificial Sequence
<220> FEATURE:
<223> OTHER INFORMATION: Probe

<400> SEQUENCE: 159
catcctccac gcacccccac c                                         21

<210> SEQ ID NO 160

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 160
gcctggcagc ccctgtccag                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 161
ggcctggcag ccctgtcca                                                20

<210> SEQ ID NO 162
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 162
gggcctggca gccctgtcc                                                20

<210> SEQ ID NO 163
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 163
atggcccctc cccgggccgg                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 164
catggcccct ccccgggccg                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 165
ccatggcccc tccccgggcc                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 166
```

```
accatggccc ctccccgggc                                              20

<210> SEQ ID NO 167
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 167
caccatggcc cctccccggg                                              20

<210> SEQ ID NO 168
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 168
gcaccatggc ccctccccgg                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 169
agcaccatgg ccctccccg                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 170
cagcaccatg gccctcccc                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 171
gcagcaccat ggccctccc                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 172
ggcagcacca tggcccctcc                                              20

<210> SEQ ID NO 173
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 173
caggcagcac catggcccct                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 174
acaggcagca ccatggcccc                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 175
ggacaggcag caccatggcc                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 176
tggacaggca gcaccatggc                                              20

<210> SEQ ID NO 177
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 177
ttggacaggc agcaccatgg                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 178
gttggacagg cagcaccatg                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 179
tgttggacag gcagcaccat                                              20
```

<210> SEQ ID NO 180
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 180
atgttggaca ggcagcacca                                               20

<210> SEQ ID NO 181
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 181
catgttggac aggcagcacc                                               20

<210> SEQ ID NO 182
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 182
acatgttgga caggcagcac                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 183
gacatgttgg acaggcagca                                               20

<210> SEQ ID NO 184
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 184
tgacatgttg gacaggcagc                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 185
ctgacatgtt ggacaggcag                                               20

<210> SEQ ID NO 186
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 186
gctgacatgt tggacaggca                                                      20

<210> SEQ ID NO 187
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 187
ggctgacatg ttggacaggc                                                      20

<210> SEQ ID NO 188
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 188
cggctgacat gttggacagg                                                      20

<210> SEQ ID NO 189
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 189
tcggctgaca tgttggacag                                                      20

<210> SEQ ID NO 190
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 190
ctcggctgac atgttggaca                                                      20

<210> SEQ ID NO 191
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 191
cctcggctga catgttggac                                                      20

<210> SEQ ID NO 192
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 192
acctcggctg acatgttgga                                                      20
```

```
<210> SEQ ID NO 193
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 193
cacctcggct gacatgttgg                                                   20

<210> SEQ ID NO 194
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 194
gcacctcggc tgacatgttg                                                   20

<210> SEQ ID NO 195
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 195
cgcacctcgg ctgacatgtt                                                   20

<210> SEQ ID NO 196
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 196
ccgcacctcg gctgacatgt                                                   20

<210> SEQ ID NO 197
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 197
gccgcacctc ggctgacatg                                                   20

<210> SEQ ID NO 198
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 198
agccgcacct cggctgacat                                                   20

<210> SEQ ID NO 199
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 199
cagccgcacc tcggctgaca						20

<210> SEQ ID NO 200
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 200
tcagccgcac ctcggctgac						20

<210> SEQ ID NO 201
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 201
ctcagccgca cctcggctga						20

<210> SEQ ID NO 202
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 202
cctcagccgc acctcggctg						20

<210> SEQ ID NO 203
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 203
gcctcagccg cacctcggct						20

<210> SEQ ID NO 204
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 204
ccaacaccag ctgctggagc						20

<210> SEQ ID NO 205
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 205
tccaacacca gctgctggag						20

<210> SEQ ID NO 206
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 206
gtccaacacc agctgctgga                                              20

<210> SEQ ID NO 207
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 207
gggtccaaca ccagctgctg                                              20

<210> SEQ ID NO 208
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 208
ggctccagcc ccaggaagcc                                              20

<210> SEQ ID NO 209
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 209
gggctccagc cccaggaagc                                              20

<210> SEQ ID NO 210
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 210
caggagaagg tcgagcaggg                                              20

<210> SEQ ID NO 211
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 211
cccaggagaa ggtcgagcag                                              20

<210> SEQ ID NO 212
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 212
```

```
gcccaggaga aggtcgagca                                          20

<210> SEQ ID NO 213
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 213
cgcccaggag aaggtcgagc                                          20

<210> SEQ ID NO 214
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 214
acgcccagga gaaggtcgag                                          20

<210> SEQ ID NO 215
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 215
tcctgggcca gttcggaggc                                          20

<210> SEQ ID NO 216
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 216
gtcctgggcc agttcggagg                                          20

<210> SEQ ID NO 217
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 217
tgtcctgggc cagttcggag                                          20

<210> SEQ ID NO 218
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 218
ttgtcctggg ccagttcgga                                          20

<210> SEQ ID NO 219
<211> LENGTH: 20
<212> TYPE: DNA
<213> ORGANISM: Artificial Sequence
```

<220> FEATURE:
<223> OTHER INFORMATION: Synthetic oligonucleotide

<400> SEQUENCE: 219
cttgtcctgg gccagttcgg    20

<210> SEQ ID NO 220
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 220
acttgtcctg ggccagttcg    20

<210> SEQ ID NO 221
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 221
tacttgtcct gggccagttc    20

<210> SEQ ID NO 222
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 222
gtacttgtcc tgggccagtt    20

<210> SEQ ID NO 223
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 223
cgtacttgtc ctgggccagt    20

<210> SEQ ID NO 224
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 224
actgcaagaa gtcggccacg    20

<210> SEQ ID NO 225
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 225
ccactgcaag aagtcggcca    20

```
<210> SEQ ID NO 226
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 226
cccactgcaa gaagtcggcc                                                   20

<210> SEQ ID NO 227
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 227
gcccactgca agaagtcggc                                                   20

<210> SEQ ID NO 228
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 228
cgcccactgc aagaagtcgg                                                   20

<210> SEQ ID NO 229
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 229
ccgcccactg caagaagtcg                                                   20

<210> SEQ ID NO 230
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 230
tccgcccact gcaagaagtc                                                   20

<210> SEQ ID NO 231
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 231
ctccgcccac tgcaagaagt                                                   20

<210> SEQ ID NO 232
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 232
gctccgccca ctgcaagaag                                               20

<210> SEQ ID NO 233
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 233
ggctccgccc actgcaagaa                                               20

<210> SEQ ID NO 234
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 234
gggctccgcc cactgcaaga                                               20

<210> SEQ ID NO 235
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 235
tgggctccgc ccactgcaag                                               20

<210> SEQ ID NO 236
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 236
atgggctccg cccactgcaa                                               20

<210> SEQ ID NO 237
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 237
gatgggctcc gcccactgca                                               20

<210> SEQ ID NO 238
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 238
cgatgggctc cgcccactgc                                               20

<210> SEQ ID NO 239
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 239
acgatgggct ccgcccactg                                              20

<210> SEQ ID NO 240
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 240
cacgatgggc tccgcccact                                              20

<210> SEQ ID NO 241
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 241
ccacgatggg ctccgcccac                                              20

<210> SEQ ID NO 242
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 242
accacgatgg gctccgccca                                              20

<210> SEQ ID NO 243
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 243
caccacgatg ggctccgccc                                              20

<210> SEQ ID NO 244
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 244
tcaccacgat gggctccgcc                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 245
```
ctcaccacga tgggctccgc 20

<210> SEQ ID NO 246
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 246
cctcaccacg atgggctccg 20

<210> SEQ ID NO 247
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 247
gcctcaccac gatgggctcc 20

<210> SEQ ID NO 248
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 248
agcctcacca cgatgggctc 20

<210> SEQ ID NO 249
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 249
aagcctcacc acgatgggct 20

<210> SEQ ID NO 250
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 250
taagcctcac cacgatgggc 20

<210> SEQ ID NO 251
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 251
ttaagcctca ccacgatggg 20

<210> SEQ ID NO 252
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 252
cttaagcctc accacgatgg                                                    20

<210> SEQ ID NO 253
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 253
ccttaagcct caccacgatg                                                    20

<210> SEQ ID NO 254
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 254
tccttaagcc tcaccacgat                                                    20

<210> SEQ ID NO 255
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 255
ctccttaagc ctcaccacga                                                    20

<210> SEQ ID NO 256
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 256
cctccttaag cctcaccacg                                                    20

<210> SEQ ID NO 257
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 257
acctccttaa gcctcaccac                                                    20

<210> SEQ ID NO 258
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 258
gacctcctta agcctcacca                                                    20
```

<210> SEQ ID NO 259
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 259
ggacctcctt aagcctcacc                                       20

<210> SEQ ID NO 260
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 260
cggacctcct taagcctcac                                       20

<210> SEQ ID NO 261
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 261
tcggacctcc ttaagcctca                                       20

<210> SEQ ID NO 262
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 262
gtcggacctc cttaagcctc                                       20

<210> SEQ ID NO 263
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 263
cagtcggacc tccttaagcc                                       20

<210> SEQ ID NO 264
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 264
gcagtcggac tccttaagc                                        20

<210> SEQ ID NO 265
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 265
tgcagtcgga cctccttaag					20

<210> SEQ ID NO 266
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 266
ccttcagaat ctcgaagtcg					20

<210> SEQ ID NO 267
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 267
accttcagaa tctcgaagtc					20

<210> SEQ ID NO 268
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 268
tcaccttcag aatctcgaag					20

<210> SEQ ID NO 269
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 269
atcaccttca gaatctcgaa					20

<210> SEQ ID NO 270
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 270
gatcaccttc agaatctcga					20

<210> SEQ ID NO 271
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 271
ccgatcacct tcagaatctc					20

```
<210> SEQ ID NO 272
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 272
tccgatcacc ttcagaatct                                            20

<210> SEQ ID NO 273
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 273
gtccgatcac cttcagaatc                                            20

<210> SEQ ID NO 274
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 274
cgtccgatca ccttcagaat                                            20

<210> SEQ ID NO 275
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 275
cccgtctgct tcatcttcac                                            20

<210> SEQ ID NO 276
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 276
gcccgtctgc ttcatcttca                                            20

<210> SEQ ID NO 277
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 277
ggcccgtctg cttcatcttc                                            20

<210> SEQ ID NO 278
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 278
tggcccgtct gcttcatctt                                               20

<210> SEQ ID NO 279
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 279
ctggcccgtc tgcttcatct                                               20

<210> SEQ ID NO 280
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 280
cctggcccgt ctgcttcatc                                               20

<210> SEQ ID NO 281
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 281
acctggcccg tctgcttcat                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 282
cacctggccc gtctgcttca                                               20

<210> SEQ ID NO 283
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 283
acacctggcc cgtctgcttc                                               20

<210> SEQ ID NO 284
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 284
tacacctggc ccgtctgctt                                               20

<210> SEQ ID NO 285
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 285
ttgttcatga tcttcatggc                                              20

<210> SEQ ID NO 286
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 286
acttgttcat gatcttcatg                                              20

<210> SEQ ID NO 287
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 287
cacttgttca tgatcttcat                                              20

<210> SEQ ID NO 288
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 288
ccacttgttc atgatcttca                                              20

<210> SEQ ID NO 289
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 289
cccacttgtt catgatcttc                                              20

<210> SEQ ID NO 290
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 290
tcccacttgt tcatgatctt                                              20

<210> SEQ ID NO 291
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 291
```
gtcccacttg ttcatgatct                                              20

<210> SEQ ID NO 292
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 292
tgtcccactt gttcatgatc                                              20

<210> SEQ ID NO 293
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 293
atgtcccact tgttcatgat                                              20

<210> SEQ ID NO 294
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 294
catgtcccac ttgttcatga                                              20

<210> SEQ ID NO 295
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 295
gcatgtccca cttgttcatg                                              20

<210> SEQ ID NO 296
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 296
agcatgtccc acttgttcat                                              20

<210> SEQ ID NO 297
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 297
cagcatgtcc cacttgttca                                              20

<210> SEQ ID NO 298
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 298
tcagcatgtc ccacttgttc                                              20

<210> SEQ ID NO 299
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 299
ttcagcatgt cccacttgtt                                              20

<210> SEQ ID NO 300
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 300
cttcagcatg tcccacttgt                                              20

<210> SEQ ID NO 301
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 301
tcttcagcat gtcccacttg                                              20

<210> SEQ ID NO 302
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 302
cctcttcagc atgtcccact                                              20

<210> SEQ ID NO 303
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 303
ccctcttcag catgtcccac                                              20

<210> SEQ ID NO 304
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 304
cccctcttca gcatgtccca                                              20
```

<210> SEQ ID NO 305
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 305
gcccctcttc agcatgtccc                                           20

<210> SEQ ID NO 306
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 306
cgcccctctt cagcatgtcc                                           20

<210> SEQ ID NO 307
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 307
tcgcccctct tcagcatgtc                                           20

<210> SEQ ID NO 308
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 308
ctcgcccctc ttcagcatgt                                           20

<210> SEQ ID NO 309
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 309
cctcgcccct cttcagcatg                                           20

<210> SEQ ID NO 310
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 310
acctcgcccc tcttcagcat                                           20

<210> SEQ ID NO 311
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 311
cacctcgccc ctcttcagca                                              20

<210> SEQ ID NO 312
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 312
acacctcgcc cctcttcagc                                              20

<210> SEQ ID NO 313
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 313
gacacctcgc ccctcttcag                                              20

<210> SEQ ID NO 314
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 314
gccaggcgga tgtggccaca                                              20

<210> SEQ ID NO 315
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 315
accgcaccgt tccatctgcc                                              20

<210> SEQ ID NO 316
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 316
gaccgcaccg ttccatctgc                                              20

<210> SEQ ID NO 317
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 317
acagcctgca ggatctcggg                                              20

<210> SEQ ID NO 318
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 318
cacagcctgc aggatctcgg                                                    20

<210> SEQ ID NO 319
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 319
ccacagcctg caggatctcg                                                    20

<210> SEQ ID NO 320
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 320
cccacagcct gcaggatctc                                                    20

<210> SEQ ID NO 321
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 321
gcccacagcc tgcaggatct                                                    20

<210> SEQ ID NO 322
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 322
cgcccacagc ctgcaggatc                                                    20

<210> SEQ ID NO 323
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 323
ccgcccacag cctgcaggat                                                    20

<210> SEQ ID NO 324
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 324
```
accgcccaca gcctgcagga                                              20

<210> SEQ ID NO 325
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 325
caccgcccac agcctgcagg                                              20

<210> SEQ ID NO 326
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 326
ccaccgccca cagcctgcag                                              20

<210> SEQ ID NO 327
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 327
cccaccgccc acagcctgca                                              20

<210> SEQ ID NO 328
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 328
gcccaccgcc cacagcctgc                                              20

<210> SEQ ID NO 329
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 329
ggcccaccgc ccacagcctg                                              20

<210> SEQ ID NO 330
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 330
aggcccaccg cccacagcct                                              20

<210> SEQ ID NO 331
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 331
caggcccacc gcccacagcc                                              20

<210> SEQ ID NO 332
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 332
ccaggcccac cgcccacagc                                              20

<210> SEQ ID NO 333
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 333
cccaggccca ccgcccacag                                              20

<210> SEQ ID NO 334
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 334
tcccaggccc accgcccaca                                              20

<210> SEQ ID NO 335
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 335
gtcccaggcc caccgcccac                                              20

<210> SEQ ID NO 336
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 336
tgtcccaggc ccaccgccca                                              20

<210> SEQ ID NO 337
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 337
ctgtcccagg cccaccgccc                                              20
```

<210> SEQ ID NO 338
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 338
cctgtcccag gcccaccgcc                                           20

<210> SEQ ID NO 339
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 339
gcctgtccca ggcccaccgc                                           20

<210> SEQ ID NO 340
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 340
tgcctgtccc aggcccaccg                                           20

<210> SEQ ID NO 341
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 341
ctgcctgtcc caggcccacc                                           20

<210> SEQ ID NO 342
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 342
gctgcctgtc ccaggcccac                                           20

<210> SEQ ID NO 343
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 343
agctgcctgt cccaggccca                                           20

<210> SEQ ID NO 344
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 344
tagctgcctg tcccaggccc                                        20

<210> SEQ ID NO 345
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 345
gtagctgcct gtcccaggcc                                        20

<210> SEQ ID NO 346
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 346
cgtagctgcc tgtcccaggc                                        20

<210> SEQ ID NO 347
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 347
ccgtagctgc ctgtcccagg                                        20

<210> SEQ ID NO 348
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 348
cccgtagctg cctgtcccag                                        20

<210> SEQ ID NO 349
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 349
gcccgtagct gcctgtccca                                        20

<210> SEQ ID NO 350
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 350
ggcccgtagc tgcctgtccc                                        20

```
<210> SEQ ID NO 351
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 351
tagaacattt cataggcgaa                                              20

<210> SEQ ID NO 352
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 352
tctccgccgt ggaatccgcg                                              20

<210> SEQ ID NO 353
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 353
gtctccgccg tggaatccgc                                              20

<210> SEQ ID NO 354
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 354
ggtctccgcc gtggaatccg                                              20

<210> SEQ ID NO 355
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 355
aggtctccgc cgtggaatcc                                              20

<210> SEQ ID NO 356
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 356
taggtctccg ccgtggaatc                                              20

<210> SEQ ID NO 357
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 357
ttgtagtgga cgatcttgcc                                         20

<210> SEQ ID NO 358
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 358
cttgtagtgg acgatcttgc                                         20

<210> SEQ ID NO 359
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 359
ccttgtagtg gacgatcttg                                         20

<210> SEQ ID NO 360
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 360
tccttgtagt ggacgatctt                                         20

<210> SEQ ID NO 361
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 361
ctccttgtag tggacgatct                                         20

<210> SEQ ID NO 362
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 362
gctccttgta gtggacgatc                                         20

<210> SEQ ID NO 363
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 363
tgctccttgt agtggacgat                                         20

<210> SEQ ID NO 364
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 364
gtgctccttg tagtggacga                                                     20

<210> SEQ ID NO 365
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 365
ggtgctcctt gtagtggacg                                                     20

<210> SEQ ID NO 366
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 366
aggtgctcct tgtagtggac                                                     20

<210> SEQ ID NO 367
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 367
gaggtgctcc ttgtagtgga                                                     20

<210> SEQ ID NO 368
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 368
agaggtgctc cttgtagtgg                                                     20

<210> SEQ ID NO 369
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 369
gagaggtgct ccttgtagtg                                                     20

<210> SEQ ID NO 370
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 370
```
agagaggtgc tccttgtagt                                          20

<210> SEQ ID NO 371
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 371
gagagaggtg ctccttgtag                                          20

<210> SEQ ID NO 372
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 372
agagagaggt gctccttgta                                          20

<210> SEQ ID NO 373
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 373
cagagagagg tgctccttgt                                          20

<210> SEQ ID NO 374
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 374
ggcagagaga ggtgctcctt                                          20

<210> SEQ ID NO 375
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 375
cggcagagag aggtgctcct                                          20

<210> SEQ ID NO 376
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 376
gcggcagaga gaggtgctcc                                          20

<210> SEQ ID NO 377
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 377
agcggcagag agaggtgctc                                                     20

<210> SEQ ID NO 378
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 378
cagcggcaga gagaggtgct                                                     20

<210> SEQ ID NO 379
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 379
ccagcggcag agagaggtgc                                                     20

<210> SEQ ID NO 380
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 380
ggcccagccg tgtctccggg                                                     20

<210> SEQ ID NO 381
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 381
cggcccagcc gtgtctccgg                                                     20

<210> SEQ ID NO 382
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 382
ccggcccagc cgtgtctccg                                                     20

<210> SEQ ID NO 383
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 383
cccggcccag ccgtgtctcc                                                     20
```

<210> SEQ ID NO 384
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 384
ccccggccca gccgtgtctc                                              20

<210> SEQ ID NO 385
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 385
accccggccc agccgtgtct                                              20

<210> SEQ ID NO 386
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 386
caccccggcc cagccgtgtc                                              20

<210> SEQ ID NO 387
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 387
ccaccccggc ccagccgtgt                                              20

<210> SEQ ID NO 388
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 388
tccaccccgg cccagccgtg                                              20

<210> SEQ ID NO 389
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 389
ctccaccccg gcccagccgt                                              20

<210> SEQ ID NO 390
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 390
gctccacccc ggcccagccg                                               20

<210> SEQ ID NO 391
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 391
tgctccaccc cggcccagcc                                               20

<210> SEQ ID NO 392
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 392
ctgctccacc ccggcccagc                                               20

<210> SEQ ID NO 393
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 393
aagggatgtg tccggaagtc                                               20

<210> SEQ ID NO 394
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 394
gaagggatgt gtccggaagt                                               20

<210> SEQ ID NO 395
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 395
agaagggatg tgtccggaag                                               20

<210> SEQ ID NO 396
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 396
aagaagggat gtgtccggaa                                               20

<210> SEQ ID NO 397
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 397
gaagaaggga tgtgtccgga                                                   20

<210> SEQ ID NO 398
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 398
agaagaaggg atgtgtccgg                                                   20

<210> SEQ ID NO 399
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 399
aagaagaagg gatgtgtccg                                                   20

<210> SEQ ID NO 400
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 400
aaagaagaag ggatgtgtcc                                                   20

<210> SEQ ID NO 401
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 401
caaagaagaa gggatgtgtc                                                   20

<210> SEQ ID NO 402
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 402
ccaaagaaga agggatgtgt                                                   20

<210> SEQ ID NO 403
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 403
```
ggccaaagaa gaagggatgt                                              20

<210> SEQ ID NO 404
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 404
aggccaaaga agaagggatg                                              20

<210> SEQ ID NO 405
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 405
gaggccaaag aagaagggat                                              20

<210> SEQ ID NO 406
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 406
cgaggccaaa gaagaaggga                                              20

<210> SEQ ID NO 407
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 407
tcgaggccaa agaagaaggg                                              20

<210> SEQ ID NO 408
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 408
gtcgaggcca agaagaaggg                                              20

<210> SEQ ID NO 409
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 409
agtcgaggcc aaagaagaag                                              20

<210> SEQ ID NO 410
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 410
cagtcgaggc caaagaagaa                                                   20

<210> SEQ ID NO 411
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 411
ccagtcgagg ccaaagaaga                                                   20

<210> SEQ ID NO 412
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 412
cccagtcgag gccaaagaag                                                   20

<210> SEQ ID NO 413
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 413
tcccagtcga ggccaaagaa                                                   20

<210> SEQ ID NO 414
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 414
atcccagtcg aggccaaaga                                                   20

<210> SEQ ID NO 415
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 415
catcccagtc gaggccaaag                                                   20

<210> SEQ ID NO 416
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 416
ccatcccagt cgaggccaaa                                                   20
```

<210> SEQ ID NO 417
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 417
accatcccag tcgaggccaa                                               20

<210> SEQ ID NO 418
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 418
gaccatccca gtcgaggcca                                               20

<210> SEQ ID NO 419
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 419
agaccatccc agtcgaggcc                                               20

<210> SEQ ID NO 420
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 420
gagaccatcc cagtcgaggc                                               20

<210> SEQ ID NO 421
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 421
ggagaccatc ccagtcgagg                                               20

<210> SEQ ID NO 422
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 422
ttcgaaatcc ggtgtaaagg                                               20

<210> SEQ ID NO 423
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 423
cttcgaaatc cggtgtaaag						20

<210> SEQ ID NO 424
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 424
ccttcgaaat ccggtgtaaa						20

<210> SEQ ID NO 425
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 425
accttcgaaa tccggtgtaa						20

<210> SEQ ID NO 426
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 426
caccttcgaa atccggtgta						20

<210> SEQ ID NO 427
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 427
gcaccttcga atccggtgt						20

<210> SEQ ID NO 428
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 428
ggcaccttcg aaatccggtg						20

<210> SEQ ID NO 429
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 429
tggcaccttc gaaatccggt						20

```
<210> SEQ ID NO 430
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 430
gtggcacctt cgaaatccgg                                          20

<210> SEQ ID NO 431
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 431
ggtggcacct tcgaaatccg                                          20

<210> SEQ ID NO 432
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 432
cggtggcacc ttcgaaatcc                                          20

<210> SEQ ID NO 433
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 433
tcggtggcac cttcgaaatc                                          20

<210> SEQ ID NO 434
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 434
gtcggtggca ccttcgaaat                                          20

<210> SEQ ID NO 435
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 435
tgtcggtggc accttcgaaa                                          20

<210> SEQ ID NO 436
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 436
gtgtcggtgg caccttcgaa                                                    20

<210> SEQ ID NO 437
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 437
tgtgtcggtg gcaccttcga                                                    20

<210> SEQ ID NO 438
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 438
atgtgtcggt ggcaccttcg                                                    20

<210> SEQ ID NO 439
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 439
catgtgtcgg tggcaccttc                                                    20

<210> SEQ ID NO 440
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 440
gcatgtgtcg gtggcacctt                                                    20

<210> SEQ ID NO 441
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 441
tgcatgtgtc ggtggcacct                                                    20

<210> SEQ ID NO 442
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 442
ttgcatgtgt cggtggcacc                                                    20

<210> SEQ ID NO 443
<211> LENGTH: 20

<212> TYPE: DNA
<213> ORGANISM: Artificial Sequence
<220> FEATURE:
<223> OTHER INFORMATION: Synthetic oligonucleotide

<400> SEQUENCE: 443
gttgcatgtg tcggtggcac                                        20

<210> SEQ ID NO 444
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 444
agttgcatgt gtcggtggca                                        20

<210> SEQ ID NO 445
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 445
aagttgcatg tgtcggtggc                                        20

<210> SEQ ID NO 446
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 446
gaagttgcat gtgtcggtgg                                        20

<210> SEQ ID NO 447
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 447
cgaagttgca tgtgtcggtg                                        20

<210> SEQ ID NO 448
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 448
gtcgaagttg catgtgtcgg                                        20

<210> SEQ ID NO 449
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 449
agtcgaagtt gcatgtgtcg                                               20

<210> SEQ ID NO 450
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 450
aagtcgaagt tgcatgtgtc                                               20

<210> SEQ ID NO 451
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 451
caagtcgaag ttgcatgtgt                                               20

<210> SEQ ID NO 452
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 452
ccaagtcgaa gttgcatgtg                                               20

<210> SEQ ID NO 453
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 453
accaagtcga agttgcatgt                                               20

<210> SEQ ID NO 454
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 454
caccaagtcg aagttgcatg                                               20

<210> SEQ ID NO 455
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 455
ccaccaagtc gaagttgcat                                               20

<210> SEQ ID NO 456
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 456
tccaccaagt cgaagttgca                                               20

<210> SEQ ID NO 457
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 457
ctccaccaag tcgaagttgc                                               20

<210> SEQ ID NO 458
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 458
cctccaccaa gtcgaagttg                                               20

<210> SEQ ID NO 459
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 459
tcctccacca agtcgaagtt                                               20

<210> SEQ ID NO 460
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 460
gtcctccacc aagtcgaagt                                               20

<210> SEQ ID NO 461
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 461
cgtcctccac caagtcgaag                                               20

<210> SEQ ID NO 462
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 462
ccgtcctcca ccaagtcgaa                                               20
```

<210> SEQ ID NO 463
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 463
cccgtcctcc accaagtcga                                               20

<210> SEQ ID NO 464
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 464
gcccgtcctc caccaagtcg                                               20

<210> SEQ ID NO 465
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 465
agcccgtcct ccaccaagtc                                               20

<210> SEQ ID NO 466
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 466
gagcccgtcc tccaccaagt                                               20

<210> SEQ ID NO 467
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 467
tgagcccgtc ctccaccaag                                               20

<210> SEQ ID NO 468
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 468
ggttccgagc ctctgcctcg                                               20

<210> SEQ ID NO 469
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 469
cggttccgag cctctgcctc                                              20

<210> SEQ ID NO 470
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 470
ccggttccga gcctctgcct                                              20

<210> SEQ ID NO 471
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 471
cccggttccg agcctctgcc                                              20

<210> SEQ ID NO 472
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 472
tcccggttcc gagcctctgc                                              20

<210> SEQ ID NO 473
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 473
gtcccggttc cgagcctctg                                              20

<210> SEQ ID NO 474
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 474
aggtcccggt tccgagcctc                                              20

<210> SEQ ID NO 475
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 475
taggtcccgg ttccgagcct                                              20

<210> SEQ ID NO 476
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 476
ctaggtcccg gttccgagcc                                                20

<210> SEQ ID NO 477
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 477
tctaggtccc ggttccgagc                                                20

<210> SEQ ID NO 478
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 478
ctctaggtcc cggttccgag                                                20

<210> SEQ ID NO 479
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 479
cctctaggtc ccggttccga                                                20

<210> SEQ ID NO 480
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 480
gcctctaggt cccggttccg                                                20

<210> SEQ ID NO 481
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 481
catccgctcc tgcaactgcc                                                20

<210> SEQ ID NO 482
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 482
```
ccatccgctc ctgcaactgc                                          20

<210> SEQ ID NO 483
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 483
tccatccgct cctgcaactg                                          20

<210> SEQ ID NO 484
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 484
ctccatccgc tcctgcaact                                          20

<210> SEQ ID NO 485
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 485
actccatccg ctcctgcaac                                          20

<210> SEQ ID NO 486
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 486
aactccatcc gctcctgcaa                                          20

<210> SEQ ID NO 487
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 487
caactccatc cgctcctgca                                          20

<210> SEQ ID NO 488
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 488
agcaactcca tccgctcctg                                          20

<210> SEQ ID NO 489
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 489
cagcaactcc atccgctcct                                                    20

<210> SEQ ID NO 490
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 490
gcagcaactc catccgctcc                                                    20

<210> SEQ ID NO 491
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 491
cagctgtggc tccctctgcc                                                    20

<210> SEQ ID NO 492
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 492
acagctgtgg ctccctctgc                                                    20

<210> SEQ ID NO 493
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 493
gacagctgtg gctccctctg                                                    20

<210> SEQ ID NO 494
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 494
tgacagctgt ggctccctct                                                    20

<210> SEQ ID NO 495
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 495
gtgacagctg tggctccctc                                                    20
```

<210> SEQ ID NO 496
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 496
cgtgacagct gtggctccct        20

<210> SEQ ID NO 497
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 497
ccgtgacagc tgtggctccc        20

<210> SEQ ID NO 498
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 498
cccgtgacag ctgtggctcc        20

<210> SEQ ID NO 499
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 499
ccccgtgaca gctgtggctc        20

<210> SEQ ID NO 500
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 500
cccccgtgac agctgtggct        20

<210> SEQ ID NO 501
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 501
acccccgtga cagctgtggc        20

<210> SEQ ID NO 502
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 502 gaccccgtg acagctgtgg                                          20

<210> SEQ ID NO 503
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 503 ggaccccgt gacagctgtg                                          20

<210> SEQ ID NO 504
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 504 gggaccccg tgacagctgt                                          20

<210> SEQ ID NO 505
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 505
gaaggtggat ccgtggcccg                                         20

<210> SEQ ID NO 506
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 506
ggaaggtgga tccgtggccc                                         20

<210> SEQ ID NO 507
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 507
gggaaggtgg atccgtggcc                                         20

<210> SEQ ID NO 508
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 508
tgggaaggtg gatccgtggc                                         20

```
<210> SEQ ID NO 509
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 509
atgggaaggt ggatccgtgg                                                    20

<210> SEQ ID NO 510
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 510
gatgggaagg tggatccgtg                                                    20

<210> SEQ ID NO 511
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 511
tagatgggaa ggtggatccg                                                    20

<210> SEQ ID NO 512
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 512
ctagatggga aggtggatcc                                                    20

<210> SEQ ID NO 513
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 513
tctagatggg aaggtggatc                                                    20

<210> SEQ ID NO 514
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 514
atctagatgg gaaggtggat                                                    20

<210> SEQ ID NO 515
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 515
ccatctagat gggaaggtgg                                                    20

<210> SEQ ID NO 516
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 516
gccatctaga tgggaaggtg                                                    20

<210> SEQ ID NO 517
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 517
ggccatctag atgggaaggt                                                    20

<210> SEQ ID NO 518
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 518
caccagcggg cactggccca                                                    20

<210> SEQ ID NO 519
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 519
ccaccagcgg gcactggccc                                                    20

<210> SEQ ID NO 520
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 520
cccaccagcg ggcactggcc                                                    20

<210> SEQ ID NO 521
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 521
ccccaccagc gggcactggc                                                    20

<210> SEQ ID NO 522
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 522
ggccccacca gcgggcactg                                              20

<210> SEQ ID NO 523
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 523
tggccccacc agcgggcact                                              20

<210> SEQ ID NO 524
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 524
ctggccccac cagcgggcac                                              20

<210> SEQ ID NO 525
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 525
cctggcccca ccagcgggca                                              20

<210> SEQ ID NO 526
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 526
gcctggcccc accagcgggc                                              20

<210> SEQ ID NO 527
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 527
gggcctggcc ccaccagcgg                                              20

<210> SEQ ID NO 528
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 528
```
aggtggcggc ggtgcatggg                                                  20

<210> SEQ ID NO 529
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 529
caggtggcgg cggtgcatgg                                                  20

<210> SEQ ID NO 530
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 530
gcaggtggcg gcggtgcatg                                                  20

<210> SEQ ID NO 531
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 531
agcaggtggc ggcggtgcat                                                  20

<210> SEQ ID NO 532
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 532
cagcaggtgg cggcggtgca                                                  20

<210> SEQ ID NO 533
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 533
gcagcaggtg gcggcggtgc                                                  20

<210> SEQ ID NO 534
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 534
agcagcaggt ggcggcggtg                                                  20

<210> SEQ ID NO 535
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 535
gagcagcagg tggcggcggt                                              20

<210> SEQ ID NO 536
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 536
ggagcagcag gtggcggcgg                                              20

<210> SEQ ID NO 537
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 537
gggagcagca ggtggcggcg                                              20

<210> SEQ ID NO 538
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 538
agggagcagc aggtggcggc                                              20

<210> SEQ ID NO 539
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 539
cagggagcag caggtggcgg                                              20

<210> SEQ ID NO 540
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 540
gcagggagca gcaggtggcg                                              20

<210> SEQ ID NO 541
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 541
ggcagggagc agcaggtggc                                              20
```

<210> SEQ ID NO 542
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 542
tggcagggag cagcaggtgg                                                   20

<210> SEQ ID NO 543
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 543
ctggcaggga gcagcaggtg                                                   20

<210> SEQ ID NO 544
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 544
ccctggcagg gagcagcagg                                                   20

<210> SEQ ID NO 545
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 545
accctggcag ggagcagcag                                                   20

<210> SEQ ID NO 546
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 546
gaccctggca gggagcagca                                                   20

<210> SEQ ID NO 547
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 547
ggaccctggc agggagcagc                                                   20

<210> SEQ ID NO 548
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 548
ggcctaggga ccctggcagg                                              20

<210> SEQ ID NO 549
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 549
aggcctaggg accctggcag                                              20

<210> SEQ ID NO 550
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 550
ccaggcctag ggaccctggc                                              20

<210> SEQ ID NO 551
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 551
gccaggccta gggaccctgg                                              20

<210> SEQ ID NO 552
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 552
ggccaggcct agggaccctg                                              20

<210> SEQ ID NO 553
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 553
aggccaggcc tagggaccct                                              20

<210> SEQ ID NO 554
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 554
taggccaggc ctagggaccc                                              20

<210> SEQ ID NO 555
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 555
ataggccagg cctagggacc                                              20

<210> SEQ ID NO 556
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 556
gataggccag gcctagggac                                              20

<210> SEQ ID NO 557
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 557
cgataggcca ggcctaggga                                              20

<210> SEQ ID NO 558
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 558
ccgataggcc aggcctaggg                                              20

<210> SEQ ID NO 559
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 559
tccgataggc caggcctagg                                              20

<210> SEQ ID NO 560
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 560
ctccgatagg ccaggcctag                                              20

<210> SEQ ID NO 561
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 561
```

```
cctccgatag gccaggccta                                              20

<210> SEQ ID NO 562
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 562
gcctccgata ggccaggcct                                              20

<210> SEQ ID NO 563
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 563
gcgcctccga taggccaggc                                              20

<210> SEQ ID NO 564
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 564
aacaggagca gggaaagcgc                                              20

<210> SEQ ID NO 565
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 565
gaacaggagc agggaaagcg                                              20

<210> SEQ ID NO 566
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 566
cgaacaggag cagggaaagc                                              20

<210> SEQ ID NO 567
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 567
gcgaacagga gcagggaaag                                              20

<210> SEQ ID NO 568
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 568
ggcgaacagg agcagggaaa                                                  20

<210> SEQ ID NO 569
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 569
cggcgaacag gagcagggaa                                                  20

<210> SEQ ID NO 570
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 570
acggcgaaca ggagcaggga                                                  20

<210> SEQ ID NO 571
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 571
aacggcgaac aggagcaggg                                                  20

<210> SEQ ID NO 572
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 572
caacggcgaa caggagcagg                                                  20

<210> SEQ ID NO 573
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 573
gggcggcggc acgagacaga                                                  20

<210> SEQ ID NO 574
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 574
agggcggcgg cacgagacag                                                  20
```

<210> SEQ ID NO 575
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 575
cagggcggcg gcacgagaca         20

<210> SEQ ID NO 576
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 576
ccagggcggc ggcacgagac         20

<210> SEQ ID NO 577
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 577
cccagggcgg cggcacgaga         20

<210> SEQ ID NO 578
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 578
gcccagggcg gcggcacgag         20

<210> SEQ ID NO 579
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 579
agcccagggc ggcggcacga         20

<210> SEQ ID NO 580
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 580
cagcccaggg cggcggcacg         20

<210> SEQ ID NO 581
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 581
gcagcccagg gcggcggcac                                                 20

<210> SEQ ID NO 582
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 582
ctgcggtgag ttggccggcg                                                 20

<210> SEQ ID NO 583
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 583
actgcggtga gttggccggc                                                 20

<210> SEQ ID NO 584
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 584
gactgcggtg agttggccgg                                                 20

<210> SEQ ID NO 585
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 585
agactgcggt gagttggccg                                                 20

<210> SEQ ID NO 586
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 586
cagactgcgg tgagttggcc                                                 20

<210> SEQ ID NO 587
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 587
ccagactgcg gtgagttggc                                                 20

```
<210> SEQ ID NO 588
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 588
gccagactgc ggtgagttgg                                            20

<210> SEQ ID NO 589
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 589
cgccagactg cggtgagttg                                            20

<210> SEQ ID NO 590
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 590
aagacagttc tagggttcag                                            20

<210> SEQ ID NO 591
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 591
gaagacagtt ctagggttca                                            20

<210> SEQ ID NO 592
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 592
cgaagacagt tctagggttc                                            20

<210> SEQ ID NO 593
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 593
tcgaagacag ttctagggtt                                            20

<210> SEQ ID NO 594
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 594
gtcgaagaca gttctagggt                                               20

<210> SEQ ID NO 595
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 595
agtcgaagac agttctaggg                                               20

<210> SEQ ID NO 596
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 596
gagtcgaaga cagttctagg                                               20

<210> SEQ ID NO 597
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 597
ggagtcgaag acagttctag                                               20

<210> SEQ ID NO 598
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 598
cggagtcgaa gacagttcta                                               20

<210> SEQ ID NO 599
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 599
ccggagtcga agacagttct                                               20

<210> SEQ ID NO 600
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 600
cccggagtcg aagacagttc                                               20

<210> SEQ ID NO 601
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 601
ccccggagtc gaagacagtt                                               20

<210> SEQ ID NO 602
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 602
gccccggagt cgaagacagt                                               20

<210> SEQ ID NO 603
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 603
ggccccggag tcgaagacag                                               20

<210> SEQ ID NO 604
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 604
gggccccgga gtcgaagaca                                               20

<210> SEQ ID NO 605
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 605
aggcggtggg cgcggcttct                                               20

<210> SEQ ID NO 606
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 606
caggcggtgg gcgcggcttc                                               20

<210> SEQ ID NO 607
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 607
```

```
gcaggcggtg ggcgcggctt                                              20

<210> SEQ ID NO 608
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 608
tggcaggcgg tgggcgcggc                                              20

<210> SEQ ID NO 609
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 609
actggcaggc ggtgggcgcg                                              20

<210> SEQ ID NO 610
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 610
gaactggcag gcggtgggcg                                              20

<210> SEQ ID NO 611
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 611
tgaactggca ggcggtgggc                                              20

<210> SEQ ID NO 612
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 612
tgtgaactgg caggcggtgg                                              20

<210> SEQ ID NO 613
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 613
tggagctggg cggagaccca                                              20

<210> SEQ ID NO 614
<211> LENGTH: 20
<212> TYPE: DNA
<213> ORGANISM: Artificial Sequence
```

<220> FEATURE:
<223> OTHER INFORMATION: Synthetic oligonucleotide

<400> SEQUENCE: 614
actggagctg ggcggagacc                                              20

<210> SEQ ID NO 615
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 615
gactggagct gggcggagac                                              20

<210> SEQ ID NO 616
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 616
aggactggag ctgggcggag                                              20

<210> SEQ ID NO 617
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 617
acaggactgg agctgggcgg                                              20

<210> SEQ ID NO 618
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 618
cacaggactg gagctgggcg                                              20

<210> SEQ ID NO 619
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 619
tcacaggact ggagctgggc                                              20

<210> SEQ ID NO 620
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 620
gcctcagcct ggccgaaaga                                              20

<210> SEQ ID NO 621
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 621
ggcctcagcc tggccgaaag                                                  20

<210> SEQ ID NO 622
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 622
tggtggagcc aagccctccc                                                  20

<210> SEQ ID NO 623
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 623
gggcaccctc agagcctgaa                                                  20

<210> SEQ ID NO 624
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 624
accccactgc aagaagtcgg                                                  20

<210> SEQ ID NO 625
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 625
gccccaggat gggaggatct                                                  20

<210> SEQ ID NO 626
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 626
cataggacag agaaatgttg                                                  20

<210> SEQ ID NO 627
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 627
tgctgacctt actctgcccc                                       20

<210> SEQ ID NO 628
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 628
taagccatgg ctctgagtca                                       20

<210> SEQ ID NO 629
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 629
agagaggcca tgggaggctg                                       20

<210> SEQ ID NO 630
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 630
ctggccctcc tggcttgccc                                       20

<210> SEQ ID NO 631
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 631
agctgcccca tgctggccct                                       20

<210> SEQ ID NO 632
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 632 gccctggca gctgccccat                                        20

<210> SEQ ID NO 633
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 633
ctgtcggctg cgcccctggc                                       20

<210> SEQ ID NO 634

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 634
cgccgaacac ctgcctgtcg                                              20

<210> SEQ ID NO 635
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 635
cctcccagtg cctgggcacc                                              20

<210> SEQ ID NO 636
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 636
gcgcctgtct gcaaagctgg                                              20

<210> SEQ ID NO 637
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 637
cccaaagttg tccctcctgg                                              20

<210> SEQ ID NO 638
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 638
acacccagaa gaacccaaag                                              20

<210> SEQ ID NO 639
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 639
ctgacccaca cggctcatag                                              20

<210> SEQ ID NO 640
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 640
```
tggccccagg ccctggaaag                                               20

<210> SEQ ID NO 641
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 641
gacaaggcag ctggcagaag                                               20

<210> SEQ ID NO 642
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 642
aagaaaccag tgaccagtga                                               20

<210> SEQ ID NO 643
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 643
ctgtgaaatg ggaggaggag                                               20

<210> SEQ ID NO 644
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 644
gaaggttttt ccagaggctg                                               20

<210> SEQ ID NO 645
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 645
ggccaggaga gtcattaggg                                               20

<210> SEQ ID NO 646
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 646
ccacaaaagg agtgctcctc                                               20

<210> SEQ ID NO 647
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 647 cctttttaagg cagcaggaac                                              20

<210> SEQ ID NO 648
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 648
ctaggactgt ctgcttccca                                               20

<210> SEQ ID NO 649
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 649
gtcattcatc aatttctaag                                               20

<210> SEQ ID NO 650
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 650
ggaggagctg cagccggaga                                               20

<210> SEQ ID NO 651
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 651
gcacccggag gagctgcagc                                               20

<210> SEQ ID NO 652
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 652
gcacgacacc tgcagggcac                                               20

<210> SEQ ID NO 653
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 653
agctcaccag gtagttctca                                               20
```

<210> SEQ ID NO 654
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 654
gcttcctctc cccacctcct                                               20

<210> SEQ ID NO 655
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 655
gcagcacccc caatcctaga                                               20

<210> SEQ ID NO 656
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 656
gcccctcatc cacctgacac                                               20

<210> SEQ ID NO 657
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 657
ttccaggtaa gagaccccccc                                              20

<210> SEQ ID NO 658
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 658
agaataggtc ccagacactc                                               20

<210> SEQ ID NO 659
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 659
ctccccctga gatgttctgg                                               20

<210> SEQ ID NO 660
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 660
ccccagccca gagataacca                                               20

<210> SEQ ID NO 661
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 661
cctgatccat cacggatggc                                               20

<210> SEQ ID NO 662
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 662
tactccatga ccaggtactg                                               20

<210> SEQ ID NO 663
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 663
gctctgacct tccaagaacc                                               20

<210> SEQ ID NO 664
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 664
ctcccttctg tggtcccacc                                               20

<210> SEQ ID NO 665
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 665
gtcgggtttg atgtccctgc                                               20

<210> SEQ ID NO 666
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 666
agggcactgg ctcaccgttc                                               20

-continued

```
<210> SEQ ID NO 667
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 667
gggccctcct tccaaccact                                                  20

<210> SEQ ID NO 668
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 668
gcccacccct ctgggcccac                                                  20

<210> SEQ ID NO 669
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 669
aggagcagag cgaggcttgg                                                  20

<210> SEQ ID NO 670
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 670
caccttgtag tggacgatct                                                  20

<210> SEQ ID NO 671
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 671
ctaccccgcc cccgctcacc                                                  20

<210> SEQ ID NO 672
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 672
ctaggtcact gctgggtcct                                                  20

<210> SEQ ID NO 673
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 673
ctcagatagc tccccactcc                                                    20

<210> SEQ ID NO 674
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 674
aattctctaa ttctctagac                                                    20

<210> SEQ ID NO 675
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 675
tacctgaggg ccatgcagga                                                    20

<210> SEQ ID NO 676
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 676
gttccaagac tgatcctgca                                                    20

<210> SEQ ID NO 677
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 677
aggagggcgg tggcgcggcg                                                    20

<210> SEQ ID NO 678
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 678
tgacagctgg aaggagaaga                                                    20

<210> SEQ ID NO 679
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 679
catgggaagg tggatccgtg                                                    20

<210> SEQ ID NO 680
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 680
ggaggttatc tagggagatc                                           20

<210> SEQ ID NO 681
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 681
gaagggacag gtgacccgat                                           20

<210> SEQ ID NO 682
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 682
cgtaccctgg cagggagcag                                           20

<210> SEQ ID NO 683
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 683
ggactcgccc cgcctacgcc                                           20

<210> SEQ ID NO 684
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 684
ctcctgggac tcgccccgcc                                           20

<210> SEQ ID NO 685
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 685
gctcctggga ctcgccccgc                                           20

<210> SEQ ID NO 686
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 686
```

```
attggctcct gggactcgcc                                              20

<210> SEQ ID NO 687
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 687
gattggctcc tgggactcgc                                              20

<210> SEQ ID NO 688
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 688
gcctctgatt ggctcctggg                                              20

<210> SEQ ID NO 689
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 689
gcatgggcct ctgattggct                                              20

<210> SEQ ID NO 690
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 690
cacccggcat gggcctctga                                              20

<210> SEQ ID NO 691
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 691
gccaggccta gggacctgcg                                              20

<210> SEQ ID NO 692
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 692
ttcctccccc aaccctgatt                                              20

<210> SEQ ID NO 693
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 693
aagtttgcag caactttct                                                  20

<210> SEQ ID NO 694
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 694
gcccctcgga attcccggct                                                 20

<210> SEQ ID NO 695
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 695
catctcggcc tgcgctccgc                                                 20

<210> SEQ ID NO 696
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 696
gcaggccccc acattcccca                                                 20

<210> SEQ ID NO 697
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 697
cttctgcacg cctccgtctc                                                 20

<210> SEQ ID NO 698
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 698
tggcccacag ccacggccgg                                                 20

<210> SEQ ID NO 699
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 699
ggcctggccc caccagcggg                                                 20
```

<210> SEQ ID NO 700
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 700
cctggcaggg agcagcaggt                                                   20

<210> SEQ ID NO 701
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 701
cagccgcact tcggctgaca                                                   20

<210> SEQ ID NO 702
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 702
gcctgggtcc agcaccagct                                                   20

<210> SEQ ID NO 703
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 703
gtcccaggaa gcctgggtcc                                                   20

<210> SEQ ID NO 704
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 704
cgttagcagg tccccgccca                                                   20

<210> SEQ ID NO 705
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 705
gtctatggcc atgacaatct                                                   20

<210> SEQ ID NO 706
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 706
gtagcccagc cggtgcacgg                                              20

<210> SEQ ID NO 707
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 707
gggtgcccac agccaccagc                                              20

<210> SEQ ID NO 708
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 708
tggcccgtag ctgcctgccc                                              20

<210> SEQ ID NO 709
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 709
ggaaatcacc tgccccacct                                              20

<210> SEQ ID NO 710
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 710
ggatgtttct ggaaatcacc                                              20

<210> SEQ ID NO 711
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 711
gtggcaccct cgaagtctgg                                              20

<210> SEQ ID NO 712
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 712
ccccgctcac catggcagtg                                              20

<210> SEQ ID NO 713

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 713
ggtccgggac ctgattgtct                                          20

<210> SEQ ID NO 714
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 714
gctgcatgtc tgcccgtccc                                          20

<210> SEQ ID NO 715
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 715
ggccccagaa ccctagctgc                                          20

<210> SEQ ID NO 716
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 716
tcacagggcc tggctgcccc                                          20

<210> SEQ ID NO 717
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 717
ggctgacatg ttgggcaggc                                          20

<210> SEQ ID NO 718
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 718
tgtccaggcc ccagaaccct                                          20

<210> SEQ ID NO 719
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 719
```
ggccaggcct agggatctgc                                                     20

<210> SEQ ID NO 720
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 720
cgcctcggat aggccaggcc                                                     20

<210> SEQ ID NO 721
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 721
ggcttggagt cttagggttc                                                     20

<210> SEQ ID NO 722
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 722
tccccggccg ccaggtggca                                                     20

<210> SEQ ID NO 723
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 723
ggtgctgggc acgagccctg                                                     20

<210> SEQ ID NO 724
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 724
gcccagctgc tgcagcagcg                                                     20

<210> SEQ ID NO 725
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 725
ccgtgtgtgc tggcagaggt                                                     20

<210> SEQ ID NO 726
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 726
ataaataccg aggaatgtcg                                                 20

<210> SEQ ID NO 727
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 727
gggacagaca ataaataccg                                                 20

<210> SEQ ID NO 728
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 728
gtgcagccca gtgtggcggc                                                 20

<210> SEQ ID NO 729
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 729
cctggagaag ttctggttgg                                                 20

<210> SEQ ID NO 730
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 730
ggtgacccga tcggagccca                                                 20

<210> SEQ ID NO 731
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 731
agctggagag agaagggaca                                                 20

<210> SEQ ID NO 732
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 732
gtgagggact cgcctgcggc                                                 20
```

<210> SEQ ID NO 733
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 733
gcggctgcgg tgccccagcc                                                 20

<210> SEQ ID NO 734
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 734
gggccatcta gctggagaga                                                 20

<210> SEQ ID NO 735
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 735
ccccactgca agaagtcggc                                                 20

<210> SEQ ID NO 736
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 736
ttgagccctt ttaaggcagc                                                 20

<210> SEQ ID NO 737
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 737
tgaccaggta ctgggagcgg                                                 20

<210> SEQ ID NO 738
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 738
cctggagctg gatcagtccc                                                 20

<210> SEQ ID NO 739
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 739
acatgggaag gtggatccgt                                                        20

<210> SEQ ID NO 740
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 740
gtgggacata ccctggcagg                                                        20

<210> SEQ ID NO 741
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 741
gccaggccta gggatctgca                                                        20

<210> SEQ ID NO 742
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 742
ggaagcacga cacctcgcct                                                        20

<210> SEQ ID NO 743
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 743
cctcaccatt ccatcaggct                                                        20

<210> SEQ ID NO 744
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 744
cggcagcgac aagtgttccc                                                        20

<210> SEQ ID NO 745
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 745
gtctctgaag gccatgcagc                                                        20

```
<210> SEQ ID NO 746
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 746
cagccacttg atccggtggg                                                    20

<210> SEQ ID NO 747
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 747
aggtcggcct cttcagccac                                                    20

<210> SEQ ID NO 748
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 748
gttggctgga gaagttctgg                                                    20

<210> SEQ ID NO 749
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 749
ccccgtgatg gctgcggctc                                                    20

<210> SEQ ID NO 750
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 750
aggccaggcc tagggatcct                                                    20

<210> SEQ ID NO 751
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 751
ggcgcggtgc cccagcctgg                                                    20

<210> SEQ ID NO 752
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 752
gtcctggccc caccagcggg                                               20

<210> SEQ ID NO 753
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 753
ccaggcctag gaatcctggc                                               20

<210> SEQ ID NO 754
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 754
gcgcctcgga tagccaggcc                                               20

<210> SEQ ID NO 755
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 755
cccagtgtgg cgcagcagcc                                               20

<210> SEQ ID NO 756
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 756
gtgtttcatc ttcaccaccg                                               20

<210> SEQ ID NO 757
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 757
aggtcagcct cttcagccac                                               20

<210> SEQ ID NO 758
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 758
ggccatatgg gaaggtggat                                               20

<210> SEQ ID NO 759
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 759
ggaggatttg gcgagaagca                                               20

<210> SEQ ID NO 760
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 760
cgaagtctgc cccacctcga                                               20

<210> SEQ ID NO 761
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 761
gtggcaccct cgaagtctgc                                               20

<210> SEQ ID NO 762
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 762
gggtccattg taaggaagct                                               20

<210> SEQ ID NO 763
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 763
ggtgcccaca gccaccaggg                                               20

<210> SEQ ID NO 764
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 764
tccatggcag tgagccggtc                                               20

<210> SEQ ID NO 765
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 765
```
gggaccactt gatccggtgg                                                    20

<210> SEQ ID NO 766
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 766
ggatcagagt tgggaccact                                                    20

<210> SEQ ID NO 767
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 767
ccccgtgatg gctgcggttc                                                    20

<210> SEQ ID NO 768
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 768
gtgtgtcctc atacccngcc                                                    20

<210> SEQ ID NO 769
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 769
gcaccctcga agtctcgacc                                                    20

<210> SEQ ID NO 770
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 770
gctctgaagg ccatgcagca                                                    20

<210> SEQ ID NO 771
<211> LENGTH: 25
<212> TYPE: DNA
<213> ORGANISM: Artificial Sequence
<220> FEATURE:
<223> OTHER INFORMATION: Primer

<400> SEQUENCE: 771
gacatatgcc aagattgtgc actac                                              25

<210> SEQ ID NO 772
<211> LENGTH: 21
<212> TYPE: DNA
<213> ORGANISM: Artificial Sequence

```
<220> FEATURE:
<223> OTHER INFORMATION: Primer

<400> SEQUENCE: 772
cacgaatgag gtcctgagct t                                              21

<210> SEQ ID NO 773
<211> LENGTH: 22
<212> TYPE: DNA
<213> ORGANISM: Artificial Sequence
<220> FEATURE:
<223> OTHER INFORMATION: Probe

<400> SEQUENCE: 773
aacacttgtc gctgccgctg gc                                             22

<210> SEQ ID NO 774
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 774
agcgaggctt cacttggcgc                                                20

<210> SEQ ID NO 775
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 775
gggaagcgag gcttcacttg                                                20

<210> SEQ ID NO 776
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 776
gcggtcagcg atcccagggt                                                20

<210> SEQ ID NO 777
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 777
gggtgccagc gcggtgatct                                                20

<210> SEQ ID NO 778
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 778
tgttacaaag aaagtgactg                                                20
```

<210> SEQ ID NO 779
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 779
cgatggcagc aacggaagtt                                              20

<210> SEQ ID NO 780
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 780
gtcagtttac gatggcagca                                              20

<210> SEQ ID NO 781
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 781
cagggctttg tttcgaaaaa                                              20

<210> SEQ ID NO 782
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 782
ccattttctt ccacagggct                                              20

<210> SEQ ID NO 783
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 783
atgcttcttc aagttttcca                                              20

<210> SEQ ID NO 784
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 784
cagaatgact ttaatgcttc                                              20

<210> SEQ ID NO 785
<211> LENGTH: 21
<212> TYPE: DNA
<213> ORGANISM: Artificial Sequence
<220> FEATURE:
<223> OTHER INFORMATION: Primer

<400> SEQUENCE: 785
ccaccgcaaa tgcttctaga c                                              21

<210> SEQ ID NO 786
<211> LENGTH: 20
<212> TYPE: DNA
<213> ORGANISM: Artificial Sequence
<220> FEATURE:
<223> OTHER INFORMATION: Primer

<400> SEQUENCE: 786 ccccccatt gagaagattc                                                 20

<210> SEQ ID NO 787
<211> LENGTH: 24
<212> TYPE: DNA
<213> ORGANISM: Artificial Sequence
<220> FEATURE:
<223> OTHER INFORMATION: Probe

<400> SEQUENCE: 787
ctccacctcc agcacgcgac ttct                                           24

<210> SEQ ID NO 788
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 788
gcggtcagcg atcccagggt                                                20

<210> SEQ ID NO 789
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 789
agcagcagca gcagcagcag cagca                                          25

<210> SEQ ID NO 790
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 790
agcagcagca gcagcagcag                                                20

<210> SEQ ID NO 791
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 791
gcagcagcag cagca                                                     15

<210> SEQ ID NO 792

<400> SEQUENCE: 792

000

<210> SEQ ID NO 793
<211> LENGTH: 2611
<212> TYPE: DNA
<213> ORGANISM: Mus musculus

<400> SEQUENCE: 793

| | | | | | |
|---|---|---|---|---|---|
| cgggaagacc | ccgagctccg | gcccggggag | gggccatggt | gttgcctgcc | caacatgtca | 60 |
| gccgaagtgc | ggctgaggca | gctccagcag | ctggtgctgg | acccaggctt | cctgggactg | 120 |
| gagcccctgc | tcgaccttct | cctgggcgtc | caccaggagc | tgggtgcctc | tcacctagcc | 180 |
| caggacaagt | atgtggccga | cttcttgcag | tgggtggagc | ccattgcagc | aaggcttaag | 240 |
| gaggtccgac | tgcagaggga | tgattttgag | attttgaagg | tgatcgggcg | tggggcgttc | 300 |
| agcgaggtag | cggtggtgaa | gatgaaacag | acgggccaag | tgtatgccat | gaagattatg | 360 |
| aataagtggg | acatgctgaa | gagaggcgag | gtgtcgtgct | ccgggaaga | aagggatgta | 420 |
| ttagtgaaag | gggaccggcg | ctggatcaca | cagctgcact | tgccttcca | ggatgagaac | 480 |
| tacctgtacc | tggtcatgga | atactacgtg | ggcggggacc | tgctaacgct | gctgagcaag | 540 |
| tttggggagc | ggatccccgc | cgagatggct | cgcttctacc | tggccgagat | tgtcatggcc | 600 |
| atagactccg | tgcaccggct | gggctacgtg | cacagggaca | tcaaaccaga | taacattctg | 660 |
| ctggaccgat | gtgggcacat | tcgcctggca | gacttcggct | cctgcctcaa | actgcagcct | 720 |
| gatggaatgg | tgaggtcgct | ggtggctgtg | ggcaccccgg | actacctgtc | tcctgagatt | 780 |
| ctgcaggccg | ttggtggagg | gcctggggca | ggcagctacg | gccagagtg | tgactggtgg | 840 |
| gcactgggcg | tgttcaccta | tgagatgttc | tatgggcaga | ccccttcta | cgcggactcc | 900 |
| acagccgaga | catatgccaa | gattgtgcac | tacagggaac | acttgtcgct | gccgctggca | 960 |
| gacacagttg | tccccgagga | agctcaggac | ctcattcgtg | ggctgctgtg | tcctgctgag | 1020 |
| ataaggctag | tcgaggtgg | ggcagacttc | gagggtgcca | cggacacatg | caatttcgat | 1080 |
| gtggtggagg | accggctcac | tgccatggtg | agcggggggcg | gggagacgct | gtcagacatg | 1140 |
| caggaagaca | tgccccttgg | ggtgcgcctg | cccttcgtgg | gctactccta | ctgctgcatg | 1200 |
| gccttcagag | acaatcaggt | cccggacccc | accctatgg | aactagaggc | cctgcagttg | 1260 |
| cctgtgtcag | acttgcaagg | gcttgacttg | cagcccccag | tgtccccacc | ggatcaagtg | 1320 |
| gctgaagagg | ctgacctagt | ggctgtccct | gccctgtgg | ctgaggcaga | gaccacggta | 1380 |
| acgctgcagc | agctccagga | agccctggaa | gaagaggttc | tcacccggca | gagcctgagc | 1440 |
| cgcgagctgg | aggccatccg | gaccgccaac | cagaacttct | ccagccaact | acaggaggcc | 1500 |
| gaggtccgaa | accgagacct | ggaggcgcat | gttcggcagc | tacaggaacg | gatggagatg | 1560 |
| ctgcaggccc | caggagccgc | agccatcacg | ggggtcccca | gtcccggc | cacggatcca | 1620 |
| ccttcccatc | tagatggccc | cccggccgtg | gctgtgggcc | agtgcccgct | ggtggggcca | 1680 |
| ggccccatgc | accgccgtca | cctgctgctc | cctgccagga | tcctaggcc | tggcctatcc | 1740 |
| gaggcgcgtt | gcctgctcct | gttcgccgct | gctctggctg | ctgccgccac | actgggctgc | 1800 |
| actgggttgg | tggcctatac | cggcggtctc | accccagtct | ggtgtttccc | gggagccacc | 1860 |
| ttcgcccct | gaaccctaag | actccaagcc | atctttcatt | taggcctcct | aggaaggtcg | 1920 |
| agcgaccagg | gagcgaccca | aagcgtctct | gtgcccatcg | cccccccccc | ccccccacc | 1980 |

```
gctccgctcc acacttctgt gagcctgggt ccccacccag ctccgctcct gtgatccagg    2040
cctgccacct ggcggccggg gagggaggaa cagggctcgt gcccagcacc cctggttcct    2100
gcagagctgg tagccaccgc tgctgcagca gctgggcatt cgccgacctt gctttactca    2160
gccccgacgt ggatgggcaa actgctcagc tcatccgatt tcacttttc actctcccag     2220 ccatcagtta caagccataa gcatgagccc cctatttcca gggacatccc attcccatag    2280
tgatggatca gcaagacctc tgccagcaca cacggagtct ttggcttcgg acagcctcac    2340
tcctgggggt tgctgcaact ccttccccgt gtacacgtct gcactctaac aacggagcca    2400
cagctgcact ccccctccc ccaaagcagt gtgggtattt attgatcttg ttatctgact     2460
cactgacaga ctccgggacc cacgttttag atgcattgag actcgacatt cctcggtatt    2520
tattgtctgt ccccacctac gacctccact cccgacccctt gcgaataaaa tacttctggt   2580
ctgccctaaa aaaaaaaaaa aaaaaaaaaa a                                   2611
```

<210> SEQ ID NO 794
<211> LENGTH: 988
<212> TYPE: DNA
<213> ORGANISM: Mus musculus
<220> FEATURE:
<221> NAME/KEY: misc_feature
<222> LOCATION: 531, 942
<223> OTHER INFORMATION: n = A,T,C or G

<400> SEQUENCE: 794

```
gctggaccgg tccggaattc tccggatcgc cagcctttgt gggccatatt cgtcatccct    60
cctggcttct catctgcttt tgtggtccta gctcaagacc tctaattcct ctgctgactt    120
aaatgccctt ccccagaggt cttctcaggc ctagtggaca agcttggagc cttatctgct   180
cctgcccaac attgagccaa agctccagct taccccagct tccttacaat ggaccccatt   240
gcagcaaggc ttaaggaggt ccgactgcag agggatgatt ttgagatttt gaaggtgatc   300
gggcgtgggg cgttcagcga ggtagcggtg gtgaagatga aacagacggg ccaagtgtat   360
gccatgaaga ttatgaataa gtgggacatg ctgaagagag gcgaggtgtc gtgcttccgg   420
gaagaaaggg atgtattagt gaaagggggac cggcgctgga tcacacagct gcactttgcc   480
ttccaggatg agaactacct gtacctggtc atggaatact acgtgggcgg ngacctgcta   540
acgctgctga gcaagttttg gggagcggat ccccgccgag atggctcgct tctacctggc   600
cgagattgtc atggccatag actccgtgca ccggctgggc tacgtgcaca gggacatcaa   660
accagataac attctgctgg accgatgtgg gcacattcgc ctggcagact tcggctcctg   720
gcctcaactg cagcctgatg gaatggtgga gtcccctggt ggctgtgggc accccggac    780 tacctgtctc ctgaaattct gcagggcctt ggtgggaggc cctggggaag gcaactacgg   840
gccaaaagtt ggaagggggg ggcctggggg gggttcccct atgaaaagtt ctatggggag   900 gaccccttt aagcggaatc ccaggccgaa aaatatgccc angattgggc cctaacaggg    960
aaaacttttc ccctgcccct gggacaat                                      988
```

<210> SEQ ID NO 795
<211> LENGTH: 649
<212> TYPE: DNA
<213> ORGANISM: Mus musculus

<400> SEQUENCE: 795

```
ggcgtgttcg cctatgagat gttctatggg cagacccct tctacgcgga ctccacagcc     60
gagacatatg ccaagattgt gcactacagg gaacacttgt cgctgccgct ggcagacaca   120
```

```
gttgtccccg aggaagctca ggacctcatt cgtgggctgc tgtgtcctgc tgagataagg      180
ctaggtcgag gtggggcagg tgatttccag aaacatcctt tcttctttgg ccttgattgg      240
gagggtctcc gagacagtgt accccccttt acaccagact tcgagggtgc cacggacaca      300
tgcaatttcg atgtggtgga ggaccggctc actgccatgg agacgctgtc agacatgcag      360
gaagacatgc cccttggggt gcgcctgccc ttcgtgggct actcctactg ctgcatggcc      420
ttcagagaca atcaggtccc ggaccccacc cctatgaaac tagaggccct gcagttgcct      480
gtgtcagact tgcaagggct tgacttgcag cccccagtgt ccccaccgga tcaagtggtc      540
ccaactctga tccccaccga caggctgaag aggctgacct agtggctgtc cctgcccctg      600
tggctgaggc agagccacgg taacgctgca gcagctccag gaagccctg                  649
```

`<210>` SEQ ID NO 796
`<211>` LENGTH: 527
`<212>` TYPE: DNA
`<213>` ORGANISM: Mus musculus

`<400>` SEQUENCE: 796

```
atttcgatgt ggtggaggac cggctcactg ccatggtgag cgggggcggg gagacgctgt       60
cagacatgca ggaagacatg ccccttgggg tgcgcctgcc cttcgtgggc tactcctact      120
gctgcatggc cttcagagac aatcaggtcc cggaccccac ccctatggaa ctagaggccc      180
tgcagttgcc tgtgtcagac ttgcaagggc ttgacttgca gccccagtg tccccaccgg       240 atcaagtggc tgaagaggct gacctagtgg ctgtccctgc cctgtggct gaggcagaga      300 ccacggtaac gctgcagcag ctccaggaag ccctggaaga agaggttctc acccggcaga      360
gcctgagccg cgagctggag gccatccgga ccgccaacca gaacttctcc aggaggccga      420
ggtccgaaac cgagacctgg aggcgcatgt tcggcagcta caggaacgga tggagatgct      480
gcaggcccca ggaaccgcag ccatcacggg ggtccccagt ccccgg                     527
```

`<210>` SEQ ID NO 797
`<211>` LENGTH: 567
`<212>` TYPE: DNA
`<213>` ORGANISM: Mus musculus

`<400>` SEQUENCE: 797

```
atggtgaggt cgctggtggc tgtgggcacc ccggactacc tgtctcctga gattctgcag       60
gccgttggtg gagggcctgg ggcaggcagc tacgggccag agtgtgactg gtgggcactg      120
ggcgtgttcg cctatgagat gttctatggg cagaccccct tctacgcgga ctccacagcc      180
gagacatatg ccaagattgt gcactacagg gaacacttgt cgctgccgct ggcagacaca      240
gttgtccccg aggaagctca ggacctcatt cgtgggctgc tgtgtcctgc tgagataagg      300
ctaggtcgag gtggggcagg tgatttccag aaacatcctt tcttctttgg ccttgattgg      360
gagggtctcc gagacagtgt accccccttt acaccagact tcgagggtgc cacggacaca      420
tgcaatttcg atgtggtgga ggaccggctc actgccatgg tgagcggggg cggggtatga      480
ggacacacag gtgaccagtc cccaagacag tgagtgaggc ttcactcttg gcagtactaa      540
aattgaatgt agggggctgg gctcttg                                          567
```

`<210>` SEQ ID NO 798
`<211>` LENGTH: 2474
`<212>` TYPE: DNA
`<213>` ORGANISM: Mus musculus

<400> SEQUENCE: 798

```
ccgggaagaa agggatgtat tagtgaaagg ggaccggcgc tggatcacac agctgcactt      60
tgccttccag gatgagaact acctgtacct ggtcatggaa tactacgtgg gcggggacct     120
gctaacgctg ctgagcaagt ttggggagcg gatccccgcc gagatggctc gcttctacct     180
ggccgagatt gtcatggcca tagactccgt gcaccggctg ggctacgtgc acagggacat     240
caaaccagat aacattctgc tggaccgatg tgggcacatt cgcctggcag acttcggctc     300
ctgcctcaaa ctgcagcctg atggaatggt gaggtcgctg gtggctgtgg gcaccccgga     360
ctacctgtct cctgagattc tgcaggccgt tggtggaggg cctggggcag gcagctacgg     420
gccagagtgt gactggtggg cactgggcgt gttcgcctat gagatgttct atgggcagac     480
ccccttctac gcggactcca cagccgagac atatgccaag attgtgcact acagggaaca     540
cttgtcgctg ccgctggcag acacagttgt ccccgaggaa gctcaggacc tcattcgtgg     600
gctgctgtgt cctgctgaga taaggctagg tcgagacttc gagggtgcca cggacacatg     660
caatttcgat gtggtggagg accggctcac tgccatggtg agcgggggcg gggagacgct     720
gtcagacatg caggaagaca tgcccccttgg ggtgcgcctg cccttcgtgg gctactccta     780
ctgctgcatg gccttcagag acaatcaggt cccggacccc accccctatgg aactagaggc     840
cctgcagttg cctgtgtcag acttgcaagg gcttgacttg cagccccag tgtccccacc     900
ggatcaagtg gctgaagagg ccgacctagt ggctgtccct gcccctgtgg ctgaggcaga     960
gaccacggta acgctgcagc agctccagga agccctggaa gaagaggttc tcacccggca    1020
gagcctgagc cgcgagctgg aggccatccg gaccgccaac cagaacttct ccagccaact    1080
acaggaggcc gaggtccgaa accgagacct ggaggcgcat gttcggcagc tacaggaacg    1140
gatggagatg ctgcaggccc caggagccgc aggcgagtcc ctcacctgct tccagccaag    1200
ggggcactgg gtggagatgg ggggcatgtt gggtgtgtga accctcgggg caggggagga    1260
gtccaggctg gggcaccgca gccgcgccac tgcctttctc ctccatcctc cacactccat    1320
acacctctct cttctccttc cagccatcac gggggtcccc agtccccggg ccacggatcc    1380
accttcccat gcttctcgcc aaatcctccc caagggaact ccctagactc ccgttctggc    1440
ctcgactaga ttcccgcact gcctctcgcc ctgctgctgg gctccgatcg ggtcacctgt    1500
cccttctctc tccagctaga tggccccccg gccgtggctg tgggccagtg cccgctggtg    1560
gggccaggcc ccatgcaccg ccgtcacctg ctgctccctg ccaggatccc taggcctggc    1620
ctatccgagg cgcgttgcct gctcctgttc gccgctgctc tggctgctgc cgccacactg    1680
ggctgcactg ggttggtggc ctataccggc ggtctcaccc cagtctggtg tttcccggga    1740
gccaccttcg cccctgaac cctaagactc caagccatct ttcatttagg cctcctagga    1800
agatcgagcg accagggagc gacccaaagc gtctctgtgc ccatcgcccc cccccccc    1860
cccaccgctc cgctccacac ttctgtgagc ctgggtcccc acccagctcc gctcctgtga    1920
tccaggcctg ccacctggcg gccggggagg gaggaacagg gctcgtgccc agcacccctg    1980
gttcctgcag agctggtagc caccgctgct gcagcagctg ggcattcgcc gaccttgctt    2040
tactcagccc tgacgtggat gggctaactg ctcagctcat ccgatttcac tttttcactc    2100
tcccagccat cagttacaag ccataagcat gagcccccta tttccaggga catcccattc    2160
ccatagtgat ggatcagcaa gacctctgcc agcacacacg gagtctttgg cttcggacag    2220
cctcactcct gggggttgct gcaactcctt ccccgtgtac acgtctgcac tctaacaacg    2280
gagccacagc tgcactcccc cctcccccaa agcagtgtgg gtatttattg atcttgttat    2340
```

| | | |
|---|---|---|
| ctgactcact gacagactcc gggacccacg ttttagatgc attgagactc gacattcctc | 2400 | |
| ggtatttatt gtctgtcccc acctacgacc tccactcccg acccttgcga ataaaatact | 2460 | |
| tctggtctgc ccta | 2474 | |

<210> SEQ ID NO 799
<211> LENGTH: 2135
<212> TYPE: DNA
<213> ORGANISM: Mus musculus

<400> SEQUENCE: 799

| | |
|---|---|
| ccgggaagaa agggatgtat tagtgaaagg ggaccggcgc tggatcacac agctgcactt | 60 |
| tgccttccag gatgagaact acctgtacct ggtcatggaa tactacgtgg gcggggacct | 120 |
| gctaacgctg ctgagcaagt ttggggagcg gatccccgcc gagatggctc gcttctacct | 180 |
| ggccgagatt gtcatggcca tagactccgt gcaccggctg ggctacgtgc acagggacat | 240 |
| caaaccagat aacattctgc tggaccgatg tgggcacatt cgcctggcag acttcggctc | 300 |
| ctgcctcaaa ctgcagcctg atggaatggt gaggtcgctg gtggctgtgg gcaccccgga | 360 |
| ctacctgtct cctgagattc tgcaggccgt tggtggaggg cctggggcag gcagctacgg | 420 |
| gccagagtgt gactggtggg cactgggcgt gttcgcctat gagatgttct atgggcagac | 480 |
| ccccttctac gcggactcca cagccgagac atatgccaag attgtgcact acagggaaca | 540 |
| cttgtcgctg ccgctggcag acacagttgt ccccgaggaa gctcaggacc tcattcgtgg | 600 |
| gctgctgtgt cctgctgaga taaggctagg tcgaggtggg gcaggtgatt ccagaaaaca | 660 |
| tcctttcttc tttggccttg attgggaggg tctccgagac agtgtacccc cctttacacc | 720 |
| agacttcgag ggtgccacgg acacatgcaa tttcgatgtg gtggaggacc ggctcactgc | 780 |
| catggagacg ctgtcagaca tgcaggaaga catgccccct ggggtgcgcc tgcccttcgt | 840 |
| gggctactcc tactgctgca tggccttcag agctgaagag gccgacctag tggctgtccc | 900 |
| tgcccctgtg gctgaggcag agaccacggt aacgctgcag cagctccagg aagccctgga | 960 |
| agaagaggtt ctcaccccggc agagcctgag ccgcgagctg gaggccatcc ggaccgccaa | 1020 |
| ccagaacttc tccagccaac tacaggaggc cgaggtccga aaccgagacc tggaggcgca | 1080 |
| tgttcggcag ctacaggaac ggatggagat gctgcaggcc ccaggagccg cagccatcac | 1140 |
| gggggtcccc agtccccggg ccacggatcc accttcccat atggcccccc ggccgtggct | 1200 |
| gtgggccagt gcccgctggt ggggccaggc cccatgcacc gccgtcacct gctgctccct | 1260 |
| gccaggatcc ctaggcctgg cctatccgag gcgcgttgcc tgctcctgtt cgccgctgct | 1320 |
| ctggctgctg ccgccacact gggctgcact gggttggtgg cctataccgg cggtctcacc | 1380 |
| ccagtctggt gtttcccggg agccaccttc gcccctgaa ccctaagact ccaagccatc | 1440 |
| tttcatttag gcctcctagg aagatcgagc gaccagggag cgacccaaag cgtctctgtg | 1500 |
| cccatcgccc cccccccccc ccccaccgct ccgctccaca cttctgtgag cctgggtccc | 1560 |
| cacccagctc cgctcctgtg atccaggcct gccacctggc ggccggggag ggaggaacag | 1620 |
| ggctcgtgcc cagcacccct ggttcctgca gagctggtag ccaccgctgc tgcagcagct | 1680 |
| gggcattcgc cgaccttgct ttactcagcc ctgacgtgga tgggctaact gctcagctca | 1740 |
| tccgatttca cttttcact ctcccagcca tcagttacaa gccataagca tgagccccct | 1800 |
| atttccaggg acatcccatt cccatagtga tggatcagca agacctctgc cagcacacac | 1860 |
| ggagtctttg gcttcggaca gcctcactcc tgggggttgc tgcaactcct tccccgtgta | 1920 |

-continued

| | |
|---|---|
| cacgtctgca ctctaacaac ggagccacag ctgcactccc ccctccccca aagcagtgtg | 1980 |
| ggtatttatt gatcttgtta tctgactcac tgacagactc cgggacccac gttttagatg | 2040 |
| cattgagact cgacattcct cggtatttat tgtctgtccc cacctacgac ctccactccc | 2100 |
| gacccttgcg aataaaatac ttctggtctg cccta | 2135 |

<210> SEQ ID NO 800
<211> LENGTH: 2873
<212> TYPE: DNA
<213> ORGANISM: Homo sapiens

<400> SEQUENCE: 800

| | |
|---|---|
| agggggctg gaccaagggg tggggagaag gggaggaggc ctcggccggc cgcagagaga | 60 |
| agtggccaga gaggcccagg ggacagccag ggacaggcag acatgcagcc agggctccag | 120 |
| ggcctggaca ggggctgcca ggccctgtga caggaggacc ccgagccccc ggcccgggga | 180 |
| ggggccatgg tgctgcctgt ccaacatgtc agccgaggtg cggctgaggc ggctccagca | 240 |
| gctggtgttg gacccgggct tcctggggct ggagcccctg ctcgaccttc tcctgggcgt | 300 |
| ccaccaggag ctgggcgcct cgaactggc caggacaag tacgtggccg acttcttgca | 360 |
| gtgggcggag cccatcgtgg tgaggcttaa ggaggtccga ctgcagaggg acgacttcga | 420 |
| gattctgaag gtgatcggac gcgggcgtt cagcgaggta gcggtagtga agatgaagca | 480 |
| gacgggccga gtgtatgcca tgaagatcat gaacaagtgg gacatgctga gaggggcga | 540 |
| ggtgtcgtgc ttccgtgagg agagggacgt gttggtgaat ggggaccggc ggtggatcac | 600 |
| gcagctgcac ttcgccttcc aggatgagaa ctacctgtac ctggtcatgg agtattacgt | 660 |
| gggcggggac ctgctgacac tgctgagcaa gtttggggag cggattccgg ccgagatggc | 720 |
| gcgcttctac ctgcggagaa ttgtcatggc catagactcg gtgcaccggc ttggctacgt | 780 |
| gcacagggac atcaaacccg acaacatcct gctggaccgc tgtggccaca tccgcctggc | 840 |
| cgacttcggc tcttgcctca agctgcgggc agatggaacg gtgcggtcgc tggtggctgt | 900 |
| gggcacccca gactacctgt cccccgagat cctgcaggct gtgggcggtg ggcctgggac | 960 |
| aggcagctac gggcccgagt gtgactggtg ggcgctgggg gtattcgcct atgaaatgtt | 1020 |
| ctatgggcag acgcccttct acgcggattc cacggcggag acctatggca agatcgtcca | 1080 |
| ctacaaggag cacctctctc tgccgctggt ggacgaaggg gtccctgagg aggctcgaga | 1140 |
| cttcattcag cggttgctgt gtccccggga gacacggctg ggccggggtg gagcaggcga | 1200 |
| cttccggaca catcccttct ctttggcct cgactgggat ggtctccggg acagcgtgcc | 1260 |
| cccctttaca ccggatttcg aaggtgccac cgacacatgc aacttcgact tggtggagga | 1320 |
| cgggctcact gccatggaga cactgtcgga cattcgggaa ggtgcgccgc tagggggtcca | 1380 |
| cctgcctttt gtgggctact cctactcctg catggccctc agggacagtg aggtcccagg | 1440 |
| ccccacaccc atggaactgg aggccgagca gctgcttgag ccacgcgtgc aagcgcccag | 1500 |
| cctggagccc tcggtgtccc cacaggatga aacagctgaa gtggcagttc cagcggctgt | 1560 |
| ccctgcggca gaggctgagg ccgaggtgac gctgcgggag ctccaggaag ccctggagga | 1620 |
| ggaggtgctc acccggcaga gcctgagccg ggagatggag gccatccgca cggacaacca | 1680 |
| gaacttcgcc agtcaactac gcgaggcaga ggctcggaac cgggacctag aggcacacgt | 1740 |
| ccggcagttg caggagcgga tggagttgct gcaggcagag ggagccacag ctgtcacggg | 1800 |
| ggtccccagt ccccgggcca cggatccacc ttcccatatg gccccccggc cgtggctgtg | 1860 |
| ggccagtgcc cgctggtggg gccaggcccc atgcaccgcc gccacctgct gctccctgcc | 1920 |

```
agggtcccta ggcctggcct atcggaggcg cttcccctgc tcctgttcgc cgttgttctg    1980
tctcgtgccg ccgccctggg ctgcattggg ttggtggccc acgccggcca actcaccgca    2040
gtctggcgcc gcccaggagc cgcccgcgct ccctgaaccc tagaactgtc ttcgactccg    2100
gggccccgtt ggaagactga gtgccggggg cacggcacag aagccgcgcc caccgcctgc    2160
cagttcacaa ccgctccgag cgtgggtctc cgcccagctc cagtcctgtg atccgggccc    2220 gcccctagc ggccggggag ggaggggccg ggtccgcggc cggcgaacgg ggctcgaagg     2280
gtccttgtag ccgggaatgc tgctgctgct gctgctgctg ctgctgctgt gctgctgct    2340 gctgctgctg ctgctgctgg ggggatcaca gaccatttct ttctttcggc caggctgagg    2400
ccctgacgtg gatgggcaaa ctgcaggcct gggaaggcag caagccgggc cgtccgtgtt    2460
ccatcctcca cgcacccca cctatcgttg gttcgcaaag tgcaaagctt tcttgtgcat     2520
gacgccctgc tctggggagc gtctggcgcg atctctgcct gcttactcgg gaaatttgct    2580
tttgccaaac ccgcttttc ggggatcccg cgcccctc ctcacttgcg ctgctctcgg       2640
agccccagcc ggctccgccc gcttcggcgg tttggatatt tattgacctc gtcctccgac    2700
tcgctgacag gctacaggac ccccaacaac cccaatccac gttttggatg cactgagacc    2760
ccgacattcc tcggtattta ttgtctgtcc ccacctagga ccccaccc cgaccctcgc      2820 gaataaaagg ccctccatct gcccaaaaaa aaaaaaaaa aaaaaaaaaa aaa             2873
```

<210> SEQ ID NO 801
<211> LENGTH: 1509
<212> TYPE: DNA
<213> ORGANISM: Homo sapiens

<400> SEQUENCE: 801

```
ccaccgcagc ggacagcgcc aagtgaagcc tcgcttcccc tccgcggcga ccagggcccg    60
agccgagagt agcagttgta gctacccgcc cagaaactag acacaatgtg cgacgaagac   120
gagaccaccg ccctcgtgtg cgacaatggc tccggcctgg tgaaagccgg cttcgccggg   180
gatgacgccc ctagggccgt gttccccgtcc atcgtgggcc gccccgaca ccagggcgtc   240 atggtcggta tgggtcagaa agattcctac gtgggcgacg aggctcagag caagagaggt   300
atcctgaccc tgaagtaccc tatcgagcac ggcatcatca ccaactggga tgacatggag   360
aagatctggc accacccttt ctacaacgag cttcgcgtgg ctcccgagga gcaccccacc   420
ctgctcaccg aggccccct caatcccaag gccaaccgcg agaagatgac ccagatcatg   480
tttgagacct tcaacgtgcc cgccatgtac gtggccatcc aggccgtgct gtccctctac   540
gcctccggca ggaccaccgg catcgtgctg gactccggcg acggcgtcac ccacaacgtg   600
cccatttatg agggctacgc gctgccgcac gccatcatgc gcctggacct ggcgggccgc   660
gatctcaccg actacctgat gaagatcctc actgagcgtg gctactcctt cgtgaccaca   720
gctgagcgcg agatcgtgcg cgacatcaag gagaagctgt gctacgtggc cctggacttc   780
gagaacgaga tggcgacggc cgcctcctcc tcctccctgg aaaagagcta cgagctgcca   840
gacgggcagg tcatcaccat cggcaacgag cgcttccgct gcccggagac gctcttccag   900
ccctccttca tcggtatgga gtcggcgggc attcacgaga ccacctacaa cagcatcatg   960
aagtgtgaca tcgacatcag gaaggacctg tatgccaaca acgtcatgtc ggggggcacc  1020
acgatgtacc ctgggatcgc tgaccgcatg cagaaagaga tcaccgcgct ggcacccagc  1080
accatgaaga tcaagatcat cgccccgccg gagcgcaaat actcggtgtg gatcggcggc  1140
```

```
tccatcctgg cctcgctgtc caccttccag cagatgtgga tcaccaagca ggagtacgac    1200
gaggccggcc cttccatcgt ccaccgcaaa tgcttctaga cacactccac ctccagcacg    1260
cgacttctca ggacgacgaa tcttctcaat ggggggggcgg ctgagctcca gccaccccgc    1320
agtcactttc tttgtaacaa cttccgttgc tgccatcgta aactgacaca gtgtttataa    1380
cgtgtacata cattaactta ttacctcatt ttgttatttt tcgaaacaaa gccctgtgga    1440
agaaaatgga aaacttgaag aagcattaaa gtcattctgt taagctgcgt aaaaaaaaaa    1500
aaaaaaaaa                                                           1509
```

<210> SEQ ID NO 802
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 802

```
gcagcagcag cagcagcag                                                 19
```

<210> SEQ ID NO 803
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 803

```
gcagcagcag cagcagcag                                                 19
```

<210> SEQ ID NO 804
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 804

```
agcagcagca gcagcagcag                                                20
```

<210> SEQ ID NO 805
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 805

```
gcagcagcag cagcagca                                                  18
```

<210> SEQ ID NO 806
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 806

```
agcagcagca gcagcagca                                                 19
```

<210> SEQ ID NO 807
<211> LENGTH: 16
<212> TYPE: DNA
<213> ORGANISM: Artificial Sequence

```
<220> FEATURE:
<223> OTHER INFORMATION: Synthetic oligonucleotide

<400> SEQUENCE: 807
agcagcagca gcagca                                                       16

<210> SEQ ID NO 808
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 808
ctcccgacaa gctcca                                                       16

<210> SEQ ID NO 809
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 809
tcccgacaag ctcc                                                         14

<210> SEQ ID NO 810
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 810
gcttgcacgt gtggct                                                       16

<210> SEQ ID NO 811
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 811
cttgcacgtg tggc                                                         14

<210> SEQ ID NO 812
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 812
ggttgtgaac tggcag                                                       16

<210> SEQ ID NO 813
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 813
gttgtgaact ggca                                                         14
```

<210> SEQ ID NO 814
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 814
gagcggttgt gaactg                                                     16

<210> SEQ ID NO 815
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 815
agcggttgtg aact                                                       14

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 816
gctgccttcc caggcc                                                     16

<210> SEQ ID NO 817
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 817
ctgccttccc aggc                                                       14

<210> SEQ ID NO 818
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 818
gcactttgcg aaccaa                                                     16

<210> SEQ ID NO 819
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 819
cactttgcga acca                                                       14

<210> SEQ ID NO 820
<211> LENGTH: 16
<212> TYPE: DNA
<213> ORGANISM: Artificial Sequence
<220> FEATURE:
<223> OTHER INFORMATION: Synthetic oligonucleotide

```
<400> SEQUENCE: 820
gaaagctttg cacttt                                                      16

<210> SEQ ID NO 821
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 821
aaagctttgc actt                                                        14

<210> SEQ ID NO 822
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 822
cggaggacga ggtcaa                                                      16

<210> SEQ ID NO 823
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 823
ggaggacgag gtca                                                        14

<210> SEQ ID NO 824
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 824
agcctgtcag cgagtc                                                      16

<210> SEQ ID NO 825
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 825
gcctgtcagc gagt                                                        14

<210> SEQ ID NO 826
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 826
tcctgtagcc tgtcag                                                      16

<210> SEQ ID NO 827
```

```
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 827
cctgtagcct gtca                                                      14

<210> SEQ ID NO 828
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 828
gaagcgaggc ttcact                                                    16

<210> SEQ ID NO 829
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 829
aagcgaggct tcac                                                      14

<210> SEQ ID NO 830
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 830
acctgcccgt ctggca                                                    16

<210> SEQ ID NO 831
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 831
cctgcccgtc tggc                                                      14

<210> SEQ ID NO 832
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 832
ggtcagcgat cccagg                                                    16

<210> SEQ ID NO 833
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 833
```

```
gtcagcgatc ccag                                                        14

<210> SEQ ID NO 834
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 834
attttcttcc acaggg                                                      16

<210> SEQ ID NO 835
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 835
ttttcttcca cagg                                                        14

<210> SEQ ID NO 836
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 836 gaatgactttt aatgct                                                     16

<210> SEQ ID NO 837
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 837
aatgacttta atgc                                                        14
```